US012760109B2

(12) United States Patent
Holmes

(10) Patent No.: US 12,760,109 B2
(45) Date of Patent: Oct. 13, 2026

(54) ANTI BDCA-2 ANTIBODIES

(71) Applicant: Centessa Pharmaceuticals (UK) Limited, Altrincham (GB)

(72) Inventor: Steve Holmes, Altrincham (GB)

(73) Assignee: Centessa Pharmaceuticals (UK) Limited, Altrincham (GB)

( * ) Notice: Subject to any disclaimer, the term of this patent is extended or adjusted under 35 U.S.C. 154(b) by 1226 days.

(21) Appl. No.: 17/665,239

(22) Filed: Feb. 4, 2022

(65) Prior Publication Data

US 2022/0162322 A1 May 26, 2022

Related U.S. Application Data

(63) Continuation of application No. PCT/EP2020/072051, filed on Aug. 5, 2020.

(30) Foreign Application Priority Data

Aug. 5, 2019 (GB) ..................................... 1911188
Jan. 20, 2020 (GB) ..................................... 2000814

(51) Int. Cl.
*C07K 16/28* (2006.01)
*A61P 37/02* (2006.01)

(52) U.S. Cl.
CPC .......... *C07K 16/2851* (2013.01); *A61P 37/02* (2018.01); *C07K 2317/24* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 6,180,370 | B1 * | 1/2001 | Queen | A61P 19/02 435/69.6 |
| 7,030,228 | B1 | 4/2006 | Schmitz et al. | |
| 8,183,039 | B2 | 5/2012 | Schmitz et al. | |
| 9,670,283 | B2 | 6/2017 | Su | |
| 9,902,775 | B2 * | 2/2018 | Caravella | A61P 17/06 |
| 9,914,780 | B2 | 3/2018 | Su | |
| 10,214,587 | B2 | 2/2019 | Su | |
| 10,294,301 | B2 | 5/2019 | Nakao et al. | |
| 10,407,486 | B2 | 9/2019 | Schmitz et al. | |
| 11,028,175 | B2 | 6/2021 | Su | |
| 11,046,770 | B2 | 6/2021 | Nakao et al. | |
| 11,634,495 | B2 | 4/2023 | Burger et al. | |
| 12,410,225 | B2 | 9/2025 | Kley et al. | |
| 2013/0315820 | A1 | 11/2013 | Fournier et al. | |
| 2015/0238632 | A1 | 8/2015 | Clark et al. | |
| 2019/0002567 | A1 | 1/2019 | Chtourou et al. | |
| 2019/0248904 | A1 | 8/2019 | Nakao et al. | |
| 2019/0284281 | A1 | 9/2019 | Krebs et al. | |
| 2024/0018246 | A1 | 1/2024 | Gaudreault et al. | |
| 2024/0092914 | A1 | 3/2024 | Jiang | |
| 2025/0179191 | A1 | 6/2025 | Lai et al. | |
| 2025/0289895 | A1 | 9/2025 | Krebs et al. | |
| 2025/0304700 | A1 | 10/2025 | Caravella et al. | |
| 2025/0346673 | A1 | 11/2025 | Li et al. | |

FOREIGN PATENT DOCUMENTS

| | | | |
|---|---|---|---|
| EP | 3088519 | A1 | 11/2016 |
| JP | 2016505556 | A | 2/2016 |
| RU | 2419450 | C2 | 5/2011 |
| WO | PCT/US92/09965 | | 6/1993 |
| WO | WO94/13804 | | 6/1994 |
| WO | 2006113331 | A1 | 10/2006 |
| WO | 2014093396 | A1 | 6/2014 |
| WO | 2015098813 | A1 | 2/2015 |
| WO | 2018/185284 | A1 | 10/2018 |
| WO | 2022246764 | A1 | 12/2022 |
| WO | 2023034762 | A2 | 3/2023 |
| WO | 2023227033 | A1 | 11/2023 |
| WO | 2024010118 | A1 | 1/2024 |
| WO | 2024140838 | A1 | 7/2024 |
| WO | 2024230774 | A1 | 11/2024 |
| WO | 2024255683 | A1 | 12/2024 |
| WO | 2025051083 | A1 | 3/2025 |
| WO | 2025067469 | A1 | 4/2025 |
| WO | 2025118871 | A1 | 6/2025 |
| WO | 2025216667 | A1 | 10/2025 |
| WO | 2025242094 | A1 | 11/2025 |
| WO | 2026008012 | A1 | 1/2026 |

(Continued)

OTHER PUBLICATIONS

Baumgart, D. C., et al. "Aberrant plasmacytoid dendritic cell distribution and function in patients with Crohn's disease and ulcerative colitis." Clinical & Experimental Immunology 166.1 (2011): 46-54 (Year: 2011).*
Tang, Fei et al. "Plasmacytoid dendritic cells in antiviral immunity and autoimmunity." Science China. Life sciences vol. 53,2 (2010): 172-82. doi:10.1007/s11427-010-0045-0 (Year: 2010).*
Furie, Richard A., et al. "Trial of anti-BDCA2 antibody litifilimab for systemic lupus erythematosus." New England Journal of Medicine 387.10 (2022): 894-904 (Year: 2022).*
Nestle, Frank O et al. "Plasmacytoid predendritic cells initiate psoriasis through interferon-alpha production." The Journal of experimental medicine vol. 202,1 (2005): 135-43. doi: 10.1084/jem.20050500 (Year: 2005).*

(Continued)

*Primary Examiner* — Misook Yu
*Assistant Examiner* — Lia E Taylor
(74) *Attorney, Agent, or Firm* — Leydig, Voit & Mayer, Ltd.

(57) ABSTRACT

The present invention relates antigen binding molecules, particularly antibodies, fragments and variants thereof, that bind to BDCA-2 (CLEC4C), and the use of said antigen binding molecules in treating and/or preventing inflammatory disorders and immune disorders such as autoimmune diseases.

25 Claims, 19 Drawing Sheets

Specification includes a Sequence Listing.

(56) References Cited

FOREIGN PATENT DOCUMENTS

WO 2026067736 A1 4/2026

OTHER PUBLICATIONS

Ross, Rebecca L et al. "Targeting human plasmacytoid dendritic cells through BDCA2 prevents skin inflammation and fibrosis in a novel xenotransplant mouse model of scleroderma." Annals of the rheumatic diseases vol. 80,7 (2021): 920-929. doi:10.1136/annrheumdis-2020-218439 (Year: 2021).*

Nehmar, Ramzi et al. "Therapeutic Modulation of Plasmacytoid Dendritic Cells in Experimental Arthritis." Arthritis & rheumatology (Hoboken, N.J.) vol. 69,11 (2017): 2124-2135. doi:10.1002/art.40225 (Year: 2017).*

Morel, Penelope A. "Dendritic cell subsets in type 1 diabetes: friend or foe?." Frontiers in immunology 4 (2013): 415 (Year: 2013).*

Ramadan, Nehmat et al. "Possible Role for Plasmacytoid Dendritic Cells in Pemphigus." Annals of dermatology vol. 31,4 (2019): 454-457. doi:10.5021/ad.2019.31.4.454 (Year: 2019).*

Zhao, Zhendan et al. "Causal role of immune cells in Hashimoto's thyroiditis: Mendelian randomization study." Frontiers in endocrinology vol. 15 1352616. May 13, 2024, doi:10.3389/fendo.2024.1352616 (Year: 2024).*

Starosz, Aleksandra et al. "Evaluating the Role of Circulating Dendritic Cells in Methimazole-Treated Pediatric Graves' Disease Patients." Genes vol. 12,2 164. Jan. 26, 2021, doi:10.3390/genes12020164 (Year: 2021).*

Lundberg, Ingrid E., and Cecilia Grundtman. "Developments in the scientific and clinical understanding of inflammatory myopathies." Arthritis research & therapy 10 (2008): 1-10) (Year: 2008).*

Werth, Victoria P., et al. "Trial of anti-BDCA2 antibody litifilimab for cutaneous lupus erythematosus." New England Journal of Medicine 387.4 (2022): 321-331 (Year: 2022).*

Bates, Adam, and Christine A. Power. "David vs. Goliath: the structure, function, and clinical prospects of antibody fragments." Antibodies 8.2 (2019): 28 (Year: 2019).*

"Secondary Antibody Specific Binding Locations." Bio-Rad Antibodies. Accessed Mar. 8, 2024 (Year: 2024).*

Zhou, Jing, Xiaofeng Zhang, and Qing Yu. "Plasmacytoid dendritic cells promote the pathogenesis of sjögren's syndrome." Biochimica et Biophysica Acta (BBA)-Molecular Basis of Disease 1868.2 (2022): 166302 (Year: 2022).*

Cummins, Martin J et al. "Treatment of primary Sjögren's syndrome with low-dose human interferon alfa administered by the oromucosal route: combined phase III results." Arthritis and rheumatism vol. 49,4 (2003): 585-93. doi:10.1002/art.11199 (Year: 2003).*

Dzionek, A et al. "BDCA-2, a novel plasmacytoid dendritic cell-specific type II C-type lectin, mediates antigen capture and is a potent inhibitor of interferon alpha/beta induction." The Journal of experimental medicine vol. 194,12 (2001): 1823-34. doi:10.1084/jem.194.12.1823 (Year: 2001).*

Gilliet, Michel, Wei Cao, and Yong-Jun Liu. "Plasmacytoid dendritic cells: sensing nucleic acids in viral infection and autoimmune diseases." Nature Reviews Immunology 8.8 (2008): 594-606. (Year: 2008).*

Silva, Inês S., Beatriz H. Ferreira, and Catarina R. Almeida. "Molecular mechanisms behind the role of plasmacytoid dendritic cells in systemic sclerosis." Biology 12.2 (2023): 285 (Year: 2023).*

Turner, Mark D., et al. "Cytokines and chemokines: At the crossroads of cell signalling and inflammatory disease." Biochimica et Biophysica Acta (BBA)-Molecular Cell Research 1843.11 (2014): 2563-2582. (Year: 2014).*

Cao, Wei et al. "BDCA2/Fc epsilon RI gamma complex signals through a novel BCR-like pathway in human plasmacytoid dendritic cells." PLoS biology vol. 5,10 (2007): e248. doi:10.1371/journal.pbio.0050248 (Year: 2007).*

Janeway, Charles A. "Immunobiology: The Immune System in Health and Disease." 2001 (Year: 2001).*

Kipriyanov, Sergey M., and Fabrice Le Gall. "Generation and production of engineered antibodies." Molecular biotechnology 26.1 (2004): 39-60. (Year: 2004).*

Office Action issued in corresponding European Patent Application No. EP20761155.9, dated Jun. 22, 2023, 11 pages.

Brkic Z, et al. Ann Rheum Dis 2016; 75: 1567-73.

Fei T, et al. Sci China Life Sci. 2010; 53: 497-503.

Van Bon L, et al. Current Opinion in Rheumatology 2011; 23: 505-51.

Banchereau J and Pascual V. Immunity 2006; 25: 383-392.

Colonna M, et al. Nat. Immunol. 2004; 5: 1219-1226.

Gilliet M, et al. Nat. Rev. Immunol. 2008; 8: 594-606.

Swiecki M and Colonna M. Immunol. Rev. 2010; 234:142-162.

Barrat FJ et al. J. Exp. Med. 2005, 202: 1131-1139.

Hagberg N and Ronnblom L Scand. J. Immunol. 2015, 82:199-207.

Lande R et al. Nature 2007, 449; 564-569.

Deane, JA et al. Immunity 2007; 27: 801-810.

Guiducci C, et al. J. Exp. Med. 2013; 210: 2903-2919.

Mayes MD, et al. Arthritis Rheum. 2003; 48: 2246-2255.

Ah Kioon et al. Sci. Transl. Med. 2018;1 0: eaam8458.

Liu X, et al. Arthritis Rheum. 2013; 65: 226-35.

Van Bon L, et al. N Engl J Med. 2014; 370: 433-43.

Lande et al. Nat Commun. 2019; 10: 1731.

Dzionek A, et al. J. Exp. Med. 2001 ;194: 1823-1834.

Crocker PR et al. Nat Rev Immunol. 2007; 7: 255-66.

Cao W, et al. PLoS Biol. 2007; 5: e248.

Li et al. Front Immunol. 2017; 8: 1268.

Eloranta et al. Arthritis Rheum. 2013;65:853-863.

Ward, E.S. et al., Nature. 1989; 341: 544-546.

Bird et al., Science. 1988; 242: 423-426.

Huston et al., PNAS. 1988; 85: 5879-5883.

P. Hollinger et al., Proc. Natl. Acad. Sci. 1993; 90: 6444-6448.

Hollinger & Winter, Current Opinion Biotechnol. 1993; 4: 446-449.

Traunecker et al., EMBO Journal. 1991; 10: 3655-3659.

Devereux, et al., Nucleic Acids Research. 1984; 12, 387.

Alculumbre et al. Nat Immunol. 2018; 19: 63-75.

Karlin and Altschul, Proc. Natl. Acad. Sci. 1990; 87: 2264-2268.

Karlin and Altschul, Proc. Natl. Acad. Sci. 1993; 90: 5873-5877.

Altschul, et al. J. Mol. Biol. 1990; 215: 403-410.

Altschul et al. Nucleic Acids Res. 1997; 25: 3389-3402.

Torellis and Robotti, Comput. Appl. Biosci. 1994; 10: 3-5.

Pearson and Lipman, Proc. Natl. Acad. Sci. 1988; 85: 2444-8.

Yamamoto et al. J Rheumatol. 1999; 26: 2628-34.

Rajpal et al., Proc Natl Acad Sci. 2005, 102 (24):8466-71.

Steinwand et al., MAbs. 2014, 6(1): 204-18.

Wiley, Handbook of Therapeutic Antibodies. 2014, Chapter 6, Antibody Affinity (pp. 115-140).

Frenzel et al., "Expression of Recombinant Antibodies", Front Immunol, 2013, 4: 217.

Roguska et al. Protein Eng. 1996; 9: 895-904.

Jones et al., "Deimmunization of monoclonal antibodies", Methods Mol Biol, 2009, 525: 405-23.

Pharmaceutical Research, 3(6), 318 (1986).

Fanning SL et al. J Immunol. 2006; 177: 5829-39.

Rock J et al. Eur J Immunol. 2007; 37: 3564-75.

Furie R et al. J Clin Invest. 2019; 129: 1359-1371.

Jahn, PS., et al., Cell Immunol, 2010. 265: 15-22.

Mathian et al. J. Immunology 2005; 174:2499, 2005.

Jego Immunity, 2003; 19:255-34.

International Search Report mailed Nov. 16, 2020 for International Patent Application No. PCT/EP2020/072051.

Written Opinion mailed Nov. 16, 2020 for International Patent Application No. PCT/EP2020/072051.

International Preliminary Report on Patentability completed Nov. 30, 2021 for International Patent Application No. PCT/EP2020/072051.

Davison LM and Jorgensen TN. "New Treatments for Systemic Lupus Erythematosus on the Horizon: Targeting Plasmacytoid Dendritic Cells to Inhibit Cytokine Production." J. Clin. Cell. Immunol., vol. 8, No. 6, Dec. 2017, pp. 1-4.

Biliouris, K., et al., "A pre-clinical quantitative model predicts the pharmacokinetics/harmacodynamics of an anti-BDCA-2 monoclo-

(56) References Cited

OTHER PUBLICATIONS nal antibody in humans," Journal of Pharmacokinetics and Pharmacodynamics, 2018, vol. 45, pp. 817-827.
Pellerin, A., et al., "Anti-BDCA2 monoclonal antibody inhibits plasmacytoid dendritic cell activation through Fc-dependent and Fc-independent mechanisms," EMBO Molecular Medicine, 2015, vol. 7, No. 4, pp. 464-476.

* cited by examiner

>3E5_VL (SEQ ID NO: 1)

(SEQ ID NO: 2) (SEQ ID NO: 3)

DIVLTQSPASLAVSLGQRATISCKASQSVDYDGDSSMNWYQQKPGQPPKLLICAASTLESGIPARFSGSGSG

TDFTLNIHPVEEEDAATYYCQQTNEDPPTFGGGTKLEIK (SEQ ID NO: 4)

>3E5_VL_1 (SEQ ID NO: 11)

(SEQ ID NO: 12) (SEQ ID NO: 13)

DIVMTQSPDSLAVSLGERATINCKASQSVDYDGDSSMNWYQQKPGQPPKLLISAASTLESGVPSRFSGSGSG

TDFTLTISSLQAEDVAVYYCQQTNEDPPTFGGGTKVEIK (SEQ ID NO: 14)

>3E5_VL_2 (SEQ ID NO: 21)

(SEQ ID NO: 22) (SEQ ID NO: 23)

DIVMTQSPDSLAVSLGERATINCKSSQSVDYDGDSSMNWYQQKPGQPPKLLISAASTLESGVPSRFSGSGSG

TDFTLTISSLQAEDVATYYCQQTNEDPPTFGGGTKVEIK (SEQ ID NO: 24)

>3E5_VL_3 (SEQ ID NO: 31)

(SEQ ID NO: 32) (SEQ ID NO: 33)

DIVMTQSPDSLAVSLGERATINCKSSQSVDYDGDSSMNWYQQKPGQPPKLLIYAASTLESGVPSRFSGSGSG

TDFTLTISSLQAEDVATYYCQQTNEDPPTFGGGTKVEIK (SEQ ID NO: 34)

>3E5_VL_4 (SEQ ID NO: 41)

(SEQ ID NO: 42) (SEQ ID NO: 43)

DIVMTQSPDSLAVSLGERATINCKASQSVDYEGDSSMNWYQQKPGQPPKLLISAASTLESGVPSRFSGSGSG

TDFTLTISSLQAEDVAVYYCQQTNEDPPTFGGGTKVEIK (SEQ ID NO: 44)

Fig. 12A

>3E5_VH (SEQ ID NO: 5)

EVKLVESGGGLVKPGGSLKLSCAASGFTFSSYTMSWVRQTPEKRLEWVAYISSGGGNTYYPDSVKGRFTISR
DNARNTLYLQMSSLRSEDTAMYYCARHDYYDGGLYYAMDYWGQGTSVTVSS (SEQ ID NO: 6) (SEQ ID NO: 7) (SEQ ID NO: 8)

>3E5_VH_1 (SEQ ID NO: 15)

EVQLVESGGGLVKPGGSLRLSCAASGFTFSSYTMSWVRQAPGKGLEWVAYISSGGGNTYYPDSVKGRFTISR
DNAKNSLYLQMNSLRAEDTAVYYCARHDYYDGGLYYAMDYWGQGTLVTVSS (SEQ ID NO: 16) (SEQ ID NO: 17) (SEQ ID NO: 18)

>3E5_VH_2 (SEQ ID NO: 25)

QVQLVESGGGLVKPGGSLRLSCAASGFTFSSYTMSWVRQAPGKGLEWVSYISSGGGNTYYADSVKGRFTISR
DNAKNSLYLQMNSLRAEDTAVYYCARHDYYDGGLYYAMDYWGQGTLVTVSS (SEQ ID NO: 26) (SEQ ID NO: 27) (SEQ ID NO: 28)

>3E5_VH_3 (SEQ ID NO: 35)

EVQLVESGGGLVKPGGSLRLSCAASGFTFSSYTMSWVRQAPGKGLEWVAYISSGGGQTYYPDSVKGRFTISR
DNAKNSLYLQMNSLRAEDTAVYYCARHDYYDGGLYYAMDYWGQGTLVTVSS (SEQ ID NO: 36) (SEQ ID NO: 37) (SEQ ID NO: 38)

>3E5_VH_4 (SEQ ID NO: 45)

EVQLVESGGGLVKPGGSLRLSCAASGFTFSSYTMSWVRQAPGKGLEWVAYISSGGGQTYYPDSVKGRFTISR
DNAKNSLYLQMNSLRAEDTAVYYCARHDYYEGGLYYAMDYWGQGTLVTVSS (SEQ ID NO: 46) (SEQ ID NO: 47) (SEQ ID NO: 48)

Fig. 12B

>3E5_VL (SEQ ID NO: 1)

(SEQ ID NO: 2) (SEQ ID NO: 3)

DIVLTQSPASLAVSLGQRATISC[KASQSVDYDGDSSMN]WYQQKPGQPPKLLIC[AASTLES]GIPARFSGSGSG
TDFTLNIHPVEEEDAATYYC[QQTNEDPPT]FGGGTKLEIK (SEQ ID NO: 4)

>3E5_VL_1 (SEQ ID NO: 11)

(SEQ ID NO: 12) (SEQ ID NO: 13)

DIVMTQSPDSLAVSLGERATINC[KASQSVDYDGDSSMN]WYQQKPGQPPKLLIS[AASTLES]GVPSRFSGSGSG
TDFTLTISSLQAEDVAVYYC[QQTNEDPPT]FGGGTKVEIK (SEQ ID NO: 14)

>3E5_VL_2 (SEQ ID NO: 21)

(SEQ ID NO: 22) (SEQ ID NO: 23)

DIVMTQSPDSLAVSLGERATINC[KSSQSVDYDGDSSMN]WYQQKPGQPPKLLIS[AASTLES]GVPSRFSGSGSG
TDFTLTISSLQAEDVATYYC[QQTNEDPPT]FGGGTKVEIK (SEQ ID NO: 24)

>3E5_VL_3 (SEQ ID NO: 31)

(SEQ ID NO: 32) (SEQ ID NO: 33)

DIVMTQSPDSLAVSLGERATINC[KSSQSVDYDGDSSMN]WYQQKPGQPPKLLIY[AASTLES]GVPSRFSGSGSG
TDFTLTISSLQAEDVATYYC[QQTNEDPPT]FGGGTKVEIK (SEQ ID NO: 34)

>3E5_VL_4 (SEQ ID NO: 41)

(SEQ ID NO: 42) (SEQ ID NO: 43)

DIVMTQSPDSLAVSLGERATINC[KASQSVDYEGDSSMN]WYQQKPGQPPKLLIS[AASTLES]GVPSRFSGSGSG
TDFTLTISSLQAEDVAVYYC[QQTNEDPPT]FGGGTKVEIK (SEQ ID NO: 44)

Fig. 12C

>3E5_VH (SEQ ID NO: 5)

(SEQ ID NO: 9) (SEQ ID NO: 10)

EVKLVESGGGLVKPGGSLKLSCAAS[GFTFSSY]TMSWVRQTPEKRLEWVAYI[SSGGGNTY]YPDSVKGRFTISR

DNARNTLYLQMSSLRSEDTAMYYCAR[HDYYDGGLYYAMDY]WGQGTSVTVSS (SEQ ID NO: 8)

>3E5_VH_1 (SEQ ID NO: 15)

(SEQ ID NO: 19) (SEQ ID NO: 20)

EVQLVESGGGLVKPGGSLRLSCAAS[GFTFSSY]TMSWVRQAPGKGLEWVAYI[SSGGGNTY]YPDSVKGRFTISR

DNAKNSLYLQMNSLRAEDTAVYYCAR[HDYYDGGLYYAMDY]WGQGTLVTVSS (SEQ ID NO: 18)

>3E5_VH_2 (SEQ ID NO: 25)

(SEQ ID NO: 29) (SEQ ID NO: 30)

QVQLVESGGGLVKPGGSLRLSCAAS[GFTFSSY]TMSWVRQAPGKGLEWVSYI[SSGGGNTY]YADSVKGRFTISR

DNAKNSLYLQMNSLRAEDTAVYYCAR[HDYYDGGLYYAMDY]WGQGTLVTVSS (SEQ ID NO: 28)

>3E5_VH_3 (SEQ ID NO: 35)

(SEQ ID NO: 39) (SEQ ID NO: 40)

EVQLVESGGGLVKPGGSLRLSCAAS[GFTFSSY]TMSWVRQAPGKGLEWVAYI[SSGGGQTY]YPDSVKGRFTISR

DNAKNSLYLQMNSLRAEDTAVYYCAR[HDYYDGGLYYAMDY]WGQGTLVTVSS (SEQ ID NO: 38)

>3E5_VH_4 (SEQ ID NO: 45)

(SEQ ID NO: 49) (SEQ ID NO: 50)

EVQLVESGGGLVKPGGSLRLSCAAS[GFTFSSY]TMSWVRQAPGKGLEWVAYI[SSGGGQTY]YPDSVKGRFTISR

DNAKNSLYLQMNSLRAEDTAVYYCAR[HDYYEGGLYYAMDY]WGQGTLVTVSS (SEQ ID NO: 48)

Fig. 12D

ANTI BDCA-2 ANTIBODIES

CROSS-REFERENCE TO RELATED APPLICATIONS

This application is a continuation application of International PCT Patent Application No. PCT/EP2020/072051, filed on Aug. 5, 2020, which claims priority to United Kingdom Patent Application Nos. 1911188.9, filed on Aug. 5, 2019 and 2000914.0, filed on Jan. 20, 2020, each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: 20220204_SequenceListing; date created: Jan. 28, 2022; file size: 51.0 Kb).

FIELD OF THE INVENTION

The present invention relates antigen binding molecules, particularly antibodies, fragments and variants thereof, that bind to BDCA-2 (CLEC4C), and the use of said antigen binding molecules in treating and/or preventing inflammatory disorders and immune disorders such as autoimmune diseases.

BACKGROUND TO THE INVENTION

It is critical for the immune system to avoid the recognition of self-DNA and self-RNA while retaining the ability to sense microbial nucleic acids. The innate immune system appears to have elaborated several distinct mechanisms to discriminate pathogen-derived exogenous nucleic acids and host-derived self-nucleic acids. However, there is considerable emerging evidence that Toll-like receptors (TLR) recognition of self-nucleic acids occurs under certain circumstances although the innate immune system evolves distinct mechanisms to prevent self-recognition. The chronically activated plasmacytoid dendritic cells (pDCs) and the IFN-α that they produce in response to self-nucleic acids are contributing factors in the pathogenesis of some autoimmune diseases, such as Scleroderma (SSc), Systemic Lupus Erythematosus (SLE), and Sjogren syndrome psoriasis (Bekic Z, et al. Ann Rheum Dis 2016; 75:1567-73; Fei T, et al. Sci China Life Sci. 2010; 53: 172-182; van Bon L, et al. Current Opinion in Rheumatology 2011; 23:505-510; Banchereau J and Pascual V. Immunity 2006; 25:383-392).

Plasmacytoid dendritic cells (pDC) are bone marrow-derived cells specialized in the secretion of type I IFN (Colonna M, et al. Nat. Immunol. 2004; 5:1219-1226; Gilliet M, et al. Nat. Rev. Immunol. 2008; 8: 594-606). pDC are mainly found in peripheral blood and in primary and secondary lymphoid organs. pDC promptly detect viral nucleic acids, which are endocytosed and delivered to endosomes containing TLR7 and TLR9. Engagement of these receptors results in the immediate release of type I IFN, providing a very early defence against viral infections (Swiecki M and Colonna M. Immunol. Rev. 2010; 234:142-162). pDC also secrete type I IFN in response to endogenous nucleic acids that are released during cell necrosis and/or apoptosis or are bound to antinuclear autoantibodies.

Substantial evidence has pointed to the involvement of self-nucleic acid recognition in inflammatory and autoimmune diseases. In particular the contribution of TLRs to autoimmunity has been highlighted in multiple disease models. The best example is the role played by TLR9 and TLR7 in lupus following the accumulation of self-DNA/RNA via immune complexes (Barrat F J et al. J. Exp. Med. 2005, 202:1131-1139; Hagberg N and Ronnblom L Scand. J. Immunol. 2015,82:199-207). Another example is the importance of self-antimicrobial peptides in promoting autoimmunity (Lande R et al. Nature 2007, 449; 564-569). It has been shown that the overexpression of TLRs alone is sufficient to induce autoimmunity in otherwise wild type animals, as shown for TLR7 or TLR8 (Deane, J A et al. Immunity 2007; 27:801-810; Guiducci C, et al. J. Exp. Med. 2013; 210:2903-2919).

SSc is a multisystem, fibrosing disorder in which vasculopathy, autoimmunity, and inflammation lead to diverse life altering and life-threatening clinical manifestations. SSc has the highest degree of morbidity and mortality of the rheumatic diseases with a 10-year mortality rate of 23 to 45% (Mayes M D, et al. Arthritis Rheum. 2003; 48:2246-2255). The female predominance is about 4:1, and the usual age of onset is 35 to 55 years. The pathophysiology of SSc is not completely understood, but substantial evidence shows interplay between immunologic derangement, endothelial dysfunction, and profibrotic mechanisms.

Evidence is pointing to the role of pDC in SSc. pDCs infiltrate the skin of SSc patients and are chronically activated, leading to secretion of IFNα and CXCL4, which are both hallmarks of the disease. Ah Kioon et al. (Sci. Transl. Med. 2018; 10:eaam8458) demonstrated that the secretion of CXCL4 is due to the aberrant presence of TLR8 on pDCs of SSc patients, which is not seen in healthy donors and that CXCL4 primarily acts by potentiating TLR8- but also TLR9-induced IFN production by pDCs. Other studies on IFN inducible chemokines in SSC (Liu X, et al. Arthritis Rheum. 2013; 65:226-35) and the report on CXCL4 as biomarker of SSc (van Bon L, et al. N Engl J Med. 2014; 370:433-43), a growing interest has built on the role of IFN in the progression and early phases of SSc. Another recent paper shows that the IFN signature (previously associated with active SSc) is present before the onset of clinical fibrosis (Brkic Z et al. Ann Rheum Dis. 2016; 75:1567-73). In addition, in vivo data has shown that depleting pDCs can prevent disease in a mouse model of scleroderma and could revert fibrosis in mice with established disease (Ah Kioon et al. Sci. Transl. Med. 2018; 10: eaam8458).

pDC express multiple receptors that inhibit type I IFN secretion, preventing immune surveillance. One of these receptors is CLEC4C, also known as blood dendritic cell antigen-2 (BDCA-2) and CD303 (Dzionek A, et al. J. Exp. Med. 2001; 194:1823-1834). CLEC4C is a type II transmembrane glycoprotein that belongs to the C-type lectin (CTLs) superfamily (Crocker P R et al. Nat Rev Immunol. 2007; 7:255-66). BDCA-2 is the most specific marker for human pDC and is only expressed in primates. BDCA-2 consists of a single extracellular carbohydrate recognition domain, a transmembrane region, and a short cytoplasmic domain without an obvious signaling motif. BDCA-2 transmits intracellular signals through an associated transmembrane adaptor, the FcεRγ, which recruits the protein tyrosine kinase Syk, inducing protein tyrosine phosphorylation and calcium mobilization (Cao W, et al. PLoS Biol. 2007; 5:e248). Although it promotes cellular activation in other lymphoid and myeloid cells, the FcεRγ-Syk signaling pathway interferes with TLR7 and 9-induced activation of pDC, inhibiting type I IFN secretion (Dzionek A, et al. J. Exp. Med. 2001; 194:1823-1834).

pDCs are abnormally activated in peripheral blood or diseased sites and produce IFNα in large amounts, as well as other inflammatory cytokines and chemokines, in autoimmune diseases such as SLE, SSc, polymyositis and dermatomyositis, psoriasis, Sjogren's syndrome, rheumatoid arthritis, Grave's disease and Hashimoto's disease (Li et al. Front Immunol. 2017; 8:1268; Eloranta et al. Arthritis Rheum. 2013; 65:853-863).

SUMMARY OF THE INVENTION

In a first aspect of the invention there is provided an antigen binding molecule or fragment or variant thereof comprising a heavy chain variable region comprising a VHCDR3 and/or a light chain variable region comprising a VLCDR3, wherein the antigen binding molecule binds to BDCA-2 (CLEC4C).

In a second aspect of the invention there is provided an antigen binding molecule or fragment or variant thereof comprising a heavy chain variable region and/or a light chain variable region, each comprising 3 CDR regions, wherein the antigen binding molecule binds to BDCA-2 (CLEC4C).

In a third aspect of the invention, there is provided an anti-BDCA-2 (CLEC4C) antigen binding molecule, wherein the antigen binding molecule has an equilibrium dissociation constant ($K_D$) for BDCA-2 (CLEC4C) of less than about 2 nM. In some embodiments, the antigen binding molecule has an equilibrium dissociation constant (Ko) for BDCA-2 (CLEC4C) of less than about 0.01 nM.

In a fourth aspect of the invention, there is provided an anti-BDCA-2 (CLEC4C) antigen binding molecule, wherein the antigen binding molecule has a half maximal inhibitory concentration (IC50) for inhibition of IFN secretion of less than about 2 nM. In some embodiments, the antigen binding molecule has a half maximal inhibitory concentration (IC50) for inhibition of IFN secretion of less than about 0.1 nM.

In a fifth aspect of the invention, there is provided an anti-BDCA-2 (CLEC4C) antigen binding molecule, wherein the antigen binding molecule has an IC90 for inhibition of IFN secretion of less than about 20 nM. In some embodiments, the antigen binding molecule has an IC90 for inhibition of IFN secretion of less than about 5 nM.

In a sixth aspect of the invention, there is provided an anti-BDCA-2 (CLEC4C) antigen binding molecule, wherein the antigen binding molecule comprises a VHCDR3 comprising the amino acid sequence of any one of SEQ ID NOs 48, 28, 8, 38, 58, 68 and 78; and/or a VLCDR3 comprising the amino acid sequence of any one of SEQ ID NOs 34, 24, 44, 4, 14, 54, 64 and 74.

In a seventh aspect of the invention, there is provided an anti-BDCA-2 (CLEC4C) antigen binding molecule, wherein the antigen binding molecule comprises: a VHCDR1 comprising the amino acid sequence of any one of SEQ ID NOs 46, 49, 26, 29, 6, 9, 16, 19, 36, 39, 56, 59, 66, 69, 76 and 79; a VHCDR2 comprising the amino acid sequence of any one of SEQ ID NOs 47, 50, 27, 30, 7, 10, 17, 20, 37, 40, 57, 60, 67, 70, 77 and 80; and a VHCDR3 comprising the amino acid sequence of any one of SEQ ID NOs 48, 28, 8, 18, 38, 58, 68 and 78; and/or a VLCDR1 comprising the amino acid sequence of any one of SEQ ID NOs 32, 22, 42, 2, 12, 52, 62 and 72; a VLCDR2 comprising the amino acid sequence of any one of SEQ ID NOs 33, 23, 43, 3, 13, 53, 63 and 73; and a VLCDR3 comprising the amino acid sequence of any one of SEQ ID NOs 34, 24, 44, 4, 14, 54, 64 and 74.

In an eighth aspect of the invention, there is provided an anti-BDCA-2 (CLEC4C) antigen binding molecule, wherein the antigen binding molecule comprises a heavy chain variable region having the amino acid sequence selected from the group consisting of SEQ ID NO:45, SEQ ID NO: 25, SEQ ID NO: 5, SEQ ID NO: 15, SEQ ID NO: 35, SEQ ID NO: 55, SEQ ID NO: 65 and SEQ ID NO: 75, and/or a light chain variable region having the amino acid sequence selected from the group consisting of SEQ ID NO: 31, SEQ ID NO: 21, SEQ ID NO: 41, SEQ ID NO: 1, SEQ ID NO: 11, SEQ ID NO: 51, SEQ ID NO: 61 and SEQ ID NO: 71

In a ninth aspect of the invention, there is provided an anti-BDCA-2 (CLEC4C) antigen binding molecule, wherein the antigen binding molecule is an antibody that specifically binds to BDCA-2 (CLEC4C) and is selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06, 28B01. The present invention also provides fragments and variants derived from said antibodies.

In a further aspect of the invention there is provided an antigen binding molecule or fragment or variant thereof, that binds to BDCA-2 (CLEC4C) and competes for binding to BDCA-2 (CLEC4C) with an antigen binding molecule of any of the first to ninth aspects of the invention.

In a further aspect of the invention, there is provided an antigen binding molecule that specifically binds to an epitope of BDCA-2 (CLEC4C) that is bound by an antigen binding molecule of any of the first to ninth aspects of the invention.

In a further aspect of the invention, there is provided an antigen binding molecule that specifically binds to BDCA-2 (CLEC4C) and inhibits the binding of BDCA-2 (CLEC4C) to an antigen binding molecule of any of the first to ninth aspects of the invention.

In a further aspect of the invention, there is provided an anti-BDCA-2 (CLEC4C) antigen binding molecule comprising 1 to 10, 1 to 5 or 1 to 2 amino acid substitutions from the antigen binding molecule of any the first to ninth aspects of the invention.

In a further aspect of the invention, there is provided an anti-BDCA-2 (CLEC4C) antigen binding molecule, wherein the anti-BDCA-2 (CLEC4C) antigen binding molecule is a humanised or deimmunised derivative of an anti-BDCA-2 (CLEC4C) antigen binding molecule of the invention.

In a further aspect of the invention, there is provided an affinity matured mutant of an antigen binding molecule or antibody of the invention.

In a further aspect of the invention there is provided a pharmaceutical composition comprising an antigen binding molecule of the invention, or a fragment, variant or affinity matured mutant thereof.

In a still further aspect of the invention there is provided the antigen binding molecules or pharmaceutical compositions of the invention for use in medicine.

In another aspect, there is provided the antigen binding molecules or pharmaceutical compositions of the invention for use in preventing and/or treating an inflammatory disorder or disease.

In another aspect, there is provided the use of antigen binding molecules or pharmaceutical compositions of the invention for the manufacture of a medicament for use in treatment of an inflammatory disorder or disease.

In a further aspect, there is provided a method of treating or preventing an inflammatory disorder or disease in a subject in need thereof, comprising administering to the subject a therapeutically effective amount of an antigen binding molecule or pharmaceutical composition of the invention.

Also provided are nucleic acids encoding the antigen binding molecules of the invention. There is also provided a vector or a plasmid comprising the nucleic acids of the invention. The invention also provides a host cell comprising a nucleic acid, vector or plasmid of the invention.

The invention also provides methods of producing cell that expresses an anti-BDCA-2 (CLEC4C) antigen binding molecule, comprising transfecting said cell with a plasmid or vector of the invention The invention also provides methods for the production of an anti-BDCA-2 (CLEC4C) antigen binding molecule, comprising culturing a host cell of the invention in a cell culture medium under conditions to express the encoding nucleic acid sequence of the plasmid or vector inside the cell, and optionally collecting the anti-BDCA-2 (CLEC4C) antigen binding molecule from the cell supernatant.

The invention also provides kits comprising an anti-BDCA-2 (CLEC4C) antigen binding molecule or other aspect of the invention, optionally further comprising instructions for use.

BRIEF DESCRIPTION OF FIGURES

FIG. 7A shows global RNA-seq analysis of three independent human pDCs donors (Lineage$^{-}$HLA-DR$^{+}$ CD123$^{+}$CD304$^{+}$) with and without ODN stimulation and the pathway analysis of differentially expressed genes (DEG). FIG. 7B illustrates 3E5 inhibition of ODN stimulated pDC DEGs, which exhibits an expression profile similar to non-stimulated pDC.

FIG. 8A outlines the culture technique and air-liquid interface (ALI).

FIGS. 12A, B, C and D. Sequences of parental 3E5 heavy and light chain variable sequences and 4 humanised/deimmunised variants 1 to 4 (SEQ ID NOs 1, 11, 21, 31, 41, 5, 15, 25, 35 and 45), together making up the 16 variant antibodies based on the parental 3E5 antibody. Figures A and B identify the 6 CDRs according to the Kabat scheme. Figures C and D identify the 6 CDRs according to the Chothia scheme. These figures also provide the SEQ ID NO for each of the sequences (heavy, light, CDRs both Kabat and Chothia) related to the 3E5 parental antibody and its 16 variants (SEQ ID NOs: 1 to 50). In the event of any discrepancies between the sequences of these Figures and the sequences in the accompanying sequence listing or elsewhere in this description, the sequences of these Figures shall prevail.

DETAILED DESCRIPTION

Figure 1:
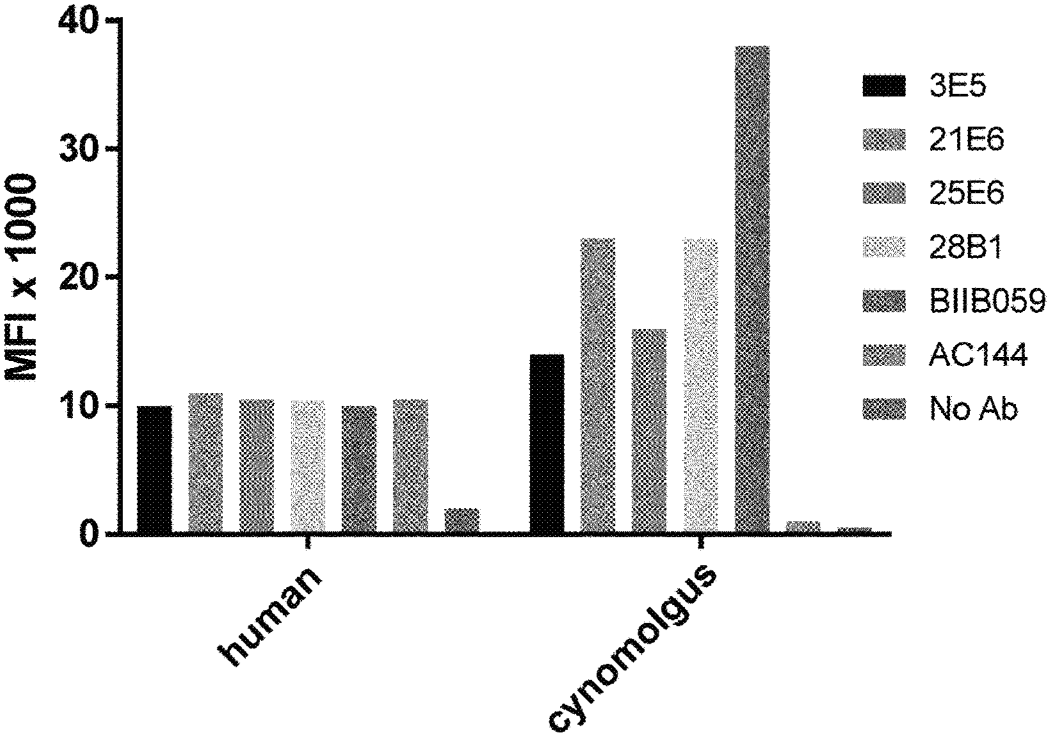
FIG. 1. Chimeric mAbs binding to human and cynomolgus cell expressed BDCA-2. 5 ug/ml of purified mAbs were tested against human or cynomolgus expressed BDCA-2. Positive controls used were anti-BDCA-2 mAbs, AC144 (Miltenyi Biotec, cat. no. 130-090-690) and BIIB059 (patent WO2014093396) and the negative control was buffer (no Ab).

As used herein, an "antigen binding molecule" is a member of a pair of molecules which have binding specificity for one another. The members of an antigen binding pair may be naturally derived or wholly or partially synthetically produced. One member of the pair of molecules has an area on its surface, which may be a protrusion or a cavity, which specifically binds to and is therefore complementary to a particular spatial and polar organisation of the other member of the pair of molecules. Thus, the members of the pair have the property of binding specifically to each other. Examples of types of antigen binding pairs are antigen-antibody, biotin-avidin, hormone-hormone receptor, receptor-ligand and enzyme-substrate. The present invention is generally concerned with antigen-antibody type interactions. The antigen binding molecule used in the present invention binds specifically to BDCA-2 (CLEC4C) or an epitope of BDCA-2 (CLEC4C). The binding affinity of the antigen binding molecule to BDCA-2 (CLEC4C) or an epitope of BDCA-2 (CLEC4C) can be measured using the dissociation constant ($K_D$). The binding affinity of the antigen binding molecule to BDCA-2 (CLEC4C) or an epitope of BDCA-2 (CLEC4C) can be measured using the association constant ($K_a$). The $K_D$ value of the antigen binding molecule for an epitope of BDCA-2 (CLEC4C) bound by a antigen binding molecule of the invention will be lower than the $K_D$ value of the antigen binding molecule for an alternative epitope of BDCA-2 (CLEC4C) or a non-BDCA-2 (CLEC4C) epitope.

Antigen binding molecules which bind to BDCA-2 (CLEC4C) include anti-BDCA-2 (CLEC4C) antibodies and antigen-binding fragments thereof. The antigen binding molecule used in the present invention is typically an antibody.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. Antibodies may be polyclonal or monoclonal. These can be derived from natural sources, or they may be partly or wholly synthetically produced. Antibodies are polypeptides that typically contain two identical heavy chains and two identical light chains, which are smaller than the heavy chains. In mammals there are two types of light chain, which are called lambda (λ) and kappa (κ). Each of the heavy chains and each of the light chains are composed of a variable region and a constant region. The heavy chain variable region is referred to as the VH region and the light chain variable region is referred to as the VL region. For kappa light chains, the VL region can also be referred to as the VK region. Each of the variable regions of the heavy and light chains comprise three complementarity determining regions (CDRs), CDR1, CDR2 and CDR3. These are named VLCDR1, VLCDR2, VLCDR3, VHCDR1, VHCDR2 and VHCDR3 respectively. Examples of antibodies are the immunoglobulin isotypes (e.g., IgG, IgE, IgM, IgD and IgA) and their isotypic subclasses; fragments which comprise an antigen binding domain, such as Fab, F(ab')2, Fv, scFv, dAb, Fd; and diabodies.

Fragments of Antibodies and Antigen Binding Molecules

The antigen binding molecule of the invention can be a fragment of an antibody, specifically an antigen binding fragment of an antibody. The antigen binding fragments comprise one or more antigen binding regions. It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341:544-546 (1989)) which consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a peptide linker which allows the two domains to associate to form an antigen binding site (Bird et al., Science 242:423-426 (1988); Huston et al., PNAS USA 85:5879-5883 (1988)); (viii) bispecific single chain Fv dimers (PCT/US92/09965) and (ix) "diabodies", multivalent or multispecific fragments constructed by gene fusion (WO94/13804; P. Hollinger et al., Proc. Natl. Acad. Sci. USA 90: 6444-6448 (1993)). Typically, the fragment is a Fab, F(ab')2 or Fv fragment or an scFv molecule.

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associated with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Hollinger & Winter, Current Opinion Biotechnol. 4:446-449 (1993)), e.g. prepared chemically or from hybrid hybridomas, or may be any of the bispecific antibody fragments mentioned below. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., EMBO Journal 10:3655-3659 (1991).

A bispecific antibody is one which can bind to two target molecules simultaneously, such as two antigens or two epitopes. Bispecific antibodies may also be referred to as dual binding antibodies. Examples of bispecific antibody formats include, but are not limited to; (mAb)2, Fcab, F(mAb')2, quadromas, scFv (single chain variable fragments), bsDb (bispecific diabodies), scBsDb (single chain bispecific diabodies), BiTE (bispecific T cell engagers), DART (dual affinity re-targeting antibodies), charge pairs, tandem antibodies, tandem scFv-Fc, Fab-scFv-Fc, Fab-scFv, minibodies, zybodies, DNL-F(ab)3 (dock-and-lock trivalent Fabs), bssdAb (bispecific single domain antibodies) and knobs-in-holes.

Bispecific diabodies, as opposed to bispecific whole antibodies, may also be useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

The antigen binding molecules of the invention may be provided in a format that allows crosslinking between adjacent antigen-binding molecules. For example, antigen binding molecules comprising an Fc region (such as those in a monoclonal antibody format) allow cross-linking between the Fc regions of two adjacent molecules (and hence cross-linking between adjacent BDCA-2 molecules due to co-localisation). In some cases, this may promote internalisation of BDCA2 and inhibition of IFN secretion. In other embodiments, the antigen binding molecules may be provided in a format that does not allow for crosslinking between adjacent antigen-binding molecules. For example, antigen binding molecules lacking an Fc region (such as those in a Fab format, or similar), may not cross-link. Nevertheless, it has been demonstrated that the antigen-binding molecules of the invention (specifically, antigen binding molecules having the sequences disclosed herein) are still able to promote internalisation of BDCA2 and inhibition of IFN secretion in a dose-dependent manner, even when provided in a format that does not permit crosslinking. This means both types of antigen binding molecules (those formats allowing for cross-linking and those formats that do not allow for cross-linking) can be provided, increasing the utility and functionality of the antigen binding molecules of the present invention over those of the prior art.

Furthermore, the antigen-binding molecules of the invention are able to promote internalisation of BDCA2 and inhibition of IFN secretion in a dose-dependent manner, even when the antigen-binding molecules are provided in a format that bind in a monovalent manner to BDCA2. For example, antigen-binding molecules in a Fab format, which bind to BDCA-2 in a monovalent manner (i.e. a ratio of one antigen-binding molecule to one BDCA2 molecule), have been shown to promote internalisation of BDCA2 and inhibition of IFN secretion in a dose-dependent manner. This is again in contrast to the anti-BDCA2 molecules of the prior art.

Accordingly, in some embodiments, the antigen-binding molecules bind BDCA2 in a monovalent manner (i.e. a ratio of one antigen-binding molecule to one BDCA2 molecule). In some embodiments, the antigen-binding molecules do not cross-link with one another. Fab formats achieve both these aims, since they neither cross-link with each other (due to the lack of an Fc region) and they bind their antigen in a monovalent manner. In some embodiments, the present invention provides antigen-binding molecules having sequences that promote internalisation of BDCA2 and inhibition of IFN secretion (in vitro or in vivo). Advantages of the antigen-binding molecules of the invention include the ability to promote internalisation of BDCA2 and inhibition of IFN secretion regardless of the ability of the antigen-binding molecules to cross-link with each other (and hence co-localise BDCA2 molecules) and regardless of the binding valency (i.e. monovalent or bivalent binding).

Identity and Homology

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptides or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100). Generally, references to % identity herein refer to % identity along the entire length of the molecule, unless the context specifies or implies otherwise.

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad.

Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention.

To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

Typically, the amino acid sequence of the CDRs of the antigen binding molecules provided in the invention have at least 70% identity, for example using the default parameters of the BLAST computer program (Atschul et al., J. Mol. Biol. 215, 403-410 (1990)) provided by HGMP (Human Genome Mapping Project), at the amino acid level, to the amino acid sequences of the CDRs described below. More typically, the CDR sequence has at least 75%, 80%, 85%, 90%, 91%, 92%, 93%, 94%, 95%, 96%, 97%, 98% or at least 99% identity, at the amino acid level, to the sequences shown below. Typically, each of the CDR sequences of the antigen binding molecule used in the invention has this level of identity to the amino acid sequences of the CDRs set out below. Alternatively, any 1, 2, 3, 4 or 5 of the CDRs of the antigen binding molecule used in the invention has this level of identity to the amino acid sequences of the CDRs set out below.

The amino acid sequence of the VH and VL regions of the antigen binding molecules provided in the invention have at least 70% identity, for example using the default parameters of the BLAST computer program (Atschul et al., J. Mol. Biol. 215, 403-410 (1990)) provided by HGMP (Human Genome Mapping Project), at the amino acid level, to the amino acid sequences of the VH and VL regions described below. More typically, the VH and VL regions have at least 75%, 80%, 85%, 90%, 91%, 92%, 93%, 94%, 95%, 96%, 97%, 98% or at least 99% identity, at the amino acid level, to the sequences shown below. Typically, each of the VH and VL regions of the antigen binding molecule used in the invention has this level of identity to the amino acid sequences of the VH and VL regions set out below. Alternatively, only one of the VH and VL regions of the antigen binding molecule used in the invention has this level of identity to the amino acid sequences of the VH and VL regions set out below.

Identity, as used herein, is used interchangeably with "homology" and "similarity". References to particular % identities apply equally to % homology and % similarity. Homology and similarity may be determined using appropriate algorithms, such as FASTA, BLAST and Gapped BLAST. Software for performing these analyses are publicly available.

In some embodiments, in particular for any embodiments referencing sequences having a particular sequence identity to a reference sequence, the % sequence identity may be calculated without the sequence of all 6 CDRs of the specified heavy or light chain variable region. In such embodiments, the variations in sequence occur only in the framework regions.

Variants

The present invention also extends to variants of peptide sequences referred to below. As used herein the term "variant" relates to proteins that have a similar amino acid sequence and/or that retain the same function. For instance, the term "variant" encompasses proteins or polypeptides which include one or more amino acid additions, deletions, substitutions or the like. An example of a variant of the present invention is a protein comprising a peptide as defined below, apart from the substitution of one or more amino acids with one or more other amino acids. Amino acid substitutions may be made to, for example, reduce or eliminate liabilities in the amino acid sequences. Alternatively, amino acid substitutions may be made to improve antigen affinity or to humanise or deimmunise the antibodies, if required. Affinity matured variants, humanised variants and deimmunised variants of the specified antibodies are provided herein, as well as variants comprising amino acid substitutions to reduce or eliminate any liabilities in the sequences of the antibodies.

As noted above, in some embodiments, any substitutions may occur only in the framework regions. In such embodiments, the original CDR sequences are retained, but variation may occur in one or more framework regions.

Variant antigen-binding molecules having the one or more amino acid substitutions may retain the functional activity (for example EC50, IC50, IC90 and/or Kd) of the antigen-binding molecule from which the variant antigen-binding molecule is derived. Variant antigen-binding molecules of the invention can be used and formulated in the same ways as described for the antigen-binding molecules from which they are derived.

Substitutions

The skilled person is aware that various amino acids have similar properties. One or more such amino acids of a substance can often be substituted by one or more other such amino acids without eliminating a desired activity of that substance.

Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

Using the three letter and one letter codes the naturally occurring amino acids may be referred to as follows: glycine (G or Gly), alanine (A or Ala), valine (V or Val), leucine (L or Leu), isoleucine (I or lie), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gin), cysteine (C or Cys), methionine (M or Met), serine (S or Ser) and Threonine (T or Thr). Where a residue may be aspartic acid or asparagine, the symbols Asx or B may be used. Where a residue may be glutamic acid or glutamine, the symbols Glx or Z may be used. References to aspartic acid include aspartate, and glutamic acid include glutamate, unless the context specifies otherwise.

Amino acid deletions or insertions can also be made relative to the amino acid sequence for the fusion protein referred to below. Thus, for example, amino acids which do not have a substantial effect on the activity of the polypeptide, or at least which do not eliminate such activity, can be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

In some embodiments, the following amino acids can be exchange for each other for conservative amino acid substitutions:

| Class | Exchangeable amino acids |
|---|---|
| Aliphatic | Glycine, Alanine, Valine, Leucine, Isoleucine |
| Hydroxyl or Sulfur/Selenium-containing | Serine, Cysteine, Threonine, Methionine |
| Aromatic | Phenylalanine, Tyrosine, Tryptophan |
| Basic | Histidine, Lysine, Arginine |
| Acidic and their Amide | Aspartate, Glutamate, Asparagine, Glutamine |

Therefore, references to "conservative" amino acid substitutions refer to amino acid substitutions in which one or more of the amino acids in the sequence of the antibody (e.g. in the CDRs or in the VH or VL sequences) is substituted with another amino acid in the same class as indicated above. Conservative amino acid substitutions may be preferred in the CDR regions to minimise adverse effects on the function of the antibody. However, conservative amino acid substitutions may also occur in the framework regions.

Amino acid changes relative to the sequence given below can be made using any suitable technique e.g. by using site-directed mutagenesis or solid-state synthesis.

It should be appreciated that amino acid substitutions or insertions within the scope of the present invention can be made using naturally occurring or non-naturally occurring amino acids, although naturally occurring amino acids may be preferred. Whether or not natural or synthetic amino acids are used, it may be preferred that only L-amino acids are present.

In one embodiment of the invention there is provided antigen binding molecule, or antigen binding fragment thereof, of the invention comprising from 1 to 10, preferably from 1 to 5, amino acid substitutions in the antibody binding domain or antigen binding domains. For example, in one embodiment of the invention, there is provided an anti-BDCA-2 (CLEC4C) antibody or antigen binding fragment thereof, wherein the anti-BDCA-2 (CLEC4C) antibody antigen binding fragment thereof comprises the 6 CDR regions of an antibody selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01, wherein the antigen binding molecule has from 1 to 10 amino acid substitutions across all of its CDR regions, preferably from 1 to 5 amino acid substitutions. In a further embodiment of the invention, there is provided an anti-BDCA-2 (CLEC4C) antigen binding molecule or antigen binding fragment thereof, wherein the anti-BDCA-2 (CLEC4C) antibody antigen binding fragment thereof comprises the VH and VL sequences of an antibody selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01, wherein the antigen binding molecule has from 1 to 10 amino acid substitutions across its VH and VL sequences, preferably from 1 to 5 amino acid substitutions. In a still further embodiment of the invention, there is provided an anti-BDCA-2 (CLEC4C) antibody, wherein the anti-BDCA-2 (CLEC4C) antibody is an antibody selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01, wherein the antibody has from 1 to 10 amino acid substitutions, preferably from 1 to 5 amino acid substitutions. Substitutions are of course substitutions with reference to the original CDR or variable chain sequences of the starting antibody.

In some embodiments, the one or more amino acid substitutions are in the CDR region or regions. In other embodiments, the one or more amino acid substitutions are in the framework regions, i.e. in the variable heavy and light chains but not in the CDR region or regions. In other embodiments, the one or more amino acid substitutions may be at any position in the variable heavy and/or variable light regions. In some embodiments, the amino acid substitutions do not occur in a CDR sequence.

In some embodiments, the amino acid substitutions do not adversely affect the binding specificity and/or affinity of the antibody. Accordingly, the variant antibody may have the same or superior functional profile as the antibody from which is it derived.

Affinity Matured Variants

Other variants that are within the scope of the present invention include antigen binding molecules of the invention that are modified to have increased affinity for BDCA-2 (CLEC4C). In one embodiment, the antigen binding molecule of the invention is an affinity-matured antibody. In one embodiment, the antigen binding molecules of the invention are humanised affinity-matured antibodies.

Any known methods can be used to increase the affinity of the antigen binding molecules of the invention to generate affinity-matured antibodies or humanised affinity-matured antibodies with an increased affinity for BDCA-2 (CLEC4C).

The present invention provides affinity matured variants of the provided antigen binding agents. The affinity matured variants bind to BDCA-2 (CLEC4C) with greater affinity than the parental antibody. Preferably the produced antibody binds to BDCA-2 (CLEC4C) with at least 20%, at least 30%, at least 40%, more preferably at least 50% greater affinity than the parental antibody binds to BDCA-2 (CLEC4C), for example as measured by the Kd.

In some embodiments the invention provides a method of preparing antigen binding molecules of the invention comprising providing an antigen binding molecule as herein described (e.g., anti-BDCA-2 (CLEC4C) binding molecule or antibody or an antigen binding fragment or variant thereof), and subjecting the antibody to affinity maturation, wherein the antibody produced binds to BDCA-2 (CLEC4C) with greater affinity than the parental antibody. Preferably the produced antibody binds to BDCA-2 (CLEC4C) with at least 20%, at least 30%, at least 40%, more preferably at least 50% greater affinity than the parental antibody binds to BDCA-2 (CLEC4C), for example as measured by the Kd. Methods for measuring affinity are known in the art and described in the Examples below. The affinity matured antibodies produced by such methods can be formulated and used as described herein for the other anti-BDCA-2 (CLEC4C) binding molecules.

Affinity maturation may be carried out according to any suitable method known to the skilled person. For example, in vitro antibody display systems are widely used for the generation of specific antibodies with high affinity. In these systems, the phenotype (i.e., the antibody fragment) is coupled to the genotype (i.e., the antibody gene) allowing the direct determination of the sequence of the antibody. Several systems have been developed to achieve display of antibody repertoires to allow subsequent selection of binders and by increasing the stringency of selection allows for the selection of higher and higher affinity variants. The antibody fragments can be expressed in yeast, ribosomes, phage display particles or by direct coupling to DNA.

Current antibody affinity maturation methods belong to two mutagenesis categories: stochastic and non-stochastic. Error-prone polymerase chain reaction (PCR), mutator bacterial strains, and saturation mutagenesis are typical examples of stochastic mutagenesis methods. Non-stochastic techniques often use alanine-scanning or site-directed mutagenesis to generate limited collections of specific variants. In addition, shuffling approaches to obtain shuffled variants of the parent antibody can also be used to improve antibodies' affinity further.

Accordingly, in one embodiment of the invention, the method of affinity maturation is selected from the group consisting of stochastic mutagenesis (for example error-prone polymerase chain reaction (PCR), mutator bacterial strains, or saturation mutagenesis), non-stochastic mutagenesis (for example alanine-scanning or site-directed mutagenesis), shuffling (for example DNA shuffling, chain shuffling or CDR shuffling) and the use of the CRISPR-Cas9 system to introduce modifications.

Affinity maturation methods are described in, for example, Rajpal et al., Proc Natl Acad Sci USA, 2005, 102(24):8466-71, Steinwand et al., MAbs, 2014, 6(1):204-18, as well as in Handbook of Therapeutic Antibodies, Wiley, 2014, Chapter 6, Antibody Affinity (pages 115-140).

In some embodiments there is provided a method of preparing a pharmaceutical composition comprising providing an antibody prepared according to a method above, (i.e. for producing an antibody by affinity maturation) and co-formulating the antibody with at least one or more pharmaceutically acceptable excipients. The antibody used in the preparation of the pharmaceutical composition can be an affinity matured variant of 3E05, 21E06, 25E06 or 28B01. The antibody used in the preparation of the pharmaceutical composition can also be an affinity matured variant of 3E05_var12, 3E05_var6, 3E05_var14, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15 or 3E05_var16. The pharmaceutical compositions produced by such methods can be used in the methods of treatment of the present invention as described herein for the other anti-BDCA-2 (CLEC4C) binding molecules.

There are therefore provided antigen binding molecules that are affinity matured mutants or variants of the antigen binding molecules of the invention. For example, in one embodiment there is provided an affinity-matured variant of an antibody selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01. Generally, the affinity matured mutants have a higher affinity for BDCA-2 (CLEC4C) (in particular human BDCA-2 (CLEC4C)) than the parent antibody (the antibody from which the mutant is derived). Also provided by the present invention are antigen binding molecules and antibodies obtainable or obtained by affinity maturation of an antigen binding molecule or antibody of the invention.

Other Variants

The antigen binding molecule of the invention is typically an antibody, more typically a monoclonal antibody. In a preferred embodiment, the monoclonal antibody of the present invention is a humanised antibody. In some embodiments, the antibody is a fully-human monoclonal antibody, in which the human constant region is employed.

Methods for the production of monoclonal antibodies are well known to the skilled person, for examples as described in Frenzel et al., "Expression of Recombinant Antibodies", *Front Immunol,* 2013, 4:217, the contents of which is hereby incorporated by reference.

The monoclonal antibodies of the present invention can be humanised by modifying the amino acid sequence of the antibody. Methods to reduce the immunogenicity of the antigen binding molecules of the invention include CDR grafting on to a suitable antibody framework scaffold or variable surface residues remodelling, e.g. by site-directed mutagenesis or other commonly used molecular biological techniques (Roguska et al Protein Eng. 9 895-904 (1996)).

Other methods applicable can include the identification of potential T-cell epitopes within the molecule, and the subsequent removal of these e.g. by site-directed mutagenesis (de-immunisation). Humanisation of the antigen binding molecule may be desired where the molecule is to be used as a therapeutic agent. Humanisation of the CDR regions or of the surrounding framework sequence can be carried out as desired.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin. A hybridoma or other cell producing an antibody may be subject to genetic mutation or other changes, which may or may not alter the binding specificity of antibodies produced.

In one embodiment, the heavy chain variable region and/or the light chain variable region are at least 85% humanised, at least 90% humanized, at least 95% humanized, at least 96% humanized, at least 97% humanized, at least 98% humanized or at least 99% humanized. In some embodiments, the antibodies are conservatively humanised, for example to retain better antigen binding. In such conservatively humanised antibodies, fewer antibody substations may be made, compared to humanised antibodies.

The antigen binding molecules of the invention are, in some embodiments, deimmunised, for example using methods described in Jones et al., "Deimmunization of monoclonal antibodies", *Methods Mol Biol,* 2009, 525:405-23, the contents of which are hereby incorporated by reference. Deimmunisation removes T-cell epitopes from the sequences using a combined immunological and molecular biology technique.

In some embodiments of the invention, there is therefore provided a deimmunised anti-BDCA-2 (CLEC4C) antigen binding molecule or antigen binding fragment thereof, wherein the anti-BDCA-2 (CLEC4C) antigen binding molecule or antigen binding fragment thereof comprises deimmunised variants of the 6 CDR regions of an antibody selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01. In a further embodiment of the invention, there is provided a deimmunised anti-BDCA-2 (CLEC4C) antigen binding molecule or antigen binding fragment thereof, wherein the anti-BDCA-2 (CLEC4C) antigen binding molecule or antigen binding fragment thereof comprises deimmunised variants of the VH and/or VL sequences from an antibody selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01. In a still further embodiment of the invention, there is provided a deimmunised anti-BDCA-2 (CLEC4C) antibody, wherein the anti-BDCA-2 (CLEC4C) antibody is a deimmunised variant of an antibody selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01.

The antigen binding molecules and antigen binding fragments thereof are based on 4 parental antibodies 3E05, 21E06, 25E06 and 28B01. In addition to the parental antibodies, the invention is particularly concerned with humanised and deimmunised derivatives of one of the parental antibodies, 3E05, including 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15 and 3E05_var16. In preferred embodiments, the invention is particularly concerned with humanised and deimmunised derivatives of 3E05, including 3E05_var12, 3E05_var6 and 3E05_var14. However, humanised and deimmunised derivatives of the remaining 3 parental antibodies are also provided. The invention is also based on antibody-fragments comprising one more antigen binding domains from the parental or humanised/deimmunised antibodies of the invention, as well as further variants such as antigen binding domains containing 1 or more conservative amino acid substitutions (such as from 1 to 10, or preferably from 1 to 5 substitutions) and affinity matured variants of the antigen binding molecules of the invention. All of the antigen binding molecules of the invention specifically bind BDCA-2 (CLEC4C).

Humanised and deimmunised variants of antibodies provided herein may have at least 90% sequence identity, for example at least 95% sequence identity to the original, parental, sequence(s) that is/are humanised or deimmunised.

The antigen binding molecules of the invention, in particular antibodies, may be of any suitable type, including IgA, IgD, IgE, IgG, IgM and IgY, although IgG may be preferred. IgG1 backbones may be most preferred. In relevant embodiments, the constant region of the antibodies of the invention may be modified for advantageous effect, for example to increase stability and reduce Fc gamma receptor interaction. Such modifications include S241P and L248E substitutions in the Fc region. Other suitable modifications are known to the skilled person.

"Specific binding", "bind specifically", and "specifically bind" are understood to mean that the anti-BDCA-2 (CLEC4C) antigen binding molecule has a dissociation constant ($K_d$) for BDCA-2 (CLEC4C) of less than about $10^{-6}$ M, $10^{-7}$ M, $10^{-8}$ M, $10^{-9}$ M, $10^{-10}$ M, $10^{-11}$ M or $10^{-12}$ M. In a preferred embodiment, the dissociation constant is less than $10^{-8}$ M, for instance in the range of $10^{-9}$ M, $10^{-10}$ M, $10^{-11}$ M or $10^{-12}$ M. In accordance with some embodiments of the invention, "Specific binding", "bind specifically", and "specifically bind" may refer to affinity and/or avidity. In some embodiments, the affinity of the anti-BDCA-2 (CLEC4C) antigen binding molecule is from $10^{-8}$ to $10^{-6}$ M (for example about $10^{-7}$ M). In some embodiments of the invention, the avidity of the anti-BDCA-2 (CLEC4C) antigen binding molecule is about from $10^{-10}$ to $10^{-8}$ M (for example about $10^{-9}$ M). In some embodiments of the invention, the affinity and/or avidity of the anti-BDCA-2 (CLEC4C) antigen binding molecule is about from 1 nM to 700 nM, or about from 1 to 600 nM, or about from 1 to 500 nM, or about from 1 to 400 nM, or about from 1 to 300 nM.

Manufacturing Liabilities

Therapeutic proteins such as antibodies are heterogenous and complex by nature due to chemical modifications and post-translational modifications (PTMs). Modifications can be caused by a number of factors such as the host cell system, processes used in manufacture or conditions during storage or manufacture. Modifications can relate to the chemical stability of the molecule itself or the aggregation potential and the effect this has on intrinsic physical stability of the antibody. Amino acid motifs or residues in a given antibody sequence that may undergo spontaneous modification during manufacture or storage are referred to as liabilities. Accordingly, mutations may be made to the antibody sequence to address the liabilities to reduce the susceptibility of the antibody to modification and degradation.

Such modifications as a result of liabilities in the antibody sequences may include glycosylation, deamidation, oxidation and variations of C- and N-termini. Such modifications may arise during manufacture. Certain residues and structural or sequence motifs are more liable to certain modifications. Examples of such liabilities to modification include Asn N-linked glycosylation, Ser/Thr O-linked glycosylation, Asn deamidation, Asp isomerisation/fragmentation, Lys glycation, Met/Trp oxidation, free thiol groups, pyroglutamates, C-terminal Lys.

A skilled person is aware that computational tools can be used to predict and identify structural and sequence liabilities which could potentially result in modifications. To minimise the occurrence of modifications alterations to the manufacturing process can be made. Protein engineering may also be considered to reduce the risk. For example, selective mutation of these liabilities can help to identify and reduce the risk of a modification endangering the stability of an antibody.

Aspartic acid residues (Asp) may undergo spontaneous modification. Asp containing motifs, such as Asp-Gly sequences may undergo spontaneous isomerization to form isoaspartic acid. Formation of isoaspartate may debilitate or completely abrogate the binding of the antibody. This is of additional importance if the Asp residue appears in the CDR of an antibody.

Aspartic acid residues (Asp) can therefore be substituted with any naturally occurring amino acid to reduce this liability to modification. Optionally, aspartic acid residues (Asp) can be substituted with alanine (Ala), glutamine (Gln) or glutamic acid (Glu) to reduce this liability to modification. Optimization of production/formulation can also be investigated to reduce isomerization. Alternatively, Asp-Gly motifs may be modified by substituting the glycine residue with another naturally occurring amino acid to inhibit deamidation, rather than by substitution of the Asp residue.

Methionine residues (Met) may undergo spontaneous modification. The presence of methionine (Met) in a CDR, especially if exposed to solvent, can create a problem if the methionine is oxidized and this interferes with binding. Methionine residues can therefore be substituted with any other naturally occurring amino acid to reduce this liability to modification. Methionine residues may preferably be substituted with Ala or Leu. Optimization of production/formulation can also be investigated to reduce oxidation.

Therefore, variant antibodies derived from any of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01 but comprising one or more amino substitutions to address one or more of any potential liabilities as described above are also provided herein.

For example, for any antigen binding molecules defined by one or more amino acid sequences herein, if there are one or more Met residues present, the one or more Met residues may each and independently be substituted with an Ala residue or a Leu residue. If there are one or more Asp residues present, the one or more Asp residues may each and independently be substituted with an Ala residue, a Gin residue, or a Glu residue.

Summary of Antigen Binding Molecules Provided

A summary of the antigen binding molecules provided by the present invention is provided below, with identification of the assigned SEQ ID NO. in the accompanying sequence listing. Antigen binding variants, derivatives and fragments thereof are also provided as part of the present invention:

TABLE 1

Summary of parental mouse antibodies and conservatively humanised, humanised and deimmunised versions of two parental antibodies

| | SEQ ID NOs | | | | | | | | | |
|---|---|---|---|---|---|---|---|---|---|---|
| Antibody | VL | VLCDR1 (Kabat/ Chothia) | VLCDR2 (Kabat/ Chothia) | VLCDR3 (Kabat/ Chothia) | VH | VHCDR1 (Kabat) | VHCDR2 (Kabat) | VHCDR3 (Kabat/ Chothia) | VHCDR1 (Chothia) | VHCDR2 (Chothia) |
| Parental 3E05 | 1 | 2 | 3 | 4 | 5 | 6 | 7 | 8 | 9 | 10 |
| 3E05_var1 | 11 | 12 | 13 | 14 | 15 | 16 | 17 | 18 | 19 | 20 |
| 3E05_var2 | 11 | 12 | 13 | 14 | 25 | 26 | 27 | 28 | 29 | 30 |
| 3E05_var3 | 11 | 12 | 13 | 14 | 35 | 36 | 37 | 38 | 39 | 40 |
| 3E05_var4 | 11 | 12 | 13 | 14 | 45 | 46 | 47 | 48 | 49 | 50 |
| 3E05_var5 | 21 | 22 | 23 | 24 | 15 | 16 | 17 | 18 | 19 | 20 |
| 3E05_var6 | 21 | 22 | 23 | 24 | 25 | 26 | 27 | 28 | 29 | 30 |
| 3E05_var7 | 21 | 22 | 23 | 24 | 35 | 36 | 37 | 38 | 39 | 40 |
| 3E05_var8 | 21 | 22 | 23 | 24 | 45 | 46 | 47 | 48 | 49 | 50 |
| 3E05_var9 | 31 | 32 | 33 | 34 | 15 | 16 | 17 | 18 | 19 | 20 |
| 3E05_var10 | 31 | 32 | 33 | 34 | 25 | 26 | 27 | 28 | 29 | 30 |
| 3E05_var11 | 31 | 32 | 33 | 34 | 35 | 36 | 37 | 38 | 39 | 40 |
| 3E05_var12 | 31 | 32 | 33 | 34 | 45 | 46 | 47 | 48 | 49 | 50 |
| 3E05_var13 | 41 | 42 | 43 | 44 | 15 | 16 | 17 | 18 | 19 | 20 |
| 3E05_var14 | 41 | 42 | 43 | 44 | 25 | 26 | 27 | 28 | 29 | 30 |
| 3E05_var15 | 41 | 42 | 43 | 44 | 35 | 36 | 37 | 38 | 39 | 40 |
| 3E05_var16 | 41 | 42 | 43 | 44 | 45 | 46 | 47 | 48 | 49 | 50 |
| Parental 21E06 | 51 | 52 | 53 | 54 | 55 | 56 | 57 | 58 | 59 | 60 |
| Parental 25E06 | 61 | 62 | 63 | 64 | 65 | 66 | 67 | 68 | 69 | 70 |
| Parental 28B01 | 71 | 72 | 73 | 74 | 75 | 76 | 77 | 78 | 79 | 80 |

TABLE 2

Combination of humanised/deimmunised heavy and light chain variable regions produces 16 antibodies derived from the 3E05 parent antibody

| Variant Name | Light chain | SEQ ID NO. | Heavy chain | SEQ ID NO. |
|---|---|---|---|---|
| 3E05 | 3E05_VL | 1 | 3E05_VH | 5 |
| 3E05_var1 | 3E05_VL_1 | 11 | 3E05_VH_1 | 15 |
| 3E05_var2 | 3E05_VL_1 | 11 | 3E05_VH_2 | 25 |
| 3E05_var3 | 3E05_VL_1 | 11 | 3E05_VH_3 | 35 |
| 3E05_var4 | 3E05_VL_1 | 11 | 3E05_VH_4 | 45 |
| 3E05_var5 | 3E05_VL_2 | 21 | 3E05_VH_1 | 15 |

TABLE 2-continued

Combination of humanised/deimmunised heavy and light chain variable regions produces 16 antibodies derived from the 3E05 parent antibody

| Variant Name | Light chain | SEQ ID NO. | Heavy chain | SEQ ID NO. |
|---|---|---|---|---|
| 3E05_var6 | 3E05_VL_2 | 21 | 3E05_VH_2 | 25 |
| 3E05_var7 | 3E05_VL_2 | 21 | 3E05_VH_3 | 35 |
| 3E05_var8 | 3E05_VL_2 | 21 | 3E05_VH_4 | 45 |
| 3E05_var9 | 3E05_VL_3 | 31 | 3E05_VH_1 | 15 |
| 3E05_var10 | 3E05_VL_3 | 31 | 3E05_VH_2 | 25 |
| 3E05_var11 | 3E05_VL_3 | 31 | 3E05_VH_3 | 35 |
| 3E05_var12 | 3E05_VL_3 | 31 | 3E05_VH_4 | 45 |
| 3E05_var13 | 3E05_VL_4 | 41 | 3E05_VH_1 | 15 |
| 3E05_var14 | 3E05_VL_4 | 41 | 3E05_VH_2 | 25 |
| 3E05_var15 | 3E05_VL_4 | 41 | 3E05_VH_3 | 35 |
| 3E05_var16 | 3E05_VL_4 | 41 | 3E05_VH_4 | 45 |

The various embodiments of the invention are now discussed in more detail.

Antigen Binding Molecules Comprising a VHCDR3 and/or a VLCDR3 Region

In one embodiment, an antibody, fragment or variant thereof, is provided comprising a heavy chain variable region comprising a VHCDR3 comprising an amino acid sequence selected from the group consisting of: SEQ ID NO: 48, 28, 8, 18, 38, 58, 68 and 78, and/or a light chain variable region comprising a VLCDR3 comprising an amino acid sequence selected from the group consisting of: SEQ ID NO: 34, 24, 44, 4, 14, 54, 64 and 74. Certain amino acid substitutions may be made to provide one or more variant antibodies as described herein.

3E05 in one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 8) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QQTNEDPPT (SEQ ID NO: 4). In one embodiment, an antigen binding molecule, for example an antibody, fragment or variant thereof is provided comprising a heavy chain variable region comprising an amino acid sequence having at least 90% identity to the amino acid sequence HDYYDGGLYYAMDY (SEQ ID NO: 8) and/or a light chain variable region comprising an amino acid sequence having at least 90% identity to the amino acid sequence QQTNEDPPT (SEQ ID NO: 4).

In one embodiment, an antigen binding molecule, for example an antibody, fragment or variant thereof is provided comprising a heavy chain variable region comprising the amino acid sequence HDYYDGGLYYAMDY (SEQ ID NO: 8) and/or a light chain variable region comprising the amino acid sequence QQTNEDPPT (SEQ ID NO: 4). In a particular embodiment, the antigen binding molecule is an antibody or fragment or variant thereof, wherein the VHCDR3 region of said antibody or fragment or variant thereof is HDYYDGGLYYAMDY (SEQ ID NO: 8) and/or the VLCDR3 region of said antibody or fragment or variant thereof is QQTNEDPPT (SEQ ID NO: 4).

Amino acid substitutions may be made to provide variant antibodies derived from 3E05, for example an antibody, fragment or variant thereof is provided comprising a heavy chain variable region comprising the amino acid sequence HDYYDGGLYYAMDY (SEQ ID NO: 8), optionally comprising 1 or 2 amino acid substitutions, and/or a light chain variable region comprising the amino acid sequence QQTNEDPPT (SEQ ID NO: 4), optionally comprising 1 or 2 amino acid substitutions. The amino acid substitutions may be conservative amino acid substitutions.

In one embodiment, the antigen binding molecule is an antibody or fragment or variant thereof, wherein the VHCDR3 region of said antibody or fragment or variant thereof is HDYYDGGLYYAMDY (SEQ ID NO: 8) and/or the VLCDR3 region of said antibody or fragment or variant thereof is QQTNEDPPT (SEQ ID NO: 4), optionally wherein the Met residues are each independently substituted with an amino acid selected from the group consisting of Ala and Leu, and/or the Asp residues are each independently substituted with an amino acid selected from the group consisting of Ala, Gln and Glu.

3E05_var 1, 5, 9 and 13

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 18) and/or a light chain variable region comprising the amino acid sequence having at least 70%, 75%, 80%, 85%, 90%, 91%, 92%, 93%, 94%, 95%, 96%, 97%, 98% or 99% identity to the amino acid sequence QQTNEDPPT (SEQ ID NO: 14). In one embodiment, the heavy chain variable region comprises an amino acid sequence having at least 90% identity to the amino acid sequence HDYYDGGLYYAMDY (SEQ ID NO: 18) and/or the light chain variable region comprises an amino acid sequence having at least 90% identity to the amino acid sequence QQTNEDPPT (SEQ ID NO: 14).

In one embodiment, an antibody, fragment or variant thereof is provided comprising a heavy chain variable region comprising the amino acid sequence HDYYDGGLYYAMDY (SEQ ID NO: 18) and/or a light chain variable region comprising the amino acid sequence QQTNEDPPT (SEQ ID NO: 14). In a particular embodiment, an antibody, fragment or variant thereof is provided, wherein the VHCDR3 region of said antibody or fragment or variant thereof is HDYYDGGLYYAMDY (SEQ ID NO: 18) and/or the VLCDR3 region of said antibody or fragment or variant thereof is QQTNEDPPT (SEQ ID NO: 14).

Amino acid substitutions may be made to provide variant antibodies derived from 3E05 var 1, 5, 9 or 13, for example an antibody, fragment or variant thereof is provided comprising a heavy chain variable region comprising the amino acid sequence HDYYDGGLYYAMDY (SEQ ID NO: 18), optionally comprising 1 or 2 amino acid substitutions, and/or a light chain variable region comprising the amino acid sequence QQTNEDPPT (SEQ ID NO: 14), optionally comprising 1 or 2 amino acid substitutions. The amino acid substitutions may be conservative amino acid substitutions.

In one embodiment, the antigen binding molecule is an antibody or fragment or variant thereof, wherein the VHCDR3 region of said antibody or fragment or variant thereof is HDYYDGGLYYAMDY (SEQ ID NO: 18) and/or the VLCDR3 region of said antibody or fragment or variant thereof is QQTNEDPPT (SEQ ID NO: 14), optionally wherein the Met residues are each independently substituted with an amino acid selected from the group consisting of Ala and Leu, and/or the Asp residues are each independently substituted with an amino acid selected from the group consisting of Ala, Gln and Glu.

3E05 Var2.6. 10 and 14

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence HDYYDG-GLYYAMDY (SEQ ID NO: 28) and/or a light chain variable region comprising the amino acid sequence having at least 70%, 75%, 80%, 85%, 90%, 91%, 92%, 93%, 94%, 95%, 96%, 97%, 98% or 99% identity to the amino acid sequence QQTNEDPPT (SEQ ID NO: 14). In one embodiment, the heavy chain variable region comprises an amino acid sequence having at least 90% identity to the amino acid sequence HDYYDGGLYYAMDY (SEQ ID NO: 28) and/or the light chain variable region comprises an amino acid sequence having at least 90% identity to the amino acid sequence QQTNEDPPT (SEQ ID NO: 14).

In one embodiment, an antibody, fragment or variant thereof is provided comprising a heavy chain variable region comprising the amino acid sequence HDYYDG-GLYYAMDY (SEQ ID NO: 28) and/or a light chain variable region comprising the amino acid sequence QQTNEDPPT (SEQ ID NO: 14). In a particular embodiment, an antibody, fragment or variant thereof is provided, wherein the VHCDR3 region of said antibody or fragment or variant thereof is HDYYDGGLYYAMDY (SEQ ID NO: 28) and/or the VLCDR3 region of said antibody or fragment or variant thereof is QQTNEDPPT (SEQ ID NO: 14).

Amino acid substitutions may be made to provide variant antibodies derived from 3E05 var 2, 6, 10 or 14, for example an antibody, fragment or variant thereof is provided comprising a heavy chain variable region comprising the amino acid sequence HDYYDGGLYYAMDY (SEQ ID NO: 28), optionally comprising 1 or 2 amino acid substitutions, and/or a light chain variable region comprising the amino acid sequence QQTNEDPPT (SEQ ID NO: 14), optionally comprising 1 or 2 amino acid substitutions. The amino acid substitutions may be conservative amino acid substitutions.

In one embodiment, the antigen binding molecule is an antibody or fragment or variant thereof, wherein the VHCDR3 region of said antibody or fragment or variant thereof is HDYYDGGLYYAMDY (SEQ ID NO: 28), optionally comprising 1 or 2 amino acid substitutions, and/or a light chain variable region comprising the amino acid sequence QQTNEDPPT (SEQ ID NO: 14), optionally wherein the Met residues are each independently substituted with an amino acid selected from the group consisting of Ala and Leu, and/or the Asp residues are each independently substituted with an amino acid selected from the group consisting of Ala, Gln and Glu.

3E05_var 3, 7, 11 and 15

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence HDYYDG-GLYYAMDY (SEQ ID NO: 38) and/or a light chain variable region comprising the amino acid sequence having at least 70%, 75%, 80%, 85%, 90%, 91%, 92%, 93%, 94%, 95%, 96%, 97%, 98% or 99% identity to the amino acid sequence QQTNEDPPT (SEQ ID NO: 14). In one embodiment, the heavy chain variable region comprises an amino acid sequence having at least 90% identity to the amino acid sequence HDYYDGGLYYAMDY (SEQ ID NO: 38) and/or the light chain variable region comprises an amino acid sequence having at least 90% identity to the amino acid sequence QQTNEDPPT (SEQ ID NO: 14).

In one embodiment, an antibody, fragment or variant thereof is provided comprising a heavy chain variable region comprising the amino acid sequence HDYYDG-GLYYAMDY (SEQ ID NO: 38) and/or a light chain variable region comprising the amino acid sequence QQTNEDPPT (SEQ ID NO: 14). In a particular embodiment, an antibody, fragment or variant thereof is provided, wherein the VHCDR3 region of said antibody or fragment or variant thereof is HDYYDGGLYYAMDY (SEQ ID NO: 38) and/or the VLCDR3 region of said antibody or fragment or variant thereof is QQTNEDPPT (SEQ ID NO: 14).

Amino acid substitutions may be made to provide variant antibodies derived from 3E05 var 3, 7, 11 or 15, for example an antibody, fragment or variant thereof is provided comprising a heavy chain variable region comprising the amino acid sequence HDYYDGGLYYAMDY (SEQ ID NO: 38), optionally comprising 1 or 2 amino acid substitutions, and/or a light chain variable region comprising the amino acid sequence QQTNEDPPT (SEQ ID NO: 14), optionally comprising 1 or 2 amino acid substitutions. The amino acid substitutions may be conservative amino acid substitutions.

In one embodiment, the antigen binding molecule is an antibody or fragment or variant thereof, wherein the VHCDR3 region of said antibody or fragment or variant thereof is HDYYDGGLYYAMDY (SEQ ID NO: 38), optionally comprising 1 or 2 amino acid substitutions, and/or a light chain variable region comprising the amino acid sequence QQTNEDPPT (SEQ ID NO: 14), optionally wherein the Met residues are each independently substituted with an amino acid selected from the group consisting of Ala and Leu, and/or the Asp residues are each independently substituted with an amino acid selected from the group consisting of Ala, Gln and Glu.

3E05_var 4. 8, 12 and 16

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence HDYYEGGLYYAMDY (SEQ ID NO: 48) and/or a light chain variable region comprising the amino acid sequence having at least 70%, 75%, 80%, 85%, 90%, 91%, 92%, 93%, 94%, 95%, 96%, 97%, 98% or 99% identity to the amino acid sequence QQTNEDPPT (SEQ ID NO: 14). In one embodiment, the heavy chain variable region comprises an amino acid sequence having at least 90% identity to the amino acid sequence HDYYEGGLYYAMDY (SEQ ID NO: 48) and/or the light chain variable region comprises an amino acid sequence having at least 90% identity to the amino acid sequence QQTNEDPPT (SEQ ID NO: 14).

In one embodiment, an antibody, fragment or variant thereof is provided comprising a heavy chain variable region comprising the amino acid sequence HDYYEG-GLYYAMDY (SEQ ID NO: 48) and/or a light chain variable region comprising the amino acid sequence QQTNEDPPT (SEQ ID NO: 14). In a particular embodiment, an antibody, fragment or variant thereof is provided, wherein the VHCDR3 region of said antibody or fragment or variant thereof is HDYYEGGLYYAMDY (SEQ ID NO: 48) and/or the VLCDR3 region of said antibody or fragment or variant thereof is QQTNEDPPT (SEQ ID NO: 14).

Amino acid substitutions may be made to provide variant antibodies derived from 3E05 var 4, 8, 12 or 16, for example an antibody, fragment or variant thereof is provided comprising a heavy chain variable region comprising the amino acid sequence HDYYEGGLYYAMDY (SEQ ID NO: 48), optionally comprising 1 or 2 amino acid substitutions, and/or a light chain variable region comprising the amino acid sequence QQTNEDPPT (SEQ ID NO: 14), optionally comprising 1 or 2 amino acid substitutions. The amino acid substitutions may be conservative amino acid substitutions.

In one embodiment, the antigen binding molecule is an antibody or fragment or variant thereof, wherein the VHCDR3 region of said antibody or fragment or variant thereof is HDYYEGGLYYAMDY (SEQ ID NO: 48) and/or the VLCDR3 region of said antibody or fragment or variant thereof is QQTNEDPPT (SEQ ID NO: 14), optionally wherein the Met residues are each independently substituted with an amino acid selected from the group consisting of Ala and Leu, and/or the Asp residues are each independently substituted with an amino acid selected from the group consisting of Ala, Gln and Glu.

21E06

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence HLYYGDYFYVMDY (SEQ ID NO: 58) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QQSNEDPPT (SEQ ID NO: 54). In one embodiment, an antigen binding molecule, for example an antibody, fragment or variant thereof is provided comprising a heavy chain variable region comprising an amino acid sequence having at least 90% identity to the amino acid sequence HLYYGDYFYVMDY (SEQ ID NO: 58) and/or a light chain variable region comprising an amino acid sequence having at least 90% identity to the amino acid sequence QQSNEDPPT (SEQ ID NO: 54).

In one embodiment, an antigen binding molecule, for example an antibody, fragment or variant thereof is provided comprising a heavy chain variable region comprising the amino acid sequence HLYYGDYFYVMDY (SEQ ID NO: 58) and/or a light chain variable region comprising the amino acid sequence QQSNEDPPT (SEQ ID NO: 54). In a particular embodiment, the antigen binding molecule is an antibody or fragment or variant thereof, wherein the VHCDR3 region of said antibody or fragment or variant thereof is HLYYGDYFYVMDY (SEQ ID NO: 58) and/or the VLCDR3 region of said antibody or fragment or variant thereof is QQSNEDPPT (SEQ ID NO: 54).

Amino acid substitutions may be made to provide variant antibodies derived from 21E06, for example an antibody, fragment or variant thereof is provided comprising a heavy chain variable region comprising the amino acid sequence HLYYGDYFYVMDY (SEQ ID NO: 58), optionally comprising 1 or 2 amino acid substitutions, and/or a light chain variable region comprising the amino acid sequence QQSNEDPPT (SEQ ID NO: 54), optionally comprising 1 or 2 amino acid substitutions. The amino acid substitutions may be conservative amino acid substitutions.

In one embodiment, the antigen binding molecule is an antibody or fragment or variant thereof, wherein the VHCDR3 region of said antibody or fragment or variant thereof is HLYYGDYFYVMDY (SEQ ID NO: 58) and/or the VLCDR3 region of said antibody or fragment or variant thereof is QQSNEDPPT (SEQ ID NO: 54), optionally wherein the Met residues are each independently substituted with an amino acid selected from the group consisting of Ala and Leu, and/or the Asp residues are each independently substituted with an amino acid selected from the group consisting of Ala, Gln and Glu.

25E06

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence HHYSHYFWYFDV (SEQ ID NO: 68) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QQSNEDPPT (SEQ ID NO: 64). In one embodiment, an antigen binding molecule, for example an antibody, fragment or variant thereof is provided comprising a heavy chain variable region comprising an amino acid sequence having at least 90% identity to the amino acid sequence HHYSHYFWYFDV (SEQ ID NO: 68) and/or a light chain variable region comprising an amino acid sequence having at least 90% identity to the amino acid sequence QQSNEDPPT (SEQ ID NO: 64).

In one embodiment, an antigen binding molecule, for example an antibody, fragment or variant thereof is provided comprising a heavy chain variable region comprising the amino acid sequence HHYSHYFWYFDV (SEQ ID NO: 68) and/or a light chain variable region comprising the amino acid sequence QQSNEDPPT (SEQ ID NO: 64). In a particular embodiment, the antigen binding molecule is an antibody or fragment or variant thereof, wherein the VHCDR3 region of said antibody or fragment or variant thereof is HHYSHYFWYFDV (SEQ ID NO: 68) and/or the VLCDR3 region of said antibody or fragment or variant thereof is QQSNEDPPT (SEQ ID NO: 64).

Amino acid substitutions may be made to provide variant antibodies derived from 25E06, for example an antibody, fragment or variant thereof is provided comprising a heavy chain variable region comprising the amino acid sequence HHYSHYFWYFDV (SEQ ID NO: 68), optionally comprising 1 or 2 amino acid substitutions, and/or a light chain variable region comprising the amino acid sequence QQSNEDPPT (SEQ ID NO: 64), optionally comprising 1 or 2 amino acid substitutions. The amino acid substitutions may be conservative amino acid substitutions.

In one embodiment, the antigen binding molecule is an antibody or fragment or variant thereof, wherein the VHCDR3 region of said antibody or fragment or variant thereof is HHYSHYFWYFDV (SEQ ID NO: 68) and/or the VLCDR3 region of said antibody or fragment or variant thereof is QQSNEDPPT (SEQ ID NO: 64), optionally wherein the Met residues are each independently substituted with an amino acid selected from the group consisting of Ala and Leu, and/or the Asp residues are each independently substituted with an amino acid selected from the group consisting of Ala, Gin and Glu.

28B01

In one embodiment, an antigen binding molecule, for example an antibody, fragment or variant thereof is provided comprising a heavy chain variable region comprising an amino acid sequence having at least 70%, 75%, 80%, 85%, 90%, 91%, 92%, 93%, 94%, 95%, 96%, 97%, 98% or 99% identity to the amino acid sequence HHYSNYFWYFDV (SEQ ID NO: 78) and/or a light chain variable region comprising an amino acid sequence having at least 70%, 75%, 80%, 85%, 90%, 91%, 92%, 93%, 94%, 95%, 96%, 97%, 98% or 99% identity to the amino acid sequence QQSNEDPPT (SEQ ID NO: 74). In one embodiment, an antigen binding molecule, for example an antibody, fragment or variant thereof is provided comprising a heavy chain variable region comprising an amino acid sequence having at least 90% identity to the amino acid sequence HHYSNYFWYFDV (SEQ ID NO: 78) and/or a light chain variable region comprising an amino acid sequence having at least 90% identity to the amino acid sequence QQSNEDPPT (SEQ ID NO: 74).

In one embodiment, an antigen binding molecule, for example an antibody, fragment or variant thereof is provided comprising a heavy chain variable region comprising the amino acid sequence HHYSNYFWYFDV (SEQ ID NO: 78) and/or a light chain variable region comprising the amino acid sequence QQSNEDPPT (SEQ ID NO: 74). In a particular embodiment, the antigen binding molecule is an antibody or fragment or variant thereof, wherein the VHCDR3 region of said antibody or fragment or variant thereof is HHYSNYFWYFDV (SEQ ID NO: 78) and/or the VLCDR3 region of said antibody or fragment or variant thereof is QQSNEDPPT (SEQ ID NO: 74).

Amino acid substitutions may be made to provide variant antibodies derived from 28B01, for example an antibody, fragment or variant thereof is provided comprising a heavy chain variable region comprising the amino acid sequence HHYSNYFWYFDV (SEQ ID NO: 78), optionally comprising 1 or 2 amino acid substitutions, and/or a light chain variable region comprising the amino acid sequence QQSNEDPPT (SEQ ID NO: 74), optionally comprising 1 or 2 amino acid substitutions. The amino acid substitutions may be conservative amino acid substitutions.

In one embodiment, the antigen binding molecule is an antibody or fragment or variant thereof, wherein the VHCDR3 region of said antibody or fragment or variant thereof is HHYSNYFWYFDV (SEQ ID NO: 78) and/or the VLCDR3 region of said antibody or fragment or variant thereof is QQSNEDPPT (SEQ ID NO: 74), optionally wherein the Met residues are each independently substituted with an amino acid selected from the group consisting of Ala and Leu, and/or the Asp residues are each independently substituted with an amino acid selected from the group consisting of Ala, Gln and Glu.

Heavy and/or Light Chain CDRs

In one embodiment, an antibody, fragment or variant thereof, is provided comprising:

- a heavy chain variable region comprising:
  - a VHCDR1 comprising an amino acid sequence selected from the group consisting of: SEQ ID NO: 46, 49, 26, 29, 6, 9, 16, 19, 36, 39, 56, 59, 66, 69, 76 and 79;
  - a VHCDR2 comprising an amino acid sequence selected from the group consisting of: SEQ ID NO: 47, 50, 27, 30, 7, 10, 17, 20, 37, 40, 57, 60, 67, 70, 77 and 80; and
  - a VHCDR3 comprising an amino acid sequence selected from the group consisting of: SEQ ID NO: 48, 28, 8, 18, 38, 58, 68 and 78; and
- a light chain variable region comprising:
  - a VLCDR1 comprising an amino acid sequence selected from the group consisting of: SEQ ID NO: 32, 22, 42, 2, 12, 52, 62 and 72;
  - a VLCDR2 comprising an amino acid sequence selected from the group consisting of: SEQ ID NO: 33, 23, 43, 3, 13, 53, 63 and 73; and
  - a VLCDR3 comprising an amino acid sequence selected from the group consisting of: SEQ ID NO: 34, 24, 44, 4, 14, 54, 64 and 74.

Certain amino acid substitutions may be made to provide one or more variant antibodies as described herein.

3E05

In one embodiment, an antibody, fragment or variant thereof, is provided comprising:

- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 6), a VHCDR2 comprising at least 70%, 75%, 80%, 85%, 90%, 91%, 92%, 93%, 94%, 95%, 96%, 97%, 98% or 99% identity to the amino acid sequence YISSGGGNTYYPDSVKG (SEQ ID NO: 7) and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 8); and/or
- a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDSSMN (SEQ ID NO: 2), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 3) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 4).

In one embodiment, an antibody, fragment or variant thereof, is provided comprising:

- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 9), a VHCDR2 comprising at least 70%, 75%, 80%, 85%, 90%, 91%, 92%, 93%, 94%, 95%, 96%, 97%, 98% or 99% identity to the amino acid sequence SSGGGNTY (SEQ ID NO: 10) and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 8); and/or
- a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDSSMN (SEQ ID NO: 2), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 3) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 4).

In one embodiment, an antibody, fragment or variant thereof, is provided comprising:

- a heavy chain variable region comprising a VHCDR1 comprising at least 90% identity to the amino acid sequence SYTMS (SEQ ID NO: 6), a VHCDR2 comprising at least 90% identity to the amino acid sequence YISSGGGNTYYPDSVKG (SEQ ID NO: 7) and a VHCDR3 comprising at least 90% identity to the amino acid sequence HDYYDGGLYYAMDY (SEQ ID NO: 8); and/or a light chain variable region comprising a VLCDR1 comprising the at least 90% identity to amino acid sequence KASQSVDYDGDSSMN (SEQ ID NO: 2), a VLCDR2 comprising at least 90% identity to the amino acid sequence AASTLES (SEQ ID NO: 3) and a VLCDR3 comprising at least 90% identity to the amino acid sequence QQTNEDPPT (SEQ ID NO: 4).

In one embodiment, an antibody, fragment or variant thereof, is provided comprising:

a heavy chain variable region comprising a VHCDR1 comprising at least 90% identity to the amino acid sequence GFTFSSY (SEQ ID NO: 9), a VHCDR2 comprising at least 90% identity to the amino acid sequence SSGGGNTY (SEQ ID NO: 10) and a VHCDR3 comprising at least 90% identity to the amino acid sequence HDYYDGGLYYAMDY (SEQ ID NO: 8); and/or a light chain variable region comprising a VLCDR1 comprising the at least 90% identity to amino acid sequence KASQSVDYDGDSSMN (SEQ ID NO: 2), a VLCDR2 comprising at least 90% identity to the amino acid sequence AASTLES (SEQ ID NO: 3) and a VLCDR3 comprising at least 90% identity to the amino acid sequence QQTNEDPPT (SEQ ID NO: 4).

In one embodiment, an antibody, fragment or variant thereof, is provided comprising:

a heavy chain variable region comprising a VHCDR1 comprising the amino acid sequence SYTMS (SEQ ID NO: 6), a VHCDR2 comprising the amino acid sequence YISSGGGNTYYPDSVKG (SEQ ID NO: 7) and a VHCDR3 comprising the amino acid sequence HDYYDGGLYYAMDY (SEQ ID NO: 8); and a light chain variable region comprising a VLCDR1 comprising the amino acid sequence KASQSVDYDGDSSMN (SEQ ID NO: 2), a VLCDR2 comprising the amino acid sequence AASTLES (SEQ ID NO: 3) and a VLCDR3 comprising the amino acid sequence QQTNEDPPT (SEQ ID NO: 4).

Amino acid substitutions may be made to provide variant antibodies derived from 3E05, for example an antibody, fragment or variant thereof is provided comprising a heavy chain variable region comprising a VHCDR1 comprising the amino acid sequence SYTMS (SEQ ID NO: 6) optionally comprising 1 or 2 amino acid substitutions, a VHCDR2 comprising the amino acid sequence YISSGGGNTYYPDSVKG (SEQ ID NO: 7) optionally comprising 1 or 2 amino acid substitutions, and a VHCDR3 comprising the amino acid sequence HDYYDGGLYYAMDY (SEQ ID NO: 8) optionally comprising 1 or 2 amino acid substitutions; and/or a light chain variable region comprising a VLCDR1 comprising the amino acid sequence KASQSVDYDGDSSMN (SEQ ID NO: 2) optionally comprising 1 or 2 amino acid substitutions, a VLCDR2 comprising the amino acid sequence AASTLES (SEQ ID NO: 3) optionally comprising 1 or 2 amino acid substitutions and a VLCDR3 comprising the amino acid sequence QQTNEDPPT (SEQ ID NO: 4) optionally comprising 1 or 2 amino acid substitutions. The amino acid substitutions may be conservative amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 6), a VHCDR2 comprising the amino acid sequence YISSGGGNTYYPDSVKG (SEQ ID NO: 7) and a VHCDR3 comprising the amino acid sequence HDYYDGGLYYAMDY (SEQ ID NO: 8); and a light chain variable region comprising a VLCDR1 comprising the amino acid sequence KASQSVDYDGDSSMN (SEQ ID NO: 2), a VLCDR2 comprising the amino acid sequence AASTLES (SEQ ID NO: 3) and a VLCDR3 comprising the amino acid sequence QQTNEDPPT (SEQ ID NO: 4);

optionally wherein the Met residues are each independently substituted with an amino acid selected from the group consisting of Ala and Leu, and/or the Asp residues are each independently substituted with an amino acid selected from the group consisting of Ala, Gin and Glu.

In one embodiment, an antibody, fragment or variant thereof, is provided comprising:

a heavy chain variable region comprising a VHCDR1 comprising the amino acid sequence GFTFSSY (SEQ ID NO: 9), a VHCDR2 comprising the amino acid sequence SSGGGNTY (SEQ ID NO: 10), and a VHCDR3 comprising the amino acid sequence HDYYDGGLYYAMDY (SEQ ID NO: 8); and a light chain variable region comprising a VLCDR1 comprising the amino acid sequence KASQSVDYDGDSSMN (SEQ ID NO: 2), a VLCDR2 comprising the amino acid sequence AASTLES (SEQ ID NO: 3) and a VLCDR3 comprising the amino acid sequence QQTNEDPPT (SEQ ID NO: 4).

Amino acid substitutions may be made to provide variant antibodies derived from 3E05, for example an antibody, fragment or variant thereof is provided comprising a heavy chain variable region comprising a VHCDR1 comprising the amino acid sequence GFTFSSY (SEQ ID NO: 9) optionally comprising 1 or 2 amino acid substitutions, a VHCDR2 comprising the amino acid sequence SSGGGNTY (SEQ ID NO: 10) optionally comprising 1 or 2 amino acid substitutions, and a VHCDR3 comprising the amino acid sequence HDYYDGGLYYAMDY (SEQ ID NO: 8) optionally comprising 1 or 2 amino acid substitutions; and/or a light chain variable region comprising a VLCDR1 comprising the amino acid sequence KASQSVDYDGDSSMN (SEQ ID NO: 2) optionally comprising 1 or 2 amino acid substitutions, a VLCDR2 comprising the amino acid sequence AASTLES (SEQ ID NO: 3) optionally comprising 1 or 2 amino acid substitutions and a VLCDR3 comprising the amino acid sequence QQTNEDPPT (SEQ ID NO: 4) optionally comprising 1 or 2 amino acid substitutions. The amino acid substitutions may be conservative amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 9), a VHCDR2 comprising the amino acid sequence SSGGGNTY (SEQ ID NO: 10), and a VHCDR3 comprising the amino acid sequence HDYYDGGLYYAMDY (SEQ ID NO: 8); and a light chain variable region comprising a VLCDR1 comprising the amino acid sequence KASQSVDYDGDSSMN (SEQ ID NO: 2), a VLCDR2 comprising the amino acid sequence AASTLES (SEQ ID NO: 3) and a VLCDR3 comprising the amino acid sequence QQTNEDPPT (SEQ ID NO: 4);

optionally wherein the Met residues are each independently substituted with an amino acid selected from the group consisting of Ala and Leu, and/or the Asp residues are each independently substituted with an amino acid selected from the group consisting of Ala, Gln and Glu.

3E05_var 12

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 46), a VHCDR2 comprising at least 70%, 75%, 80%, 85%, 90%, 91%, 92%, 93%, 94%, 95%, 96%, 97%, 98% or 99% identity to the amino acid sequence YISSGGGQTYYPDSVKG (SEQ ID NO: 47), and a VHCDR3 comprising at least 70%, 75%, 80%, 85%, 90%, 91%, 92%, 93%, 94%, 95%, 96%, 97%, 98% or 99% identity to the amino acid sequence HDYYEGGLYYAMDY (SEQ ID NO: 48); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 32), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 33) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 34).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 49), a VHCDR2 comprising at least 70%, 75%, 80%, 85%, 90%, 91%, 92%, 93%, 94%, 95%, 96%, 97%, 98% or 99% identity to the amino acid sequence SSGGGQTY (SEQ ID NO: 50), and a VHCDR3 comprising at least 70%, 75%, 80%, 85%, 90%, 91%, 92%, 93%, 94%, 95%, 96%, 97%, 98% or 99% identity to the amino acid sequence HDYYEGGLYYAMDY (SEQ ID NO: 48); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 32), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 33) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 34).

In one embodiment, an antibody, fragment or variant thereof, is provided comprising:

a heavy chain variable region comprising a VHCDR1 comprising at least 90% identity to the amino acid sequence SYTMS (SEQ ID NO: 46), a VHCDR2 comprising at least 90% identity to the amino acid sequence YISSGGGQTYYPDSVKG (SEQ ID NO: 47), and a VHCDR3 comprising at least 90% identity to the amino acid sequence HDYYEGGLYYAMDY (SEQ ID NO: 48); and/or a light chain variable region comprising a VLCDR1 comprising the at least 90% identity to amino acid sequence KSSQSVDYDGDSSMN (SEQ ID NO: 32), a VLCDR2 comprising at least 90% identity to the amino acid sequence AASTLES (SEQ ID NO: 33) and a VLCDR3 comprising at least 90% identity to the amino acid sequence QQTNEDPPT (SEQ ID NO: 34).

In one embodiment, an antibody, fragment or variant thereof, is provided comprising:

a heavy chain variable region comprising a VHCDR1 comprising at least 90% identity to the amino acid sequence GFTFSSY (SEQ ID NO: 49), a VHCDR2 comprising at least 90% identity to the amino acid sequence SSGGGQTY (SEQ ID NO: 50), and a VHCDR3 comprising at least 90% identity to the amino acid sequence HDYYEGGLYYAMDY (SEQ ID NO: 48); and/or a light chain variable region comprising a VLCDR1 comprising the at least 90% identity to amino acid sequence KSSQSVDYDGDSSMN (SEQ ID NO: 32), a VLCDR2 comprising at least 90% identity to the amino acid sequence AASTLES (SEQ ID NO: 33) and a VLCDR3 comprising at least 90% identity to the amino acid sequence QQTNEDPPT (SEQ ID NO: 34).

In one embodiment, an antibody, fragment or variant thereof, is provided comprising:

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), and a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34).

Amino acid substitutions may be made to provide variant antibodies derived from 3E05_var 12, for example an antibody, fragment or variant thereof is provided comprising a heavy chain variable region comprising a VHCDR1 comprising the amino acid sequence SYTMS (SEQ ID NO: 46) optionally comprising 1 or 2 amino acid substitutions, a VHCDR2 comprising the amino acid sequence YISSGGGQTYYPDSVKG (SEQ ID NO: 47) optionally comprising 1 or 2 amino acid substitutions, and a VHCDR3 comprising the amino acid sequence HDYYEGGLYYAMDY (SEQ ID NO: 48) optionally comprising 1 or 2 amino acid substitutions; and/or a light chain variable region comprising a VLCDR1 comprising the amino acid sequence KSSQSVDYDGDSSMN (SEQ ID NO: 32) optionally comprising 1 or 2 amino acid substitutions, a VLCDR2 comprising the amino acid sequence AASTLES (SEQ ID NO: 33) optionally comprising 1 or 2 amino acid substitutions and a VLCDR3 comprising the amino acid sequence QQTNEDPPT (SEQ ID NO: 34) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), and a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

optionally wherein the Met residues are each independently substituted with an amino acid selected from the group consisting of Ala and Leu, and/or the Asp residues are each independently substituted with an amino acid selected from the group consisting of Ala, Gln and Glu.

In one embodiment, an antibody, fragment or variant thereof, is provided comprising:

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), and a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34).

Amino acid substitutions may be made to provide variant antibodies derived from 3E05_var 12, for example an antibody, fragment or variant thereof is provided comprising a heavy chain variable region comprising a VHCDR1 comprising the amino acid sequence GFTFSSY (SEQ ID NO: 49) optionally comprising 1 or 2 amino acid substitutions, a VHCDR2 comprising the amino acid sequence SSGGGQTY (SEQ ID NO: 50) optionally comprising 1 or 2 amino acid substitutions, and a VHCDR3 comprising the amino acid sequence HDYYEGGLYYAMDY (SEQ ID NO: 48) optionally comprising 1 or 2 amino acid substitutions; and/or a light chain variable region comprising a VLCDR1 comprising the amino acid sequence KSSQSVDYDGDSSMN (SEQ ID NO: 32) optionally comprising 1 or 2 amino acid substitutions, a VLCDR2 comprising the amino acid sequence AASTLES (SEQ ID NO: 33) optionally comprising 1 or 2 amino acid substitutions and a VLCDR3 comprising the amino acid sequence QQTNEDPPT (SEQ ID NO: 34) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), and a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

optionally wherein the Met residues are each independently substituted with an amino acid selected from the group consisting of Ala and Leu, and/or the Asp residues are each independently substituted with an amino acid selected from the group consisting of Ala, Gin and Glu.

Antigen binding molecules of or derived from 3E05_var12 (for example antibodies having one or more amino acid substitutions) may have a $K_D$ of less than about 0.01 nM, an IC50 for IFN secretion of less than about 0.5M, and/or an IC90 for IFN secretion of less than about 5 nM. In a specific embodiment, antigen binding molecules of or derived from 3E05_var12 (for example antibodies having one or more amino acid substitutions) may have a $K_D$ of less than about 0.01 nM, an IC50 for IFN secretion of less than about 0.2 nM, and/or an IC90 for IFN secretion of less than about 2 nM 3E05_var 6

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 26), a VHCDR2 comprising at least 70%, 75%, 80%, 85%, 90%, 91%, 92%, 93%, 94%, 95%, 96%, 97%, 98% or 99% identity to the amino acid sequence YISSGGGNTYYADSVKG (SEQ ID NO: 27), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 28); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 22), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 23) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 24).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 29), a VHCDR2 comprising at least 70%, 75%, 80%, 85%, 90%, 91%, 92%, 93%, 94%, 95%, 96%, 97%, 98% or 99% identity to the amino acid sequence SSGGGNTY (SEQ ID NO: 30), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 28); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 22), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 23) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 24).

In one embodiment, an antibody, fragment or variant thereof, is provided comprising:

a heavy chain variable region comprising a VHCDR1 comprising at least 90% identity to the amino acid sequence SYTMS (SEQ ID NO: 26), a VHCDR2 comprising at least 90% identity to the amino acid sequence YISSGGGNTYYADSVKG (SEQ ID NO: 27), and a VHCDR3 comprising at least 90% identity to the amino acid sequence HDYYDGGLYYAMDY (SEQ ID NO: 28); and/or a light chain variable region comprising a VLCDR1 comprising the at least 90% identity to amino acid sequence KSSQSVDYDGDSSMN (SEQ ID NO: 22), a VLCDR2 comprising at least 90% identity to the amino acid sequence AASTLES (SEQ ID NO: 23) and a VLCDR3 comprising at least 90% identity to the amino acid sequence QQTNEDPPT (SEQ ID NO: 24).

In one embodiment, an antibody, fragment or variant thereof, is provided comprising:

a heavy chain variable region comprising a VHCDR1 comprising at least 90% identity to the amino acid sequence GFTFSSY (SEQ ID NO: 29), a VHCDR2 comprising at least 90% identity to the amino acid sequence SSGGGNTY (SEQ ID NO: 30), and a VHCDR3 comprising at least 90% identity to the amino acid sequence HDYYDGGLYYAMDY (SEQ ID NO: 28); and/or a light chain variable region comprising a VLCDR1 comprising the at least 90% identity to amino acid sequence KSSQSVDYDGDSSMN (SEQ ID NO: 22), a VLCDR2 comprising at least 90% identity to the amino acid sequence AASTLES (SEQ ID NO: 23) and a VLCDR3 comprising at least 90% identity to the amino acid sequence QQTNEDPPT (SEQ ID NO: 24).

In one embodiment, an antibody, fragment or variant thereof, is provided comprising:

a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), and a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24).

Amino acid substitutions may be made to provide variant antibodies derived from 3E05_var 6, for example an antibody, fragment or variant thereof is provided comprising a heavy chain variable region comprising a VHCDR1 comprising the amino acid sequence SYTMS (SEQ ID NO: 26) optionally comprising 1 or 2 amino acid substitutions, a VHCDR2 comprising the amino acid sequence YISSGGGNTYYADSVKG (SEQ ID NO: 27) optionally comprising 1 or 2 amino acid substitutions, and a VHCDR3 comprising the amino acid sequence HDYYDGGLYYAMDY (SEQ ID NO: 28) optionally comprising 1 or 2 amino acid substitutions; and/or a light chain variable region comprising a VLCDR1 comprising the amino acid sequence KSSQSVDYDGDSSMN (SEQ ID NO: 22) optionally comprising 1 or 2 amino acid substitutions, a VLCDR2 comprising the amino acid sequence AASTLES (SEQ ID NO: 23) optionally comprising 1 or 2 amino acid substitutions and a VLCDR3 comprising the amino acid sequence QQTNEDPPT (SEQ ID NO: 24) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), and a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

optionally wherein the Met residues are each independently substituted with an amino acid selected from the group consisting of Ala and Leu, and/or the Asp residues are each independently substituted with an amino acid selected from the group consisting of Ala, Gin and Glu.

In one embodiment, an antibody, fragment or variant thereof, is provided comprising:

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), and a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24).

Amino acid substitutions may be made to provide variant antibodies derived from 3E05_var 6, for example an antibody, fragment or variant thereof is provided comprising a heavy chain variable region comprising a VHCDR1 comprising the amino acid sequence GFTFSSY (SEQ ID NO: 29) optionally comprising 1 or 2 amino acid substitutions, a VHCDR2 comprising the amino acid sequence SSGGGNTY (SEQ ID NO: 30) optionally comprising 1 or 2 amino acid substitutions, and a VHCDR3 comprising the amino acid sequence HDYYDGGLYYAMDY (SEQ ID NO: 28) optionally comprising 1 or 2 amino acid substitutions; and/or a light chain variable region comprising a VLCDR1 comprising the amino acid sequence KSSQSVDYDGDSSMN (SEQ ID NO: 22) optionally comprising 1 or 2 amino acid substitutions, a VLCDR2 comprising the amino acid sequence AASTLES (SEQ ID NO: 23) optionally comprising 1 or 2 amino acid substitutions and a VLCDR3 comprising the amino acid sequence QQTNEDPPT (SEQ ID NO: 24) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), and a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

optionally wherein the Met residues are each independently substituted with an amino acid selected from the group consisting of Ala and Leu, and/or the Asp residues are each independently substituted with an amino acid selected from the group consisting of Ala, Gin and Glu.

Antigen binding molecules of or derived from 3E05_var6 (for example antibodies having one or more amino acid substitutions) may have a $K_D$ of less than about 0.01 nM, an IC50 for IFN secretion of less than about 0.5M, and/or an IC90 for IFN secretion of less than about 5 nM. In a specific embodiment, antigen binding molecules of or derived from 3E05_var6 (for example antibodies having one or more amino acid substitutions) may have a $K_D$ of less than about 0.01 nM, an IC50 for IFN secretion of less than about 0.1 nM, and/or an IC90 for IFN secretion of less than about 1 nM 3E05_var 14

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 26), a VHCDR2 comprising at least 70%, 75%, 80%, 85%, 90%, 91%, 92%, 93%, 94%, 95%, 96%, 97%, 98% or 99% identity to the amino acid sequence YISSGGGNTYYADSVKG (SEQ ID NO: 27), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 28); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYEGDSSMN (SEQ ID NO: 42), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 43) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 44).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 29), a VHCDR2 comprising at least 70%, 75%, 80%, 85%, 90%, 91%, 92%, 93%, 94%, 95%, 96%, 97%, 98% or 99% identity to the amino acid sequence SSGGGNTY (SEQ ID NO: 30), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 28); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYEGDSSMN (SEQ ID NO: 42), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 43) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 44).

In one embodiment, an antibody, fragment or variant thereof, is provided comprising:

a heavy chain variable region comprising a VHCDR1 comprising at least 90% identity to the amino acid sequence SYTMS (SEQ ID NO: 26), a VHCDR2 comprising at least 90% identity to the amino acid sequence YISSGGGNTYYADSVKG (SEQ ID NO: 27), and a VHCDR3 comprising at least 90% identity to the amino acid sequence HDYYDGGLYYAMDY (SEQ ID NO: 28); and/or a light chain variable region comprising a VLCDR1 comprising the at least 90% identity to amino acid sequence KASQSVDYEGDSSMN (SEQ ID NO: 42), a VLCDR2 comprising at least 90% identity to the amino acid sequence AASTLES (SEQ ID NO: 43) and a VLCDR3 comprising at least 90% identity to the amino acid sequence QQTNEDPPT (SEQ ID NO: 44).

In one embodiment, an antibody, fragment or variant thereof, is provided comprising:

a heavy chain variable region comprising a VHCDR1 comprising at least 90% identity to the amino acid sequence GFTFSSY (SEQ ID NO: 29), a VHCDR2 comprising at least 90% identity to the amino acid sequence SSGGGNTY (SEQ ID NO: 30), and a VHCDR3 comprising at least 90% identity to the amino acid sequence HDYYDGGLYYAMDY (SEQ ID NO: 28); and/or a light chain variable region comprising a VLCDR1 comprising the at least 90% identity to amino acid sequence KASQSVDYEGDSSMN (SEQ ID NO: 42), a VLCDR2 comprising at least 90% identity to the amino acid sequence AASTLES (SEQ ID NO: 43) and a VLCDR3 comprising at least 90% identity to the amino acid sequence QQTNEDPPT (SEQ ID NO: 44).

In one embodiment, an antibody, fragment or variant thereof, is provided comprising:

a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), and a VHCDR3 comprising the amino acid sequence HDYYDGGLYYAMDY (SEQ ID NO: 28); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44).

Amino acid substitutions may be made to provide variant antibodies derived from 3E05_var 14, for example an antibody, fragment or variant thereof is provided comprising a heavy chain variable region comprising a VHCDR1 comprising the amino acid sequence SYTMS (SEQ ID NO: 26) optionally comprising 1 or 2 amino acid substitutions, a VHCDR2 comprising the amino acid sequence YISSGGGNTYYADSVKG (SEQ ID NO: 27) optionally comprising 1 or 2 amino acid substitutions, and a VHCDR3 comprising the amino acid sequence HDYYDGGLYYAMDY (SEQ ID NO: 28) optionally comprising 1 or 2 amino acid substitutions; and/or a light chain variable region comprising a VLCDR1 comprising the amino acid sequence KASQSVDYEGDSSMN (SEQ ID NO: 42) optionally comprising 1 or 2 amino acid substitutions, a VLCDR2 comprising the amino acid sequence AASTLES (SEQ ID NO: 43) optionally comprising 1 or 2 amino acid substitutions and a VLCDR3 comprising the amino acid sequence QQTNEDPPT (SEQ ID NO: 44) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), and a VHCDR3 comprising the amino acid sequence HDYYDGGLYYAMDY (SEQ ID NO: 28); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

optionally wherein the Met residues are each independently substituted with an amino acid selected from the group consisting of Ala and Leu, and/or the Asp residues are each independently substituted with an amino acid selected from the group consisting of Ala, Gin and Glu.

In one embodiment, an antibody, fragment or variant thereof, is provided comprising:

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), and a VHCDR3 comprising the amino acid sequence HDYYDGGLYYAMDY (SEQ ID NO: 28); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44).

Amino acid substitutions may be made to provide variant antibodies derived from 3E05_var 14, for example an antibody, fragment or variant thereof is provided comprising a heavy chain variable region comprising a VHCDR1 comprising the amino acid sequence GFTFSSY (SEQ ID NO: 29) optionally comprising 1 or 2 amino acid substitutions, a VHCDR2 comprising the amino acid sequence SSGGGNTY (SEQ ID NO: 30) optionally comprising 1 or 2 amino acid substitutions, and a VHCDR3 comprising the amino acid sequence HDYYDGGLYYAMDY (SEQ ID NO: 28) optionally comprising 1 or 2 amino acid substitutions; and/or a light chain variable region comprising a VLCDR1 comprising the amino acid sequence KASQSVDYEGDSSMN (SEQ ID NO: 42) optionally comprising 1 or 2 amino acid substitutions, a VLCDR2 comprising the amino acid sequence AASTLES (SEQ ID NO: 43) optionally comprising 1 or 2 amino acid substitutions and a VLCDR3 comprising the amino acid sequence QQTNEDPPT (SEQ ID NO: 44) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), and a VHCDR3 comprising the amino acid sequence HDYYDGGLYYAMDY (SEQ ID NO: 28); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

optionally wherein the Met residues are each independently substituted with an amino acid selected from the group consisting of Ala and Leu, and/or the Asp residues are each independently substituted with an amino acid selected from the group consisting of Ala, Gin and Glu.

Antigen binding molecules of or derived from 3E05_var14 (for example antibodies having one or more amino acid substitutions) may have a $K_D$ of less than about 0.01 nM, an IC50 for IFN secretion of less than about 0.5M, and/or an IC90 for IFN secretion of less than about 5 nM. In a specific embodiment, antigen binding molecules of or derived from 3E05_var14 (for example antibodies having one or more amino acid substitutions) may have a $K_D$ of less than about 0.01 nM, an IC50 for IFN secretion of less than about 0.2 nM, and/or an IC90 for IFN secretion of less than about 2 nM 3E05_var 1

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 16), a VHCDR2 comprising at least 70%, 75%, 80%, 85%, 90%, 91%, 92%, 93%, 94%, 95%, 96%, 97%, 98% or 99% identity to the amino acid sequence YISSGGGNTYYPDSVKG (SEQ ID NO: 17), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 18); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDSSMN (SEQ ID NO: 12), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 13) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 14).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 19), a VHCDR2 comprising at least 70%, 75%, 80%, 85%, 90%, 91%, 92%, 93%, 94%, 95%, 96%, 97%, 98% or 99% identity to the amino acid sequence SSGGGNTY (SEQ ID NO: 20), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 18); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDSSMN (SEQ ID NO: 12), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 13) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 14).

In one embodiment, an antibody, fragment or variant thereof, is provided comprising:

a heavy chain variable region comprising a VHCDR1 comprising at least 90% identity to the amino acid sequence SYTMS (SEQ ID NO: 16), a VHCDR2 comprising at least 90% identity to the amino acid sequence YISSGGGNTYYPDSVKG (SEQ ID NO: 17), and a VHCDR3 comprising at least 90% identity to the amino acid sequence HDYYDGGLYYAMDY (SEQ ID NO: 18); and/or a light chain variable region comprising a VLCDR1 comprising the at least 90% identity to amino acid sequence KASQSVDYDGDSSMN (SEQ ID NO: 12), a VLCDR2 comprising at least 90% identity to the amino acid sequence AASTLES (SEQ ID NO: 13) and a VLCDR3 comprising at least 90% identity to the amino acid sequence QQTNEDPPT (SEQ ID NO: 14).

In one embodiment, an antibody, fragment or variant thereof, is provided comprising:

a heavy chain variable region comprising a VHCDR1 comprising at least 90% identity to the amino acid sequence GFTFSSY (SEQ ID NO: 19), a VHCDR2 comprising at least 90% identity to the amino acid sequence SSGGGNTY (SEQ ID NO: 20), and a VHCDR3 comprising at least 90% identity to the amino acid sequence HDYYDGGLYYAMDY (SEQ ID NO: 18); and a light chain variable region comprising a VLCDR1 comprising the at least 90% identity to amino acid sequence KASQSVDYDGDSSMN (SEQ ID NO: 12), a VLCDR2 comprising at least 90% identity to the amino acid sequence AASTLES (SEQ ID NO: 13) and a VLCDR3 comprising at least 90% identity to the amino acid sequence QQTNEDPPT (SEQ ID NO: 14).

In one embodiment, an antibody, fragment or variant thereof, is provided comprising:

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), and a VHCDR3 comprising the amino acid sequence HDYYDGGLYYAMDY (SEQ ID NO: 18); and/or a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14).

Amino acid substitutions may be made to provide variant antibodies derived from 3E05_var 1, for example an antibody, fragment or variant thereof is provided comprising:

a heavy chain variable region comprising a VHCDR1 comprising the amino acid sequence SYTMS (SEQ ID NO: 16) optionally comprising 1 or 2 amino acid substitutions, a VHCDR2 comprising the amino acid sequence YISSGGGNTYYPDSVKG (SEQ ID NO: 17) optionally comprising 1 or 2 amino acid substitutions, and a VHCDR3 comprising the amino acid sequence HDYYDGGLYYAMDY (SEQ ID NO: 18) optionally comprising 1 or 2 amino acid substitutions; and/or a light chain variable region comprising a VLCDR1 comprising the amino acid sequence KASQSVDYDGDSSMN (SEQ ID NO: 12) optionally comprising 1 or 2 amino acid substitutions, a VLCDR2 comprising the amino acid sequence AASTLES (SEQ ID NO: 13) optionally comprising 1 or 2 amino acid substitutions and a VLCDR3 comprising the amino acid sequence QQTNEDPPT (SEQ ID NO: 14) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), and a VHCDR3 comprising the amino acid sequence HDYYDGGLYYAMDY (SEQ ID NO: 18); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

optionally wherein the Met residues are each independently substituted with an amino acid selected from the group consisting of Ala and Leu, and/or the Asp residues are each independently substituted with an amino acid selected from the group consisting of Ala, Gin and Glu.

In one embodiment, an antibody, fragment or variant thereof, is provided comprising:

a heavy chain variable region comprising a VHCDR1 comprising the amino acid sequence GFTFSSY (SEQ ID NO: 19), a VHCDR2 comprising the amino acid sequence SSGGGNTY (SEQ ID NO: 20), and a VHCDR3 comprising the amino acid sequence HDYYDGGLYYAMDY (SEQ ID NO: 18); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14).

Amino acid substitutions may be made to provide variant antibodies derived from 3E05_var 1, for example an antibody, fragment or variant thereof is provided comprising:

a heavy chain variable region comprising a VHCDR1 comprising the amino acid sequence GFTFSSY (SEQ ID NO: 19) optionally comprising 1 or 2 amino acid substitutions, a VHCDR2 comprising the amino acid sequence SSGGGNTY (SEQ ID NO: 20) optionally comprising 1 or 2 amino acid substitutions, and a VHCDR3 comprising the amino acid sequence HDYYDGGLYYAMDY (SEQ ID NO: 18) optionally comprising 1 or 2 amino acid substitutions; and/or a light chain variable region comprising a VLCDR1 comprising the amino acid sequence KASQSVDYDGDSSMN (SEQ ID NO: 12) optionally comprising 1 or 2 amino acid substitutions, a VLCDR2 comprising the amino acid sequence AASTLES (SEQ ID NO: 13) optionally comprising 1 or 2 amino acid substitutions and a VLCDR3 comprising the amino acid sequence QQTNEDPPT (SEQ ID NO: 14) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 19), a VHCDR2 comprising the amino acid sequence SSGGGNTY (SEQ ID NO: 20), and a VHCDR3 comprising the amino acid sequence HDYYDGGLYYAMDY (SEQ ID NO: 18); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

optionally wherein the Met residues are each independently substituted with an amino acid selected from the group consisting of Ala and Leu, and/or the Asp residues are each independently substituted with an amino acid selected from the group consisting of Ala, Gln and Glu.

Antigen binding molecules of or derived from 3E05_var1 (for example antibodies having one or more amino acid substitutions) may have a $K_D$ of less than about 0.01 nM. Such antigen binding molecules may additionally or alternatively exhibit an IC50 for IFN secretion of less than about 0.5 nM and/or an IC90 for IFN secretion of less than about 5 nM.

3E05_var 2

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 26), a VHCDR2 comprising at least 70%, 75%, 80%, 85%, 90%, 91%, 92%, 93%, 94%, 95%, 96%, 97%, 98% or 99% identity to the amino acid sequence YISSGGGNTYYADSVKG (SEQ ID NO: 27), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 28); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDSSMN (SEQ ID NO: 12), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 13) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 14).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 29), a VHCDR2 comprising at least 70%, 75%, 80%, 85%, 90%, 91%, 92%, 93%, 94%, 95%, 96%, 97%, 98% or 99% identity to the amino acid sequence SSGGGNTY (SEQ ID NO: 30), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 28); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDSSMN (SEQ ID NO: 12), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 13) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 14).

In one embodiment, an antibody, fragment or variant thereof, is provided comprising:

a heavy chain variable region comprising a VHCDR1 comprising at least 90% identity to the amino acid sequence SYTMS (SEQ ID NO: 26), a VHCDR2 comprising at least 90% identity to the amino acid sequence YISSGGGNTYYADSVKG (SEQ ID NO: 27), and a VHCDR3 comprising at least 90% identity to the amino acid sequence HDYYDGGLYYAMDY (SEQ ID NO: 28); and/or a light chain variable region comprising a VLCDR1 comprising the at least 90% identity to amino acid sequence KASQSVDYDGDSSMN (SEQ ID NO: 12), a VLCDR2 comprising at least 90% identity to the amino acid sequence AASTLES (SEQ ID NO: 13) and a VLCDR3 comprising at least 90% identity to the amino acid sequence QQTNEDPPT (SEQ ID NO: 14).

In one embodiment, an antibody, fragment or variant thereof, is provided comprising:

a heavy chain variable region comprising a VHCDR1 comprising at least 90% identity to the amino acid sequence GFTFSSY (SEQ ID NO: 29), a VHCDR2 comprising at least 90% identity to the amino acid sequence SSGGGNTY (SEQ ID NO: 30), and a VHCDR3 comprising at least 90% identity to the amino acid sequence HDYYDGGLYYAMDY (SEQ ID NO: 28); and/or a light chain variable region comprising a VLCDR1 comprising the at least 90% identity to amino acid sequence KASQSVDYDGDSSMN (SEQ ID NO: 12), a VLCDR2 comprising at least 90% identity to the amino acid sequence AASTLES (SEQ ID NO: 13) and a VLCDR3 comprising at least 90% identity to the amino acid sequence QQTNEDPPT (SEQ ID NO: 14).

In one embodiment, an antibody, fragment or variant thereof, is provided comprising:

a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), and a VHCDR3 comprising the amino acid sequence HDYYDGGLYYAMDY (SEQ ID NO: 28); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14).

Amino acid substitutions may be made to provide variant antibodies derived from 3E05_var 2, for example an antibody, fragment or variant thereof is provided comprising:

a heavy chain variable region comprising a VHCDR1 comprising the amino acid sequence SYTMS (SEQ ID NO: 26) optionally comprising 1 or 2 amino acid substitutions, a VHCDR2 comprising the amino acid sequence YISSGGGNTYYADSVKG (SEQ ID NO: 27) optionally comprising 1 or 2 amino acid substitutions, and a VHCDR3 comprising the amino acid sequence HDYYDGGLYYAMDY (SEQ ID NO: 28) optionally comprising 1 or 2 amino acid substitutions; and/or a light chain variable region comprising a VLCDR1 comprising the amino acid sequence KASQSVDYDGDSSMN (SEQ ID NO: 12) optionally comprising 1 or 2 amino acid substitutions, a VLCDR2 comprising the amino acid sequence AASTLES (SEQ ID NO: 13) optionally comprising 1 or 2 amino acid substitutions and a VLCDR3 comprising the amino acid sequence QQTNEDPPT (SEQ ID NO: 14) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), and a VHCDR3 comprising the amino acid sequence HDYYDGGLYYAMDY (SEQ ID NO: 28); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14).

optionally wherein the Met residues are each independently substituted with an amino acid selected from the group consisting of Ala and Leu, and/or the Asp residues are each independently substituted with an amino acid selected from the group consisting of Ala, Gln and Glu.

In one embodiment, an antibody, fragment or variant thereof, is provided comprising:

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), and a VHCDR3 comprising the amino acid sequence HDYYDGGLYYAMDY (SEQ ID NO: 28); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14).

Amino acid substitutions may be made to provide variant antibodies derived from 3E05_var 2, for example an antibody, fragment or variant thereof is provided comprising:

a heavy chain variable region comprising a VHCDR1 comprising the amino acid sequence GFTFSSY (SEQ ID NO: 29) optionally comprising 1 or 2 amino acid substitutions, a VHCDR2 comprising the amino acid sequence SSGGGNTY (SEQ ID NO: 30) optionally comprising 1 or 2 amino acid substitutions, and a VHCDR3 comprising the amino acid sequence HDYYDGGLYYAMDY (SEQ ID NO: 28) optionally comprising 1 or 2 amino acid substitutions; and/or a light chain variable region comprising a VLCDR1 comprising the amino acid sequence KASQSVDYDGDSSMN (SEQ ID NO: 12) optionally comprising 1 or 2 amino acid substitutions, a VLCDR2 comprising the amino acid sequence AASTLES (SEQ ID NO: 13) optionally comprising 1 or 2 amino acid substitutions, and a VLCDR3 comprising the amino acid sequence QQTNEDPPT (SEQ ID NO: 14) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), and a VHCDR3 comprising the amino acid sequence HDYYDGGLYYAMDY (SEQ ID NO: 28); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

optionally wherein the Met residues are each independently substituted with an amino acid selected from the group consisting of Ala and Leu, and/or the Asp residues are each independently substituted with an amino acid selected from the group consisting of Ala, Gin and Glu.

Antigen binding molecules of or derived from 3E05_var2 (for example antibodies having one or more amino acid substitutions) may have a $K_D$ of less than about 0.5 nM. Such antigen binding molecules may additionally or alternatively exhibit an IC50 for IFN secretion of less than about 0.5 nM and/or an IC90 for IFN secretion of less than about 5 nM.

3E05_var 3

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 36), a VHCDR2 comprising at least 70%, 75%, 80%, 85%, 90%, 91%, 92%, 93%, 94%, 95%, 96%, 97%, 98% or 99% identity to the amino acid sequence YISSGGGQTYYPDSVKG (SEQ ID NO: 37), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 38); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDSSMN (SEQ ID NO: 12), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 13) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 14).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 39), a VHCDR2 comprising at least 70%, 75%, 80%, 85%, 90%, 91%, 92%, 93%, 94%, 95%, 96%, 97%, 98% or 99% identity to the amino acid sequence SSGGGQTY (SEQ ID NO: 40), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 38); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDSSMN (SEQ ID NO: 12), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 13) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 14).

In one embodiment, an antibody, fragment or variant thereof, is provided comprising:

a heavy chain variable region comprising a VHCDR1 comprising at least 90% identity to the amino acid sequence SYTMS (SEQ ID NO: 36), a VHCDR2 comprising at least 90% identity to the amino acid sequence YISSGGGQTYYPDSVKG (SEQ ID NO: 37), and a VHCDR3 comprising at least 90% identity to the amino acid sequence HDYYDGGLYYAMDY (SEQ ID NO: 38); and/or a light chain variable region comprising a VLCDR1 comprising the at least 90% identity to amino acid sequence KASQSVDYDGDSSMN (SEQ ID NO: 12), a VLCDR2 comprising at least 90% identity to the amino acid sequence AASTLES (SEQ ID NO: 13) and a VLCDR3 comprising at least 90% identity to the amino acid sequence QQTNEDPPT (SEQ ID NO: 14).

In one embodiment, an antibody, fragment or variant thereof, is provided comprising:

a heavy chain variable region comprising a VHCDR1 comprising at least 90% identity to the amino acid sequence GFTFSSY (SEQ ID NO: 39), a VHCDR2 comprising at least 90% identity to the amino acid sequence SSGGGQTY (SEQ ID NO: 40), and a VHCDR3 comprising at least 90% identity to the amino acid sequence HDYYDGGLYYAMDY (SEQ ID NO: 38); and/or a light chain variable region comprising a VLCDR1 comprising the at least 90% identity to amino acid sequence KASQSVDYDGDSSMN (SEQ ID NO: 12), a VLCDR2 comprising at least 90% identity to the amino acid sequence AASTLES (SEQ ID NO: 13) and a VLCDR3 comprising at least 90% identity to the amino acid sequence QQTNEDPPT (SEQ ID NO: 14).

In one embodiment, an antibody, fragment or variant thereof, is provided comprising:

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), and a VHCDR3 comprising the amino acid sequence HDYYDGGLYYAMDY (SEQ ID NO: 38); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14).

Amino acid substitutions may be made to provide variant antibodies derived from 3E05_var 3, for example an antibody, fragment or variant thereof is provided comprising:

a heavy chain variable region comprising a VHCDR1 comprising the amino acid sequence SYTMS (SEQ ID NO: 36) optionally comprising 1 or 2 amino acid substitutions, a VHCDR2 comprising the amino acid sequence YISSGGGQTYYPDSVKG (SEQ ID NO: 37) optionally comprising 1 or 2 amino acid substitutions, and a VHCDR3 comprising the amino acid sequence HDYYDGGLYYAMDY (SEQ ID NO: 38) optionally comprising 1 or 2 amino acid substitutions; and/or a light chain variable region comprising a VLCDR1 comprising the amino acid sequence KASQSVDYDGDSSMN (SEQ ID NO: 12) optionally comprising 1 or 2 amino acid substitutions, a VLCDR2 comprising the amino acid sequence AASTLES (SEQ ID NO: 13) optionally comprising 1 or 2 amino acid substitutions and a VLCDR3 comprising the amino acid sequence QQTNEDPPT (SEQ ID NO: 14) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), and a VHCDR3 comprising the amino acid sequence HDYYDGGLYYAMDY (SEQ ID NO: 38); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

optionally wherein the Met residues are each independently substituted with an amino acid selected from the group consisting of Ala and Leu, and/or the Asp residues are each independently substituted with an amino acid selected from the group consisting of Ala, Gin and Glu.

In one embodiment, an antibody, fragment or variant thereof, is provided comprising:

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), and a VHCDR3 comprising the amino acid sequence HDYYDGGLYYAMDY (SEQ ID NO: 38); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14).

Amino acid substitutions may be made to provide variant antibodies derived from 3E05_var 3, for example an antibody, fragment or variant thereof is provided comprising:

a heavy chain variable region comprising a VHCDR1 comprising the amino acid sequence GFTFSSY (SEQ ID NO: 39) optionally comprising 1 or 2 amino acid substitutions, a VHCDR2 comprising the amino acid sequence SSGGGQTY (SEQ ID NO: 40) optionally comprising 1 or 2 amino acid substitutions, and a VHCDR3 comprising the amino acid sequence HDYYDGGLYYAMDY (SEQ ID NO: 38) optionally comprising 1 or 2 amino acid substitutions; and/or a light chain variable region comprising a VLCDR1 comprising the amino acid sequence KASQSVDYDGDSSMN (SEQ ID NO: 12) optionally comprising 1 or 2 amino acid substitutions, a VLCDR2 comprising the amino acid sequence AASTLES (SEQ ID NO: 13) optionally comprising 1 or 2 amino acid substitutions and a VLCDR3 comprising the amino acid sequence QQTNEDPPT (SEQ ID NO: 14) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), and a VHCDR3 comprising the amino acid sequence HDYYDGGLYYAMDY (SEQ ID NO: 38); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

optionally wherein the Met residues are each independently substituted with an amino acid selected from the group consisting of Ala and Leu, and/or the Asp residues are each independently substituted with an amino acid selected from the group consisting of Ala, Gin and Glu.

Antigen binding molecules of or derived from 3E05_var3 (for example antibodies having one or more amino acid substitutions) may have a $K_D$ of less than about 0.01 nM. Such antigen binding molecules may additionally or alternatively exhibit an IC50 for IFN secretion of less than about 0.5 nM and/or an IC90 for IFN secretion of less than about 5 nM.

3E05_var4

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 46), a VHCDR2 comprising at least 70%, 75%, 80%, 85%, 90%, 91%, 92%, 93%, 94%, 95%, 96%, 97%, 98% or 99% identity to the amino acid sequence YISSGGGQTYYPDSVKG (SEQ ID NO: 47), and a VHCDR3 comprising at least 70%, 75%, 80%, 85%, 90%, 91%, 92%, 93%, 94%, 95%, 96%, 97%, 98% or 99% identity to the amino acid sequence HDYYEGGLYYAMDY (SEQ ID NO: 48); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDSSMN (SEQ ID NO: 12), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 13) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 14).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 49), a VHCDR2 comprising at least 70%, 75%, 80%, 85%, 90%, 91%, 92%, 93%, 94%, 95%, 96%, 97%, 98% or 99% identity to the amino acid sequence SSGGGQTY (SEQ ID NO: 50), and a VHCDR3 comprising at least 70%, 75%, 80%, 85%, 90%, 91%, 92%, 93%, 94%, 95%, 96%, 97%, 98% or 99% identity to the amino acid sequence HDYYEGGLYYAMDY (SEQ ID NO: 48); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDSSMN (SEQ ID NO: 12), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 13) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 14).

In one embodiment, an antibody, fragment or variant thereof, is provided comprising:

a heavy chain variable region comprising a VHCDR1 comprising at least 90% identity to the amino acid sequence SYTMS (SEQ ID NO: 46), a VHCDR2 comprising at least 90% identity to the amino acid sequence YISSGGGQTYYPDSVKG (SEQ ID NO: 47), and a VHCDR3 comprising at least 90% identity to the amino acid sequence HDYYEGGLYYAMDY (SEQ ID NO: 48); and/or a light chain variable region comprising a VLCDR1 comprising the at least 90% identity to amino acid sequence KASQSVDYDGDSSMN (SEQ ID NO: 12), a VLCDR2 comprising at least 90% identity to the amino acid sequence AASTLES (SEQ ID NO: 13) and a VLCDR3 comprising at least 90% identity to the amino acid sequence QQTNEDPPT (SEQ ID NO: 14).

In one embodiment, an antibody, fragment or variant thereof, is provided comprising:

a heavy chain variable region comprising a VHCDR1 comprising at least 90% identity to the amino acid sequence GFTFSSY (SEQ ID NO: 49), a VHCDR2 comprising at least 90% identity to the amino acid sequence SSGGGQTY (SEQ ID NO: 50), and a VHCDR3 comprising at least 90% identity to the amino acid sequence HDYYEGGLYYAMDY (SEQ ID NO: 48); and/or a light chain variable region comprising a VLCDR1 comprising the at least 90% identity to amino acid sequence KASQSVDYDGDSSMN (SEQ ID NO: 12), a VLCDR2 comprising at least 90% identity to the amino acid sequence AASTLES (SEQ ID NO: 13) and a VLCDR3 comprising at least 90% identity to the amino acid sequence QQTNEDPPT (SEQ ID NO: 14).

In one embodiment, an antibody, fragment or variant thereof, is provided comprising:

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), and a VHCDR3 comprising the amino acid sequence HDYYEGGLYYAMDY (SEQ ID NO: 48); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14).

Amino acid substitutions may be made to provide variant antibodies derived from 3E05_var 4, for example an antibody, fragment or variant thereof is provided comprising:

a heavy chain variable region comprising a VHCDR1 comprising the amino acid sequence SYTMS (SEQ ID NO: 46) optionally comprising 1 or 2 amino acid substitutions, a VHCDR2 comprising the amino acid sequence YISSGGGQTYYPDSVKG (SEQ ID NO: 47) optionally comprising 1 or 2 amino acid substitutions, and a VHCDR3 comprising the amino acid sequence HDYYEGGLYYAMDY (SEQ ID NO: 48) optionally comprising 1 or 2 amino acid substitutions; and/or a light chain variable region comprising a VLCDR1 comprising the amino acid sequence KASQSVDYDGDSSMN (SEQ ID NO: 12) optionally comprising 1 or 2 amino acid substitutions, a VLCDR2 comprising the amino acid sequence AASTLES (SEQ ID NO: 13) optionally comprising 1 or 2 amino acid substitutions and a VLCDR3 comprising the amino acid sequence QQTNEDPPT (SEQ ID NO: 14) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), and a VHCDR3 comprising the amino acid sequence HDYYEGGLYYAMDY (SEQ ID NO: 48); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

optionally wherein the Met residues are each independently substituted with an amino acid selected from the group consisting of Ala and Leu, and/or the Asp residues are each independently substituted with an amino acid selected from the group consisting of Ala, Gin and Glu.

In one embodiment, an antibody, fragment or variant thereof, is provided comprising:

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), and a VHCDR3 comprising the amino acid sequence HDYYEGGLYYAMDY (SEQ ID NO: 48); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14).

Amino acid substitutions may be made to provide variant antibodies derived from 3E05_var 4, for example an antibody, fragment or variant thereof is provided comprising a heavy chain variable region comprising a VHCDR1 comprising the amino acid sequence GFTFSSY (SEQ ID NO: 49) optionally comprising 1 or 2 amino acid substitutions, a VHCDR2 comprising the amino acid sequence SSGGGQTY (SEQ ID NO: 50) optionally comprising 1 or 2 amino acid substitutions, and a VHCDR3 comprising the amino acid sequence HDYYEGGLYYAMDY (SEQ ID NO: 48); and/or a light chain variable region comprising a VLCDR1 comprising the amino acid sequence KASQSVDYDGDSSMN (SEQ ID NO: 12) optionally comprising 1 or 2 amino acid substitutions, a VLCDR2 comprising the amino acid sequence AASTLES (SEQ ID NO: 13) optionally comprising 1 or 2 amino acid substitutions and a VLCDR3 comprising the amino acid sequence QQTNEDPPT (SEQ ID NO: 14) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), and a VHCDR3 comprising the amino acid sequence HDYYEGGLYYAMDY (SEQ ID NO: 48); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

optionally wherein the Met residues are each independently substituted with an amino acid selected from the group consisting of Ala and Leu, and/or the Asp residues are each independently substituted with an amino acid selected from the group consisting of Ala, Gin and Glu.

Antigen binding molecules of or derived from 3E05_var4 (for example antibodies having one or more amino acid substitutions) may have a $K_D$ of less than about 0.01 nM. Such antigen binding molecules may additionally or alternatively exhibit an IC50 for IFN secretion of less than about 0.5 nM and/or an IC90 for IFN secretion of less than about 5 nM.

3E05_var 5

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 16), a VHCDR2 comprising at least 70%, 75%, 80%, 85%, 90%, 91%, 92%, 93%, 94%, 95%, 96%, 97%, 98% or 99% identity to the amino acid sequence YISSGGGNTYYPDSVKG (SEQ ID NO: 17), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 18); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 22), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 23) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 24).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 19), a VHCDR2 comprising at least 70%, 75%, 80%, 85%, 90%, 91%, 92%, 93%, 94%, 95%, 96%, 97%, 98% or 99% identity to the amino acid sequence SSGGGNTY (SEQ ID NO: 20), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 18); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 22), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 23) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 24).

In one embodiment, an antibody, fragment or variant thereof, is provided comprising:

a heavy chain variable region comprising a VHCDR1 comprising at least 90% identity to the amino acid sequence SYTMS (SEQ ID NO: 16), a VHCDR2 comprising at least 90% identity to the amino acid sequence YISSGGGNTYYPDSVKG (SEQ ID NO: 17), and a VHCDR3 comprising at least 90% identity to the amino acid sequence HDYYDGGLYYAMDY (SEQ ID NO: 18); and/or a light chain variable region comprising a VLCDR1 comprising the at least 90% identity to amino acid sequence KSSQSVDYDGDSSMN (SEQ ID NO: 22), a VLCDR2 comprising at least 90% identity to the amino acid sequence AASTLES (SEQ ID NO: 23) and a VLCDR3 comprising at least 90% identity to the amino acid sequence QQTNEDPPT (SEQ ID NO: 24).

In one embodiment, an antibody, fragment or variant thereof, is provided comprising:

a heavy chain variable region comprising a VHCDR1 comprising at least 90% identity to the amino acid sequence GFTFSSY (SEQ ID NO: 19), a VHCDR2 comprising at least 90% identity to the amino acid sequence SSGGGNTY (SEQ ID NO: 20), and a VHCDR3 comprising at least 90% identity to the amino acid sequence HDYYDGGLYYAMDY (SEQ ID NO: 18); and/or a light chain variable region comprising a VLCDR1 comprising the at least 90% identity to amino acid sequence KSSQSVDYDGDSSMN (SEQ ID NO: 22), a VLCDR2 comprising at least 90% identity to the amino acid sequence AASTLES (SEQ ID NO: 23) and a VLCDR3 comprising at least 90% identity to the amino acid sequence QQTNEDPPT (SEQ ID NO: 24).

In one embodiment, an antibody, fragment or variant thereof, is provided comprising:

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), and a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24).

Amino acid substitutions may be made to provide variant antibodies derived from 3E05_var 5, for example an antibody, fragment or variant thereof is provided comprising a heavy chain variable region comprising a VHCDR1 comprising the amino acid sequence SYTMS (SEQ ID NO: 16) optionally comprising 1 or 2 amino acid substitutions, a VHCDR2 comprising the amino acid sequence YISSGGGNTYYPDSVKG (SEQ ID NO: 17) optionally comprising 1 or 2 amino acid substitutions, and a VHCDR3 comprising the amino acid sequence HDYYDGGLYYAMDY (SEQ ID NO: 18) optionally comprising 1 or 2 amino acid substitutions; and/or a light chain variable region comprising a VLCDR1 comprising the amino acid sequence KSSQSVDYDGDSSMN (SEQ ID NO: 22) optionally comprising 1 or 2 amino acid substitutions, a VLCDR2 comprising the amino acid sequence AASTLES (SEQ ID NO: 23) optionally comprising 1 or 2 amino acid substitutions and a VLCDR3 comprising the amino acid sequence QQTNEDPPT (SEQ ID NO: 24) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), and a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

optionally wherein the Met residues are each independently substituted with an amino acid selected from the group consisting of Ala and Leu, and/or the Asp residues are each independently substituted with an amino acid selected from the group consisting of Ala, Gin and Glu.

In one embodiment, an antibody, fragment or variant thereof, is provided comprising:

a heavy chain variable region comprising a VHCDR1 comprising the amino acid sequence GFTFSSY (SEQ ID NO: 19), a VHCDR2 comprising the amino acid sequence SSGGGNTY (SEQ ID NO: 20), and a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24).

Amino acid substitutions may be made to provide variant antibodies derived from 3E05_var 5, for example an antibody, fragment or variant thereof is provided comprising a heavy chain variable region comprising a VHCDR1 comprising the amino acid sequence GFTFSSY (SEQ ID NO: 19) optionally comprising 1 or 2 amino acid substitutions, a VHCDR2 comprising the amino acid sequence SSGGGNTY (SEQ ID NO: 20) optionally comprising 1 or 2 amino acid substitutions, and a VHCDR3 comprising the amino acid sequence HDYYDGGLYYAMDY (SEQ ID NO: 18) optionally comprising 1 or 2 amino acid substitutions; and/or a light chain variable region comprising a VLCDR1 comprising the amino acid sequence KSSQSVDYDGDSSMN (SEQ ID NO: 22) optionally comprising 1 or 2 amino acid substitutions, a VLCDR2 comprising the amino acid sequence AASTLES (SEQ ID NO: 23) optionally comprising 1 or 2 amino acid substitutions and a VLCDR3 comprising the amino acid sequence QQTNEDPPT (SEQ ID NO: 24) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 19), a VHCDR2 comprising the amino acid sequence SSGGGNTY (SEQ ID NO: 20), and a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

optionally wherein the Met residues are each independently substituted with an amino acid selected from the group consisting of Ala and Leu, and/or the Asp residues are each independently substituted with an amino acid selected from the group consisting of Ala, Gin and Glu.

Antigen binding molecules of or derived from 3E05_var5 (for example antibodies having one or more amino acid substitutions) may have a $K_D$ of less than about 0.01 nM. Such antigen binding molecules may additionally or alternatively exhibit an IC50 for IFN secretion of less than about 0.5 nM and/or an IC90 for IFN secretion of less than about 5 nM.

3E05_var 7

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 36), a VHCDR2 comprising at least 70%, 75%, 80%, 85%, 90%, 91%, 92%, 93%, 94%, 95%, 96%, 97%, 98% or 99% identity to the amino acid sequence YISSGGGQTYYPDSVKG (SEQ ID NO: 37), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 38); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 22), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 23) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 24).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 39), a VHCDR2 comprising at least 70%, 75%, 80%, 85%, 90%, 91%, 92%, 93%, 94%, 95%, 96%, 97%, 98% or 99% identity to the amino acid sequence SSGGGQTY (SEQ ID NO: 40), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 38); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 22), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 23) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 24).

In one embodiment, an antibody, fragment or variant thereof, is provided comprising:

a heavy chain variable region comprising a VHCDR1 comprising at least 90% identity to the amino acid sequence SYTMS (SEQ ID NO: 36), a VHCDR2 comprising at least 90% identity to the amino acid sequence YISSGGGQTYYPDSVKG (SEQ ID NO: 37), and a VHCDR3 comprising at least 90% identity to the amino acid sequence HDYYDGGLYYAMDY (SEQ ID NO: 38); and/or a light chain variable region comprising a VLCDR1 comprising the at least 90% identity to amino acid sequence KSSQSVDYDGDSSMN (SEQ ID NO: 22), a VLCDR2 comprising at least 90% identity to the amino acid sequence AASTLES (SEQ ID NO: 23) and a VLCDR3 comprising at least 90% identity to the amino acid sequence QQTNEDPPT (SEQ ID NO: 24).

In one embodiment, an antibody, fragment or variant thereof, is provided comprising:

a heavy chain variable region comprising a VHCDR1 comprising at least 90% identity to the amino acid sequence GFTFSSY (SEQ ID NO: 39), a VHCDR2 comprising at least 90% identity to the amino acid sequence SSGGGQTY (SEQ ID NO: 40), and a VHCDR3 comprising at least 90% identity to the amino acid sequence HDYYDGGLYYAMDY (SEQ ID NO: 38); and/or a light chain variable region comprising a VLCDR1 comprising the at least 90% identity to amino acid sequence KSSQSVDYDGDSSMN (SEQ ID NO: 22), a VLCDR2 comprising at least 90% identity to the amino acid sequence AASTLES (SEQ ID NO: 23) and a VLCDR3 comprising at least 90% identity to the amino acid sequence QQTNEDPPT (SEQ ID NO: 24).

In one embodiment, an antibody, fragment or variant thereof, is provided comprising:

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), and a VHCDR3 comprising the amino acid sequence HDYYDGGLYYAMDY (SEQ ID NO: 38); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24).

Amino acid substitutions may be made to provide variant antibodies derived from 3E05_var 7, for example an antibody, fragment or variant thereof is provided comprising a heavy chain variable region comprising a VHCDR1 comprising the amino acid sequence SYTMS (SEQ ID NO: 36) optionally comprising 1 or 2 amino acid substitutions, a VHCDR2 comprising the amino acid sequence YISSGGGQTYYPDSVKG (SEQ ID NO: 37) optionally comprising 1 or 2 amino acid substitutions, and a VHCDR3 comprising the amino acid sequence HDYYDGGLYYAMDY (SEQ ID NO: 38) optionally comprising 1 or 2 amino acid substitutions; and/or a light chain variable region comprising a VLCDR1 comprising the amino acid sequence KSSQSVDYDGDSSMN (SEQ ID NO: 22) optionally comprising 1 or 2 amino acid substitutions, a VLCDR2 comprising the amino acid sequence AASTLES (SEQ ID NO: 23) optionally comprising 1 or 2 amino acid substitutions and a VLCDR3 comprising the amino acid sequence QQTNEDPPT (SEQ ID NO: 24) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), and a VHCDR3 comprising the amino acid sequence HDYYDGGLYYAMDY (SEQ ID NO: 38); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

optionally wherein the Met residues are each independently substituted with an amino acid selected from the group consisting of Ala and Leu, and/or the Asp residues are each independently substituted with an amino acid selected from the group consisting of Ala, Gln and Glu.

In one embodiment, an antibody, fragment or variant thereof, is provided comprising:

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), and a VHCDR3 comprising the amino acid sequence HDYYDGGLYYAMDY (SEQ ID NO: 38); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24).

Amino acid substitutions may be made to provide variant antibodies derived from 3E05_var 7, for example an antibody, fragment or variant thereof is provided comprising a heavy chain variable region comprising a VHCDR1 comprising the amino acid sequence GFTFSSY (SEQ ID NO: 39) optionally comprising 1 or 2 amino acid substitutions, a VHCDR2 comprising the amino acid sequence SSGGGQTY (SEQ ID NO: 40) optionally comprising 1 or 2 amino acid substitutions, and a VHCDR3 comprising the amino acid sequence HDYYDGGLYYAMDY (SEQ ID NO: 38) optionally comprising 1 or 2 amino acid substitutions; and/or a light chain variable region comprising a VLCDR1 comprising the amino acid sequence KSSQSVDYDGDSSMN (SEQ ID NO: 22) optionally comprising 1 or 2 amino acid substitutions, a VLCDR2 comprising the amino acid sequence AASTLES (SEQ ID NO: 23) optionally comprising 1 or 2 amino acid substitutions and a VLCDR3 comprising the amino acid sequence QQTNEDPPT (SEQ ID NO: 24) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), and a VHCDR3 comprising the amino acid sequence HDYYDGGLYYAMDY (SEQ ID NO: 38); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

optionally wherein the Met residues are each independently substituted with an amino acid selected from the group consisting of Ala and Leu, and/or the Asp residues are each independently substituted with an amino acid selected from the group consisting of Ala, Gin and Glu.

Antigen binding molecules of or derived from 3E05_var7 (for example antibodies having one or more amino acid substitutions) may have a $K_D$ of less than about 0.01 nM. Such antigen binding molecules may additionally or alternatively exhibit an IC50 for IFN secretion of less than about 0.5 nM and/or an IC90 for IFN secretion of less than about 5 nM.

3E05_var 8

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 46), a VHCDR2 comprising at least 70%, 75%, 80%, 85%, 90%, 91%, 92%, 93%, 94%, 95%, 96%, 97%, 98% or 99% identity to the amino acid sequence YISSGGGQTYYPDSVKG (SEQ ID NO: 47), and a VHCDR3 comprising at least 70%, 75%, 80%, 85%, 90%, 91%, 92%, 93%, 94%, 95%, 96%, 97%, 98% or 99% identity to the amino acid sequence HDYYEGGLYYAMDY (SEQ ID NO: 48); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 22), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 23) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 24).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 49), a VHCDR2 comprising at least 70%, 75%, 80%, 85%, 90%, 91%, 92%, 93%, 94%, 95%, 96%, 97%, 98% or 99% identity to the amino acid sequence SSGGGQTY (SEQ ID NO: 50), and a VHCDR3 comprising at least 70%, 75%, 80%, 85%, 90%, 91%, 92%, 93%, 94%, 95%, 96%, 97%, 98% or 99% identity to the amino acid sequence HDYYEGGLYYAMDY (SEQ ID NO: 48); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 22), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 23) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 24).

In one embodiment, an antibody, fragment or variant thereof, is provided comprising:

a heavy chain variable region comprising a VHCDR1 comprising at least 90% identity to the amino acid sequence SYTMS (SEQ ID NO: 46), a VHCDR2 comprising at least 90% identity to the amino acid sequence YISSGGGQTYYPDSVKG (SEQ ID NO: 47), and a VHCDR3 comprising at least 90% identity to the amino acid sequence HDYYEGGLYYAMDY (SEQ ID NO: 48); and/or a light chain variable region comprising a VLCDR1 comprising the at least 90% identity to amino acid sequence KSSQSVDYDGDSSMN (SEQ ID NO: 22), a VLCDR2 comprising at least 90% identity to the amino acid sequence AASTLES (SEQ ID NO: 23) and a VLCDR3 comprising at least 90% identity to the amino acid sequence QQTNEDPPT (SEQ ID NO: 24).

In one embodiment, an antibody, fragment or variant thereof, is provided comprising:

a heavy chain variable region comprising a VHCDR1 comprising at least 90% identity to the amino acid sequence GFTFSSY (SEQ ID NO: 49), a VHCDR2 comprising at least 90% identity to the amino acid sequence SSGGGQTY (SEQ ID NO: 50), and a VHCDR3 comprising at least 90% identity to the amino acid sequence HDYYEGGLYYAMDY (SEQ ID NO: 48); and/or a light chain variable region comprising a VLCDR1 comprising the at least 90% identity to amino acid sequence KSSQSVDYDGDSSMN (SEQ ID NO: 22), a VLCDR2 comprising at least 90% identity to the amino acid sequence AASTLES (SEQ ID NO: 23) and a VLCDR3 comprising at least 90% identity to the amino acid sequence QQTNEDPPT (SEQ ID NO: 24).

In one embodiment, an antibody, fragment or variant thereof, is provided comprising:

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), and a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24).

Amino acid substitutions may be made to provide variant antibodies derived from 3E05_var 8, for example an antibody, fragment or variant thereof is provided comprising a heavy chain variable region comprising a VHCDR1 comprising the amino acid sequence SYTMS (SEQ ID NO: 46) optionally comprising 1 or 2 amino acid substitutions, a VHCDR2 comprising the amino acid sequence YISSGGGQTYYPDSVKG (SEQ ID NO: 47) optionally comprising 1 or 2 amino acid substitutions, and a VHCDR3 comprising the amino acid sequence HDYYEGGLYYAMDY (SEQ ID NO: 48) optionally comprising 1 or 2 amino acid substitutions; and/or a light chain variable region comprising a VLCDR1 comprising the amino acid sequence KSSQSVDYDGDSSMN (SEQ ID NO: 22) optionally comprising 1 or 2 amino acid substitutions, a VLCDR2 comprising the amino acid sequence AASTLES (SEQ ID NO: 23) optionally comprising 1 or 2 amino acid substitutions and a VLCDR3 comprising the amino acid sequence QQTNEDPPT (SEQ ID NO: 24) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), and a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

optionally wherein the Met residues are each independently substituted with an amino acid selected from the group consisting of Ala and Leu, and/or the Asp residues are each independently substituted with an amino acid selected from the group consisting of Ala, Gin and Glu.

In one embodiment, an antibody, fragment or variant thereof, is provided comprising:

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), and a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24).

Amino acid substitutions may be made to provide variant antibodies derived from 3E05_var 8, for example an antibody, fragment or variant thereof is provided comprising a heavy chain variable region comprising a VHCDR1 comprising the amino acid sequence GFTFSSY (SEQ ID NO: 49) optionally comprising 1 or 2 amino acid substitutions, a VHCDR2 comprising the amino acid sequence SSGGGQTY (SEQ ID NO: 50) optionally comprising 1 or 2 amino acid substitutions, and a VHCDR3 comprising the amino acid sequence HDYYEGGLYYAMDY (SEQ ID NO: 48) optionally comprising 1 or 2 amino acid substitutions; and/or a light chain variable region comprising a VLCDR1 comprising the amino acid sequence KSSQSVDYDGDSSMN (SEQ ID NO: 22) optionally comprising 1 or 2 amino acid substitutions, a VLCDR2 comprising the amino acid sequence AASTLES (SEQ ID NO: 23) optionally comprising 1 or 2 amino acid substitutions and a VLCDR3 comprising the amino acid sequence QQTNEDPPT (SEQ ID NO: 24) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), and a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

optionally wherein the Met residues are each independently substituted with an amino acid selected from the group consisting of Ala and Leu, and/or the Asp residues are each independently substituted with an amino acid selected from the group consisting of Ala, Gin and Glu.

Antigen binding molecules of or derived from 3E05_var8 (for example antibodies having one or more amino acid substitutions) may have a $K_D$ of less than about 0.01 nM. Such antigen binding molecules may additionally or alternatively exhibit an IC50 for IFN secretion of less than about 0.5 nM and/or an IC90 for IFN secretion of less than about 5 nM.

3E05_var 9

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 16), a VHCDR2 comprising at least 70%, 75%, 80%, 85%, 90%, 91%, 92%, 93%, 94%, 95%, 96%, 97%, 98% or 99% identity to the amino acid sequence YISSGGGNTYYPDSVKG (SEQ ID NO: 17), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 18); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 32), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 33) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 34).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 19), a VHCDR2 comprising at least 70%, 75%, 80%, 85%, 90%, 91%, 92%, 93%, 94%, 95%, 96%, 97%, 98% or 99% identity to the amino acid sequence SSGGGNTY (SEQ ID NO: 20), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 18); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 32), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 33) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 34).

In one embodiment, an antibody, fragment or variant thereof, is provided comprising:

a heavy chain variable region comprising a VHCDR1 comprising at least 90% identity to the amino acid sequence SYTMS (SEQ ID NO: 16), a VHCDR2 comprising at least 90% identity to the amino acid sequence YISSGGGNTYYPDSVKG (SEQ ID NO: 17), and a VHCDR3 comprising at least 90% identity to the amino acid sequence HDYYDGGLYYAMDY (SEQ ID NO: 18); and/or a light chain variable region comprising a VLCDR1 comprising the at least 90% identity to amino acid sequence KSSQSVDYDGDSSMN (SEQ ID NO: 32), a VLCDR2 comprising at least 90% identity to the amino acid sequence AASTLES (SEQ ID NO: 33) and a VLCDR3 comprising at least 90% identity to the amino acid sequence QQTNEDPPT (SEQ ID NO: 34).

In one embodiment, an antibody, fragment or variant thereof, is provided comprising:

a heavy chain variable region comprising a VHCDR1 comprising at least 90% identity to the amino acid sequence GFTFSSY (SEQ ID NO: 19), a VHCDR2 comprising at least 90% identity to the amino acid sequence SSGGGNTY (SEQ ID NO: 20), and a VHCDR3 comprising at least 90% identity to the amino acid sequence HDYYDGGLYYAMDY (SEQ ID NO: 18); and/or a light chain variable region comprising a VLCDR1 comprising the at least 90% identity to amino acid sequence KSSQSVDYDGDSSMN (SEQ ID NO: 32), a VLCDR2 comprising at least 90% identity to the amino acid sequence AASTLES (SEQ ID NO: 33) and a VLCDR3 comprising at least 90% identity to the amino acid sequence QQTNEDPPT (SEQ ID NO: 34).

In one embodiment, an antibody, fragment or variant thereof, is provided comprising:

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), and a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34).

Amino acid substitutions may be made to provide variant antibodies derived from 3E05_var 9, for example an antibody, fragment or variant thereof is provided comprising a heavy chain variable region comprising a VHCDR1 comprising the amino acid sequence SYTMS (SEQ ID NO: 16) optionally comprising 1 or 2 amino acid substitutions, a VHCDR2 comprising the amino acid sequence YISSGGGNTYYPDSVKG (SEQ ID NO: 17) optionally comprising 1 or 2 amino acid substitutions, and a VHCDR3 comprising the amino acid sequence HDYYDGGLYYAMDY (SEQ ID NO: 18) optionally comprising 1 or 2 amino acid substitutions; and/or a light chain variable region comprising a VLCDR1 comprising the amino acid sequence KSSQSVDYDGDSSMN (SEQ ID NO: 32) optionally comprising 1 or 2 amino acid substitutions, a VLCDR2 comprising the amino acid sequence AASTLES (SEQ ID NO: 33) optionally comprising 1 or 2 amino acid substitutions and a VLCDR3 comprising the amino acid sequence QQTNEDPPT (SEQ ID NO: 34) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), and a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

optionally wherein the Met residues are each independently substituted with an amino acid selected from the group consisting of Ala and Leu, and/or the Asp residues are each independently substituted with an amino acid selected from the group consisting of Ala, Gln and Glu.

In one embodiment, an antibody, fragment or variant thereof, is provided comprising:

a heavy chain variable region comprising a VHCDR1 comprising the amino acid sequence GFTFSSY (SEQ ID NO: 19), a VHCDR2 comprising the amino acid sequence SSGGGNTY (SEQ ID NO: 20), and a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34).

Amino acid substitutions may be made to provide variant antibodies derived from 3E05_var 9, for example an antibody, fragment or variant thereof is provided comprising a heavy chain variable region comprising a VHCDR1 comprising the amino acid sequence GFTFSSY (SEQ ID NO: 19) optionally comprising 1 or 2 amino acid substitutions, a VHCDR2 comprising the amino acid sequence SSGGGNTY (SEQ ID NO: 20) optionally comprising 1 or 2 amino acid substitutions, and a VHCDR3 comprising the amino acid sequence HDYYDGGLYYAMDY (SEQ ID NO: 18) optionally comprising 1 or 2 amino acid substitutions; and/or a light chain variable region comprising a VLCDR1 comprising the amino acid sequence KSSQSVDYDGDSSMN (SEQ ID NO: 32) optionally comprising 1 or 2 amino acid substitutions, a VLCDR2 comprising the amino acid sequence AASTLES (SEQ ID NO: 33) optionally comprising 1 or 2 amino acid substitutions and a VLCDR3 comprising the amino acid sequence QQTNEDPPT (SEQ ID NO: 34) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 19), a VHCDR2 comprising the amino acid sequence SSGGGNTY (SEQ ID NO: 20), and a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

optionally wherein the Met residues are each independently substituted with an amino acid selected from the group consisting of Ala and Leu, and/or the Asp residues are each independently substituted with an amino acid selected from the group consisting of Ala, Gln and Glu.

Antigen binding molecules of or derived from 3E05_var9 (for example antibodies having one or more amino acid substitutions) may have a $K_D$ of less than about 0.01 nM. Such antigen binding molecules may additionally or alternatively exhibit an IC50 for IFN secretion of less than about 0.5 nM and/or an IC90 for IFN secretion of less than about 5 nM.

3E05_var 10

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 26), a VHCDR2 comprising at least 70%, 75%, 80%, 85%, 90%, 91%, 92%, 93%, 94%, 95%, 96%, 97%, 98% or 99% identity to the amino acid sequence YISSGGG-NTYYADSVKG (SEQ ID NO: 27), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 28); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 32), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 33) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 34).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 29), a VHCDR2 comprising at least 70%, 75%, 80%, 85%, 90%, 91%, 92%, 93%, 94%, 95%, 96%, 97%, 98% or 99% identity to the amino acid sequence SSGGGNTY (SEQ ID NO: 30), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 28); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 32), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 33) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 34).

In one embodiment, an antibody, fragment or variant thereof, is provided comprising:

a heavy chain variable region comprising a VHCDR1 comprising at least 90% identity to the amino acid sequence SYTMS (SEQ ID NO: 26), a VHCDR2 comprising at least 90% identity to the amino acid sequence YISSGGGNTYYADSVKG (SEQ ID NO: 27), and a VHCDR3 comprising at least 90% identity to the amino acid sequence HDYYDGGLYYAMDY (SEQ ID NO: 28); and/or a light chain variable region comprising a VLCDR1 comprising the at least 90% identity to amino acid sequence KSSQSVDYDGDSSMN (SEQ ID NO: 32), a VLCDR2 comprising at least 90% identity to the amino acid sequence AASTLES (SEQ ID NO: 33) and a VLCDR3 comprising at least 90% identity to the amino acid sequence QQTNEDPPT (SEQ ID NO: 34).

In one embodiment, an antibody, fragment or variant thereof, is provided comprising:

a heavy chain variable region comprising a VHCDR1 comprising at least 90% identity to the amino acid sequence GFTFSSY (SEQ ID NO: 29), a VHCDR2 comprising at least 90% identity to the amino acid sequence SSGGGNTY (SEQ ID NO: 30), and a VHCDR3 comprising at least 90% identity to the amino acid sequence HDYYDGGLYYAMDY (SEQ ID NO: 28); and/or a light chain variable region comprising a VLCDR1 comprising the at least 90% identity to amino acid sequence KSSQSVDYDGDSSMN (SEQ ID NO: 32), a VLCDR2 comprising at least 90% identity to the amino acid sequence AASTLES (SEQ ID NO: 33) and a VLCDR3 comprising at least 90% identity to the amino acid sequence QQTNEDPPT (SEQ ID NO: 34).

In one embodiment, an antibody, fragment or variant thereof, is provided comprising:

a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), and a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34).

Amino acid substitutions may be made to provide variant antibodies derived from 3E05_var 10, for example an antibody, fragment or variant thereof is provided comprising a heavy chain variable region comprising a VHCDR1 comprising the amino acid sequence SYTMS (SEQ ID NO: 26) optionally comprising 1 or 2 amino acid substitutions, a VHCDR2 comprising the amino acid sequence YISSGGGNTYYADSVKG (SEQ ID NO: 27) optionally comprising 1 or 2 amino acid substitutions, and a VHCDR3 comprising the amino acid sequence HDYYDGGLYYAMDY (SEQ ID NO: 28) optionally comprising 1 or 2 amino acid substitutions; and/or a light chain variable region comprising a VLCDR1 comprising the amino acid sequence KSSQSVDYDGDSSMN (SEQ ID NO: 32) optionally comprising 1 or 2 amino acid substitutions, a VLCDR2 comprising the amino acid sequence AASTLES (SEQ ID NO: 33) optionally comprising 1 or 2 amino acid substitutions and a VLCDR3 comprising the amino acid sequence QQTNEDPPT (SEQ ID NO: 34) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), and a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

optionally wherein the Met residues are each independently substituted with an amino acid selected from the group consisting of Ala and Leu, and/or the Asp residues are each independently substituted with an amino acid selected from the group consisting of Ala, Gln and Glu.

In one embodiment, an antibody, fragment or variant thereof, is provided comprising:

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), and a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34).

Amino acid substitutions may be made to provide variant antibodies derived from 3E05_var 10, for example an antibody, fragment or variant thereof is provided comprising a heavy chain variable region comprising a VHCDR1 comprising the amino acid sequence GFTFSSY (SEQ ID NO: 29) optionally comprising 1 or 2 amino acid substitutions, a VHCDR2 comprising the amino acid sequence SSGGGNTY (SEQ ID NO: 30) optionally comprising 1 or 2 amino acid substitutions, and a VHCDR3 comprising the amino acid sequence HDYYDGGLYYAMDY (SEQ ID NO: 28) optionally comprising 1 or 2 amino acid substitutions; and/or a light chain variable region comprising a VLCDR1 comprising the amino acid sequence KSSQSVDYDGDSSMN (SEQ ID NO: 32) optionally comprising 1 or 2 amino acid substitutions, a VLCDR2 comprising the amino acid sequence AASTLES (SEQ ID NO: 33) optionally comprising 1 or 2 amino acid substitutions and a VLCDR3 comprising the amino acid sequence QQTNEDPPT (SEQ ID NO: 34) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), and a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

optionally wherein the Met residues are each independently substituted with an amino acid selected from the group consisting of Ala and Leu, and/or the Asp residues are each independently substituted with an amino acid selected from the group consisting of Ala, Gln and Glu.

Antigen binding molecules of or derived from 3E05_var10 (for example antibodies having one or more amino acid substitutions) may have a $K_D$ of less than about 1 nM. Such antigen binding molecules may additionally or alternatively exhibit an IC50 for IFN secretion of less than about 0.5 nM and/or an IC90 for IFN secretion of less than about 5 nM.

3E05_var 11

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 36), a VHCDR2 comprising at least 70%, 75%, 80%, 85%, 90%, 91%, 92%, 93%, 94%, 95%, 96%, 97%, 98% or 99% identity to the amino acid sequence YISSGGGQTYYPDSVKG (SEQ ID NO: 37), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 38); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 32), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 33) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 34).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 39), a VHCDR2 comprising at least 70%, 75%, 80%, 85%, 90%, 91%, 92%, 93%, 94%, 95%, 96%, 97%, 98% or 99% identity to the amino acid sequence SSGGGQTY (SEQ ID NO: 40), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 38); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KSSQSVDYDGDSSMN (SEQ ID NO: 32), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 33) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 34).

In one embodiment, an antibody, fragment or variant thereof, is provided comprising:

a heavy chain variable region comprising a VHCDR1 comprising at least 90% identity to the amino acid sequence SYTMS (SEQ ID NO: 36), a VHCDR2 comprising at least 90% identity to the amino acid sequence YISSGGGQTYYPDSVKG (SEQ ID NO: 37), and a VHCDR3 comprising at least 90% identity to the amino acid sequence HDYYDGGLYYAMDY (SEQ ID NO: 38); and/or a light chain variable region comprising a VLCDR1 comprising the at least 90% identity to amino acid sequence KSSQSVDYDGDSSMN (SEQ ID NO: 32), a VLCDR2 comprising at least 90% identity to the amino acid sequence AASTLES (SEQ ID NO: 33) and a VLCDR3 comprising at least 90% identity to the amino acid sequence QQTNEDPPT (SEQ ID NO: 34).

In one embodiment, an antibody, fragment or variant thereof, is provided comprising:

a heavy chain variable region comprising a VHCDR1 comprising at least 90% identity to the amino acid sequence GFTFSSY (SEQ ID NO: 39), a VHCDR2 comprising at least 90% identity to the amino acid sequence SSGGGQTY (SEQ ID NO: 40), and a VHCDR3 comprising at least 90% identity to the amino acid sequence HDYYDGGLYYAMDY (SEQ ID NO: 38); and/or a light chain variable region comprising a VLCDR1 comprising the at least 90% identity to amino acid sequence KSSQSVDYDGDSSMN (SEQ ID NO: 32), a VLCDR2 comprising at least 90% identity to the amino acid sequence AASTLES (SEQ ID NO: 33) and a VLCDR3 comprising at least 90% identity to the amino acid sequence QQTNEDPPT (SEQ ID NO: 34).

In one embodiment, an antibody, fragment or variant thereof, is provided comprising:

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), and a VHCDR3 comprising the amino acid sequence HDYYDGGLYYAMDY (SEQ ID NO: 38); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34).

Amino acid substitutions may be made to provide variant antibodies derived from 3E05_var 11, for example an antibody, fragment or variant thereof is provided comprising a heavy chain variable region comprising a VHCDR1 comprising the amino acid sequence SYTMS (SEQ ID NO: 36) optionally comprising 1 or 2 amino acid substitutions, a VHCDR2 comprising the amino acid sequence YISSGGGQTYYPDSVKG (SEQ ID NO: 37) optionally comprising 1 or 2 amino acid substitutions, and a VHCDR3 comprising the amino acid sequence HDYYDGGLYYAMDY (SEQ ID NO: 38) optionally comprising 1 or 2 amino acid substitutions; and/or a light chain variable region comprising a VLCDR1 comprising the amino acid sequence KSSQSVDYDGDSSMN (SEQ ID NO: 32) optionally comprising 1 or 2 amino acid substitutions, a VLCDR2 comprising the amino acid sequence AASTLES (SEQ ID NO: 33) optionally comprising 1 or 2 amino acid substitutions and a VLCDR3 comprising the amino acid sequence QQTNEDPPT (SEQ ID NO: 34) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), and a VHCDR3 comprising the amino acid sequence HDYYDGGLYYAMDY (SEQ ID NO: 38); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

optionally wherein the Met residues are each independently substituted with an amino acid selected from the group consisting of Ala and Leu, and/or the Asp residues are each independently substituted with an amino acid selected from the group consisting of Ala, Gln and Glu.

In one embodiment, an antibody, fragment or variant thereof, is provided comprising:

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), and a VHCDR3 comprising the amino acid sequence HDYYDGGLYYAMDY (SEQ ID NO: 38); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34).

Amino acid substitutions may be made to provide variant antibodies derived from 3E05_var 11, for example an antibody, fragment or variant thereof is provided comprising a heavy chain variable region comprising a VHCDR1 comprising the amino acid sequence GFTFSSY (SEQ ID NO: 39) optionally comprising 1 or 2 amino acid substitutions, a VHCDR2 comprising the amino acid sequence SSGGGQTY (SEQ ID NO: 40) optionally comprising 1 or 2 amino acid substitutions, and a VHCDR3 comprising the amino acid sequence HDYYDGGLYYAMDY (SEQ ID NO: 38) optionally comprising 1 or 2 amino acid substitutions; and/or a light chain variable region comprising a VLCDR1 comprising the amino acid sequence KSSQSVDYDGDSSMN (SEQ ID NO: 32) optionally comprising 1 or 2 amino acid substitutions, a VLCDR2 comprising the amino acid sequence AASTLES (SEQ ID NO: 33) optionally comprising 1 or 2 amino acid substitutions and a VLCDR3 comprising the amino acid sequence QQTNEDPPT (SEQ ID NO: 34) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), and a VHCDR3 comprising the amino acid sequence HDYYDGGLYYAMDY (SEQ ID NO: 38); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

optionally wherein the Met residues are each independently substituted with an amino acid selected from the group consisting of Ala and Leu, and/or the Asp residues are each independently substituted with an amino acid selected from the group consisting of Ala, Gln and Glu.

Antigen binding molecules of or derived from 3E05_var11 (for example antibodies having one or more amino acid substitutions) may have a $K_D$ of less than about 1 nM. Such antigen binding molecules may additionally or alternatively exhibit an IC50 for IFN secretion of less than about 0.5 nM and/or an IC90 for IFN secretion of less than about 5 nM.

3E05_var 13

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 16), a VHCDR2 comprising at least 70%, 75%, 80%, 85%, 90%, 91%, 92%, 93%, 94%, 95%, 96%, 97%, 98% or 99% identity to the amino acid sequence YISSGGGNTYYPDSVKG (SEQ ID NO: 17), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 18); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYEGDSSMN (SEQ ID NO: 42), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 43) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 44).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 19), a VHCDR2 comprising at least 70%, 75%, 80%, 85%, 90%, 91%, 92%, 93%, 94%, 95%, 96%, 97%, 98% or 99% identity to the amino acid sequence SSGGGNTY (SEQ ID NO: 20), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 18); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYEGDSSMN (SEQ ID NO: 42), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 43) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 44).

In one embodiment, an antibody, fragment or variant thereof, is provided comprising:

a heavy chain variable region comprising a VHCDR1 comprising at least 90% identity to the amino acid sequence SYTMS (SEQ ID NO: 16), a VHCDR2 comprising at least 90% identity to the amino acid sequence YISSGGGNTYYPDSVKG (SEQ ID NO: 17), and a VHCDR3 comprising at least 90% identity to the amino acid sequence HDYYDGGLYYAMDY (SEQ ID NO: 18); and/or a light chain variable region comprising a VLCDR1 comprising the at least 90% identity to amino acid sequence KASQSVDYEGDSSMN (SEQ ID NO: 42), a VLCDR2 comprising at least 90% identity to the amino acid sequence AASTLES (SEQ ID NO: 43) and a VLCDR3 comprising at least 90% identity to the amino acid sequence QQTNEDPPT (SEQ ID NO: 44).

In one embodiment, an antibody, fragment or variant thereof, is provided comprising:

a heavy chain variable region comprising a VHCDR1 comprising at least 90% identity to the amino acid sequence GFTFSSY (SEQ ID NO: 19), a VHCDR2 comprising at least 90% identity to the amino acid sequence SSGGGNTY (SEQ ID NO: 20), and a VHCDR3 comprising at least 90% identity to the amino acid sequence HDYYDGGLYYAMDY (SEQ ID NO: 18); and/or a light chain variable region comprising a VLCDR1 comprising the at least 90% identity to amino acid sequence KASQSVDYEGDSSMN (SEQ ID NO: 42), a VLCDR2 comprising at least 90% identity to the amino acid sequence AASTLES (SEQ ID NO: 43) and a VLCDR3 comprising at least 90% identity to the amino acid sequence QQTNEDPPT (SEQ ID NO: 44).

In one embodiment, an antibody, fragment or variant thereof, is provided comprising:

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), and a VHCDR3 comprising the amino acid sequence HDYYDGGLYYAMDY (SEQ ID NO: 18); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44).

Amino acid substitutions may be made to provide variant antibodies derived from 3E05_var 13, for example an antibody, fragment or variant thereof is provided comprising a heavy chain variable region comprising a VHCDR1 comprising the amino acid sequence SYTMS (SEQ ID NO: 16) optionally comprising 1 or 2 amino acid substitutions, a VHCDR2 comprising the amino acid sequence YISSGGGNTYYPDSVKG (SEQ ID NO: 17) optionally comprising 1 or 2 amino acid substitutions, and a VHCDR3 comprising the amino acid sequence HDYYDGGLYYAMDY (SEQ ID NO: 18) optionally comprising 1 or 2 amino acid substitutions; and/or a light chain variable region comprising a VLCDR1 comprising the amino acid sequence KASQSVDYEGDSSMN (SEQ ID NO: 42) optionally comprising 1 or 2 amino acid substitutions, a VLCDR2 comprising the amino acid sequence AASTLES (SEQ ID NO: 43) optionally comprising 1 or 2 amino acid substitutions and a VLCDR3 comprising the amino acid sequence QQTNEDPPT (SEQ ID NO: 44) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), and a VHCDR3 comprising the amino acid sequence HDYYDGGLYYAMDY (SEQ ID NO: 18); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

optionally wherein the Met residues are each independently substituted with an amino acid selected from the group consisting of Ala and Leu, and/or the Asp residues are each independently substituted with an amino acid selected from the group consisting of Ala, Gin and Glu.

In one embodiment, an antibody, fragment or variant thereof, is provided comprising:

a heavy chain variable region comprising a VHCDR1 comprising the amino acid sequence GFTFSSY (SEQ ID NO: 19), a VHCDR2 comprising the amino acid sequence SSGGGNTY (SEQ ID NO: 20), and a VHCDR3 comprising the amino acid sequence HDYYDGGLYYAMDY (SEQ ID NO: 18); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44).

Amino acid substitutions may be made to provide variant antibodies derived from 3E05_var 13, for example an antibody, fragment or variant thereof is provided comprising a heavy chain variable region comprising a VHCDR1 comprising the amino acid sequence GFTFSSY (SEQ ID NO: 19) optionally comprising 1 or 2 amino acid substitutions, a VHCDR2 comprising the amino acid sequence SSGGGNTY (SEQ ID NO: 20) optionally comprising 1 or 2 amino acid substitutions, and a VHCDR3 comprising the amino acid sequence HDYYDGGLYYAMDY (SEQ ID NO: 18) optionally comprising 1 or 2 amino acid substitutions; and/or a light chain variable region comprising a VLCDR1 comprising the amino acid sequence KASQSVDYEGDSSMN (SEQ ID NO: 42) optionally comprising 1 or 2 amino acid substitutions, a VLCDR2 comprising the amino acid sequence AASTLES (SEQ ID NO: 43) optionally comprising 1 or 2 amino acid substitutions and a VLCDR3 comprising the amino acid sequence QQTNEDPPT (SEQ ID NO: 44) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 19), a VHCDR2 comprising the amino acid sequence SSGGGNTY (SEQ ID NO: 20), and a VHCDR3 comprising the amino acid sequence HDYYDGGLYYAMDY (SEQ ID NO: 18); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

optionally wherein the Met residues are each independently substituted with an amino acid selected from the group consisting of Ala and Leu, and/or the Asp residues are each independently substituted with an amino acid selected from the group consisting of Ala, Gln and Glu.

Antigen binding molecules of or derived from 3E05_var13 (for example antibodies having one or more amino acid substitutions) may have a $K_D$ of less than about 0.01 nM. Such antigen binding molecules may additionally or alternatively exhibit an IC50 for IFN secretion of less than about 0.5 nM and/or an IC90 for IFN secretion of less than about 5 nM.

3E05_var 15

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 36), a VHCDR2 comprising at least 70%, 75%, 80%, 85%, 90%, 91%, 92%, 93%, 94%, 95%, 96%, 97%, 98% or 99% identity to the amino acid sequence YISSGGGQTYYPDSVKG (SEQ ID NO: 37), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 38); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYEGDSSMN (SEQ ID NO: 42), a VLCDR2 comprising at least 70%, 75%, 80%, 85%, 90%, 91%, 92%, 93%, 94% a, 95%, 96%, 97%, 98% or 99% identity to the amino acid sequence AASTLES (SEQ ID NO: 43) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 44).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 39), a VHCDR2 comprising at least 70%, 75%, 80%, 85%, 90%, 91%, 92%, 93%, 94%, 95%, 96%, 97%, 98% or 99% identity to the amino acid sequence SSGGGQTY (SEQ ID NO: 40), and a VHCDR3 comprising at least 70%, 75%, 80%, 85%, 90%, 91%, 92%, 93%, 94%, 95%, 96%, 97%, 98% or 99% identity to the amino acid sequence HDYYDGGLYYAMDY (SEQ ID NO: 38); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYEGDSSMN (SEQ ID NO: 42), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 43) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 44).

In one embodiment, an antibody, fragment or variant thereof, is provided comprising:

a heavy chain variable region comprising a VHCDR1 comprising at least 90% identity to the amino acid sequence SYTMS (SEQ ID NO: 36), a VHCDR2 comprising at least 90% identity to the amino acid sequence YISSGGGQTYYPDSVKG (SEQ ID NO: 37), and a VHCDR3 comprising at least 90% identity to the amino acid sequence HDYYDGGLYYAMDY (SEQ ID NO: 38); and/or a light chain variable region comprising a VLCDR1 comprising the at least 90% identity to amino acid sequence KASQSVDYEGDSSMN (SEQ ID NO: 42), a VLCDR2 comprising at least 90% identity to the amino acid sequence AASTLES (SEQ ID NO: 43) and a VLCDR3 comprising at least 90% identity to the amino acid sequence QQTNEDPPT (SEQ ID NO: 44).

In one embodiment, an antibody, fragment or variant thereof, is provided comprising:

a heavy chain variable region comprising a VHCDR1 comprising at least 90% identity to the amino acid sequence GFTFSSY (SEQ ID NO: 39), a VHCDR2 comprising at least 90% identity to the amino acid sequence SSGGGQTY (SEQ ID NO: 40), and a VHCDR3 comprising at least 90% identity to the amino acid sequence HDYYDGGLYYAMDY (SEQ ID NO: 38); and/or a light chain variable region comprising a VLCDR1 comprising the at least 90% identity to amino acid sequence KASQSVDYEGDSSMN (SEQ ID NO: 42), a VLCDR2 comprising at least 90% identity to the amino acid sequence AASTLES (SEQ ID NO: 43) and a VLCDR3 comprising at least 90% identity to the amino acid sequence QQTNEDPPT (SEQ ID NO: 44).

In one embodiment, an antibody, fragment or variant thereof, is provided comprising:

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), and a VHCDR3 comprising the amino acid sequence HDYYDGGLYYAMDY (SEQ ID NO: 38); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44).

Amino acid substitutions may be made to provide variant antibodies derived from 3E05_var 15, for example an antibody, fragment or variant thereof is provided comprising a heavy chain variable region comprising a VHCDR1 comprising the amino acid sequence SYTMS (SEQ ID NO: 36) optionally comprising 1 or 2 amino acid substitutions, a VHCDR2 comprising the amino acid sequence YISSGGGQTYYPDSVKG (SEQ ID NO: 37) optionally comprising 1 or 2 amino acid substitutions, and a VHCDR3 comprising the amino acid sequence HDYYDGGLYYAMDY (SEQ ID NO: 38) optionally comprising 1 or 2 amino acid substitutions; and/or a light chain variable region comprising a VLCDR1 comprising the amino acid sequence KASQSVDYEGDSSMN (SEQ ID NO: 42) optionally comprising 1 or 2 amino acid substitutions, a VLCDR2 comprising the amino acid sequence AASTLES (SEQ ID NO: 43) optionally comprising 1 or 2 amino acid substitutions and a VLCDR3 comprising the amino acid sequence QQTNEDPPT (SEQ ID NO: 44) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), and a VHCDR3 comprising the amino acid sequence HDYYDGGLYYAMDY (SEQ ID NO: 38); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

optionally wherein the Met residues are each independently substituted with an amino acid selected from the group consisting of Ala and Leu, and/or the Asp residues are each independently substituted with an amino acid selected from the group consisting of Ala, Gln and Glu.

In one embodiment, an antibody, fragment or variant thereof, is provided comprising:

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), and a VHCDR3 comprising the amino acid sequence HDYYDGGLYYAMDY (SEQ ID NO: 38); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44).

Amino acid substitutions may be made to provide variant antibodies derived from 3E05_var 15, for example an antibody, fragment or variant thereof is provided comprising a heavy chain variable region comprising a VHCDR1 comprising the amino acid sequence GFTFSSY (SEQ ID NO: 39) optionally comprising 1 or 2 amino acid substitutions, a VHCDR2 comprising the amino acid sequence SSGGGQTY (SEQ ID NO: 40) optionally comprising 1 or 2 amino acid substitutions, and a VHCDR3 comprising the amino acid sequence HDYYDGGLYYAMDY (SEQ ID NO: 38) optionally comprising 1 or 2 amino acid substitutions; and/or a light chain variable region comprising a VLCDR1 comprising the amino acid sequence KASQSVDYEGDSSMN (SEQ ID NO: 42) optionally comprising 1 or 2 amino acid substitutions, a VLCDR2 comprising the amino acid sequence AASTLES (SEQ ID NO: 43) optionally comprising 1 or 2 amino acid substitutions and a VLCDR3 comprising the amino acid sequence QQTNEDPPT (SEQ ID NO: 44) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), and a VHCDR3 comprising the amino acid sequence HDYYDGGLYYAMDY (SEQ ID NO: 38); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

optionally wherein the Met residues are each independently substituted with an amino acid selected from the group consisting of Ala and Leu, and/or the Asp residues are each independently substituted with an amino acid selected from the group consisting of Ala, Gln and Glu.

Antigen binding molecules of or derived from 3E05_var15 (for example antibodies having one or more amino acid substitutions) may have a $K_D$ of less than about 0.01 nM. Such antigen binding molecules may additionally or alternatively exhibit an IC50 for IFN secretion of less than about 0.5 nM and/or an IC90 for IFN secretion of less than about 5 nM.

3E05_var 16

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 46), a VHCDR2 comprising at least 70%, 75%, 80%, 85%, 90%, 91%, 92%, 93%, 94%, 95%, 96%, 97%, 98% or 99% identity to the amino acid sequence YISSGGGQTYYPDSVKG (SEQ ID NO: 47), and a VHCDR3 comprising at least 70%, 75%, 80%, 85%, 90%, 91%, 92%, 93%, 94%, 95%, 96%, 97%, 98% or 99% identity to the amino acid sequence HDYYEGGLYYAMDY (SEQ ID NO: 48); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYEGDSSMN (SEQ ID NO: 42), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 43) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 44).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 49), a VHCDR2 comprising at least 70%, 75%, 80%, 85%, 90%, 91%, 92%, 93%, 94%, 95%, 96%, 97%, 98% or 99% identity to the amino acid sequence SSGGGQTY (SEQ ID NO: 50), and a VHCDR3 comprising at least 70%, 75%, 80%, 85%, 90%, 91%, 92%, 93%, 94%, 95%, 96%, 97%, 98% or 99% identity to the amino acid sequence HDYYEGGLYYAMDY (SEQ ID NO: 48); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYEGDSSMN (SEQ ID NO: 42), a VLCDR2 comprising at least 70%, 75%, 80%, 85%, 90%, 91%, 92%, 93%, 94%, 95%, 96%, 97%, 98% or 99% identity to the amino acid sequence AASTLES (SEQ ID NO: 43) and a VLCDR3 comprising at least 70%, 75%, 80%, 85%, 90%, 91%, 92%, 93%, 94%, 95%, 96%, 97%, 98% or 99% identity to the amino acid sequence QQTNEDPPT (SEQ ID NO: 44).

In one embodiment, an antibody, fragment or variant thereof, is provided comprising:

a heavy chain variable region comprising a VHCDR1 comprising at least 90% identity to the amino acid sequence SYTMS (SEQ ID NO: 46), a VHCDR2 comprising at least 90% identity to the amino acid sequence YISSGGGQTYYPDSVKG (SEQ ID NO: 47), and a VHCDR3 comprising at least 90% identity to the amino acid sequence HDYYEGGLYYAMDY (SEQ ID NO: 48); and/or a light chain variable region comprising a VLCDR1 comprising the at least 90% identity to amino acid sequence KASQSVDYEGDSSMN (SEQ ID NO: 42), a VLCDR2 comprising at least 90% identity to the amino acid sequence AASTLES (SEQ ID NO: 43) and a VLCDR3 comprising at least 90% identity to the amino acid sequence QQTNEDPPT (SEQ ID NO: 44).

In one embodiment, an antibody, fragment or variant thereof, is provided comprising:

a heavy chain variable region comprising a VHCDR1 comprising at least 90% identity to the amino acid sequence GFTFSSY (SEQ ID NO: 49), a VHCDR2 comprising at least 90% identity to the amino acid sequence SSGGGQTY (SEQ ID NO: 50), and a VHCDR3 comprising at least 90% identity to the amino acid sequence HDYYEGGLYYAMDY (SEQ ID NO: 48); and/or a light chain variable region comprising a VLCDR1 comprising the at least 90% identity to amino acid sequence KASQSVDYEGDSSMN (SEQ ID NO: 42), a VLCDR2 comprising at least 90% identity to the amino acid sequence AASTLES (SEQ ID NO: 43) and a VLCDR3 comprising at least 90% identity to the amino acid sequence QQTNEDPPT (SEQ ID NO: 44).

In one embodiment, an antibody, fragment or variant thereof, is provided comprising:

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), and a VHCDR3 comprising the amino acid sequence HDYYEGGLYYAMDY (SEQ ID NO: 48); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44).

Amino acid substitutions may be made to provide variant antibodies derived from 3E05_var 16, for example an antibody, fragment or variant thereof is provided comprising a heavy chain variable region comprising a VHCDR1 comprising the amino acid sequence SYTMS (SEQ ID NO: 46) optionally comprising 1 or 2 amino acid substitutions, a VHCDR2 comprising the amino acid sequence YISSGGGQTYYPDSVKG (SEQ ID NO: 47) optionally comprising 1 or 2 amino acid substitutions, and a VHCDR3 comprising the amino acid sequence HDYYEGGLYYAMDY (SEQ ID NO: 48) optionally comprising 1 or 2 amino acid substitutions; and/or a light chain variable region comprising a VLCDR1 comprising the amino acid sequence KASQSVDYEGDSSMN (SEQ ID NO: 42) optionally comprising 1 or 2 amino acid substitutions, a VLCDR2 comprising the amino acid sequence AASTLES (SEQ ID NO: 43) optionally comprising 1 or 2 amino acid substitutions and a VLCDR3 comprising the amino acid sequence QQTNEDPPT (SEQ ID NO: 44) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), and a VHCDR3 comprising the amino acid sequence HDYYEGGLYYAMDY (SEQ ID NO: 48); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

optionally wherein the Met residues are each independently substituted with an amino acid selected from the group consisting of Ala and Leu, and/or the Asp residues are each independently substituted with an amino acid selected from the group consisting of Ala, Gin and Glu.

In one embodiment, an antibody, fragment or variant thereof, is provided comprising:

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), and a VHCDR3 comprising the amino acid sequence HDYYEGGLYYAMDY (SEQ ID NO: 48); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44).

Amino acid substitutions may be made to provide variant antibodies derived from 3E05_var 16, for example an antibody, fragment or variant thereof is provided comprising a heavy chain variable region comprising a VHCDR1 comprising the amino acid sequence GFTFSSY (SEQ ID NO: 49) optionally comprising 1 or 2 amino acid substitutions, a VHCDR2 comprising the amino acid sequence SSGGGQTY (SEQ ID NO: 50) optionally comprising 1 or 2 amino acid substitutions, and a VHCDR3 comprising the amino acid sequence HDYYEGGLYYAMDY (SEQ ID NO: 48) optionally comprising 1 or 2 amino acid substitutions; and/or a light chain variable region comprising a VLCDR1 comprising the amino acid sequence KASQSVDYEGDSSMN (SEQ ID NO: 42) optionally comprising 1 or 2 amino acid substitutions, a VLCDR2 comprising the amino acid sequence AASTLES (SEQ ID NO: 43) optionally comprising 1 or 2 amino acid substitutions and a VLCDR3 comprising the amino acid sequence QQTNEDPPT (SEQ ID NO: 44) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), and a VHCDR3 comprising the amino acid sequence HDYYEGGLYYAMDY (SEQ ID NO: 48); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

optionally wherein the Met residues are each independently substituted with an amino acid selected from the group consisting of Ala and Leu, and/or the Asp residues are each independently substituted with an amino acid selected from the group consisting of Ala, Gin and Glu.

Antigen binding molecules of or derived from 3E05_var16 (for example antibodies having one or more amino acid substitutions) may have a $K_D$ of less than about 0.01 nM. Such antigen binding molecules may additionally or alternatively exhibit an IC50 for IFN secretion of less than about 0.5 nM and/or an IC90 for IFN secretion of less than about 5 nM.

21E06

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTIS (SEQ ID NO: 56), a VHCDR2 comprising at least 70%, 75%, 80%, 85%, 90%, 91%, 92%, 93%, 94%, 95%, 96%, 97%, 98% or 99% identity to the amino acid sequence YISSGGDNAYYPDSVKG (SEQ ID NO: 57), and a VHCDR3 comprising at least 70%, 75%, 80%, 85%, 90%, 91%, 92%, 93%, 94%, 95%, 96%, 97%, 98% or 99% identity to the amino acid sequence HLYYGDYFYVMDY (SEQ ID NO: 58); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDNCLH (SEQ ID NO: 52), a VLCDR2 comprising at least 70%, 75%, 80%, 85%, 90%, 91%, 92%, 93%, 94%, 95%, 96%, 97%, 98% or 99% identity to the amino acid sequence AASNLES (SEQ ID NO: 53) and a VLCDR3 comprising at least 70%, 75%, 80%, 85%, 90%, 91%, 92%, 93%, 94%, 95%, 96%, 97%, 98% or 99% identity to the amino acid sequence QQSNEDPPT (SEQ ID NO: 54).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 59), a VHCDR2 comprising at least 70%, 75%, 80%, 85%, 90%, 91%, 92%, 93%, 94%, 95%, 96%, 97%, 98% or 99% identity to the amino acid sequence SSGGDN (SEQ ID NO: 60), and a VHCDR3 comprising at least 70%, 75%, 80%, 85%, 90%, 91%, 92%, 93%, 94%, 95%, 96%, 97%, 98% or 99% identity to the amino acid sequence HLYYGDYFYVMDY (SEQ ID NO: 58); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDNCLH (SEQ ID NO: 52), a VLCDR2 comprising at least 70%, 75%, 80%, 85%, 90%, 91%, 92%, 93%, 94%, 95%, 96%, 97%, 98% or 99% identity to the amino acid sequence AASNLES (SEQ ID NO: 53) and a VLCDR3 comprising at least 70%, 75%, 80%, 85%, 90%, 91%, 92%, 93%, 94%, 95%, 96%, 97%, 98% or 99% identity to the amino acid sequence QQSNEDPPT (SEQ ID NO: 54).

In one embodiment, an antibody, fragment or variant thereof, is provided comprising:

a heavy chain variable region comprising a VHCDR1 comprising at least 90% identity to the amino acid sequence SYTIS (SEQ ID NO: 56), a VHCDR2 comprising at least 90% identity to the amino acid sequence YISSGGDNAYYPDSVKG (SEQ ID NO: 57), and a VHCDR3 comprising at least 90% identity to the amino acid sequence HLYYGDYFYVMDY (SEQ ID NO: 58); and/or a light chain variable region comprising a VLCDR1 comprising the at least 90% identity to amino acid sequence KASQSVDYDGDNCLH (SEQ ID NO: 52), a VLCDR2 comprising at least 90% identity to the amino acid sequence AASNLES (SEQ ID NO: 53) and a VLCDR3 comprising at least 90% identity to the amino acid sequence QQSNEDPPT (SEQ ID NO: 54).

In one embodiment, an antibody, fragment or variant thereof, is provided comprising:

a heavy chain variable region comprising a VHCDR1 comprising at least 90% identity to the amino acid sequence GFTFSSY (SEQ ID NO: 59), a VHCDR2 comprising at least 90% identity to the amino acid sequence SSGGDN (SEQ ID NO: 60), and a VHCDR3 comprising at least 90% identity to the amino acid sequence HLYYGDYFYVMDY (SEQ ID NO: 58); and/or a light chain variable region comprising a VLCDR1 comprising the at least 90% identity to amino acid sequence KASQSVDYDGDNCLH (SEQ ID NO: 52), a VLCDR2 comprising at least 90% identity to the amino acid sequence AASNLES (SEQ ID NO: 53) and a VLCDR3 comprising at least 90% identity to the amino acid sequence QQSNEDPPT (SEQ ID NO: 54).

In one embodiment, an antibody, fragment or variant thereof, is provided comprising:

a heavy chain variable region comprising a VHCDR1 comprising the amino acid sequence SYTIS (SEQ ID NO: 56), a VHCDR2 comprising the amino acid sequence YISSGGDNAYYPDSVKG (SEQ ID NO: 57), and a VHCDR3 comprising the amino acid sequence HLYYGDYFYVMDY (SEQ ID NO: 58); and a light chain variable region comprising a VLCDR1 comprising the amino acid sequence KASQSVDYDGDNCLH (SEQ ID NO: 52), a VLCDR2 comprising the amino acid sequence AASNLES (SEQ ID NO: 53) and a VLCDR3 comprising the amino acid sequence QQSNEDPPT (SEQ ID NO: 54).

Amino acid substitutions may be made to provide variant antibodies derived from 21E06, for example an antibody, fragment or variant thereof is provided comprising a heavy chain variable region comprising a VHCDR1 comprising the amino acid sequence SYTIS (SEQ ID NO: 56) optionally comprising 1 or 2 amino acid substitutions, a VHCDR2 comprising the amino acid sequence YISSGGDNAYYPDSVKG (SEQ ID NO: 57) optionally comprising 1 or 2 amino acid substitutions, and a VHCDR3 comprising the amino acid sequence HLYYGDYFYVMDY (SEQ ID NO: 58) optionally comprising 1 or 2 amino acid substitutions; and/or a light chain variable region comprising a VLCDR1 comprising the amino acid sequence KASQSVDYDGDNCLH (SEQ ID NO: 52) optionally comprising 1 or 2 amino acid substitutions, a VLCDR2 comprising the amino acid sequence AASNLES (SEQ ID NO: 53) optionally comprising 1 or 2 amino acid substitutions and a VLCDR3 comprising the amino acid sequence QQSNEDPPT (SEQ ID NO: 54) optionally comprising 1 or 2 amino acid substitutions. The amino acid substitutions may be conservative amino acid substitutions.

In one embodiment, an antibody, fragment or variant thereof, is provided comprising:

- a heavy chain variable region comprising a VHCDR1 comprising the amino acid sequence SYTIS (SEQ ID NO: 56), a VHCDR2 comprising the amino acid sequence YISSGGDNAYYPDSVKG (SEQ ID NO: 57), and a VHCDR3 comprising the amino acid sequence HLYYGDYFYVMDY (SEQ ID NO: 58); and
- a light chain variable region comprising a VLCDR1 comprising the amino acid sequence KASQSVDYDGDNCLH (SEQ ID NO: 52), a VLCDR2 comprising the amino acid sequence AASNLES (SEQ ID NO: 53) and a VLCDR3 comprising the amino acid sequence QQSNEDPPT (SEQ ID NO: 54).
- optionally wherein the Met residues are each independently substituted with an amino acid selected from the group consisting of Ala and Leu, and/or the Asp residues are each independently substituted with an amino acid selected from the group consisting of Ala, Gln and Glu.

In one embodiment, an antibody, fragment or variant thereof, is provided comprising:

- a heavy chain variable region comprising a VHCDR1 comprising the amino acid sequence GFTFSSY (SEQ ID NO: 59), a VHCDR2 comprising the amino acid sequence SSGGDN (SEQ ID NO: 60), and a VHCDR3 comprising the amino acid sequence HLYYGDYFYVMDY (SEQ ID NO: 58); and
- a light chain variable region comprising a VLCDR1 comprising the amino acid sequence KASQSVDYDGDNCLH (SEQ ID NO: 52), a VLCDR2 comprising the amino acid sequence AASNLES (SEQ ID NO: 53) and a VLCDR3 comprising the amino acid sequence QQSNEDPPT (SEQ ID NO: 54).

Amino acid substitutions may be made to provide variant antibodies derived from 21E06, for example an antibody, fragment or variant thereof is provided comprising:

- a heavy chain variable region comprising a VHCDR1 comprising the amino acid sequence GFTFSSY (SEQ ID NO: 59) optionally comprising 1 or 2 amino acid substitutions, a VHCDR2 comprising the amino acid sequence SSGGDN (SEQ ID NO: 60) optionally comprising 1 or 2 amino acid substitutions, and a VHCDR3 comprising the amino acid sequence HLYYGDYFYVMDY (SEQ ID NO: 58) optionally comprising 1 or 2 amino acid substitutions; and/or
- a light chain variable region comprising a VLCDR1 comprising the amino acid sequence KASQSVDYDGDNCLH (SEQ ID NO: 52) optionally comprising 1 or 2 amino acid substitutions, a VLCDR2 comprising the amino acid sequence AASNLES (SEQ ID NO: 53) optionally comprising 1 or 2 amino acid substitutions and a VLCDR3 comprising the amino acid sequence QQSNEDPPT (SEQ ID NO: 54) optionally comprising 1 or 2 amino acid substitutions. The amino acid substitutions may be conservative amino acid substitutions.

In one embodiment, an antibody, fragment or variant thereof, is provided comprising:

- a heavy chain variable region comprising a VHCDR1 comprising the amino acid sequence GFTFSSY (SEQ ID NO: 59), a VHCDR2 comprising the amino acid sequence SSGGDN (SEQ ID NO: 60), and a VHCDR3 comprising the amino acid sequence HLYYGDYFYVMDY (SEQ ID NO: 58); and

- a light chain variable region comprising a VLCDR1 comprising the amino acid sequence KASQSVDYDGDNCLH (SEQ ID NO: 52), a VLCDR2 comprising the amino acid sequence AASNLES (SEQ ID NO: 53) and a VLCDR3 comprising the amino acid sequence QQSNEDPPT (SEQ ID NO: 54).
- optionally wherein the Met residues are each independently substituted with an amino acid selected from the group consisting of Ala and Leu, and/or the Asp residues are each independently substituted with an amino acid selected from the group consisting of Ala, Gln and Glu.

25E06

In one embodiment, an antibody, fragment or variant thereof, is provided comprising:

- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence SYTMS (SEQ ID NO: 66), a VHCDR2 comprising at least 70%, 75%, 80%, 85%, 90%, 91%, 92%, 93%, 94%, 95%, 96%, 97%, 98%/or 99% identity to the amino acid sequence YISGVGGDTYYPDSVKG (SEQ ID NO: 67), and a VHCDR3 comprising at least 70%, 75%, 80%, 85%, 90%, 91%, 92%, 93%, 94%, 95%, 96%, 97%, 98% or 99% identity to the amino acid sequence HHYSHYFWYFDV (SEQ ID NO: 68); and/or
- a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDGFMN (SEQ ID NO: 62), a VLCDR2 comprising at least 70%, 75%, 80%, 85%, 90%, 91%, 92%, 93%, 94%, 95%, 96%, 97%, 98% or 99% identity to the amino acid sequence AASNLES (SEQ ID NO: 63) and a VLCDR3 comprising at least 70%, 75%, 80%, 85%, 90%, 91%, 92%, 93%, 94%, 95%, 96%, 97%, 98% or 99% identity to the amino acid sequence QQSNEDPPT (SEQ ID NO: 64).

In one embodiment, an antibody, fragment or variant thereof, is provided comprising:

- a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSSY (SEQ ID NO: 69), a VHCDR2 comprising at least 70%, 75%, 80%, 85%, 90%, 91%, 92%, 93%, 94%, 95%, 96%, 97%, 98% or 99% identity to the amino acid sequence SGVGGD (SEQ ID NO: 70), and a VHCDR3 comprising at least 70%, 75%, 80%, 85%, 90%, 91%, 92%, 93%, 94%, 95%, 96%, 97%, 98% or 99% identity to the amino acid sequence HHYSHYFWYFDV (SEQ ID NO: 68); and/or
- a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYDGDGFMN (SEQ ID NO: 62), a VLCDR2 comprising at least 70%, 75%, 80%, 85%, 90%, 91%, 92%, 93%, 94%, 95%, 96%, 97%, 98% or 99% identity to the amino acid sequence AASNLES (SEQ ID NO: 63) and a VLCDR3 comprising at least 70%, 75%, 80%, 85%, 90%, 91%, 92%, 93%, 94%, 95%, 96%, 97%, 98% or 99% identity to the amino acid sequence QQSNEDPPT (SEQ ID NO: 64).

In one embodiment, an antibody, fragment or variant thereof, is provided comprising:

a heavy chain variable region comprising a VHCDR1 comprising at least 90% identity to the amino acid sequence SYTMS (SEQ ID NO: 66), a VHCDR2 comprising at least 90% identity to the amino acid sequence YISGVGGDTYYPDSVKG (SEQ ID NO: 67), and a VHCDR3 comprising at least 90% identity to the amino acid sequence HHYSHYFWYFDV (SEQ ID NO: 68); and/or a light chain variable region comprising a VLCDR1 comprising the at least 90% identity to amino acid sequence KASQSVDYDGDGFMN (SEQ ID NO: 62), a VLCDR2 comprising at least 90% identity to the amino acid sequence AASNLES (SEQ ID NO: 63) and a VLCDR3 comprising at least 90% identity to the amino acid sequence QQSNEDPPT (SEQ ID NO: 64).

In one embodiment, an antibody, fragment or variant thereof, is provided comprising:

a heavy chain variable region comprising a VHCDR1 comprising at least 90% identity to the amino acid sequence GFTFSSY (SEQ ID NO: 69), a VHCDR2 comprising at least 90% identity to the amino acid sequence SGVGGD (SEQ ID NO: 70), and a VHCDR3 comprising at least 90% identity to the amino acid sequence HHYSHYFWYFDV (SEQ ID NO: 68); and/or a light chain variable region comprising a VLCDR1 comprising the at least 90% identity to amino acid sequence KASQSVDYDGDGFMN (SEQ ID NO: 62), a VLCDR2 comprising at least 90% identity to the amino acid sequence AASNLES (SEQ ID NO: 63) and a VLCDR3 comprising at least 90% identity to the amino acid sequence QQSNEDPPT (SEQ ID NO: 64).

In one embodiment, an antibody, fragment or variant thereof, is provided comprising:

a heavy chain variable region comprising a VHCDR1 comprising the amino acid sequence SYTMS (SEQ ID NO: 66), a VHCDR2 comprising the amino acid sequence YISGVGGDTYYPDSVKG (SEQ ID NO: 67), and a VHCDR3 comprising the amino acid sequence HHYSHYFWYFDV (SEQ ID NO: 68); and a light chain variable region comprising a VLCDR1 comprising the amino acid sequence KASQSVDYDGDGFMN (SEQ ID NO: 62), a VLCDR2 comprising the amino acid sequence AASNLES (SEQ ID NO: 63) and a VLCDR3 comprising the amino acid sequence QQSNEDPPT (SEQ ID NO: 64).

Amino acid substitutions may be made to provide variant antibodies derived from 25E06, for example an antibody, fragment or variant thereof is provided comprising:

a heavy chain variable region comprising a VHCDR1 comprising the amino acid sequence SYTMS (SEQ ID NO: 66) optionally comprising 1 or 2 amino acid substitutions, a VHCDR2 comprising the amino acid sequence YISGVGGDTYYPDSVKG (SEQ ID NO: 67) optionally comprising 1 or 2 amino acid substitutions, and a VHCDR3 comprising the amino acid sequence HHYSHYFWYFDV (SEQ ID NO: 68) optionally comprising 1 or 2 amino acid substitutions; and/or a light chain variable region comprising a VLCDR1 comprising the amino acid sequence KASQSVDYDGDGFMN (SEQ ID NO: 62) optionally comprising 1 or 2 amino acid substitutions, a VLCDR2 comprising the amino acid sequence AASNLES (SEQ ID NO: 63) optionally comprising 1 or 2 amino acid substitutions and a VLCDR3 comprising the amino acid sequence QQSNEDPPT (SEQ ID NO: 64) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence SYTMS (SEQ ID NO: 66), a VHCDR2 comprising the amino acid sequence YISGVGGDTYYPDSVKG (SEQ ID NO: 67), and a VHCDR3 comprising the amino acid sequence HHYSHYFWYFDV (SEQ ID NO: 68); and a light chain variable region comprising a VLCDR1 comprising the amino acid sequence KASQSVDYDGDGFMN (SEQ ID NO: 62), a VLCDR2 comprising the amino acid sequence AASNLES (SEQ ID NO: 63) and a VLCDR3 comprising the amino acid sequence QQSNEDPPT (SEQ ID NO: 64);

optionally wherein the Met residues are each independently substituted with an amino acid selected from the group consisting of Ala and Leu, and/or the Asp residues are each independently substituted with an amino acid selected from the group consisting of Ala, Gin and Glu.

In one embodiment, an antibody, fragment or variant thereof, is provided comprising:

a heavy chain variable region comprising a VHCDR1 comprising the amino acid sequence GFTFSSY (SEQ ID NO: 69), a VHCDR2 comprising the amino acid sequence SGVGGD (SEQ ID NO: 70), and a VHCDR3 comprising the amino acid sequence HHYSHYFWYFDV (SEQ ID NO: 68); and a light chain variable region comprising a VLCDR1 comprising the amino acid sequence KASQSVDYDGDGFMN (SEQ ID NO: 62), a VLCDR2 comprising the amino acid sequence AASNLES (SEQ ID NO: 63) and a VLCDR3 comprising the amino acid sequence QQSNEDPPT (SEQ ID NO: 64).

Amino acid substitutions may be made to provide variant antibodies derived from 25E06, for example an antibody, fragment or variant thereof is provided comprising:

a heavy chain variable region comprising a VHCDR1 comprising the amino acid sequence GFTFSSY (SEQ ID NO: 69) optionally comprising 1 or 2 amino acid substitutions, a VHCDR2 comprising the amino acid sequence SGVGGD (SEQ ID NO: 70) optionally comprising 1 or 2 amino acid substitutions, and a VHCDR3 comprising the amino acid sequence HHYSHYFWYFDV (SEQ ID NO: 68) optionally comprising 1 or 2 amino acid substitutions; and/or a light chain variable region comprising a VLCDR1 comprising the amino acid sequence KASQSVDYDGDGFMN (SEQ ID NO: 62) optionally comprising 1 or 2 amino acid substitutions, a VLCDR2 comprising the amino acid sequence AASNLES (SEQ ID NO: 63) optionally comprising 1 or 2 amino acid substitutions and a VLCDR3 comprising the amino acid sequence QQSNEDPPT (SEQ ID NO: 64) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSSY (SEQ ID NO: 69), a VHCDR2 comprising the amino acid sequence SGVGGD (SEQ ID NO: 70), and a VHCDR3 comprising the amino acid sequence HHYSHYFWYFDV (SEQ ID NO: 68); and a light chain variable region comprising a VLCDR1 comprising the amino acid sequence KASQSVDYDGDGFMN (SEQ ID NO: 62), a VLCDR2 comprising the amino acid sequence AASNLES (SEQ ID NO: 63) and a VLCDR3 comprising the amino acid sequence QQSNEDPPT (SEQ ID NO: 64);

optionally wherein the Met residues are each independently substituted with an amino acid selected from the group consisting of Ala and Leu, and/or the Asp residues are each independently substituted with an amino acid selected from the group consisting of Ala, Gln and Glu.

28B01

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence YYTMS (SEQ ID NO: 76), a VHCDR2 comprising at least 70%, 75%, 80%, 85%, 90%, 91%, 92%, 93%, 94%, 95%, 96%, 97%, 98% or 99% identity to the amino acid sequence YISSGGDNAYYPDSVRG (SEQ ID NO: 77), and a VHCDR3 comprising at least 70%, 75%, 80%, 85%, 90%, 91%, 92%, 93%, 94%, 95%, 96%, 97%, 98% or 99% identity to the amino acid sequence HHYSNYFWYFDV (SEQ ID NO: 78); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYAGDSYVN (SEQ ID NO: 72), a VLCDR2 comprising at least 70%, 75%, 80%, 85%, 90%, 91%, 92%, 93%, 94%, 95%, 96%, 97%, 98% or 99% identity to the amino acid sequence AASNLES (SEQ ID NO: 73) and a VLCDR3 comprising at least 70%, 75%, 80%, 85%, 90%, 91%, 92%, 93%, 94%, 95%, 96%, 97%, 98% or 99% identity to the amino acid sequence QQSNEDPPT (SEQ ID NO: 74).

In one embodiment, an antibody, fragment or variant thereof, is provided comprising:

a heavy chain variable region comprising a VHCDR1 comprising at least 70%, 75%, 80%, 85%, 90%, 91%, 92%, 93%, 94%, 95%, 96%, 97%, 98% or 99% identity to the amino acid sequence GFTFSYY (SEQ ID NO: 79), a VHCDR2 comprising at least 70%, 75%, 80%, 85%, 90%, 91%, 92%, 93%, 94%, 95%, 96%, 97%, 98% or 99% identity to the amino acid sequence SSGGDN (SEQ ID NO: 80), and a VHCDR3 comprising at least 70%, 75%, 80%, 85%, 90%, 91%, 92%, 93%, 94%, 95%, 96%, 97%, 98% or 99% identity to the amino acid sequence HHYSNYFWYFDV (SEQ ID NO: 78); and/or a light chain variable region comprising a VLCDR1 comprising the at least 70%, 75%, 80%, 85%, 90%, 91%, 92%, 93%, 94%, 95%, 96%, 97%, 98% or 99% identity to amino acid sequence KASQSVDYAGDSYVN (SEQ ID NO: 72), a VLCDR2 comprising at least 70%, 75%, 80%, 85%, 90%, 91%, 92%, 93%, 94%, 95%, 96%, 97%, 98% or 99% identity to the amino acid sequence AASNLES (SEQ ID NO: 73) and a VLCDR3 comprising at least 70%, 75%, 80%, 85%, 90%, 91%, 92%, 93%, 94%, 95%, 96%, 97%, 98% or 99% identity to the amino acid sequence QQSNEDPPT (SEQ ID NO: 74).

In one embodiment, an antibody, fragment or variant thereof, is provided comprising:

a heavy chain variable region comprising a VHCDR1 comprising at least 90% identity to the amino acid sequence YYTMS (SEQ ID NO: 76), a VHCDR2 comprising at least 90% identity to the amino acid sequence YISSGGDNAYYPDSVRG (SEQ ID NO: 77), and a VHCDR3 comprising at least 90% identity to the amino acid sequence HHYSNYFWYFDV (SEQ ID NO: 78); and/or a light chain variable region comprising a VLCDR1 comprising the at least 90% identity to amino acid sequence KASQSVDYAGDSYVN (SEQ ID NO: 72), a VLCDR2 comprising at least 90% identity to the amino acid sequence AASNLES (SEQ ID NO: 73) and a VLCDR3 comprising at least 90% identity to the amino acid sequence QQSNEDPPT (SEQ ID NO: 74).

In one embodiment, an antibody, fragment or variant thereof, is provided comprising:

a heavy chain variable region comprising a VHCDR1 comprising at least 90% identity to the amino acid sequence GFTFSYY (SEQ ID NO: 79), a VHCDR2 comprising at least 90% identity to the amino acid sequence SSGGDN (SEQ ID NO: 80), and a VHCDR3 comprising at least 90% identity to the amino acid sequence HHYSNYFWYFDV (SEQ ID NO: 78); and/or a light chain variable region comprising a VLCDR1 comprising the at least 90% identity to amino acid sequence KASQSVDYAGDSYVN (SEQ ID NO: 72), a VLCDR2 comprising at least 90% identity to the amino acid sequence AASNLES (SEQ ID NO: 73) and a VLCDR3 comprising at least 90% identity to the amino acid sequence QQSNEDPPT (SEQ ID NO: 74).

In one embodiment, an antibody, fragment or variant thereof, is provided comprising:

a heavy chain variable region comprising a VHCDR1 comprising the amino acid sequence YYTMS (SEQ ID NO: 76), a VHCDR2 comprising the amino acid sequence YISSGGDNAYYPDSVRG (SEQ ID NO: 77), and a VHCDR3 comprising the amino acid sequence HHYSNYFWYFDV (SEQ ID NO: 78); and a light chain variable region comprising a VLCDR1 comprising the amino acid sequence KASQSVDYAGDSYVN (SEQ ID NO: 72), a VLCDR2 comprising the amino acid sequence AASNLES (SEQ ID NO: 73) and a VLCDR3 comprising the amino acid sequence QQSNEDPPT (SEQ ID NO: 74).

Amino acid substitutions may be made to provide variant antibodies derived from 28B01, for example an antibody, fragment or variant thereof is provided comprising:

a heavy chain variable region comprising a VHCDR1 comprising the amino acid sequence YYTMS (SEQ ID NO: 76) optionally comprising 1 or 2 amino acid substitutions, a VHCDR2 comprising the amino acid sequence YISSGGDNAYYPDSVRG (SEQ ID NO: 77) optionally comprising 1 or 2 amino acid substitutions, and a VHCDR3 comprising the amino acid sequence HHYSNYFWYFDV (SEQ ID NO: 78) optionally comprising 1 or 2 amino acid substitutions; and/or a light chain variable region comprising a VLCDR1 comprising the amino acid sequence KASQSVDYAGDSYVN (SEQ ID NO: 72) optionally comprising 1 or 2 amino acid substitutions, a VLCDR2 comprising the amino acid sequence AASNLES (SEQ ID NO: 73) optionally comprising 1 or 2 amino acid substitutions and a VLCDR3 comprising the amino acid sequence QQSNEDPPT (SEQ ID NO: 74) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence YYTMS (SEQ ID NO: 76), a VHCDR2 comprising the amino acid sequence YISSGGDNAYYPDSVRG (SEQ ID NO: 77), and a VHCDR3 comprising the amino acid sequence HHYSNYFWYFDV (SEQ ID NO: 78); and a light chain variable region comprising a VLCDR1 comprising the amino acid sequence KASQSVDYAGDSYVN (SEQ ID NO: 72), a VLCDR2 comprising the amino acid sequence AASNLES (SEQ ID NO: 73) and a VLCDR3 comprising the amino acid sequence QQSNEDPPT (SEQ ID NO: 74);

optionally wherein the Met residues are each independently substituted with an amino acid selected from the group consisting of Ala and Leu, and/or the Asp residues are each independently substituted with an amino acid selected from the group consisting of Ala, Gln and Glu.

In one embodiment, an antibody, fragment or variant thereof, is provided comprising:

a heavy chain variable region comprising a VHCDR1 comprising the amino acid sequence GFTFSYY (SEQ ID NO: 79), a VHCDR2 comprising the amino acid sequence SSGGDN (SEQ ID NO: 80), and a VHCDR3 comprising the amino acid sequence HHYSNYFWYFDV (SEQ ID NO: 78); and a light chain variable region comprising a VLCDR1 comprising the amino acid sequence KASQSVDYAGDSYVN (SEQ ID NO: 72), a VLCDR2 comprising the amino acid sequence AASNLES (SEQ ID NO: 73) and a VLCDR3 comprising the amino acid sequence QQSNEDPPT (SEQ ID NO: 74).

Amino acid substitutions may be made to provide variant antibodies derived from 28B01, for example an antibody, fragment or variant thereof is provided comprising:

a heavy chain variable region comprising a VHCDR1 comprising the amino acid sequence GFTFSYY (SEQ ID NO: 79) optionally comprising 1 or 2 amino acid substitutions, a VHCDR2 comprising the amino acid sequence SSGGDN (SEQ ID NO: 80) optionally comprising 1 or 2 amino acid substitutions, and a VHCDR3 comprising the amino acid sequence HHYSNYFWYFDV (SEQ ID NO: 78) optionally comprising 1 or 2 amino acid substitutions; and/or a light chain variable region comprising a VLCDR1 comprising the amino acid sequence KASQSVDYAGDSYVN (SEQ ID NO: 72) optionally comprising 1 or 2 amino acid substitutions, a VLCDR2 comprising the amino acid sequence AASNLES (SEQ ID NO: 73) optionally comprising 1 or 2 amino acid substitutions and a VLCDR3 comprising the amino acid sequence QQSNEDPPT (SEQ ID NO: 74) optionally comprising 1 or 2 amino acid substitutions. The amino acid substitutions may be conservative amino acid substitutions.

In one embodiment, an antibody, fragment or variant thereof, is provided comprising:

a heavy chain variable region comprising a VHCDR1 comprising the amino acid sequence GFTFSYY (SEQ ID NO: 79), a VHCDR2 comprising the amino acid sequence SSGGDN (SEQ ID NO: 80), and a VHCDR3 comprising the amino acid sequence HHYSNYFWYFDV (SEQ ID NO: 78); and a light chain variable region comprising a VLCDR1 comprising the amino acid sequence KASQSVDYAGDSYVN (SEQ ID NO: 72), a VLCDR2 comprising the amino acid sequence AASNLES (SEQ ID NO: 73) and a VLCDR3 comprising the amino acid sequence QQSNEDPPT (SEQ ID NO: 74);

optionally wherein the Met residues are each independently substituted with an amino acid selected from the group consisting of Ala and Leu, and/or the Asp residues are each independently substituted with an amino acid selected from the group consisting of Ala, Gin and Glu.

Heavy and/or Light Chain Variable Regions

In one embodiment, the invention provides an antigen binding molecules, in particular an antibody that binds to BDCA-2 (CLEC4C), comprising a heavy chain variable region having at least 70%, 75%, 80%, 85%, 90%, 91%, 92%, 93%, 94%, 95%, 96%, 97%, 98% or 99% identity to an amino acid sequence selected from the group consisting of SEQ ID NO: 45, SEQ ID NO: 25, SEQ ID NO: 5, SEQ ID NO: 15, SEQ ID NO: 35, SEQ ID NO: 55, SEQ ID NO: 65 and SEQ ID NO: 75, and/or a light chain variable region having at least 70%, 75%, 80%, 85%, 90%, 91%, 92%, 93%, 94%, 95%, 96%, 97%, 98% or 99% identity to an amino acid sequence selected from the group consisting of consisting SEQ ID NO: 31, SEQ ID NO: 21, SEQ ID NO: 41, SEQ ID NO: 1, SEQ ID NO: 11, SEQ ID NO: 51, SEQ ID NO: 61 and SEQ ID NO: 71.

In one embodiment, the antibody binds to BDCA-2 (CLEC4C) and comprises a heavy chain variable region having the amino acid sequence selected from the group consisting of SEQ ID NO: 45, SEQ ID NO: 25, SEQ ID NO: 5, SEQ ID NO: 15, SEQ ID NO: 35, SEQ ID NO: 55, SEQ ID NO: 65 and SEQ ID NO: 75, and/or a light chain variable region having the amino acid sequence selected from the group consisting of SEQ ID NO: 31, SEQ ID NO: 21, SEQ ID NO: 41, SEQ ID NO: 1, SEQ ID NO: 11, SEQ ID NO: 51, SEQ ID NO: 61 and SEQ ID NO: 71.

In one embodiment, the antibody binds to BDCA-2 (CLEC4C) and comprises a heavy chain variable region having the amino acid sequence selected from the group consisting of SEQ ID NO: 45, SEQ ID NO: 25, SEQ ID NO: 5, SEQ ID NO: 15, SEQ ID NO: 35, SEQ ID NO: 55, SEQ ID NO: 65 and SEQ ID NO: 75, and/or a light chain variable region having the amino acid sequence selected from the group consisting of SEQ ID NO: 31, SEQ ID NO: 21, SEQ ID NO: 41, SEQ ID NO: 1, SEQ ID NO: 11, SEQ ID NO: 51, SEQ ID NO: 61 and SEQ ID NO: 71, optionally wherein the Met residues are each independently substituted with an amino acid selected from the group consisting of Ala and Leu, and/or the Asp residues are each independently substituted with an amino acid selected from the group consisting of Ala, Gin and Glu.

In one embodiment, an antigen binding molecule, for example an antibody, variant or fragment thereof is provided, wherein the antigen binding molecule comprises a heavy chain variable region and a light chain variable region selected from the group consisting of:

(a) a VH comprising the amino acid sequence of SEQ ID NO: 45 and a VL comprising the amino acid sequence of SEQ ID NO: 31 (or comprising VH and VL sequences that are at least 90% identical to SEQ ID NO: 45 and SEQ ID NO: 31, respectively);

(b) a VH comprising the amino acid sequence of SEQ ID NO: 25 and a VL comprising the amino acid sequence of SEQ ID NO: 21 (or comprising VH and VL sequences that are at least 90% identical to SEQ ID NO: 25 and SEQ ID NO: 21, respectively);

(c) a VH comprising the amino acid sequence of SEQ ID NO: 25 and a VL comprising the amino acid sequence of SEQ ID NO: 41 (or comprising VH and VL sequences that are at least 90% identical to SEQ ID NO: 25 and SEQ ID NO: 41, respectively);

(d) a VH comprising the amino acid sequence of SEQ ID NO: 5 and a VL comprising the amino acid sequence of SEQ ID NO: 1 (or comprising VH and VL sequences that are at least 90% identical to SEQ ID NO: 5 and SEQ ID NO: 1, respectively);

(e) a VH comprising the amino acid sequence of SEQ ID NO: 15 and a VL comprising the amino acid sequence of SEQ ID NO: 11 (or comprising VH and VL sequences that are at least 90% identical to SEQ ID NO: 15 and SEQ ID NO: 11, respectively);

(f) a VH comprising the amino acid sequence of SEQ ID NO: 25 and a VL comprising the amino acid sequence of SEQ ID NO: 11 (or comprising VH and VL sequences that are at least 90% identical to SEQ ID NO: 25 and SEQ ID NO: 11, respectively);

(g) a VH comprising the amino acid sequence of SEQ ID NO: 35 and a VL comprising the amino acid sequence of SEQ ID NO: 11 (or comprising VH and VL sequences that are at least 90% identical to SEQ ID NO: 35 and SEQ ID NO: 11, respectively);

(h) a VH comprising the amino acid sequence of SEQ ID NO: 45 and a VL comprising the amino acid sequence of SEQ ID NO: 11 (or comprising VH and VL sequences that are at least 90% identical to SEQ ID NO: 45 and SEQ ID NO: 11, respectively);

(i) a VH comprising the amino acid sequence of SEQ ID NO: 15 and a VL comprising the amino acid sequence of SEQ ID NO: 21 (or comprising VH and VL sequences that are at least 90% identical to SEQ ID NO: 15 and SEQ ID NO: 21, respectively);

(j) a VH comprising the amino acid sequence of SEQ ID NO: 35 and a VL comprising the amino acid sequence of SEQ ID NO: 21 (or comprising VH and VL sequences that are at least 90% identical to SEQ ID NO: 35 and SEQ ID NO: 21, respectively);

(k) a VH comprising the amino acid sequence of SEQ ID NO: 45 and a VL comprising the amino acid sequence of SEQ ID NO: 21 (or comprising VH and VL sequences that are at least 90% identical to SEQ ID NO: 45 and SEQ ID NO: 21, respectively);

(1) a VH comprising the amino acid sequence of SEQ ID NO: 15 and a VL comprising the amino acid sequence of SEQ ID NO: 31 (or comprising VH and VL sequences that are at least 90% identical to SEQ ID NO: 15 and SEQ ID NO: 31, respectively);

(m) a VH comprising the amino acid sequence of SEQ ID NO: 25 and a VL comprising the amino acid sequence of SEQ ID NO: 31 (or comprising VH and VL sequences that are at least 90% identical to SEQ ID NO: 25 and SEQ ID NO: 31, respectively);

(n) a VH comprising the amino acid sequence of SEQ ID NO: 35 and a VL comprising the amino acid sequence of SEQ ID NO: 31 (or comprising VH and VL sequences that are at least 90% identical to SEQ ID NO: 35 and SEQ ID NO: 31, respectively);

(o) a VH comprising the amino acid sequence of SEQ ID NO: 15 and a VL comprising the amino acid sequence of SEQ ID NO: 41 (or comprising VH and VL sequences that are at least 90% identical to SEQ ID NO: 15 and SEQ ID NO: 41, respectively);

(p) a VH comprising the amino acid sequence of SEQ ID NO: 35 and a VL comprising the amino acid sequence of SEQ ID NO: 41 (or comprising VH and VL sequences that are at least 90% identical to SEQ ID NO: 35 and SEQ ID NO: 41, respectively);

(q) a VH comprising the amino acid sequence of SEQ ID NO: 45 and a VL comprising the amino acid sequence of SEQ ID NO: 41 (or comprising VH and VL sequences that are at least 90% identical to SEQ ID NO: 45 and SEQ ID NO: 41, respectively);

(r) a VH comprising the amino acid sequence of SEQ ID NO: 55 and a VL comprising the amino acid sequence of SEQ ID NO: 51 (or comprising VH and VL sequences that are at least 90% identical to SEQ ID NO: 55 and SEQ ID NO: 51, respectively);

(s) a VH comprising the amino acid sequence of SEQ ID NO: 65 and a VL comprising the amino acid sequence of SEQ ID NO: 61 (or comprising VH and VL sequences that are at least 90% identical to SEQ ID NO: 65 and SEQ ID NO: 61, respectively); and (t) a VH comprising the amino acid sequence of SEQ ID NO: 75 and a VL comprising the amino acid sequence of SEQ ID NO: 71 (or comprising VH and VL sequences that are at least 90% identical to SEQ ID NO: 75 and SEQ ID NO: 71, respectively).

In one embodiment, an antigen binding molecule, for example an antibody, variant or fragment thereof is provided, wherein the antigen binding molecule comprises a heavy chain variable region and a light chain variable region selected from the group consisting of:

(a) a VH comprising the amino acid sequence of SEQ ID NO: 45 and a VL comprising the amino acid sequence of SEQ ID NO: 31;

(b) a VH comprising the amino acid sequence of SEQ ID NO: 25 and a VL comprising the amino acid sequence of SEQ ID NO: 21;

(c) a VH comprising the amino acid sequence of SEQ ID NO: 25 and a VL comprising the amino acid sequence of SEQ ID NO: 41;

(d) a VH comprising the amino acid sequence of SEQ ID NO: 5 and a VL comprising the amino acid sequence of SEQ ID NO: 1;

(e) a VH comprising the amino acid sequence of SEQ ID NO: 15 and a VL comprising the amino acid sequence of SEQ ID NO: 11;

(f) a VH comprising the amino acid sequence of SEQ ID NO: 25 and a VL comprising the amino acid sequence of SEQ ID NO: 11;

(g) a VH comprising the amino acid sequence of SEQ ID NO: 35 and a VL comprising the amino acid sequence of SEQ ID NO: 11;

(h) a VH comprising the amino acid sequence of SEQ ID NO: 45 and a VL comprising the amino acid sequence of SEQ ID NO: 11;

(i) a VH comprising the amino acid sequence of SEQ ID NO: 15 and a VL comprising the amino acid sequence of SEQ ID NO: 21;

(j) a VH comprising the amino acid sequence of SEQ ID NO: 35 and a VL comprising the amino acid sequence of SEQ ID NO: 21;

(k) a VH comprising the amino acid sequence of SEQ ID NO: 45 and a VL comprising the amino acid sequence of SEQ ID NO: 21;

(l) a VH comprising the amino acid sequence of SEQ ID NO: 15 and a VL comprising the amino acid sequence of SEQ ID NO: 31;
(m) a VH comprising the amino acid sequence of SEQ ID NO: 25 and a VL comprising the amino acid sequence of SEQ ID NO: 31;
(n) a VH comprising the amino acid sequence of SEQ ID NO: 35 and a VL comprising the amino acid sequence of SEQ ID NO: 31;
(o) a VH comprising the amino acid sequence of SEQ ID NO: 15 and a VL comprising the amino acid sequence of SEQ ID NO: 41;
(p) a VH comprising the amino acid sequence of SEQ ID NO: 35 and a VL comprising the amino acid sequence of SEQ ID NO: 41;
(q) a VH comprising the amino acid sequence of SEQ ID NO: 45 and a VL comprising the amino acid sequence of SEQ ID NO: 41;
(r) a VH comprising the amino acid sequence of SEQ ID NO: 55 and a VL comprising the amino acid sequence of SEQ ID NO: 51;
(s) a VH comprising the amino acid sequence of SEQ ID NO: 65 and a VL comprising the amino acid sequence of SEQ ID NO: 61; and
(t) a VH comprising the amino acid sequence of SEQ ID NO: 75 and a VL comprising the amino acid sequence of SEQ ID NO: 71.

In one embodiment, an antigen binding molecule, for example an antibody, variant or fragment thereof is provided, wherein the antigen binding molecule comprises a heavy chain variable region and a light chain variable region selected from the group consisting of:
(a) a VH comprising the amino acid sequence of SEQ ID NO: 45 optionally comprising up to 5 amino acid substitutions and a VL comprising the amino acid sequence of SEQ ID NO: 31 optionally comprising up to 5 amino acid substitutions;
(b) a VH comprising the amino acid sequence of SEQ ID NO: 25 optionally comprising up to 5 amino acid substitutions and a VL comprising the amino acid sequence of SEQ ID NO: 21 optionally comprising up to 5 amino acid substitutions;
(c) a VH comprising the amino acid sequence of SEQ ID NO: 25 optionally comprising up to 5 amino acid substitutions and a VL comprising the amino acid sequence of SEQ ID NO: 41 optionally comprising up to 5 amino acid substitutions;
(d) a VH comprising the amino acid sequence of SEQ ID NO: 5 optionally comprising up to 5 amino acid substitutions and a VL comprising the amino acid sequence of SEQ ID NO: 1 optionally comprising up to 5 amino acid substitutions;
(e) a VH comprising the amino acid sequence of SEQ ID NO: 15 optionally comprising up to 5 amino acid substitutions and a VL comprising the amino acid sequence of SEQ ID NO: 11 optionally comprising up to 5 amino acid substitutions;
(f) a VH comprising the amino acid sequence of SEQ ID NO: 25 optionally comprising up to 5 amino acid substitutions and a VL comprising the amino acid sequence of SEQ ID NO: 11 optionally comprising up to 5 amino acid substitutions;
(g) a VH comprising the amino acid sequence of SEQ ID NO: 35 optionally comprising up to 5 amino acid substitutions and a VL comprising the amino acid sequence of SEQ ID NO: 11 optionally comprising up to 5 amino acid substitutions;
(h) a VH comprising the amino acid sequence of SEQ ID NO: 45 optionally comprising up to 5 amino acid substitutions and a VL comprising the amino acid sequence of SEQ ID NO: 11 optionally comprising up to 5 amino acid substitutions;
(i) a VH comprising the amino acid sequence of SEQ ID NO: 15 optionally comprising up to 5 amino acid substitutions and a VL comprising the amino acid sequence of SEQ ID NO: 21 optionally comprising up to 5 amino acid substitutions;
(j) a VH comprising the amino acid sequence of SEQ ID NO: 35 optionally comprising up to 5 amino acid substitutions and a VL comprising the amino acid sequence of SEQ ID NO: 21 optionally comprising up to 5 amino acid substitutions;
(k) a VH comprising the amino acid sequence of SEQ ID NO: 45 optionally comprising up to 5 amino acid substitutions and a VL comprising the amino acid sequence of SEQ ID NO: 21 optionally comprising up to 5 amino acid substitutions;
(l) a VH comprising the amino acid sequence of SEQ ID NO: 15 optionally comprising up to 5 amino acid substitutions and a VL comprising the amino acid sequence of SEQ ID NO: 31 optionally comprising up to 5 amino acid substitutions;
(m) a VH comprising the amino acid sequence of SEQ ID NO: 25 optionally comprising up to 5 amino acid substitutions and a VL comprising the amino acid sequence of SEQ ID NO: 31 optionally comprising up to 5 amino acid substitutions;
(n) a VH comprising the amino acid sequence of SEQ ID NO: 35 optionally comprising up to 5 amino acid substitutions and a VL comprising the amino acid sequence of SEQ ID NO: 31 optionally comprising up to 5 amino acid substitutions;
(o) a VH comprising the amino acid sequence of SEQ ID NO: 15 optionally comprising up to 5 amino acid substitutions and a VL comprising the amino acid sequence of SEQ ID NO: 41 optionally comprising up to 5 amino acid substitutions;
(p) a VH comprising the amino acid sequence of SEQ ID NO: 35 optionally comprising up to 5 amino acid substitutions and a VL comprising the amino acid sequence of SEQ ID NO: 41 optionally comprising up to 5 amino acid substitutions;
(q) a VH comprising the amino acid sequence of SEQ ID NO: 45 optionally comprising up to 5 amino acid substitutions and a VL comprising the amino acid sequence of SEQ ID NO: 41 optionally comprising up to 5 amino acid substitutions;
(r) a VH comprising the amino acid sequence of SEQ ID NO: 55 optionally comprising up to 5 amino acid substitutions and a VL comprising the amino acid sequence of SEQ ID NO: 51 optionally comprising up to 5 amino acid substitutions;
(s) a VH comprising the amino acid sequence of SEQ ID NO: 65 optionally comprising up to 5 amino acid substitutions and a VL comprising the amino acid sequence of SEQ ID NO: 61 optionally comprising up to 5 amino acid substitutions; and
(t) a VH comprising the amino acid sequence of SEQ ID NO: 75 optionally comprising up to 5 amino acid substitutions and a VL comprising the amino acid sequence of SEQ ID NO: 71 optionally comprising up to 5 amino acid substitutions. The amino acid substitutions may be conservative amino acid substitutions. The amino acid substitutions may occur only in one or more framework regions. In some embodiments, the amino acid substitutions may be conservative amino acid substitutions and occur only in one or more framework regions.

In one embodiment, an antigen binding molecule, for example an antibody, variant or fragment thereof is provided, wherein the antigen binding molecule comprises a heavy chain variable region and a light chain variable region selected from the group consisting of:

(a) a VH comprising the amino acid sequence of SEQ ID NO: 45 optionally comprising up to 2 amino acid substitutions and a VL comprising the amino acid sequence of SEQ ID NO: 31 optionally comprising up to 2 amino acid substitutions;

(b) a VH comprising the amino acid sequence of SEQ ID NO: 25 optionally comprising up to 2 amino acid substitutions and a VL comprising the amino acid sequence of SEQ ID NO: 21 optionally comprising up to 2 amino acid substitutions;

(c) a VH comprising the amino acid sequence of SEQ ID NO: 25 optionally comprising up to 2 amino acid substitutions and a VL comprising the amino acid sequence of SEQ ID NO: 41 optionally comprising up to 2 amino acid substitutions;

(d) a VH comprising the amino acid sequence of SEQ ID NO: 5 optionally comprising up to 2 amino acid substitutions and a VL comprising the amino acid sequence of SEQ ID NO: 1 optionally comprising up to 2 amino acid substitutions;

(e) a VH comprising the amino acid sequence of SEQ ID NO: 15 optionally comprising up to 2 amino acid substitutions and a VL comprising the amino acid sequence of SEQ ID NO: 11 optionally comprising up to 2 amino acid substitutions;

(f) a VH comprising the amino acid sequence of SEQ ID NO: 25 optionally comprising up to 2 amino acid substitutions and a VL comprising the amino acid sequence of SEQ ID NO: 11 optionally comprising up to 2 amino acid substitutions;

(g) a VH comprising the amino acid sequence of SEQ ID NO: 35 optionally comprising up to 2 amino acid substitutions and a VL comprising the amino acid sequence of SEQ ID NO: 11 optionally comprising up to 2 amino acid substitutions;

(h) a VH comprising the amino acid sequence of SEQ ID NO: 45 optionally comprising up to 2 amino acid substitutions and a VL comprising the amino acid sequence of SEQ ID NO: 11 optionally comprising up to 2 amino acid substitutions;

(i) a VH comprising the amino acid sequence of SEQ ID NO: 15 optionally comprising up to 2 amino acid substitutions and a VL comprising the amino acid sequence of SEQ ID NO: 21 optionally comprising up to 2 amino acid substitutions;

(j) a VH comprising the amino acid sequence of SEQ ID NO: 35 optionally comprising up to 2 amino acid substitutions and a VL comprising the amino acid sequence of SEQ ID NO: 21 optionally comprising up to 2 amino acid substitutions;

(k) a VH comprising the amino acid sequence of SEQ ID NO: 45 optionally comprising up to 2 amino acid substitutions and a VL comprising the amino acid sequence of SEQ ID NO: 21 optionally comprising up to 2 amino acid substitutions;

(l) a VH comprising the amino acid sequence of SEQ ID NO: 15 optionally comprising up to 2 amino acid substitutions and a VL comprising the amino acid sequence of SEQ ID NO: 31 optionally comprising up to 2 amino acid substitutions;

(m) a VH comprising the amino acid sequence of SEQ ID NO: 25 optionally comprising up to 2 amino acid substitutions and a VL comprising the amino acid sequence of SEQ ID NO: 31 optionally comprising up to 2 amino acid substitutions;

(n) a VH comprising the amino acid sequence of SEQ ID NO: 35 optionally comprising up to 2 amino acid substitutions and a VL comprising the amino acid sequence of SEQ ID NO: 31 optionally comprising up to 2 amino acid substitutions;

(o) a VH comprising the amino acid sequence of SEQ ID NO: 15 optionally comprising up to 2 amino acid substitutions and a VL comprising the amino acid sequence of SEQ ID NO: 41 optionally comprising up to 2 amino acid substitutions;

(p) a VH comprising the amino acid sequence of SEQ ID NO: 35 optionally comprising up to 2 amino acid substitutions and a VL comprising the amino acid sequence of SEQ ID NO: 41 optionally comprising up to 2 amino acid substitutions;

(q) a VH comprising the amino acid sequence of SEQ ID NO: 45 optionally comprising up to 2 amino acid substitutions and a VL comprising the amino acid sequence of SEQ ID NO: 41 optionally comprising up to 2 amino acid substitutions;

(r) a VH comprising the amino acid sequence of SEQ ID NO: 55 optionally comprising up to 2 amino acid substitutions and a VL comprising the amino acid sequence of SEQ ID NO: 51 optionally comprising up to 2 amino acid substitutions;

(s) a VH comprising the amino acid sequence of SEQ ID NO: 65 optionally comprising up to 2 amino acid substitutions and a VL comprising the amino acid sequence of SEQ ID NO: 61 optionally comprising up to 2 amino acid substitutions; and (t) a VH comprising the amino acid sequence of SEQ ID NO: 75 optionally comprising up to 2 amino acid substitutions and a VL comprising the amino acid sequence of SEQ ID NO: 71 optionally comprising up to 2 amino acid substitutions. The amino acid substitutions may be conservative amino acid substitutions. The amino acid substitutions may occur only in one or more framework regions. In some embodiments, the amino acid substitutions may be conservative amino acid substitutions and occur only in one or more framework regions.

In one embodiment, an antigen binding molecule, for example an antibody, variant or fragment thereof is provided, wherein the antigen binding molecule comprises a heavy chain variable region and a light chain variable region selected from the group consisting of:

(a) a VH comprising the amino acid sequence of SEQ ID NO: 45 and a VL comprising the amino acid sequence of SEQ ID NO: 31;

(b) a VH comprising the amino acid sequence of SEQ ID NO: 25 and a VL comprising the amino acid sequence of SEQ ID NO: 21;

(c) a VH comprising the amino acid sequence of SEQ ID NO: 25 and a VL comprising the amino acid sequence of SEQ ID NO: 41;

(d) a VH comprising the amino acid sequence of SEQ ID NO: 5 and a VL comprising the amino acid sequence of SEQ ID NO: 1;

(e) a VH comprising the amino acid sequence of SEQ ID NO: 15 and a VL comprising the amino acid sequence of SEQ ID NO: 11;

(f) a VH comprising the amino acid sequence of SEQ ID NO: 25 and a VL comprising the amino acid sequence of SEQ ID NO: 11;

(g) a VH comprising the amino acid sequence of SEQ ID NO: 35 and a VL comprising the amino acid sequence of SEQ ID NO: 11;

(h) a VH comprising the amino acid sequence of SEQ ID NO: 45 and a VL comprising the amino acid sequence of SEQ ID NO: 11;

(i) a VH comprising the amino acid sequence of SEQ ID NO: 15 and a VL comprising the amino acid sequence of SEQ ID NO: 21;

(j) a VH comprising the amino acid sequence of SEQ ID NO: 35 and a VL comprising the amino acid sequence of SEQ ID NO: 21;

(k) a VH comprising the amino acid sequence of SEQ ID NO: 45 and a VL comprising the amino acid sequence of SEQ ID NO: 21;

(1) a VH comprising the amino acid sequence of SEQ ID NO: 15 and a VL comprising the amino acid sequence of SEQ ID NO: 31;

(m) a VH comprising the amino acid sequence of SEQ ID NO: 25 and a VL comprising the amino acid sequence of SEQ ID NO: 31;

(n) a VH comprising the amino acid sequence of SEQ ID NO: 35 and a VL comprising the amino acid sequence of SEQ ID NO: 31;

(o) a VH comprising the amino acid sequence of SEQ ID NO: 15 and a VL comprising the amino acid sequence of SEQ ID NO: 41;

(p) a VH comprising the amino acid sequence of SEQ ID NO: 35 and a VL comprising the amino acid sequence of SEQ ID NO: 41;

(q) a VH comprising the amino acid sequence of SEQ ID NO: 45 and a VL comprising the amino acid sequence of SEQ ID NO: 41;

(r) a VH comprising the amino acid sequence of SEQ ID NO: 55 and a VL comprising the amino acid sequence of SEQ ID NO: 51;

(s) a VH comprising the amino acid sequence of SEQ ID NO: 65 and a VL comprising the amino acid sequence of SEQ ID NO: 61; and (t) a VH comprising the amino acid sequence of SEQ ID NO: 75 and a VL comprising the amino acid sequence of SEQ ID NO: 71;

optionally wherein for any of (a) to (t) above, any Met residues are each independently substituted with an amino acid selected from the group consisting of Ala and Leu, and/or the Asp residues are each independently substituted with an amino acid selected from the group consisting of Ala, Gin and Glu. In some embodiments, any Met and/or Asp residues being substituted exist only in the framework regions.

Variants therefore are also provided, as discussed above, including humanised and affinity matured variants thereof, and variants having smaller or greater % identities or homologies, for example at least 70%, 75%, 80%, 85%, 90%, 91%, 92%, 93%, 94%, 95%, 96%, 97%, 98% or 99% identity or homology to the specified sequence(s). Variants having one or more amino acid substitutions are also provided. In some embodiments, the amino acid substitutions do not occur in a CDR sequence.

As noted above, amino acid substitutions may be made to reduce or eliminate liabilities in the heavy chain variable regions and/or light chain variable regions of the antigen-binding molecules of the invention. Such substitutions to reduce or eliminate liabilities may occur in the CDRs. Such substitutions to reduce or eliminate liabilities may occur in framework regions of the variable regions.

Nucleic Acid Sequences Encoding Antigen Binding Molecules

In one aspect of the invention, there is provided nucleic acid sequences that encode the antigen binding molecules of the invention, including fragments and variants thereof.

In one embodiment, nucleic acid molecules encoding an antigen binding molecule that binds to BDCA-2 (CLEC4C) comprising a heavy chain variable region having at least 70%, 75%, 80%, 85%, 90%, 91%, 92%, 93%, 94%, 95%, 96%, 97%, 98% or 99% identity to an amino acid sequence selected from the group consisting of SEQ ID NO: 45, SEQ ID NO: 25, SEQ ID NO: 5, SEQ ID NO: 15, SEQ ID NO: 35, SEQ ID NO: 55, SEQ ID NO: 65 and SEQ ID NO: 75, and/or a light chain variable region having at least 70%, 75%, 80%, 85%, 90%, 91%, 92%, 93%, 94%, 95%, 96%, 97%, 98% or 99% identity to an amino acid sequence selected from the group consisting SEQ ID NO: 31, SEQ ID NO: 21, SEQ ID NO: 41, SEQ ID NO: 1, SEQ ID NO: 11, SEQ ID NO: 51, SEQ ID NO: 61 and SEQ ID NO: 71 are provided.

In one embodiment, nucleic acid molecules encoding an antibody that binds to BDCA-2 (CLEC4C) comprising a heavy chain variable region having an amino acid sequence selected from the group consisting of SEQ ID NO: 45, SEQ ID NO: 25, SEQ ID NO: 5, SEQ ID NO: 15, SEQ ID NO: 35, SEQ ID NO: 55, SEQ ID NO: 65 and SEQ ID NO: 75, and/or a light chain variable region having an amino acid sequence selected from the group consisting of consisting SEQ ID NO: 31, SEQ ID NO: 21, SEQ ID NO: 41, SEQ ID NO: 1, SEQ ID NO: 11, SEQ ID NO: 51, SEQ ID NO: 61 and SEQ ID NO: 71 are provided.

The present invention also provides nucleic acid molecules encoding all of the variant antibody sequences disclosed herein comprising one or more amino acid substitutions. The present invention also provides vectors, plasmids and/or host cells comprising nucleic acid molecules, or combinations of nucleic acid molecules, encoding any antibody sequences disclosed herein or variant antibody sequences disclosed herein comprising one or more amino acid substitutions.

Also provided are nucleic acid molecules that encode an amino acid sequence according to any one of SEQ ID NOs 1 to 80

Also provided are plasmid and vectors and plasmids comprising a nucleic acid sequence encoding an antigen binding molecule of the invention. The nucleic acids may be incorporated into a plasmid or vector for expression, in particular in a eukaryotic expression system, more specifically, mammalian cell lines. Accordingly, also provided are host cells transfected with a plasmid or vector of the invention, such as NS0 muine myeloma cells or CHO cells.

Also provided is a method for the production on an anti-BDCA-2 (CLEC4C) antigen binding molecule, comprising culturing a host cell of the invention in a cell culture medium under conditions to express the encoding nucleic acid sequence of the plasmid or vector inside the cell. The method may further comprise obtaining the anti-BDCA-2 (CLEC4C) antigen binding molecule from the cell culture supernatant. The obtained antigen binding molecule may then be formulated into a pharmaceutical composition. Further, there is provided a method of producing cell that expresses an anti-BDCA-2 (CLEC4C) antigen binding molecule, comprising transfecting said cell with a plasmid or vector of the invention. Said cells can then be cultured for the production of the antigen binding molecule.

Antigens

The antigen binding molecules of the invention bind specifically to BDCA-2 (CLEC4C), in particular human BDCA-2 (CLEC4C).

BDCA-2 is a type II transmembrane glycoprotein that belongs to the C-type lectin superfamily (Crocker P R et al. Nat Rev Immunol. 2007; 7:255-66). BDCA-2 is the most specific marker for human pDC and is only expressed in primates. BDCA-2 signals through an associated transmembrane adaptor, the FcεRγ, which recruits the protein tyrosine kinase Syk, inducing protein tyrosine phosphorylation and calcium mobilization (Cao W, et al. PLoS Biol. 2007; 5:e248).

Although it promotes cellular activation in other lymphoid and myeloid cells, the FcεRγ-Syk signaling pathway interferes with TLR7 and 9-induced activation of pDC, inhibiting type I IFN secretion and other inflammatory mediators (Dzionek A, et al. J. Exp. Med. 2001; 194:1823-1834; Fanning S L et al. J Immunol. 2006; 177:5829-39.2006; Rock J et al. Eur J Immunol. 2007; 37:3564-75). For this reason, antibodies binding BDCA-2 have been explored for their potential of blocking pDC activation and as therapeutic options in other IFN mediated autoimmune conditions, such as SLE (Furie R et al. J Clin Invest. 2019; 129:1359-1371).

The amino acid sequences of BDCA-2 variants to which the antigen binding molecules of the invention bind are provided below.

```
Q8WTT0
                                (SEQ ID NOs: 82 and 90)
MVPEEEPQDREKGLWWFQLKVWSMAVVSILLLSVCFTVSSVVPHNFMYSK

TVKRLSKLREYQQYHPSLTCVMEGKDIEDWSCCPTPWTSFQSSCYFISTG

MQSWTKSQKNCSVMGADLVVINTREEQDFIIQNLKRNSSYFLGLSDPGGR

RHWQWVDQTPYNENVTFWHSGEPNNLDERCAIINFRSSEEWGWNDIHCHV

PQKSICKMKKIYI

Q8WTT0-2
                                        (SEQ ID NO: 91)
MVPEEEPQDRVPHNFMYSKTVKRLSKLREYQQYHPSLTCVMEGKDIEDWS

CCPTPWTSFQSSCYFISTGMQSWTKSQKNCSVMGADLVVINTREEQDFII

QNLKRNSSYFLGLSDPGGRRHWQWVDQTPYNENVTFWHSGEPNNLDERCA

IINFRSSEEWGWNDIHCHVPQKSICKMKKIYI
```

Q8WTT0-2 is missing amino acids 11-41 of Q8WTT0. The extra cellular domain starting at position 45 in Q8WTT0 is present in Q8WTT0-2.

The antigen binding molecules of the invention that bind membrane BDCA-2 (CLEC4C) will also therefore bind to cells that express BDCA-2 (CLEC4C). Accordingly, the present invention also provides a binding molecule having the formula TM-Ln-AM, wherein TM is a targeting moiety and is an antigen binding molecule of the invention, L is a linker, n is either 0 or 1 (so a linker may or may not be present), and AM is an active moiety. The antigen binding molecules of the invention can be used to target the active moieties to cells expressing BDCA-2 (CLEC4C). Suitable linkers include a hydrazine group, a polypeptide, a disulfide group, and a thioether group, and the linker may be cleavable by enzyme action. Suitable active moieties include pharmaceutically active components, such as anti-inflammatory agents, immunosuppressants or other such components that are suitable or desirable for use in combination with the antigen binding molecules of the invention. Suitable such agents are also discussed elsewhere.

Functional Properties of the Antigen Binding Molecules

The provided antigen binding molecules have one or more preferential functional features. The functional features may be shared across different antigen binding molecules provided herein, and/or variants and fragments derived from antigen binding molecules provided herein may preferentially retain the functional features of the antigen binding molecules from which they are derived. In some embodiments, the fragments or variants may have improved functional properties. In some embodiment, variant antibodies (such as those exhibiting one or more substitutions) will retain the advantageous functional properties of the antibodies (such as $K_D$, IC50 and/or IC90).

$K_D$

In one embodiment, the antigen binding molecules of the present invention have a $K_D$ value for BDCA-2 (CLEC4C) of less than about 2 nM. In some embodiments, the antigen binding molecules of the present invention have a $K_D$ value for BDCA-2 (CLEC4C) of less than about 1 nM. In a more preferred embodiment, the antigen binding molecules of the present invention have a $K_D$ value for BDCA-2 (CLEC4C) of less than about 0.01 nM. The term $K_D$ is well known to the skilled person and refers to an equilibrium dissociation constant that measures the strength of the binding interaction between an antibody and antigen. The $K_D$ can be measured according to any suitable means. For example, a suitable assay may be a flow-cytometry assay comprising incubating BDCA-2 (CLEC4C) expressing cells with test antigen binding molecule at a concentration of up to 70 μg/mL for 30 to 40 minutes at 4° C. In this way a dose-response curve can be determined and a $K_D$ value provided. For example, a suitable assay may be a flow-cytometry assay comprising incubating BDCA-2 (CLEC4C) expressing cells with test antigen binding molecule at concentrations of 0.1, 0.3, 1, 3, 10 and 30 μg/mL for 35 minutes at 4° C.

In some embodiments, the anti-BDCA-2 (CLEC4C) antigen binding molecule or fragment, variant or affinity matured mutant thereof, has and equilibrium dissociation constant ($K_D$) value for BDCA-2 (CLEC4C) of less than about 2 nM, in particular an anti-BDCA-2 (CLEC4C) antigen binding molecule or fragment, variant or affinity matured mutant thereof, that has $K_D$ value for BDCA-2 (CLEC4C) of less than about 1 nM, less than about 0.75 nM, less than about 0.5 nM, less than about 0.4 nM, less than about 0.3 nM, less than about 0.2 nM, less than about 0.1 nM, less than about 0.08 nM, less than about 0.06 nM, less than about 0.05 nM, less than about 0.04 nM, less than about 0.03 nM, less than about 0.02 nM or less than about 0.01 nM. In some possibly preferred embodiments, the anti-BDCA-2 (CLEC4C) antigen binding molecule or fragment, variant or affinity matured mutant thereof, has and equilibrium dissociation constant ($K_D$) value for BDCA-2 (CLEC4C) of less than about 0.01 nM.

IC50

In some embodiments, the anti-BDCA-2 (CLEC4C) antigen binding molecule or fragment, variant or affinity matured mutant thereof has a 50% of maximal inhibitory concentration (IC50) for inhibition of IFN secretion of less than about 2 nM. In some embodiments, the anti-BDCA-2 (CLEC4C) antigen binding molecule or fragment, variant or affinity matured mutant thereof has a 50% of maximal inhibitory concentration (IC50) of less than about 1.5 nM, less than about 1 nM, less than about 0.9 nM, less than about 0.8 nM, less than about 0.7 nM, less than about 0.6 nM, less than about 0.5 nM, less than about 0.4 nM, less than about 0.3 nM, less than about 0.2 nM, or less than about 0.1 nM. In some possibly preferred embodiments, the anti-BDCA-2 (CLEC4C) antigen binding molecule or fragment, variant or affinity matured mutant thereof, exhibits an IC50 of less than about 0.5 nM.

The term IC50 is well known to the skilled person and refers to the half maximal inhibitory concentration of a drug or substance, or the concentration of that substance which induces 50% inhibition. IC50 is a measure of the potency of a substance in inhibiting a specific biological or biochemical function. The lower the IC50, the greater the potency of the antagonist drug or substance as an inhibitor. The IC50 of the antigen binding molecules of the invention is the IC50 for IFN secretion from BDCA-2-expressing cells, for example plasmacytoid dendritic cells or peripheral blood mononuclear cells. The inhibition is in the inhibition of IFN secretion from cells in response to an IFN-secretion inducing agonist.

The IC50 for inhibition of IFN secretion may be measured according to a method comprising:

(a) incubating a suspension of BDCA-2 expressing cells (for example plasmacytoid dendritic cells or peripheral blood mononuclear cells) in a 96-well plate for 1 hour at 37° C. and in 5% $CO_2$;

(b) adding to the one or more wells of the 96-well plate a solution of test antibody and an IFN-secretion inducing agonist (for example a TLR7 agonist or a TLR9 agonist), wherein the test antibody is provided in a range of concentrations suitable to provide a dose-response curve for IFN secretion, for example in concentrations of from 0 to 10 μg/ml (for example 0.001, 0.003, 0.01, 0.03, 0.1, 0.3, 1, 3 and 10 μg/ml, and 0 μg/ml as a control);

(c) incubating the cells with test antibody and IFN-secretion inducing agonist for 16 hours at 37° C. and in 5% $CO_2$;

(d) quantifying the amount of IFN in the cell free supernatant for each tested concentration of antibody, for example by ELISA;

(e) providing a dose-response curve for IFN secretion against antibody concentration; and (f) determining the IC50 of the text antibody by reference to the dose response curve provided in step (e), wherein the IC50 is defined as the concentration of the test antibody that induces 50% inhibition of IFN secretion compared to the amount of IFN secretion in the absence of the test antibody.

The volume of cell suspension used may be the same as the volume of antibody solution added to each well of the plate. For example, the method may comprise incubating 50 μl of the suspension of BDCA-2 expressing cells in each well of the 96-well plate, and 50 μl of the test antibody at each of the antibody concentrations tested (or 50 μl of solution containing no test antibody, for the control).

The quantity of cells used and their media conditions can be determined by the skilled person. For example, the assay may comprise incubating 50 μl of cell suspension comprising 1 to $2\times10^4$ pDCs in cell media comprising L-glutamine and sodium bicarbonate with 10% FBS in each well of the plate and for each of the concentrations of antibody being tested. Alternatively, the assay may comprise incubating 50 μl of cell suspension comprising 1 to $2\times10^6$ PBMCs in 10% autologous serum in each well of the plate and for each of the concentrations of antibody being tested.

The IFN-secretion inducing agonist stimulates the incubated cells to secrete IFN into the supernatant. The amount of the IFN-secretion inducing agonist can be determined by the skilled person, and is provided in an amount suitable to stimulate IFN secretion from the cells. 4 μM may be a suitable amount, for example 4 μM of the TLR7 agonist or 4 μM of the TLR9 agonist. Example suitable TLR7 agonists include imiquimod. Example suitable TLR9 agonists include RNA oligoribonucleotide (ORN) agonists or a DNA oligonucleotide agonists, for example ODN 2216 (an oligonucleotide having the sequence ggGGGACGATCGTCgggggg). In some embodiments, at least 1 well of the plate is incubated with a combination of the suspension of BDCA-2 expression cells and a solution of test antibody for each concentration of antibody being tested but in the absence of the IFN-secretion inducing agonist for control purposes. The skilled person is familiar with appropriate controls required to provide a dose-response curve.

IC90

In some embodiments, the anti-BDCA-2 (CLEC4C) antigen binding molecule or fragment, variant or affinity matured mutant thereof has a 90% of maximal inhibitory concentration (IC90) for inhibition of IFN secretion of less than about 20 nM, less than about 15 nM, less than about 10 nM, less than about 9 nM, less than about 8 nM, less than about 7 nM, less than about 6 nM, less than about 5 nM, less than about 4 nM, less than about 3 nM, less than about 2 nM or less than about 1 nM. In some possibly preferred embodiments, the anti-BDCA-2 (CLEC4C) antigen binding molecule or fragment, variant or affinity matured mutant thereof, exhibits an IC90 of less than about 5 nM The term IC90 is well known to the skilled person and refers to the concentration of a substance which induces 90% inhibition. IC90 is a measure of the potency of a substance in inhibiting a specific biological or biochemical function. The lower the IC90, the greater the potency of the antagonist drug or substance as an inhibitor.

The IC90 for inhibition of IFN secretion may be measured according to the same method provided above for the IC90, except step (f) is:

(f) determining the IC90 of the text antibody by reference to the dose response curve provided in step (e), wherein the IC90 is defined as the concentration of the test antibody that induces 90% inhibition of IFN secretion compared to the amount of IFN secretion in the absence of the test antibody.

Combinations of Features

Antigen binding molecules of the invention may exhibit a combination of the functional features described herein.

For example, in some embodiments the antigen binding molecules of the present invention have:

(i) a $K_D$ value for BDCA-2 (CLEC4C) of less than about 2 nM and an IC50 for inhibition of IFN secretion of less than about 2 nM;

(ii) a $K_D$ value for BDCA-2 (CLEC4C) of less than about 2 nM and an IC90 for inhibition of IFN secretion of less than about 20 nM;

(iii) an IC50 for inhibition of IFN secretion of less than about 2 nM and an IC90 for inhibition of IFN secretion of less than about 20 nM;

(iv) a $K_D$ value for BDCA-2 (CLEC4C) of less than about 2 nM, an IC50 for inhibition of IFN secretion of less than about 2 nM, and an IC90 for inhibition of IFN secretion of less than about 20 nM;

(v) a $K_D$ value for BDCA-2 (CLEC4C) of less than about 1 nM and an IC50 for inhibition of IFN secretion of less than about 1 nM;

(vi) a $K_D$ value for BDCA-2 (CLEC4C) of less than about 1 nM and an IC90 for inhibition of IFN secretion of less than about 10 nM;

(vii) an IC50 for inhibition of IFN secretion of less than about 1 nM and an IC90 for inhibition of IFN secretion of less than about 10 nM (viii) a $K_D$ value for BDCA-2 (CLEC4C) of less than about 1 nM, an IC50 for inhibition of IFN secretion of less than about 1M, and an IC90 for inhibition of IFN secretion of less than about 10 nM;

(ix) a $K_D$ value for BDCA-2 (CLEC4C) of less than about 0.01 nM and an IC50 for inhibition of IFN secretion of less than about 0.5 nM;

(x) a $K_D$ value for BDCA-2 (CLEC4C) of less than about 0.01 nM and an IC90 for inhibition of IFN secretion of less than about 5 nM;

(xi) an IC50 for inhibition of IFN secretion of less than about 0.5 nM, and an IC90 for inhibition of IFN secretion of less than about 5 nM; or (xii) a $K_D$ value for BDCA-2 (CLEC4C) of less than about 0.01 nM, an IC50 for inhibition of IFN secretion of less than about 0.5 nM, and an IC90 for inhibition of IFN secretion of less than about 5 nM. Antigen binding molecules having such a combination of features as in (xii) may be preferred.

Other Features

Besides inhibition of TLR9 induced IFN gene expression, it was surprising to determine that 3E05, and variant antibodies, inhibited a number of genes involved in lymphocyte and myeloid migration (CXCL9, CCL3L3, CCL3L1, CCL5 and CXCL8); inflammatory mediators (MAP3K8, IL6 and PTGS2); immune response (CD274, RNF115, SLAMF7 and HLA-F) and angiogenesis and fibrosis (ENPP2 and ITGB8). In some embodiments, antigen binding molecules are provided which can inhibit expression of one or more of these genes. In some embodiments, antigen binding molecules are provided which can inhibit expression of one or more of the genes listed in FIG. 7B. In some embodiments, antigen binding molecules are provided which can inhibit expression of one or more of the genes listed in FIG. 8C. In some embodiments, antigen binding molecules are provided which can inhibit expression of one or more ODN stimulated genes, such as those listed in FIG. 7B. In some embodiments, antigen binding molecules are provided which can inhibit expression of one or more ODN stimulated genes, such as those listed in FIG. 8C.

Other Provided Antigen Binding Molecules

In one aspect, an anti-LIGHT antigen binding molecule, for example an antibody, fragment or variant thereof is provided, wherein the antigen binding molecule competes for binding to BDCA-2 (CLEC4C) with an antigen binding molecule of the invention as defined above.

For example, in one embodiment the invention provides an antigen binding molecule (preferably an antibody) wherein the antigen binding molecule specifically binds to BDCA-2 (CLEC4C), and competes for binding to BDCA-2 (CLEC4C) with an antibody selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01. Antigen binding molecules that compete with the fragments and variants thereof for binding to BDCA-2 (CLEC4C) are also provided (for example antigen binding molecules comprising the 6 CDR regions or the VH and VL sequences of the above antibodies, as well as other variants).

To determine if a test antigen binding molecule can compete for binding to the same epitope as the epitope bound by the antibodies of the present invention, a cross-blocking assay e.g., a competitive ELISA assay can be performed. In an exemplary competitive ELISA assay, BDCA-2 (CLEC4C)-coated wells of a microtiter plate, or BDCA-2 (CLEC4C)-coated sepharose beads, are pre-incubated with or without candidate competing antibody and then a biotin-labelled anti-BDCA-2 (CLEC4C) antibody of the invention is added. The amount of labelled anti-BDCA-2 (CLEC4C) antibody bound to the BDCA-2 (CLEC4C) antigen in the wells or on the beads can be measured using avidin peroxidase conjugate and appropriate substrate.

Alternatively, the anti-BDCA-2 (CLEC4C) antibody can be labelled, e.g., with a radioactive or fluorescent label or some other detectable and measurable label. The amount of labelled anti-BDCA-2 (CLEC4C) antibody that binds to the antigen will have an inverse correlation to the ability of the candidate competing antibody (test antigen binding molecule) to compete for binding to the same epitope on the antigen, i.e., the greater the affinity of the test antigen binding molecule for the same epitope, the less labelled anti-BDCA-2 (CLEC4C) antibody will be bound to the antigen-coated wells.

A candidate competing antibody is considered an antibody that binds substantially to the same epitope or that competes for binding to the same epitope as an anti-BDCA-2 (CLEC4C) antibody of the invention if the candidate competing antibody can block binding of the anti-BDCA-2 (CLEC4C) antibody by at least 20%, preferably by at least 20-50%, even more preferably, by at least 50% as compared to a control performed in parallel in the absence of the candidate competing antibody (but may be in the presence of a known noncompeting antibody). It will be understood that variations of this assay can be performed to arrive at the same quantitative value.

In one embodiment of the invention, there is provided an anti-BDCA-2 (CLEC4C) antigen binding molecule, for example an antibody, fragment or variant thereof, wherein the antigen binding molecule competes for binding to BDCA-2 (CLEC4C) with an antigen binding molecule of the invention as defined above, wherein the competing antibody can block binding of the anti-BDCA-2 (CLEC4C) antibody of the invention by at least 50% as measured in a competitive ELISA assay.

There is also provided an antigen binding molecule that specifically binds to BDCA-2 (CLEC4C) and inhibits the binding of BDCA-2 (CLEC4C) to an antigen binding molecule of the invention.

For example, in one embodiment, the antigen binding molecule (preferably an antibody) specifically binds to BDCA-2 (CLEC4C) and inhibits the binding of BDCA-2 (CLEC4C) to an antibody selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01. Antigen binding molecules that specifically bind to BDCA-2 (CLEC4C) and inhibit the binding of BDCA-2 (CLEC4C) to fragments and variants thereof are also provided (for example antigen binding molecules comprising the 6 CDR regions or the VH and VL sequences of the above antibodies, as well as other variants).

There is also provided an antigen binding molecule that specifically binds to an epitope of BDCA-2 (CLEC4C) that is bound by an antigen binding molecule of the invention.

For example, in one embodiment the invention provides an antigen binding molecule (preferably an antibody) wherein the antigen binding molecule specifically binds to an epitope of BDCA-2 (CLEC4C) that is bound by an antibody selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01. Antigen binding molecules that specifically bind to an epitope of BDCA-2 (CLEC4C) that is bound by fragments and variants thereof are also provided (for example antigen binding molecules comprising the 6 CDR regions or the VH and VL sequences of the above antibodies, as well as other variants).

Antigen binding molecules of the invention may bind an epitope comprising or consisting of the amino acid residues 166 to 179 of human BDCA-2 (SEQ ID NO: 82). The epitope may be fully contained within 166 to 179 (inclusive) of human BDCA-2. Alternatively, in some embodiments, the epitope may comprise or overlap with one or more the amino acid residues of residues 166 to 179 of human BDCA-2. The epitope may be a linear epitope (for example a linear epitope contained within amino acid residues X to X (inclusive) of human BDCA-2, or a linear epitope overlapping with amino acid residues 166 to 179 of human BDCA-2), or the epitope may be a conformational epitope (for example a conformational epitope comprising one or more amino acid residues of residues 166 to 179 of human BDCA-2, or a conformational epitope consisting of one or more amino acid residues of residues 166 to 179 of human BDCA-2). The antigen-binding molecules of the invention may also bind BDCA-2 at additional epitopes. In a preferred embodiment, the antigen binding molecules of the invention bind an epitope consisting of one or more amino acid residues of residues 166 to 179 of human BDCA-2.

Compositions

In one aspect of the invention, a pharmaceutical composition comprising an antigen binding molecule of the invention is provided.

The compositions of the invention can be formulated for use by any convenient route. The pharmaceutical composition of the invention will normally include a pharmaceutically acceptable carrier, excipient, diluent, adjuvant, vehicle, buffer or stabiliser in addition to an antigen binding molecule of the invention. Such carriers include, but are not limited to, saline, buffered saline, dextrose, liposomes, water, glycerol, polyethylene glycol, ethanol and combinations thereof.

The pharmaceutical composition may be in any suitable form depending upon the desired method of administering it to a patient.

The pharmaceutical compositions of the invention may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of formula I, doses in the range 100-1000 mg/day are provided, preferably either 100-400 mg/day, 300-600 mg/day or 500-1000 mg/day. Such doses can be provided in a single dose or as a number of discrete doses. The ultimate dose will of course depend on the condition being treated, the route of administration and the age, weight and condition of the patient and will be at the doctor's discretion.

The pharmaceutical compositions of the invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. IV administration may be preferred. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The pharmaceutical compositions of the invention can also contain one or more other therapeutically active agents in addition to the molecule of the present invention.

In some embodiments, the formulation of the active drug concentrate can comprise a pharmaceutically acceptable tonicity agent, a buffering agent, and a pharmaceutically acceptable surfactant.

Alternatively, the formulation can comprise the active ingredient plus sodium phosphate, monobasic, sodium phosphate dibasic, sodium chloride, polysorbate 80 or polysorbate 20 (surfactant to minimise risk of agitation-induced aggregation) and water (USP/Ph.Eur), optionally with a pH adjusted to about 6.0 to 7.0, e.g. around 6.5.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

In some embodiments, the pharmaceutical compositions may comprise an additional therapeutically active agent.

The present invention also provides methods of manufacture of pharmaceutical compositions, comprising formulating an antigen binding molecule of the invention with one or more pharmaceutically acceptable excipients.

The present invention also provides kits comprising an antigen binding molecule of the invention. The kits may comprise an additional therapeutically active agent. In some embodiments, the kits may comprise instructions for use.

Additional therapeutically active agents that may be use in combination with the antigen binding molecules of the invention include, for example, anti-inflammatory agents or immuno-modulating agents.

Methods of Treatment

The antigen binding molecules of the invention are useful in preventing and/or treating BDCA-2 (CLEC4C)-mediated disorders or diseases, in particular inflammatory disorders or diseases. This aspect of the invention therefore also includes a method for the treatment of a BDCA-2 (CLEC4C)-mediated disorder or disease (such as an inflammatory disorder or disease) in a subject, comprising administering to the subject an antigen binding molecule of the invention. The invention therefore also extends to the use of an antigen binding molecule of the invention in the manufacture of a medicament for use in the treatment and/or prevention of a BDCA-2 (CLEC4C)-mediate disorder or disease (such as an inflammatory disorder or disease), and use of the antigen binding molecules of the invention in prevention and/or treatment of such conditions.

The method of treatment can be of a human or an animal subject and the invention extends equally to uses in both human and/or veterinary medicine. The antigen binding molecule of the invention is preferably administered to an individual in a "therapeutically effective amount", this being sufficient to show benefit to the individual. As used herein, "treatment" includes any regime that can benefit a human or non-human animal, preferably a mammal. The treatment may be in respect of an existing condition or may be prophylactic (preventative treatment).

As used herein, the term "therapeutically effective amount" means an amount (e.g., of an agent or of a pharmaceutical composition) that is sufficient, when administered to a population suffering from or susceptible to a disease and/or condition in accordance with a therapeutic dosing regimen, to treat such disease and/or condition. A therapeutically effective amount is one that reduces the incidence and/or severity of, stabilizes, and/or delays onset of, one or more symptoms of the disease, disorder, and/or condition. Those of ordinary skill in the art will appreciate that a "therapeutically effective amount" does not in fact require successful treatment be achieved in a particular subject.

In one embodiment, the antigen binding molecules of the invention are for use in inflammation, inflammatory disorders including autoimmune diseases. In some embodiments, the antigen binding molecules of the invention are for use in treating systemic sclerosis, fibrosis (such as skin fibrosis), pemphigus vulgaris, systemic lupus erythematosus (SLE), cutaneous lupus, discoid lupus, lupus nephritis, polymyositis and dermatomyositis, psoriasis, rheumatoid arthritis, Grave's disease, morphea, inflammatory bowel disease, morphea, type I diabetes, Sjogren's disease and Hashimoto's disease. As used herein "inflammatory bowel disease" (IBD) relates to inflammatory conditions of the colon and small intestine. Of particular interest is the treatment of pemphigus vulgaris, Systemic sclerosis, lupus and Sjogren's disease.

Depending on the condition being treated, the antigen binding molecules of the invention may be used in combination with other pharmaceutically active components for simultaneous, separate or sequential use. For example, when treating an inflammatory disease or disorder, the antigen binding molecules of the invention may be used in combination with anti-inflammatory agents. Suitable anti-inflammatory agents include non-steroidal anti-inflammatory drugs (NSAIDS) and steroids. NSAIDS may be preferred, including but not limited to salicylates (such as aspirin (acetylsalicylic acid), diflunisal, salicylic acid, salsalate), propionic acid derivatives (ibuprofen, dexibuprofen, naproxen), acetic acid derivatives (indomethacin, diclofenac), enolic acid derivatives, anthranilic acid derivatives (fenamates), selective COX-2 inhibitors, and sulfonanilides.

When treating an immune-mediate disorder or disease, immunosuppressants may be used, for example glucocorticoids, cytostatics (such as alkylating agents, antimetabolites, methotrexate, azathioprine, mercaptopurine, or cytotoxic antibiotics). Of particular relevance to GvHD are glucocorticoids, such as cortisol, cortisone, prednisone, prednisolone, methylprednisolone, dexamethasone, betamethasone, triamcinolone, beclomethasone, fludrocortisone, deoxycorticosterone and aldosterone).

Further additional components that are desirable to use in combination with the antigen binding molecules of the invention include TNF-inhibitors, IL-12 inhibitors, IL-23 inhibitors and $\alpha4\beta7$ integrin inhibitors. The inhibitors may themselves be antigen binding molecules, such as antibodies and preferably monoclonal antibodies.

Suitable TNF inhibitors include infliximab (Remicade), adalimumab (Humira), certolizumab pegol (Cimzia), and golimumab (Simponi). Suitable IL-12 and IL-23 inhibitors include ustekinumab (Stelara), which is an inhibitor of both. Suitable $\alpha4\beta7$ integrin inhibitors include vedolizumab (Entyvio).

The pharmaceutical compositions of the invention may be formulated to include one or more additional pharmaceutically active components, such as those listed above. The antigen binding molecules of the invention may be provided as part of a kit. Such kits may include instructions for use and/or additional pharmaceutically active components. The antigen binding molecules may and the additional pharmaceutically active components may be disposed separately within the kit, or in some embodiments the antigen binding molecules may and the additional pharmaceutically active components may be formulated together.

In one embodiment of the invention there is provided an antibody, in particular a monoclonal antibody, that specifically binds to BDCA-2 (CLEC4C). The antibody is selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01. The antibodies are of use in the treatment of inflammatory diseases, including IBD.

In one embodiment, the invention provides an antigen binding molecule that specifically binds to an epitope of human BDCA-2 (CLEC4C), wherein the antigen binding molecule is selected from 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01, or fragments or variants thereof, for use in the treatment of systemic sclerosis, fibrosis (such as skin fibrosis), pemphigus vulgaris, systemic lupus erythematosus (SLE), cutaneous lupus, discoid lupus, lupus nephritis, polymyositis and dermatomyositis, psoriasis, rheumatoid arthritis, Grave's disease, morphea, inflammatory bowel disease, morphea, type I diabetes, Sjogren's disease and Hashimoto's disease. As used herein "inflammatory bowel disease" (IBD) relates to inflammatory conditions of the colon and small intestine. Of particular interest is the treatment of pemphigus vulgaris, Systemic sclerosis, lupus and Sjogren's disease.

This aspect of the invention therefore also extends to a method of treatment of inflammatory bowel disorders, comprising administration to the subject an antigen-binding molecule of the invention. In one embodiment, the inflammatory bowel disease may be Crohn's disease. In one embodiment, the inflammatory bowel disease may be ulcerative colitis. In an alternative embodiment, the invention may be seen as providing the use of an antigen binding molecule of the invention in the preparation of a medicament for the treatment of inflammatory bowel disorders. In one embodiment, the inflammatory bowel disease may be Crohn's disease. In one embodiment, the inflammatory bowel disease may be ulcerative colitis.

The present invention will now be further described with reference to a number of specific examples, which are presented for illustrated purposes and are not to be construed as limiting on the scope of the invention.

EXAMPLES

Cloning and Expression of BDCA-2

Approximately 2 μg of the GeneArt cassette containing either SEQ ID NO: 85 or SEQ ID NO: 87 was digested with BsmI and SbfI and the digests gel purified with a Qiagen gel extraction kit. The insert was ligated into pMQRtg using T4 ligase followed by transformation of ligation mixes (~25 ng vector) in chemocompetent *E. coli* XL1-Blue cells. Overnight cultures were performed (4 clones per construct) for miniprep followed by sequence verification and preparation of glycerol stocks. Endotoxin-free plasmid DNA of 1 sequence-verified clone was prepared with Sigma endotoxin-free maxiprep kit.

Transfection of each plasmid DNA (hIgG1-Fc-hBDCA-2 or His-hBDCA-2) was performed in 500 ml HEK293F cells using Polyplus FectoPRO DNA transfection reagent according to the manufacturer's instructions. The media was harvest at day 5 and purification of the Fc-hBDCA-2 was performed using MabSelect SuRe protein A affinity chromatography and the His-hBDCA-2 purified using Ni-NTA Agarose resin. The eluted fractions were buffered to phosphate buffered saline (PBS) by dialysis, filter sterilized (0.2 μM) and the concentration analysed by A280.

Transfection of U937 Cells with Human and Cynomolgus BDCA-2 Constructs

Human BDCA-2 (SEQ ID NO: 81) or cynomolgus BDCA-2 (SEQ ID NO: 83) was cloned into the pCDNA3.1 (+) expression vector via KpnI/NotI. $0.5\times10^6$ U937 cells (ECACC 85011440) were transfected with the plasmid using Lipofectamine 2000 transfection reagent (Invitrogen, 11668019) according to the manufacturer's instruction. 24 hours after, transfected and non-transfected cells were assayed for cell surface expression of human and cynomolgus BDCA-2 by flow cytometry assay using a FITC conjugated mouse anti-BDCA-2 antibody (Miltenyi Biotec cat. No. 130-090-510). High expressing positive BDCA-2 cells were isolated by a subcloning procedure.

Immunisation

Mice (C3H) were immunised with 100 ug of human BDCA-2-Fc (SEQ ID NO: 88) in Freund's complete adjuvant s.c. followed by 3 booster i.p. injections of human BDCA-2-Fc on days 22, 43 and 78. Test bleeds were taken on day 54 and 89 for analysis of anti-BDCA-2 antibody titres. Two mice with the highest antibody titres then received 80 ug human BDCA-2-His on day 116 followed by harvesting the spleen and electrofusion on day 121.

Electrofusion to Generate Hybridomas Secreting Anti-BDCA-2 Monoclonal Antibodies (mAbs)

Splenocytes were isolated from the immunised mice with a gentleMACS dissociator (Miltenyi Biotec) using protocols from the manufacturer. Hybridomas were generated by electrofusion (Techno Centre RU Nijmegen) of $30\times10^6$ isolated splenocytes with (NS-1) myeloma cells in a 1:1 ratio. The generated hybridoma cells were seeded into 50×96-well cell culture plates in Dulbecco's MEM F12 without glutamine (Gibco cat. No. 21331046) with 2 mM GlutaMax (Gibco cat. No. 10566016) and 1× penicillin/strep (Gibco cat. No. 15140122)+20% FBS (fetal bovine serum, Gibco). HAT selection medium (ThermoFisher cat. No. 21060017) was added and the hybridoma plates incubated for 10-14 days at 37° C. The hybridoma supernatant was then screened against BDCA-2 and BDCA-2-expressing cell lines in by ELISA and high-throughput flow cytometry.

Isolation of Plasmacytoid Dendritic Cells (pDC)

Peripheral blood mononuclear cells (PBMC) were isolated from EDTA anti-coagulated blood by density gradient separation using prefilled Leucosep™ tubes (Greiner Bio-One Ltd, UK) and pDCs were enriched from PBMC using Diamond Plasmacytoid Dendritic Cell Isolation Kit II (Miltenyi-Biotec, Bergisch Gladbach, Germany) following the manufacturer's protocol. Briefly, the isolation of PDCs is performed in a two-step procedure, firstly, the non-pDCs are indirectly magnetically labelled with a cocktail of biotin-conjugated antibodies against lineage-specific antigens and anti-biotin Microbeads. Depletion of non-pDCs (negative selection) was performed using an LD MACS® column and magnetic field MACS Separator (Miltenyi-Biotec). The pre-enriched pDCs from the first step were then libelled with pDC specific CD304 (BDCA-4/Neuropilin-1) Diamond Microbeads and isolated by positive selection over a MS MACS Column and magnetic field MACS Separator (Miltenyi-Biotec). Purified pDCs were then counted and tested for purity by FACS staining with mouse anti-human antibodies directed against lineage markers (VioBlue-CD3, CD14, CD19, CD56 and CD11c), APC-Vio770 HLA-DR, PerCPVio770-CD123 (IL-3R) and PE-CD304 (BDCA4) Abs. The purity of pDCs obtained was >98%.

Monoclonal Antibody Assays (Purified mAbs or Hybridomas) and Plasma Screening Assays for Anti-BDCA-2 Antibodies ELISA for Anti-BDCA-2 Hybridomas 96-well plates were coated with 100 ng/well his-BDCA-2 (SEQ ID NO: 86) in 100 ul of phosphate buffered saline (PBS) overnight at 4° C. The wells were then washed 3 times with PBST (PBS plus 0.05% Tween 20) and then blocked with 1% BSA (Sigma Aldrich A2934) in PBST for 1 hour at room temperature (RT). The wells were washed 3 times with PBST and 50 ul hybridoma supernatants with 50 μl 1% BSA in PBST were added for 1 hour at RT. The wells were washed 3 times with PBST and 100 μl goat anti-mouse Ig-HRP 1/5000 (ThermoFisher Scientific) in 1% BSA in PBST was added for a further 1 hour at RT. The wells were washed 3 times with PBST followed by 3 times with PBS then 50 μl TMB was added and the reaction stopped with 50 μl 2M $H_2SO_4$. The absorbance at 450 nm was measured in each well. Negative (1% FBS/PBS) and positive controls (anti-BDCA-2, AC144, 2 μg/ml, Miltenyi Biotec, cat. no. 130-090-690; anti-BDCA-2 BIIB059 from patent WO2014093396).

Flow Cytometry Assay

U937 Cells

Human and cynomolgus U937 cells were harvested and resuspended in 1% FBS/PBS at $1\times10^6$ cells/ml. 50 ul of each cell line was added to the well of a 96-well plate followed by 50 μl hybridoma supernatants to plates and incubation for 60 min in the dark on ice. The plates were then centrifuged for 7 min at 350 g, the supernatant discarded and the wells washed with 200 ul PBS followed by centrifugation and the supernatant again discarded. 50 ul per well of goat-anti-mouse PE (ThermoFisher Scientific) 1:400 in 1% FBS/PBS was added per well and incubated for 60 min at RT protected from the light. The wells were again washed and 30 μl/well 2% paraformaldehyde (PFA) in PBS was added and incubated for 20 min at 4° C., protected from light before analysis of the plates using a high-throughput IntelliCyt iQue screener.

EC50 Measurements on Cell-Expressed Target

Cells expressing human and cynomolgus BDCA-2 were resuspend at $2\times10^6$ cells/ml in FACS buffer (2% FBS/PBS) and 50 μl of the cell suspension was added per well, in a 96-well V bottom plate. The plate was centrifuge and the supernatant discarded. 12 serial, 2-fold dilutions of mAbs, starting at 50 μg/ml (range 50-0.024 μg/ml), in FACS buffer were prepared and 25 μl of the mAb dilutions added to wells, in triplicate. The plate was then incubated for 60 min at room temperature then centrifuged and washed 3× with 150 μl FACS buffer. To each well was then added 25 μl goat-anti-human PE conjugate (or goat-anti-mouse in the case of AC144), diluted 1:200 in FACS buffer. The plates were incubated for 60 min at room temperature protected from light and centrifuged and washed 3× with 150 μl FACS buffer. 25 μl per well of 2% PFA 2% was added and incubated for 20 min at 4° C., protected from light and analysed on the iQue screener.

BDCA2 Internalization

PBMC (2 million cells) were maintained for 16 h in RPM11640+10% FBS+1% PS in 96 well round bottom plate. Cells were cultured with or without 0.5 μM ODN2216 (Miltenyi Biotec) in the presence of increasing concentrations of 3E5 (0.0005-10 μg/ml). The plate was centrifuged at 300 g for 10 minutes and the cells labelled for FACS staining with mouse anti-human antibodies directed against lineage markers, APC-Vio770 HLA-DR, PerCPVio770-CD123 (IL-3R) and PE-CD304 and FITC-CD303. The gating strategy analysis detected changes in mean fluorescence intensity of cell surface CD303 expression (detected with Miltenyi Biotec clone AC144) on pDC (CD3-18-56-14-CD11C-DR+CD123+CD304+).

Intracellular Detection of Proteins and Cytokines

PBMCs from Healthy volunteers or from patients were prepared from EDTA anti-coagulated blood by density gradient separation using prefilled Leucosep™ tubes (Greiner Bio-One Ltd, UK). PBMCs ($2\times10^6$ cells) were maintained for 16-18 h in RPM11640 containing 10% Fetal Bovine Serum (FBS) and 1% Penicillin Streptomycin (Gibco Laboratories, Grand Island, NY) in a 96 well round bottom plate. Cells were cultured with or without 1 μM ODN2216 (TLR9 agonist, Miltenyi Biotec) in the presence or absence of mAb or control human IgG1 at 10 ug/mL concentration. The plate was then centrifuged at 300 g for 10 minutes and the supernatants were collected for serology studies and then the cell pellets were labelled for surface FACS staining with mouse anti-human antibodies directed against lineage markers (UV395-CD3, -CD14, -CD19, -CD56 and BV605-CD11c) all from BD Biosciences, APC-Vio770 HLA-DR, Viogreen-CD123 (IL-3R) and FITC-CD304 (BDCA4) all from Miltenyi Biotec. The plate was then incubated at 4° C. for 30 minutes and then 200 ul of FACS buffer was added to the wells, the plate centrifuged at 300 g for 10 minutes at 5° C. and the supernatants decanted.

The cell wash was repeated using 200 ul of ice cold-Dulbecco's PBS per well and the plate was centrifuged at 300 g for 10 minutes. Cells were then re-suspended in 200 ul of Fix/perm buffer (e-Biosciences) prepared according to the manufacturer instructions and the plate incubated at 4° C. for 30 minutes. The plate was again centrifuged at 300 g for 10 minutes at 4° C. and the cells were washed once by perma/wash buffer (e-Biosciences) by resuspension in 200 ul followed by centrifugation at 300 g for 10 minutes at 4° C., the supernatant decanted and the cells re-suspended in 100 ul of perm/wash buffer and labelled by antibodies directed against PE-Vio615 or APC IFN-I; PE-Vio770 TNF all from Miltenyi Biotec. The plate was incubated at 4° C. for 30 minutes then resuspended in 200 ul perm/wash buffer and centrifuged at 300 g for 10 minutes at 4° C. Finally, the cells were re-suspended in FACS buffer for flow cytometry analysis.

Functional Screening for Anti-BDCA-2 mAb Inhibition of IFNα and TNFα in pDC or PBMC When a TLR7 or TLR9 ligand such as imiquimod (InvivoGen) or ODN (InvivoGen) is added to human peripheral blood mononuclear cells (PBMC) or purified pDCs, the cells are activated and IFNα production is induced from pDCs (Dzionek et al. J Exp. Med. 2001, 194:1823-1834). The production inhibition of IFNα produced from pDCs by anti-human BDCA-2 mAbs was used as an index of the functional activity of the mAbs.

Purified healthy pDC (Stemcell), donor PBMC or SSc PBMC were used in the assay. 50 ul cells ($1\text{-}2\times10^4$ pDC in RPM11640/10% FBS or $1\text{-}2\times10^6$ PBMC in 10% autologous serum and 1% Penicillin Streptomycin from Gibco Laboratories, Grand Island, NY) were added to the well of a round bottomed 96-well plate for 1 hour at 37° C., 5% $CO_2$. 50 ul of mAbs or hybridoma supernatant was then added with or without 4 μM of the TLR7 agonist (Imiquimod, Sigma-Aldrich Corp, St. Louis, MO, USA), 1 μM of the TLR8 or TLR9 agonists (ORN and ODN2216 respectively from Miltenyi Biotec). The plate was incubated for 16 hours at 37° C., 5% CO2 and the cell free supernatant was assayed for IFN I level using a commercially available ELISA kit (PBL Assay Science, Piscataway, NJ, USA) or TNFα (ThermoFisher kit) according to the manufacturer's instructions. Negative control was buffer only and the positive control was AC144 (Miltenyi Biotec, cat. no. 130-090-690).

Intracellular Detection of Proteins and Cytokines

Cell pellets from the above assays were labelled for surface FACS staining with mouse anti-human antibodies directed against lineage markers (UV395-CD3, -CD14, -CD19, -CD56 and BV605-CD11c) (BD Biosciences), APC-Vio770 HLA-DR, Viogreen-CD123 (IL-3R) and FITC-CD304 (BDCA4) (Miltenyi Biotec). The plate was then incubated at 4° C. for 30 minutes followed by addition of 200 ul of FACS buffer and centrifugation at 300 g for 10 minutes at 4° C. Supernatants were decanted and the cells washed using 200 ul of ice cold-Dulbecco's PBS. Cell pellets were re-suspended in 200 ul of Fix/perm buffer (e-Biosciences) and the plate incubated at 4 C for 30 minutes. Following centrifugation, cells were washed once in 200 ul of perma/wash buffer (e-Biosciences) and centrifuged again. Remaining cells were re-suspended in 100 ul of perm/wash buffer and labelled by antibodies directed against PE-Vio615 or APC IFN-I; PE-Vio770 TNF (Miltenyi biotec). The plate was incubated at 4 C for 30 minutes, then resuspended in 200 ul perm/wash buffer and centrifuged. Finally, the cells were re-suspended in FACS buffer for flow cytometry analysis.

RNA Sequencing of Healthy pDC

Firstly, pDC were cultured as above in RPM11640 plus 10% FBS+1% PS (unstimulated), 1 μM ODN2216 with and without 10 ug/ml anti-BDCA-2 mAbs. RNA was extracted from the cells using RNeasy minikit (Qiagen, Hilden, Germany) according to manufacturer's protocol. Ovation® RNA-Seq System V2 (NuGEN, San Carlos, USA) was used to amplify total RNA from all samples. Briefly, first-strand cDNA was made and used to generate double-stranded cDNA followed by a SPIA® amplification. cDNA were quantified by using Qubit dsDNA BR Assay kit (Thermo Fisher Scientific, Waltham, MA) and the quality was checked by using D1000 screen tape on a Tapestation (Agilent, Santa clara, CA, USA). Covaris S2 sonicator (Woburn, MA, USA) was used to fragment all the cDNA at a size of 200 bp. 50 ng cDNA was used to make libraries by using NEBNext® Ultra™ DNA Library Prep Kit for Illumina (Ipswich, MA, USA) without any size selection.

The size distribution of the final libraries were checked using the tapestation and quantified using Quant-iT™ PicoGreen™ dsDNA Assay Kit (Thermo Fisher Scientific). All the libraries were pooled at a concentration of 10 ng and were sequenced on a Hiseq 3000 instrument (Illumina, San Diego, CA, USA). Pooled sequence data was demultiplexed using Illumina bcl2fastq software, allowing no mismatches in the read index sequences. Raw paired-end sequence data in Fastq format were quality-checked using FastQC software (Andrews 2010).

Cutadapt software (Martin 2011) was used to trim poor quality bases (Phred quality score <20) and contaminating adapter sequences from raw reads. Reads trimmed to fewer than 30 nucleotides and orphaned mate-pair reads were discarded. Reads were aligned to human hg38 analysis set reference sequences, obtained from UCSC database (Kuhn et al. 2013) using splicing-aware STAR aligner (Dobin et al. 2013). STAR aligner was run in 2-pass mode, with known splice junctions supplied in GTF file format, obtained from hg38 RefSeq gene annotation table from UCSC database using Table Browser tool (Karolchik et al. 2004).

The resulting alignments in BAM file format were checked for quality using QualiMap software (Okonechnikov et al. 2015) and Picard tools (Wysoker et al. 2013). Picard tools were used to mark PCR/Optical duplicate alignments. BAM files were sorted and indexed using Samtools software (Li et al. 2009) and visualised using IGV browser (Robinson et al. 2011). Bioconductor R package RSubread (Liao et al. 2013) was used to extract raw sequenced fragment counts per transcript using RefSeq hg38 transcript annotation set. Paired-end reads were counted as a single fragment and multi-mapping read pairs were counted as a fraction of all equivalent alignments.

Raw count data were normalised for library size differences using median ratio method (Anders and Huber 2010), as implemented in DESeq2 R Bioconductor package (Love et al. 2014). DESeq2 was also used to perform additional data QC steps and differential expression analyses. False Discovery Rate (FDR) was calculated using Benjamini-Hochberg multiple testing correction. Genes below 5% FDR threshold were considered differentially expressed. Differentially expressed gene expression was visualised as clustered heatmaps using Pheatmap R package (Kolde 2012), using log-transformed normalised gene expression values as input. Principal Component Analysis (PCA) was carried out using 'prcomp' R function, using the expression of 1000 most variable genes as input. Gene enrichment analyses and annotation were performed using R Bioconductor packages clusterProfiler (Yu et al. 2012) and ReactomePA (Yu et al. 2016). Additionally, KEGG (Kanehisa and Goto 2000) pathways were visualised using Pathview package (Luo and Brouwer 2013).

Organotypic 3D Skin Cultures

Primary normal human dermal fibroblasts and keratinocytes (from caucasian female breast tissue) (Promocell) were used to generate a skin-like 3D culture. These cells were routinely cultured in DMEM+10% FBS+1% PS and complete Keratinocyte Growth Medium 2+1% PS (Promocell), respectively, and handled according to user guidelines. Firstly, fibroblast-collagen cultures were prepared in Falcon cell culture inserts and placed into Falcon 6 Well Deep Well TC-Treated Polystyrene Plates (BD Biosciences). These cultures were prepared on ice by adding PureCol bovine type 1 collagen (Advanced Matrix), followed by 10×HBSS (ThermoFisher Scientific) (bringing to the correct pH using NaOH single droplets until media turned pink) and then 2×105 fibroblasts in FBS, following the composition ratio of 8:1:1. Using chilled stripettes, 2.5 ml of the mixture was added carefully to each well.

Cultures were left at 37° C. for 2 hours without CO2. Complete KGM™ Keratinocyte Growth Medium BulletKit™ (Lonza) was then added into the well (12.5 ml), and on top of the set collagen culture (2.5 ml) and left overnight at 37° C. with 5% CO2. Media was carefully removed from the gel and 2×106 keratinocytes were seeded in 2 ml of media/well and left overnight. Cultures were finally placed into Air-Liquid Interphase (ALI) by carefully removing all media and adding 10 ml of ALI media into the bottom of the wells. ALI contained Complete KGM Lonza media without BPE supplement, with the addition of 50 μg/ml of ascorbic acid, 1 mg/ml BSA, 10 ug/ml Transferrin, and 1.1 mM of CaCl2 (Promocell). Cultures were media changed every 2-3 days and left for 5 days. On day 5, ALI was supplemented with supernatants from pDC treated as above (CTR; no TLR9 stimulation, ODN; TLR9 stimulation, ODN+AB; TLR9 stimulation plus 10 ug/ml antibody) to produce a final concentration of 6000 pg/ml of IFN in the ODN experiment (determined via ELISA, approx. dilution of supernatants 1:20). Cultures were left for 48 hours. 3 mm punch biopsies were taken and harvested for histology analysis. Remaining culture was collected into 1 ml of TRIzol™ and processed for RNA extraction as described.

Xeno-Transplant Mouse Models of Human pDC Activation 20 female, NOD-SCID mice, aged 4 to 8 weeks, were purchased from Charles River. All mice were housed in accordance with local and Home Office regulations. Mice were shaved on the back and received topical Aldara application (5%, TLR7 agonist Imiquimod; 3M Health Care Limited). After 12 h, a second application of the cream and an intraperitoneal (i.p.) injection of 3E5 mAb (5 mg/kg) was administrated. 12 h later the mice received an intravenous (i.v.) tail injection of 2.5×105 pDC. Mice were then euthanized after a further 12 h. The skin was harvested using a punch biopsy and processed for RNA, FACS and histology analysis.

For the bleomycin induced fibrosis model, 15 female, aged 4 to 8 weeks, NOD-SCID mice were utilised. Bleomycin (BLM) (Sigma) was diluted to 200 μg/ml with PBS. Bleomycin or PBS (100 μl) were injected subcutaneously into a single location on the shaved back of the female mice once every other day for 3 weeks. Nine mice received human PDc, ($2.5\times10^5$) which were injected i.v. on days 0, 7 and 14 in a 100 μl volume. 3E5 mAb or human IgG at doses of 2.5 mg/kg were injected intra-peritoneally every 5 days starting on day −1 (n=5 i.p. injections per mouse). Masson trichrome was used to dye collagen blue and muscle red to identify the extent of fibrosis in the skin samples. Briefly, 3 dyes are used sequentially; Weigerts iron haematoxylin for nuclei, ponceau fuchsin for muscle, cytoplasm and erythrocytes, and methyl blue for collagen. In between stains, slides are washed in water. Prior to adding the final methyl blue dye, two Phoshotungstic acid incubations were performed. Slides were mounted post water rinse, dehydration in alcohol and Xylene. For epidermal and dermal measurements, each condition was performed in triplicate mice. For each mouse, one 20× H&E representative image was used to take 10 measurements. Epidermal measurement was taken from the top of the skin section to the basement membrane, while the dermal measurement also included up until the top of the muscle layer.

Soluble collagen was quantified using the Sircol soluble collagen assay (Biocolor, Belfast, UK). Punch biopsy skin samples were obtained from the NOD-SCID mice and the protein extracted and homogenised using M-PER mammalian protein extraction reagent (Thermo Scientific) and two 7 mm metal beads. The samples were then further extracted using acetic acid-pepsin solution. The samples were analyzed for collagen content according to the manufacturer's protocol. Briefly, 100 μl of sample was added to 1 ml of the colorimetric reagent and agitated for 30 min followed by centrifugation at 10,000 g for 10 min. The SR dye was released from the pellet with alkali reagent and absorbance measured at 555 nm using a microplate reader. Collagen concentration was calculated using the standard curve generated from collagen reference standards. Concentrations were normalised for total protein concentrations calculated by Pierce™ BCA Protein Assay Kit (Thermo Scientific).

RNA Extraction from Mice Skin, Organotypic 3D Skin Cultures and ISG Response Analysis RNA was extracted using TRIzol™ Plus RNA Purification Kit (Thermo Fisher Scientific, Waltham, MA) as per the manufacturer's instruction. Briefly, RNA later fixed mouse skin was homogenised in TRIzol using two 7 mm metal beads and a TissueLyser LT (Qiagen). Homogenates were centrifuged to separate an RNA containing aqueous phase, after which it was further purified by PureLink columns and genomic DNA removed by DNase (Life Technologies, Carlsbad, CA, USA). Eluted RNA was converted to cDNA using RT2 First Strand Kit (Qiagen). Next, the cDNA was mixed with an appropriate RT2 SYBR Green Mastermix (Qiagen). The mouse IFN I RT2 Profiler PCR Array (Qiagen) was performed and relative expression determined using the ΔΔCT method and normalized for 5 housekeeping genes according to manufacturer's guidance.

Histology 3 mm punch biopsies from mice, organotypic 3D skin cultures or patients were formalin-fixed and embedded in paraffin. Sections were cut at 5 μM and subjected to haematoxylin and eosin staining. Antigen retrieval was performed using 10 mM pH 6.0 sodium citrate and sections were stained with anti-MX1 antibody (abcam, Cambridge, UK) at 1:1000 dilution followed by ImmPRESS™ (Peroxidase) Polymer Anti-Rabbit IgG Reagent (Vector Laboratories, Burlingame, USA), and visualised with 3, 3-diaminobenzidine (DAB) (Vector Laboratories). Mouse spleen, healthy skin and negative staining was performed for controls. Microscopic analysis was performed using an Olympus BX50 with MicroFire (Optronics) and images captured using Stereo Investigator software at 20× magnification.

FACS on Mouse Skin Samples

Skin samples from mice were enzymatically digested to release cells using 1 mg/ml collagenase D (Roche, Basel, Switzerland), 0.5 mg/ml dispase (Roche) and 0.1 mg/ml DNase-I (Invitrogen, Carlsbad, CA, USA) in Hanks' balanced salt media (Sigma-Aldrich Corp). For FACS analysis, the released cells were stained with antibodies against human CD45, CD123, CD304 (Miltenyi Biotec). Gating strategy excluded dead cells using Aminoactinomycin D (7-AAD) (BD Biosciences) and sequential gating for human CD45+CD123+CD304+. The data acquisition was performed on LSRII 4 laser flow cytometer (BD Biosciences), and the analysis was conducted using FACS DIVA software (BD Biosciences).

Affinity Analysis of Humanized mAbs by BIAcore

A BIAcore T200 was used with BIAcore run buffer (HBS-EP) at pH7.4. 692RU of huBDCA2-Fc was immobilized to a CM5 chip (CFJB156) utilising 5 μg/ml of huBDCA2-Fc with the BIAcore EDC/NHS kit according to the manufacturer's instructions. Two-fold dilutions of the humanized mAbs were injected starting at 200 nM down to 3.1 nM with a contact time of 60 s at a flow of 30 or 60 ul/min at 25° C. followed by an off-rate wash for 5 minutes with BIAcore buffer. Regeneration of the chip was achieved with two injections of 10 μl of 10 mM NaOH/1M NaCl between samples. The BIAcore T200 software was used to calculate Ka (1/Ms), Kd (1/s) and the KD (nM).

ELISA Assay for Humanized mAbs 100 ul per well of 0.5 μg/ml of human BDCA2-Fc in PBS pH 7.4 was incubated overnight at 4 C. The wells were then washed 3 times with PBST (PBS+0.05% Tween 20) and then blocked with 250 ul 4% Skimmed Milk (Marvel, cat. no. 3023033 Lot no. 7169) in PBS for 120 min at RT. The wells were washed and then incubated with 100 ul per well of humanized mAbs at 3 fold dilutions (from 1 μg/ml to 0.001 μg/ml) in 1% Skimmed Milk PBS buffer at pH 7.4. After 60 min at RT the wells were washed 3 times in PBST and 100 ul of mouse anti-human IgG (anti-CH1-HRP; 1:1000, BD Pharmigen cat. no. 555788) or donkey anti-mouse IgG (anti-mouse IgG-HRP) at 1:5000 dilution (Jackson ImmunoResearch, Cat. no. 715-035-150) in 1% Skimmed Milk PBS was added. Development was with TMB (ThermoFisher, cat. no. 00-4201-56), 100 ul/well and the reaction stopped with 100 µl/well H2SO4 (cat. nr. J/8430/15, lot nr.) and the absorbance read at 450 nm. The EC50 was calculated using Graphpad Prism software. A negative (1% Skimmed Milk/PBS) and positive control (anti-BDCA-2, AC144, Miltenyi Biotec, cat. no. 130-090-690) were utilised in the assay.

Preparation of Chimeric mAbs

A construct containing the synthetic gene coding for the constant human IgG1 domain (mammalian codon optimized), with DNA flanking regions for correct cloning into the mammalian expression vector, was purchased from GeneWiz (GeneWiz France Ltd). The DNA was reconstituted according to the manufacturer's instructions and transformed into *E. coli* TOP10 chemically competent cells (C Cells). The DNA insert coding the constant human IgG1 domains was digested out of the construct and ligated into the mammalian expression vector. The correct generation of the human IgG1 expression vector was confirmed by DNA sequence analysis (below). Synthetic genes coding for the variable domains of four anti-BDCA-2 mouse Fabs (below) were recloned into a mammalian expression vector comprising the human IgG1 HC and human CL domains. The ExpiCHO-S Expression System (ThermoFisher cat. No. A29133) was used according to the manufacturer's instructions.

The produced chimeric mAb human IgG1 molecules were purified using HiTrap MabSelect SuRe (Sigma Aldrich) 5 ml columns in an ÄKTA pure 25 system (GE Healthcare Life Sciences) and eluted using 0.1 M sodium citrate at pH 3.0 and 1.0 ml fractions were collected in tubes containing 0.1 ml Tris-HCl pH 9.0 for neutralization. Chimeric mAb containing fractions were pooled and buffer exchanged into PBS (phosphate buffered saline) using a HiTrap Desalting column in ÄKTApure. Protein concentration was determined by measuring the optical density at 280 nm using a microvolume spectrophotometer and the purified chimeric mAbs were analysed by SDS-PAGE.

Preparation of Humanized mAbs

The wildtype and variant VH and VL sequences of mAb 28B01VHVL (VH1-3; VK1-2) (SEQ ID NO: 75 and SEQ ID NO: 71) and mAb 3E05VHVL (VH1-4; VK1-4) (SEQ ID NO: 5 and SEQ ID NO: 1) were synthesized and codon-optimised for expression in CHO cells, subcloned into heavy and light chain expression vectors, and sequence-verified to confirm identity prior to CHO transfection using plasmid midiprep DNA. The method used was the same as described for the chimeric mAb expression and purification.

Statistical Analysis

GraphPad Prism 7 software (GraphPad 50 Software, Inc., La Jolla, CA, USA) was used for statistical analysis. Pearson's correlation was used to analyse the association between all studied parameters. One-way analysis of variance combined with Mann-Whitney test or unpaired two tailed t-test were used to evaluate statistically significant differences between groups. Data were expressed as the mean±standard error (SE). Significance was considered with a P value less than 0.05.

Epitope Mapping of 3E5

For the characterization of BDCA2(CLEC4C)/3E5 (variant 12) complexes, the measurements were performed using an Autoflex II MALDI ToF ToF mass spectrometer (Bruker) equipped with a CovalX HM4 interaction module. The CovalX interaction module contains a detecting system designed to optimize detection up to 2MDa with nano-molar sensitivity. Initial experiments determined that Using High-Mass MALDI mass spectrometry and chemical cross-linking, we did not detect any non-covalent aggregates of 3E5 or multimers of CLEC4C. In order to characterize CLEC4C we submitted the sample to trypsin, chymotrypsin, Asp-N, elastase and thermolysin proteolysis followed by nLC-LTQ-Orbitrap MS/MS analysis. For the characterization, a nLC Ultimate 3000-RSLC system in line with a LTQ-Orbitrap mass spectrometer (Thermo Scientific) was used. Sample preparation was as follows:

Reduction Alkylation

10 µL of CLEC4C (15.11 µM) were mixed with 1 µL of DSS d0/d12 (2 mg/mL; DMF) before 180 minutes incubation time at room temperature. After incubation, reaction was stopped by adding 1 µL of Ammonium Bicarbonate (20 mM final concentration) before 1 h incubation time at room temperature. Then, the solution was dried using a speedvac before H2O 8M urea suspension (10 µL). After mixing, 1 µl of DTT (500 mM) was added to the solution. The mixture was then incubated 1 hour at 37° C. After incubation, 1 µl of iodoacetamide (1M) was added before 1 hour incubation time at room temperature, in a dark room. After incubation, 100 µl of the proteolytic buffer were added. The trypsin buffer contains 50 mM Ambic pH 8.5, 5% acetonitrile, the chymotrypsin buffer contains Tris HCl 100 mM, CaCL2 10 mM pH 7.8; The ASP-N buffer contains Phopshate buffer 50 MM pH 7.8; The elastase buffer contains Tris HCl 50 mM pH 8.0 and the thermolysin buffer contains Tris HCl 50 mM, CaCL2 0.5 mM pH 9.0.

Trypsin Proteolysis

100 µl of the reduced/alkyled CLEC4C were mixed with 1 µl of trypsin (Roche Diagnostic) with the ratio 1/100. The proteolytic mixture was incubated overnight at 37° C.

Chymotrypsin Proteolysis

100 µl of the reduced/alkyled CLEC4C were mixed with 0.5 µl of chymotrypsin (Roche Diagnostic) with the ratio 1/200. The proteolytic mixture was incubated overnight at 25° C.

ASP-N Proteolysis

100 µl of the reduced/alkyled CLEC4C were mixed with 0.5 µl of ASP-N(Roche Diagnostic) with the ratio 1/200. The proteolytic mixture was incubated overnight at 37° C.

Elastase Proteolysis

100 µl of the reduced/alkyled CLEC4C were mixed with 1 µl of elastase (Roche Diagnostic) with the ratio 1/100. The proteolytic mixture was incubated overnight at 37° C.

Thermolysin Proteolysis

100 µl of the reduced/alkyled CLEC4C were mixed with 2 µl of thermolysin (Roche Diagnostic) with a ratio 1/50. The proteolytic mixture was incubated overnight at 70° C. After digestion formic acid 1% final was added to the solution.

After proteolysis, 10 µl of the peptide solution generated by proteolysis were loaded onto a nano-liquid chromatography system (Ultimate 3000-RSLC) followed by LTQ-Orbitrap MS analysis.

Results:

Trypsin proteolysis: 17 peptides were identified in the sequence of CLEC4C, covering 75.74% of the sequence. Chymotrypsin proteolysis:33 peptides were identified in the sequence of CLEC4C, covering 98.81% of the sequence. ASP-N proteolysis: no peptide was identified in the sequence of CLEC4C. Elastase proteolysis: 21 peptides were identified in the sequence CLEC4C, covering 91.72% of the sequence. Thermolysin proteolysis: 28 peptides were identified in the sequence of CLEC4C, covering 83.43% of the sequence.

Figure 13:
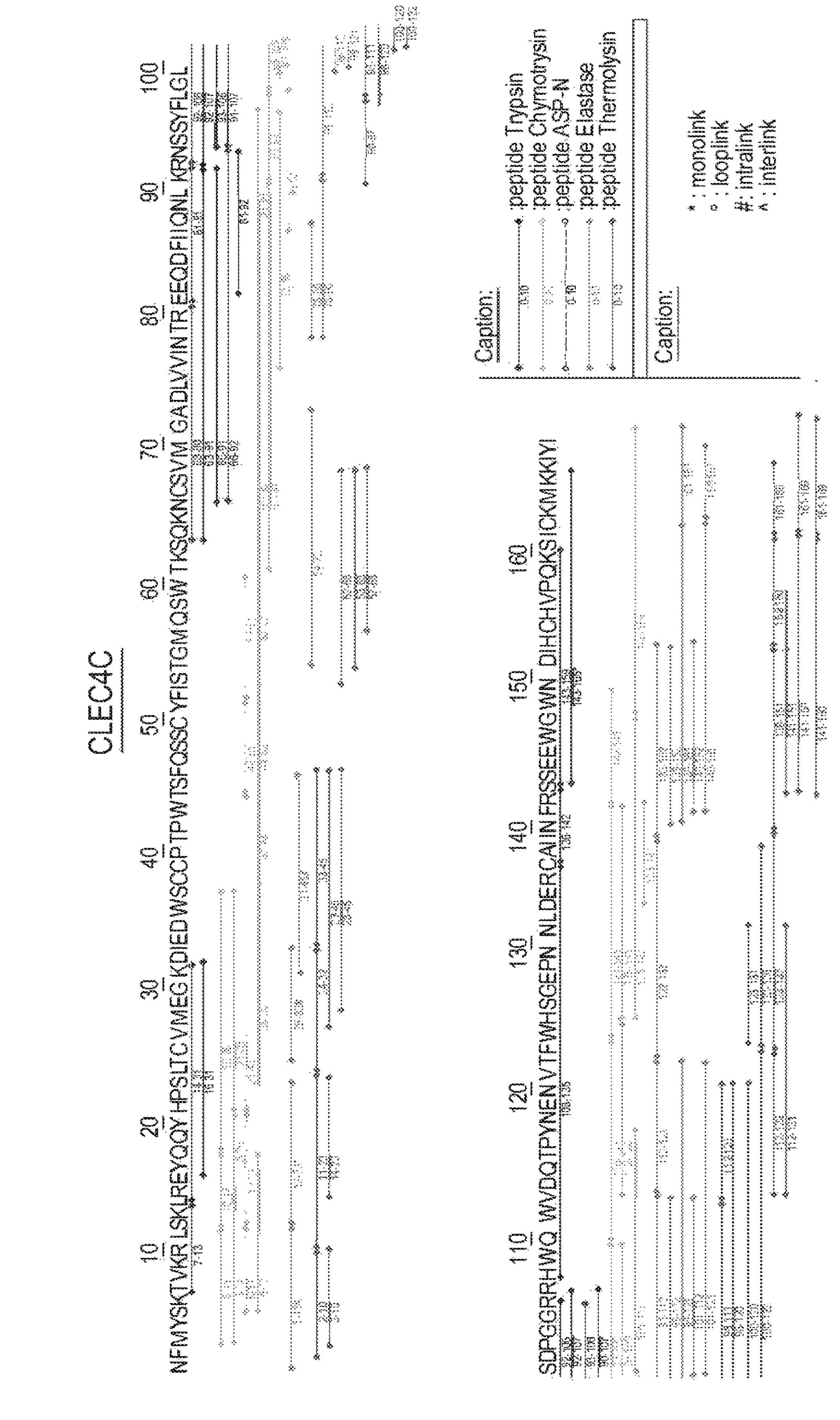
FIG. 13. Design of overlap mapping of trypsin, chymotrypsin, ASP-N, elastase and thermolysin peptides using proteolysis for epitope determination. Combining the peptides of trypsin, chymotrypsin, elastase and thermolysin proteolysis, 100% of the sequence is covered. The amino acid numbering refers to the extracellular domain of BDCA-2, amino acids 45-213 of Q8WTT0 (SEQ ID NO: 90) whereby amino acid 1 in FIG. 13 is amino acid 45 in Q8WTT0 (SEQ ID NO: 90).

Based on the results obtained, we designed overlap mapping of the trypsin, chymotrypsin, ASP-N, elastase and thermolysin peptides (FIG. 13). Combining the peptides of Trypsin, Chymotrypsin, Elastase and Thermolysin proteolysis, 100% of the sequence is covered.

Characterization of the Molecular Interfaces

In order to determine the epitope of CLEC4C/3E5 complex with high resolution, the protein complexes were incubated with deuterated cross-linkers and subjected to multi-enzymatic cleavage. After enrichment of the crosslinked peptides, the samples were analyzed by high resolution mass spectrometry (nLC-LTQ-Orbitrap MS) and the data generated were analyzed using XQuest and Stavrox software.

Sample Preparation:

Mixture of CLEC4C/3E5 was prepared with the following concentrations:

| | CLEC4C | | 3E5 | | CLEC4C/3E5 | |
|---|---|---|---|---|---|---|
| Mixture | Volume | Conc. | Volume | Conc. | Volume | Conc. |
| CLEC4C/ 3E5 | 10 µl | 5 µM | 10 µl | 2.5 µM | 20 µl | 2.5 µM/ 1.25 µM |

Reduction Alkylation

20 µL of the CLEC4C/3E5 mixtures prepared were mixed with 2 µL of DSS d0/d12 (2 mg/mL; DMF) before 180 minutes incubation time at room temperature. After incubation, reaction was stopped by adding 1 µL of Ammonium Bicarbonate (20 mM final concentration) before 1 h incubation time at room temperature. Then, the solution was dried using a speedvac before H2O 8M urea suspension (20 µL). After mixing, 2 µl of DTT (500 mM) were added to the solution. The mixture was then incubated 1 hour at 37° C. After incubation, 2 µl of iodoacetamide (1M) were added before 1 hour incubation time at room temperature, in a dark room. After incubation, 80 µl of the proteolytic buffer were added. The trypsin buffer contains 50 mM Ambic pH 8.5, 5% acetonitrile; The Chymotrypsin buffer contains Tris HCl 100 mM, CaCl2 10 mM pH 7.8; The ASP-N buffer contains Phopshate buffer 50 MM pH 7.8; The elastase buffer contains Tris HCl 50 mM pH 8.0 and the thermolysin buffer contains Tris HCl 50 mM, $CaCl_2$) 0.5 mM pH 9.0.

Trypsin Proteolysis

100 µl of the reduced/alkyled CLEC4C/3E5 mixture were mixed with 1.12 µl of trypsin (Roche Diagnostic) with the ratio 1/100. The proteolytic mixtures were incubated overnight at 37° C.

Chymotrypsin Proteolysis

100 µl of the reduced/alkyled CLEC4C/3E5 mixture were mixed with 0.56 µl of chymotrypsin (Roche Diagnostic) with the ratio 1/200. The proteolytic mixtures were incubated overnight at 25° C.

ASP-N Proteolysis

100 µl of the reduced/alkyled CLEC4C/3E5 mixture were mixed with 0.56 µl of ASP-N(Roche Diagnostic) with the ratio 1/200. The proteolytic mixtures were incubated overnight at 37° C.

Elastase Proteolysis

100 µl of the reduced/alkyled CLEC4C/3E5 mixture were mixed with 1.12 µl of elastase (Roche Diagnostic) with the ratio 1/100. The proteolytic mixtures were incubated overnight at 37° C.

Thermolysin Proteolysis

100 µl of the reduced/alkyled CLEC4C/3E5 mixture were mixed with 2.24 µl of thermolysin (Roche Diagnostic) with a ratio 1/50. The proteolytic mixtures were incubated overnight at 70° C. After digestion formic acid 1% final was added to the solution.

Results

Hybridoma Screening

Hybridomas from 96-well plates were initially screened by ELISA and 99 positives were identified and further screened on human and cynomolgus BDCA-2 U937 cells. From the second screen 34 positives were identified and the culture scaled up to 24-well plates and the mouse IgG was purified from the media and retested. Of these positive clones, 8 were selected that bound selectively to pDC. Of these positive clones, 5 showed inhibition of ODN stimulated IFNα release.

Figure 2:
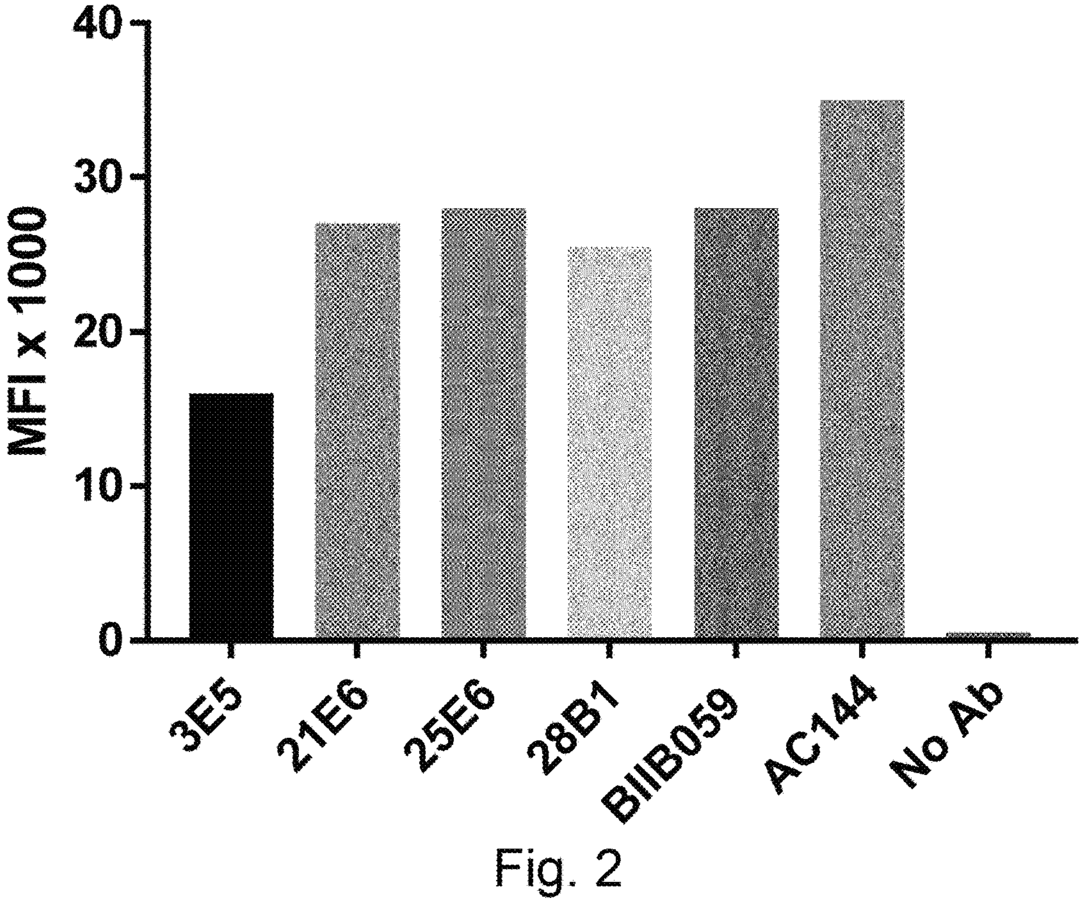
FIG. 2. Chimeric mAbs binding to plasmacytoid dendritic cells. Purified mAbs (10 ug/ml) were tested by flow cytometry to bind to purified pDC. Positive controls used were anti-BDCA-2 mAbs, AC144 (Miltenyi Biotech, cat. no. 130-090-690) and BIIB059 (patent WO2014093396) and the negative control was buffer (no Ab).

The genes encoding the heavy and light chain of the five mAbs selected (3E05, 25E06, 21E06, 28B01 and 24F3) were cloned into a human IgG1 vector, expressed, purified and retested. Four of the 5 mAbs showed good binding to both human and cynomolgus BDCA-2 in a cell binding assay (FIG. 1) whilst mAb 24F3 showed weak binding (data not shown) and was deselected from further assays. The chimeric mAbs (3E05, 28B01, 21E06 and 25E06) bound to human pDC (FIG. 2) and while mAbs 3E05 and 28B01 inhibited IFNα release from ODN stimulated pDC only weak inhibition was observed with mAbs 21E06 and 25E06.

Serial dilutions of the 4 chimeric mAbs (50-0.25 ug/ml) were prepared and incubated with cells expressing human and cynomolgus BDCA-2. After staining, the median fluorescence intensity (MFI) of the cells was measured and the data points of the dilution series were fitted on a sigmoidal curve after normalization to determine the EC50 values. Table 3 summarizes the results and shows that mAb 28B01 has equivalent EC50 values on cynomolgus and human BDCA-2 (Table 4) while the other 3 clones have a better EC50 for human than cynomolgus BDCA-2.

TABLE 3

EC50 determination of chimeric mAbs on cell expressed human and cynomolgus BDCA-2. Positive control was: AC144 (Miltenyi Biotec)

| mAb | EC50, ug/ml Human BDCA-2 | EC50, ug/ml cynomolgus BDCA-2 |
|---|---|---|
| 3E05 | 1.76 | 2.6 |
| 25E06 | 0.57 | 1.35 |
| 21E06 | 0.30 | 0.92 |
| 28B01 | 0.77 | 0.79 |

Figure 3A:
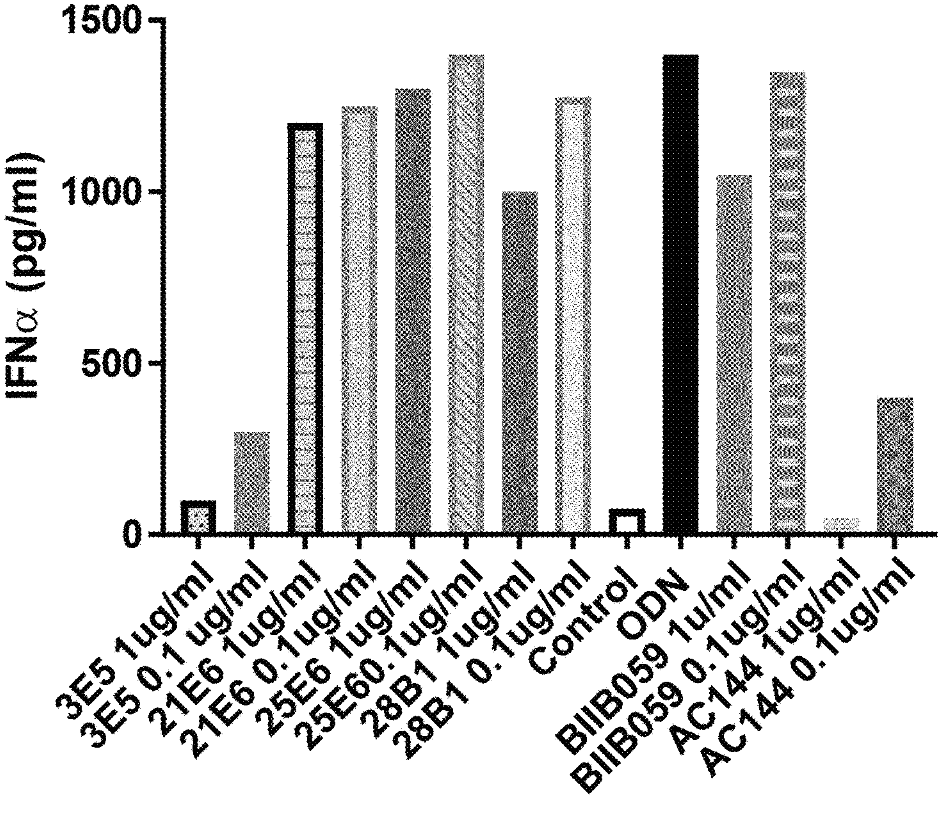
FIG. 3A. Effect of chimeric anti-BDCA-2 mAbs to inhibit IFNα from ODN stimulated pDC. mAbs were tested at 1 or 0.1 ug/ml to inhibit ODN induced IFNα from human purified pDC. Positive anti-BDCA-2 mAb controls used were: AC144 (Miltenyi Biotec, cat. no. 130-090-690) and BIIB059 (patent WO2014093396) and the negative control was buffer (no Ab).

The chimeric mAbs were also tested for their ability to inhibit ODN stimulated IFNα release from pDC (FIG. 3A).

Figure 3B:
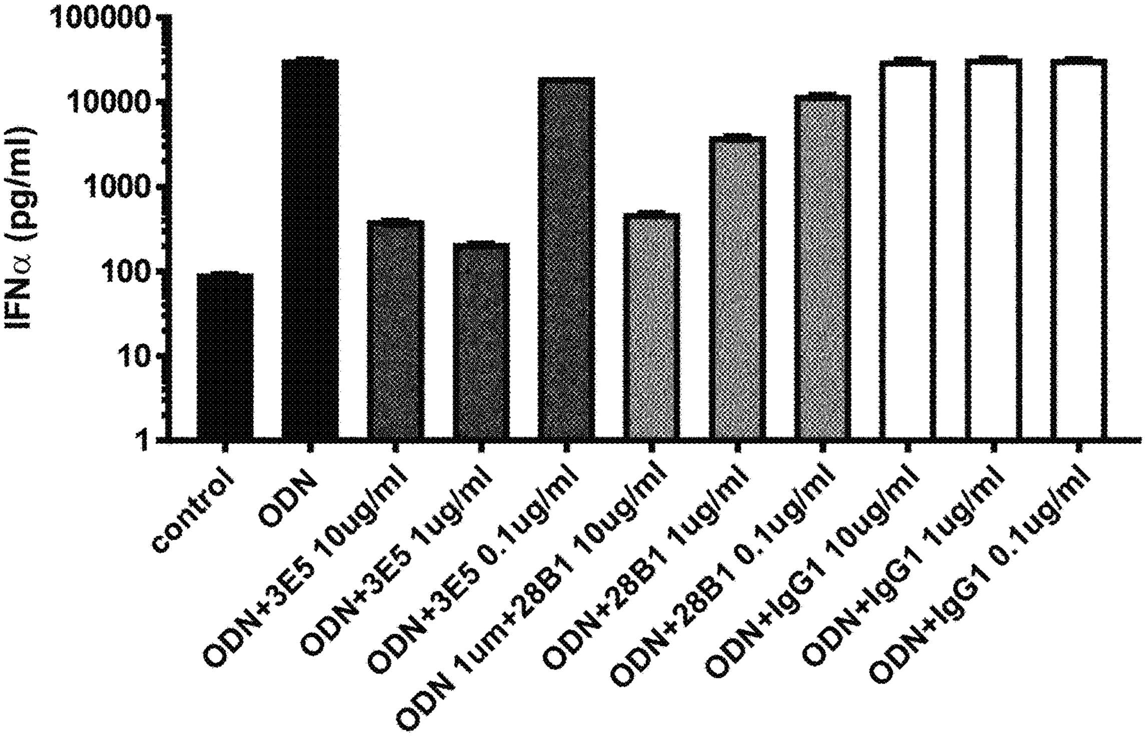
FIG. 3B. Effect of chimeric anti-BDCA-2 mAbs to inhibit IFNα from TLR9 (ODN, 1 uM) stimulated PBMC. mAbs were tested at 10, 1 or 0.1 ug/ml to inhibit ODN induced IFNα from human PBMC (500K/well). The negative controls were buffer (control) and hIgG1 at 10, 1 or 0.1 ug/ml.
Figure 3C:
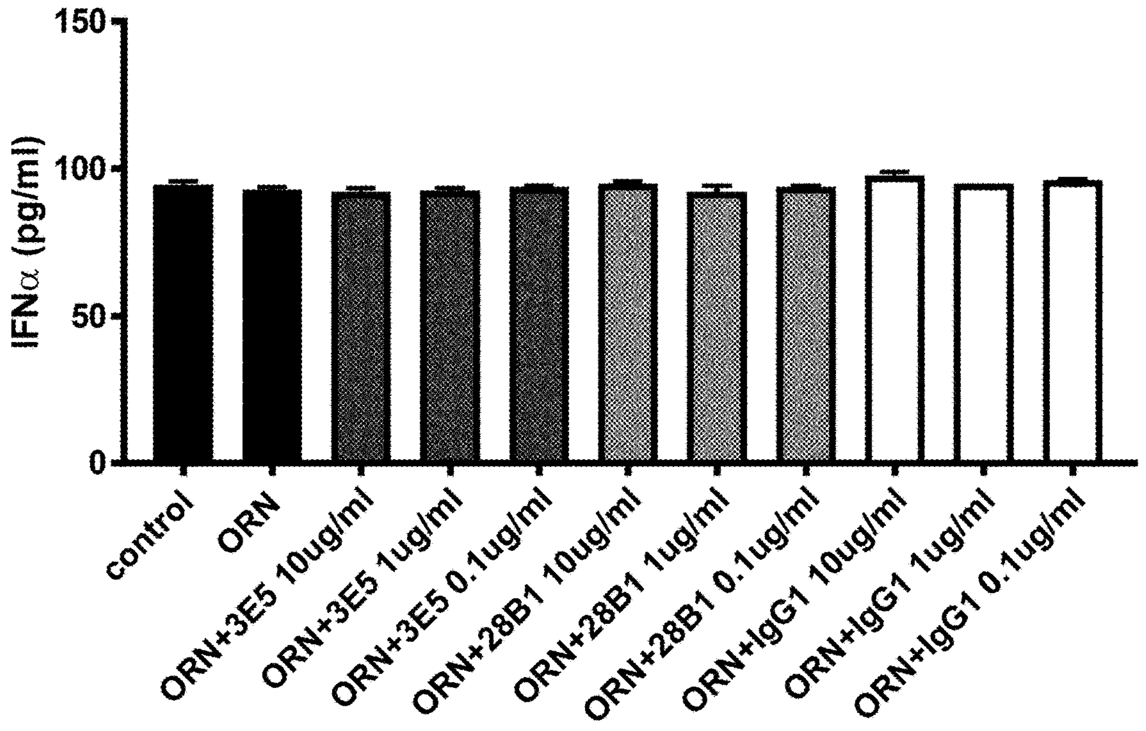
FIG. 3C. Effect of chimeric anti-BDCA-2 mAbs to inhibit IFNα from TLR8 (ORN, 1 uM) stimulated PBMC. mAbs were tested at 10, 1 or 0.1 ug/ml to inhibit ORN induced IFNα from human PBMC (500K/well). The negative controls were buffer (control) and hIgG1 at 10, 1 or 0.1 ug/ml.
Figure 3D:
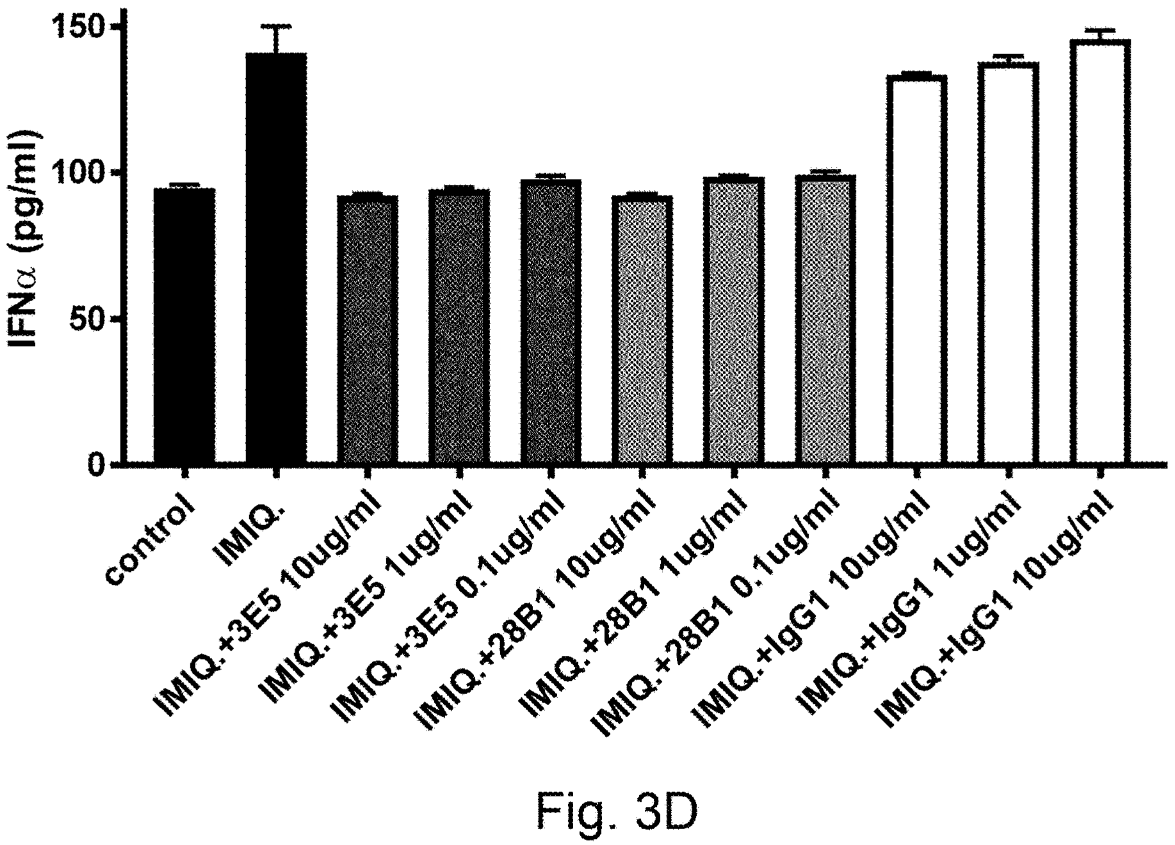
FIG. 3D. Effect of chimeric anti-BDCA-2 mAbs to inhibit IFNα from TLR7 (Imiquimod, 4 uM) stimulated PBMC. mAbs were tested at 10, 1 or 0.1 ug/ml to inhibit Imiquimod induced IFNα from human PBMC (500K/well). The negative controls were buffer (control) and hIgG1 at 10, 1 or 0.1 ug/ml.

At a concentration of 1 ug/ml chimeric mAb 3E05 inhibited IFNα to baseline levels to a similar level to the positive control AC144 mAb. Although chimeric mAb 28B01 showed inhibition of IFNα, very weak inhibition was observed with the chimeric mAbs 21E06 and 25E06. Further experiments delineated the effect of chimeric mAbs 28B01 and 3E05 to inhibit TLR9 (FIG. 3B), TLR8 (FIG. 3C) and TLR7 (FIG. 3D) agonist stimulated IFNα release from healthy PBMC. Both mAbs were very effective in the complete inhibition of TLR9 (ODN) or TLR7 (Imiquimod) stimulated IFNα release from pDC whilst no stimulation was observed with TLR8 (ORN, FIG. 3C) indicating that pDC do not possess TLR8 receptors.

Similar to the results with healthy pDC, the chimeric mAbs 3E05 and 28B01 were also able to completely inhibit IFNα secretion from ODN stimulated pDC in PBMC preparations from SSc patients (Table 4).

TABLE 4

Effect of chimeric anti-BDCA-2 mAbs to inhibit IFNα from ODN stimulated PBMC from SSc patients.
mAbs were tested at 10 ug/ml to inhibit ODN induced IFNα from SSc PBMC (500K cells; n = 3 patients) and the control was buffer (no Ab).

| Chimeric mAb 3E05 | IFNα, pg/ml (Mean ± SEM) | Chimeric mAb 28B01 | IFNα, pg/ml (Mean ± SEM) |
|---|---|---|---|
| Control | 37.0 ± 0.2 | Control | 117.5 ± 34.5 |
| 3E05 | 44.2 ± 7.0 | 28B01 | 117.5 ± 39.5 |
| ODN | 320.7 ± 127.6 | ODN | 3578 ± 2498 |
| ODN + 3E05 | 49.0 ± 5.7 | ODN + 28B01 | 246 ± 151 |

Figure 4A:
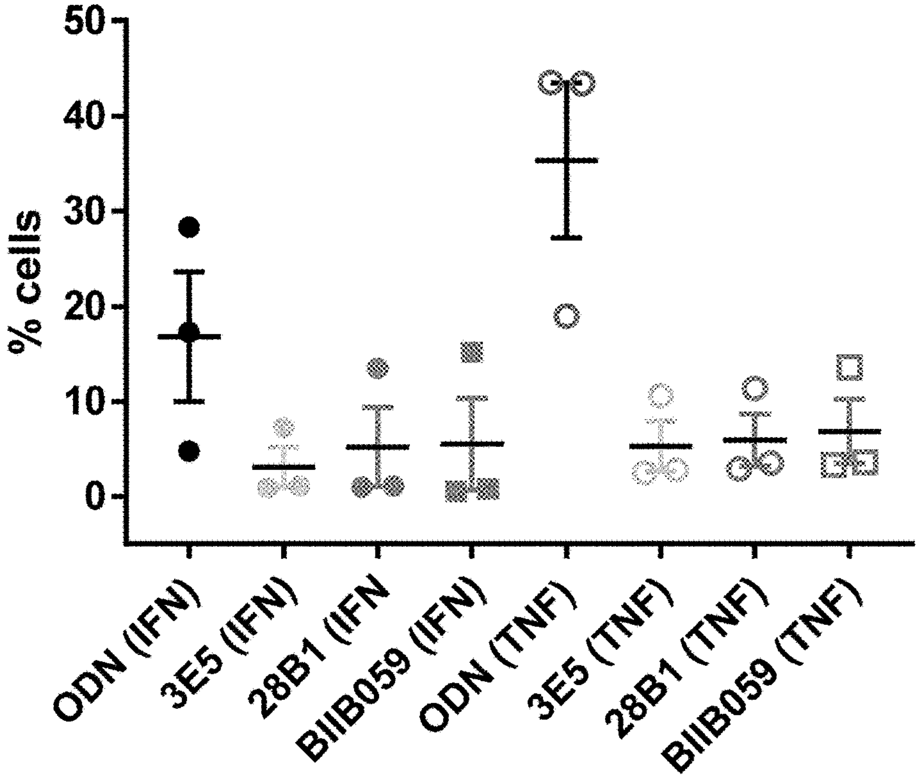
FIG. 4A. Effect of chimeric anti-BDCA-2 mAbs (10 ug/mi) to inhibit intracellular IFNα and TNFα from ODN stimulated healthy pDC. Positive control was anti-BDCA-2 mAb BIIB059 (patent WO2014093396) and the negative control was buffer (no Ab).
Figure 4B:
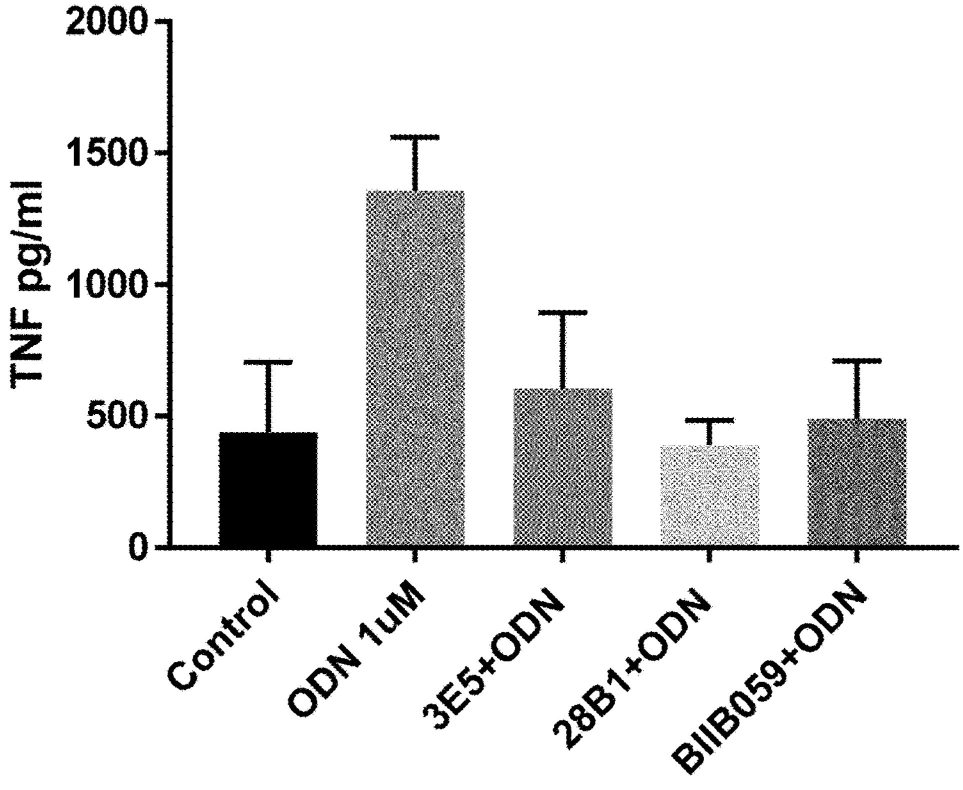
FIG. 4B. Effect of chimeric anti-BDCA-2 mAbs (10 ug/ml) to inhibit TNFα secretion from ODN stimulated healthy pDC. Positive control was anti-BDCA-2 mAb BIIB059 (patent WO2014093396) and the negative control was buffer (no Ab).

The chimeric mAbs 28B01 and 3E05 also inhibit intracellular levels of ODN stimulated pDC IFNα and TNFα as shown in FIG. 4A and ODN induced secreted levels of TNFα from pDC (FIG. 4B).

Figure 5:
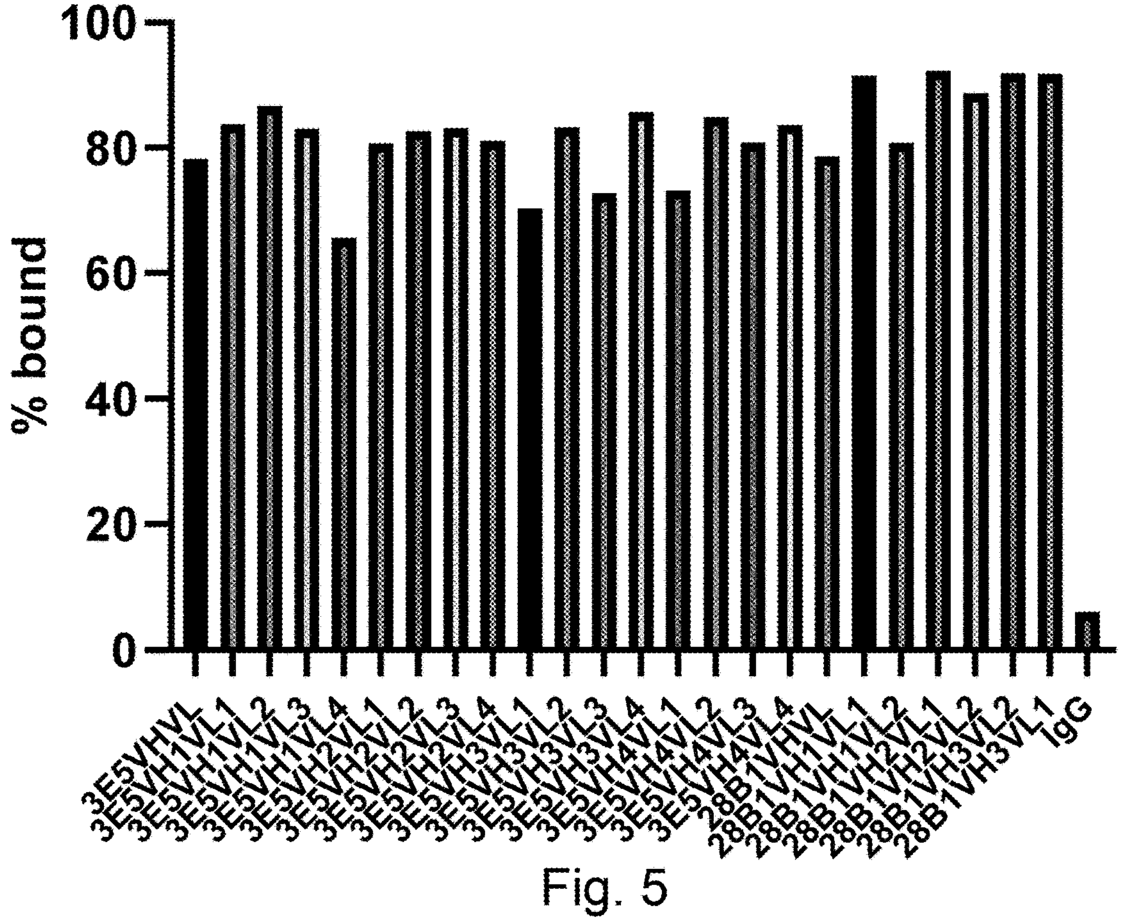
FIG. 5. Binding of humanized 3E5 and 28B1_variant mAbs to pDC by flow cytometry.
Figure 6A:
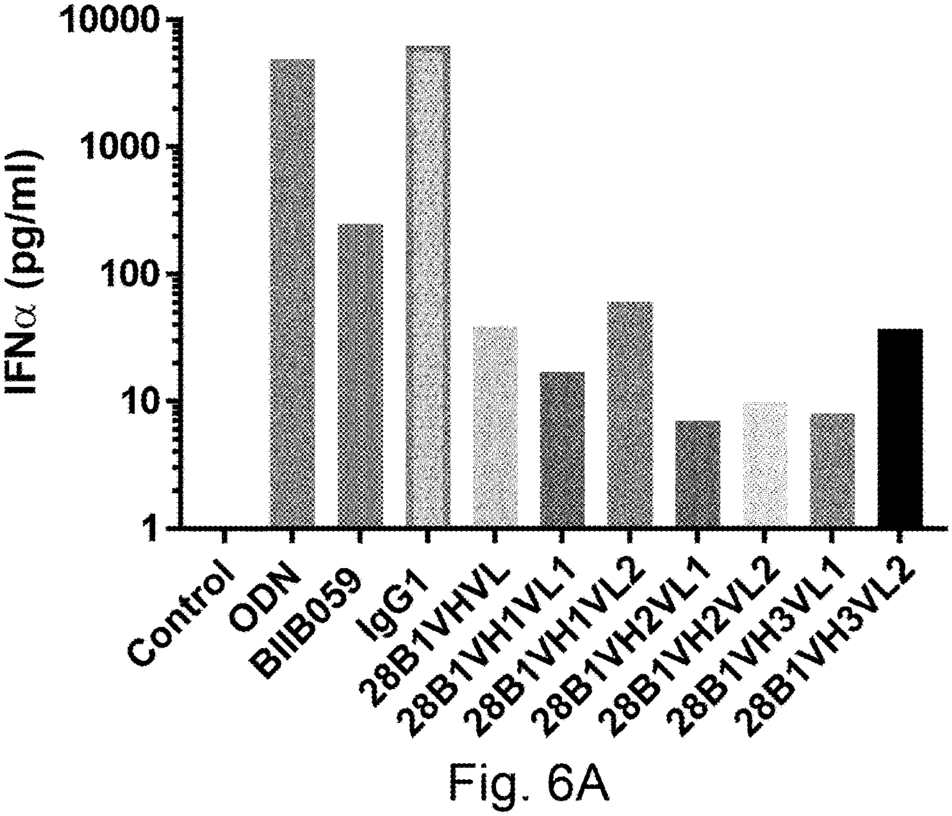
FIG. 6A. Effect of humanized 28B1 anti-BDCA-2 mAbs to inhibit IFNα secretion from ODN stimulated PBMC. Positive control was the anti-BDCA-2 mAb BIIB059 (patent WO2014093396) and the negative control was buffer (no Ab).
Figure 6B:
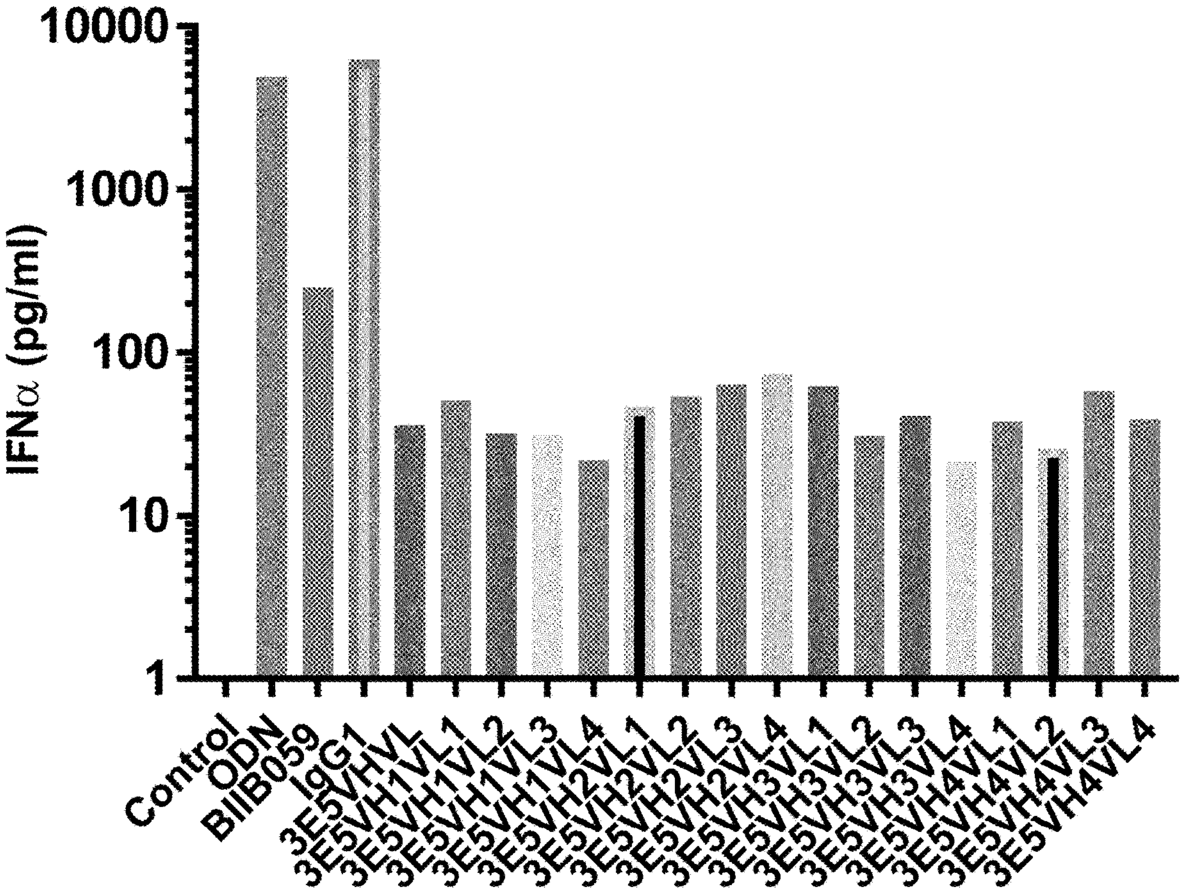
FIG. 6B. Effect of humanized 3E5 anti-BDCA-2 mAbs to inhibit IFNα secretion from ODN stimulated PBMC. Positive control was the anti-BDCA-2 mAb BIIB059 (patent WO2014093396) and the negative control was buffer (no Ab).

The mAbs 3E05 and 28B01 were selected for humanization. All humanized 28B01 and 3E05 variants bound to pDC (FIG. 5) and inhibited ODN stimulated IFNα release from pDC (FIG. 6A and FIG. 6B). From these single dose assays it was observed there was no major differences between the neutralizing activity of the humanized mAb constructs and they were also equivalent in activity to the wild type mAbs (28B01VHVL and 3E05VHVL).

Further analysis of the 3E05 humanized mAbs in terms of EC50 (BDCA-2 ELISA) and BIAcore analysis was performed and the results are shown in Tables 5 and 6.

TABLE 5

EC50 (ELISA) determination of humanized 3E05 mAbs.
The wild type mAb is 3E05 VHVL (SEQ ID NO: 5 and SEQ ID NO: 1) and the positive control was anti-BDCA-2 mAb AC144, (Miltenyi Biotec).

| mAb | EC50, nM | mAb | EC50, nM |
|---|---|---|---|
| 3E05 VL1VH1 (var_1) | 0.51 | 3E05 VL3VH1 (var_9) | 1.12 |
| 3E05 VL1VH2 (var_2) | 0.32 | 3E05 VL3VH2 (var_10) | 0.71 |
| 3E05 VL1VH3 (var_3) | 0.27 | 3E05 VL3VH3 (var_11) | 0.81 |
| 3E05 VL1VH4 (var_4) | 0.29 | 3E05 VL3VH4 (var_12) | 0.33 |
| 3E05 VL2VH1 (var_5) | 0.51 | 3E05 VL4VH1 (var_13) | 0.45 |
| 3E05 VL2VH2 (var_6) | 0.29 | 3E05 VL4VH2 (var_14) | 0.32 |
| 3E05 VL2VH3 (var_7) | 0.33 | 3E05 VL4VH3 (var_15) | 0.25 |
| 3E05 VH2VH4 (var_8) | 0.21 | 3E05 VH4VH4 (var_16) | 0.25 |
| Parental 3E05 | 0.30 | | |
| AC144 | 0.27 | | |

TABLE 6

BIAcore affinity determination of humanized 3E05 mAbs.
The wild type parental mAb is 3E05 and the positive control mAbs utilised were anti-BDCA-2 mAb, AC144, (Miltenyi Biotec) and BIIB059 (from patent WO2014093396).

| mAb | KD (nM) | mAb | KD (nM) |
|---|---|---|---|
| 3E05 VL1VH1 (var_1) | <0.01 | 3E05 VL3VH1 (var_9) | <0.01 |
| 3E05 VL1VH2 (var_2) | 0.30 | 3E05 VL3VH2 (var_10) | 0.73 |
| 3E05 VL1VH3 (var_3) | <0.01 | 3E05 VL3VH3 (var_11) | 0.94 |
| 3E05 VL1VH4 (var_4) | <0.01 | 3E05 VL3VH4 (var_12) | <0.01 |

TABLE 6-continued

BIAcore affinity determination of humanized 3E05 mAbs.
The wild type parental mAb is 3E05 and the positive control mAbs utilised were anti-BDCA-2 mAb, AC144, (Miltenyi Biotec) and BIIB059 (from patent WO2014093396).

| mAb | KD (nM) | mAb | KD (nM) |
|---|---|---|---|
| 3E05 VL2VH1 (var_5) | <0.01 | 3E05 VL4VH1 (var_13) | <0.01 |
| 3E05 VL2VH2 (var_6) | <0.01 | 3E05 VL4VH2 (var_14) | <0.01 |
| 3E05 VL2VH3 (var_7) | <0.01 | 3E05 VL4VH3 (var_15) | <0.01 |
| 3E05 VH2VH4 (var_8) | <0.01 | 3E05 VH4VH4 (var_16) | <0.01 |
| Parental 3E05 | 0.35 | | |
| AC144 | 2.3 | | |
| BIIB059 | 0.7 | | |

The ELISA EC50 analysis showed that 13 of the 16 3E05 humanized mAbs had a similar EC50 and were equivalent, in this assay, to the positive control mAb, AC144. The format of this ELISA assay may be at the limit of sensitivity. However, the BIAcore affinity analysis, which is a much more sensitive technology, revealed some surprising results regards the humanized mAb 3E05 variants. While the wild type 3E05 mAb (Parental 3E05) has a measurable KD of 350 pM the majority of the humanized mAb variants (13/16) show a dramatic improvement in KD to <10 pM (this value is at the limit of detection of the BIAcore instrument). The anti-BDCA-2 3E5 humanized variants also have a KD that is far improved on the comparator mAbs AC144 and BIIB059.

The major difference between wild type 3E05 and the humanized variants is the substitution of cysteine 53 in framework 2 (adjacent to CDR2) in the VL for serine in VL1, 2 and 4 and tyrosine in VL3. In general, the VL3 C53Y substitution is worse than the C53S in terms of EC50 analysis.

The free cysteine residue in the wild type mAb poses a modification and aggregation risk and is frequently found in antigen contact. The cysteine to serine substitution partly retains the side chain character while substituting to germline tyrosine (VL3) could influence antigen binding. Notwithstanding the VH modifications it is noticeable that in general the VL1, 2 and 4 constructs have a very high affinity for BDCA-2 ($K_D$<10 pM). The 3E05 humanized constructs: 3E05_var1, 3E05_var3, 3E05_var4, 3E05_var5, 3E05_var6, 3E05_var7, 3E05_var8, 3E05_var9, 3E05_var12, 3E05_var13, 3E05_var14, 3E05_var15, 3E05_var16 have >100 fold higher affinity than the parental wild type 3E05 as well as the anti-BDCA-2 mAb AC144.

Three mAbs (3E05_var_6, 3E05_var_12 and 3E05_var_14) were selected for further analysis by bioassay, inhibition of IFNα from ODN stimulated PBMC's from healthy donors. Four separate assays with different donor PBMC were completed and the IC50 value and the IC90 value of the mAbs were calculated by fitting a three parameter logistic curve to the normalised data (Table 7). The IC90 is a minimum value of the mAb concentration required for complete inhibition of IFNα production from human PBMC.

TABLE 7A

IFNα inhibition by the lead Humanized mAbs. Healthy donor PBMC were stimulated with ODN in the presence of mAbs (0.001-10 ug/ml) and IFNα measured in the supernatant by ELISA after an O/N incubation at 37 C. The positive control mAbs were anti-BDCA-2 mAb, AC144, (Miltenyi Biotec) and BIIB059 (from patent WO2014093396). Mean ± SEM.

| | AC144 | BII6059 | 3E05VL2VH2 (var_6) | 3E05VL3VH4 (var_12) | 3E05VL4VH2 (var_14) |
|---|---|---|---|---|---|
| IC50, ng/ml | 228 ± 66 | 128 ± 101 | 12.3 ± 1.0 | 14.3 ± 2.9 | 19.3 ± 3.5 |
| IC90, ng/ml | 2058 ± 593 | 1152 ± 916 | 110 ± 10 | 127 ± 26 | 173 ± 31 |

In Table 7A, AC 144 and BIIB059 were used as comparator positive control mAbs. It is apparent that 3E05 var_6, 3E05 var_12 and 3E05 var_14 have higher IFNα production inhibitory activity as measured by the IC50 value than the comparator mAbs AC144, 12-18 fold, and BIIB059, 7-10 fold, (Table 7A). In addition, the concentration of 3E05 var_6, 3E05 var_12 and 3E05 var_14 was lower than that of the comparator mAbs AC144 and BIIB059 for complete inhibition of IFNα production from the IC90 value by approximately 12-19 fold and 7-10 fold respectively (Table 7A). It has been reported that in SLE that a small amount of IFNα causes deterioration of pathology and that complete inhibition of IFNα is important for prevention and treatment of SLE and probably other IFNα driven diseases (Mathian et al. J. Immunology 2005; 174:2499, 2005). Thus, this level of IFN inhibition by 3E05 var_6, 12 and 14 is very encouraging for therapeutic applications.

TABLE 7B

IC50 and IC90 values in nM.

| | AC144 | BII6059 | 3E05VL2VH2 (var_6) | 3E05VL3VH4 (var_12) | 3E05VL4VH2 (var_14) |
|---|---|---|---|---|---|
| IC50, nM | 1.52 ± 0.44 | 0.85 ± 0.67 | 0.08 ± 0.01 | 0.10 ± 0.02 | 0.13 ± 0.02 |
| IC90, nM | 13.72 ± 3.95 | 7.68 ± 6.11 | 0.73 ± 0.07 | 0.85 ± 0.17 | 1.15 ± 0.21 |

To determine whether 3E5 induced BDCA2 internalization we set out to measure the mean fluorescence intensity (MFI) of BDCA2 (CD303) as measured by bound AC144 on pDC gated within PBMC and normalizing for pDC cell number by using the MFI of BDCA4 mAb (CD304), another marker of pDC. Treatment with 3E5 led to a dose-dependent decrease in BDCA2 surface expression on pDC, demonstrating BDCA2 internalization and at 14 ng/ml of 3E5, internalization of BDCA2 reached saturation. Jahn et al have shown that BDCA2 internalization and inhibition of IFN secretion are dependent on receptor cross-linking with the Fc region of the mAb and that monovalent binding of anti-BDCA2 Fab fragments was unable to inhibit ODN-induced IFN secretion (Jahn, P S., et al., Cell Immunol, 2010. 265:15-22). To determine whether the 3E5 inhibitory mechanism is dependent on Fc cross-linking, we generated digested Fab fragments of 3E5 and purified Fabs were quantified and used within the same experimental settings as in Table 7A. The 3E5 Fab was able to reduce IFN secretion in a dose-dependent manner with an IC50 of 18 nM. The Fc-containing full IgG equivalent had an approximate 100-fold lower IC50 and IC90 than the Fab. This is different to prior art anti-BDCA-2 antibodies, including AC144 (Miltenyi Biotec, cat. no. 130 090 690) and BIIB059 (Biogen) (Jahn, P S., et al., Cell Immunol, 2010. 265:15-22 and U.S. Pat. No. 9,902,775).

Figure 7A:
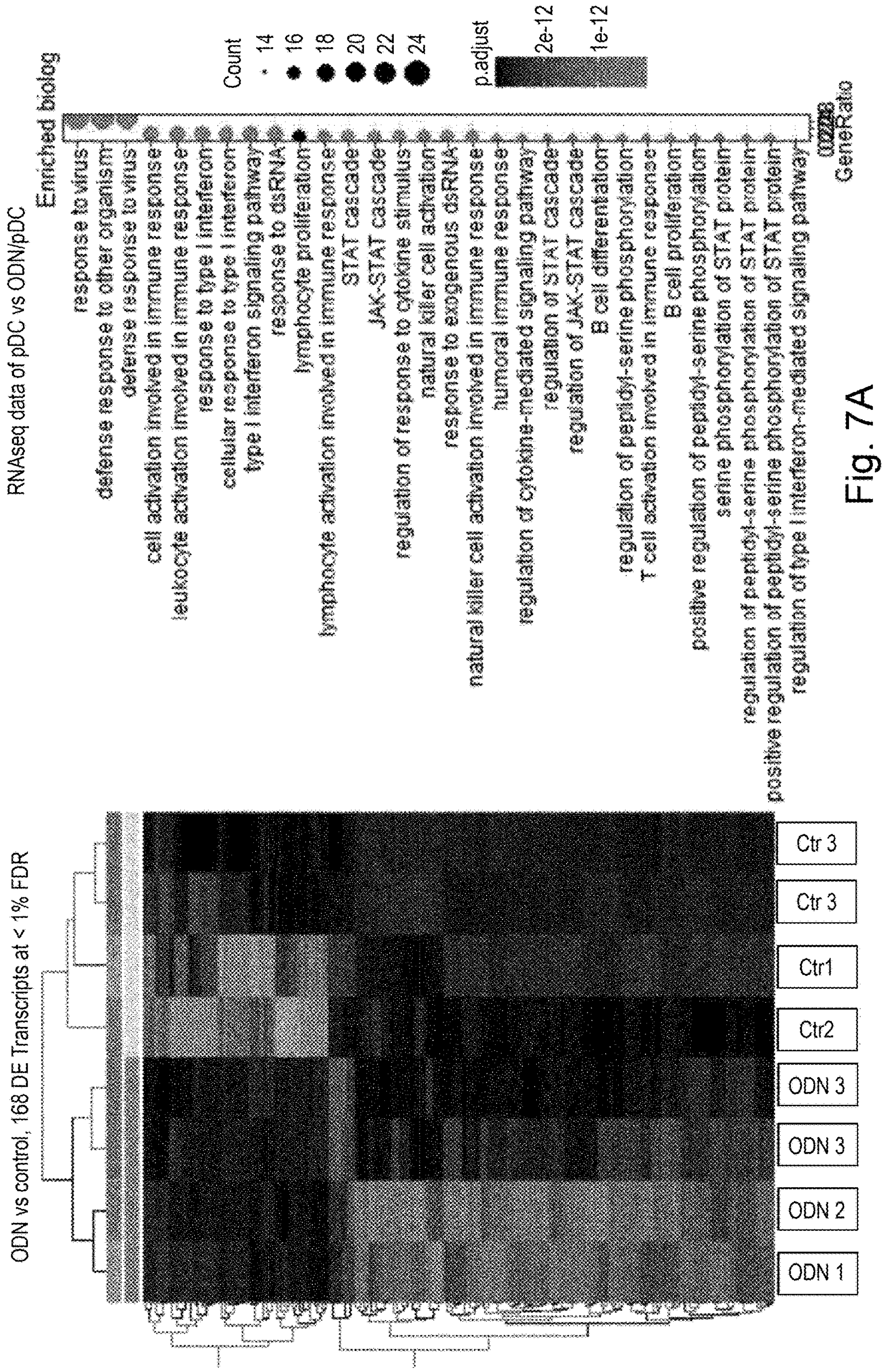
FIGS. 7A and 7B. Chimeric mAb 3E5 inhibition of BDCA2 suppresses ODN stimulated pDC transcriptome activation.
Figure 7B:
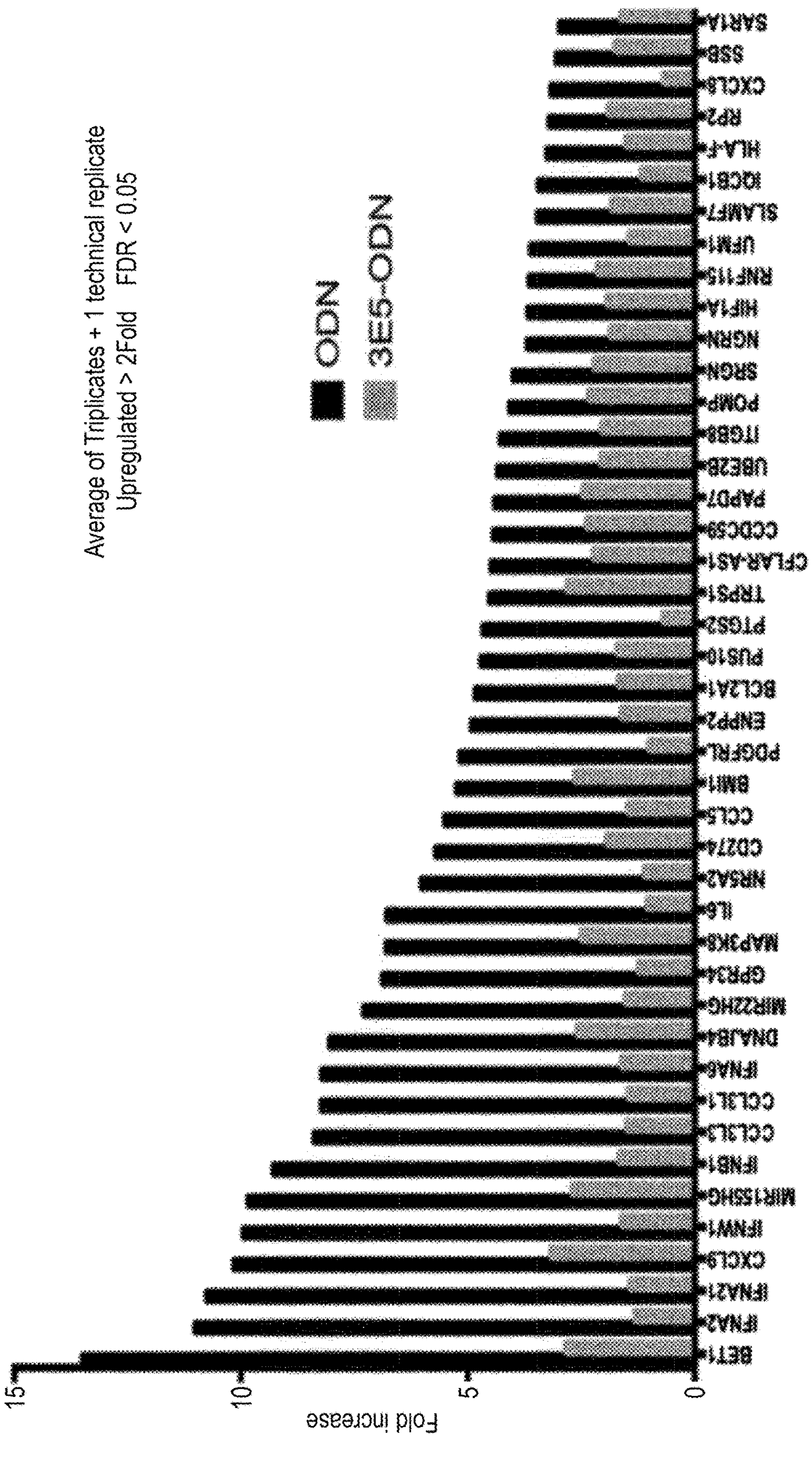

Transcriptome profiling has been widely used to describe immune cell populations, including DC subsets and pDC subpopulations (Alculumbre et al. Nat Immunol. 2018; 19:63-75). RNA-seq analysis was performed on three independent donors of human pDCs (Lineage-HLA-DR+ CD123+CD304+) with and without ODN stimulation to identify the effect of TLR9 on global pDCs and to delineate how BDCA-2 targeting affects pDCs other than reducing IFN secretion. Transcriptome analysis revealed 168 Differentially Expressed Genes (DEGs, fold change >2, FDR <1%) between unstimulated and ODN-stimulated pDCs (FIG. 7A). Pathway analysis on this set of DEGs identified genes involved in 'response to virus', defense response to other organisms', and 'defense response to virus' at the top of the enriched biological processes (FIG. 7A). Among the genes involved in these pathways, we saw upregulation of many IFN-related genes and pathway analysis also showed JAK/STAT, IL-6, NF-κB and angiogenesis pathways to be major biological processes upregulated by TLR-stimulation (FIG. 7A). Pre-treatment (15 minutes) with mAb 3E5 prevented upregulation of most DEGs, which drove an expression profile similar to non-stimulated pDCs (FIG. 7B). Besides inhibition of TLR9 induced IFN gene expression, as would be expected, it was surprising to determine that 3E5 inhibited a number of genes involved in lymphocyte and myeloid migration (CXCL9, CCL3L3, CCL3L1, CCL5 and CXCL8); inflammatory mediators (MAP3K8, IL6 and PTGS2); immune response (CD274, RNF115, SLAMF7 and HLA-F) and angiogenesis and fibrosis (ENPP2 and ITGB8).

Interestingly, CD274 expression was TLR9-induced and dependent on BDCA-2 targeting, which supports previous observations that 12-18 h flu stimulation produces mainly P1 (approximately 66%) and P2 (19%) subpopulations of pDC that are CD274+ (Alculumbre et al. Nat Immunol. 2018; 19:63-75). IL6 production was also ODN-induced and dependent on BDCA-2 targeting and has been shown to have correlated and synergistic action with IFN secretion needed for B cell differentiation (Jego Immunity. 2003; 19:225-34).

Growing evidence shows SSc patients have an induced IFN signature within the skin, pDC skin infiltration and chronically activated circulating pDCs (Brkic et al. Ann Rheum Dis. 2016; 75:1567-73; Lande et al. Nat Commun.

Figure 8A:
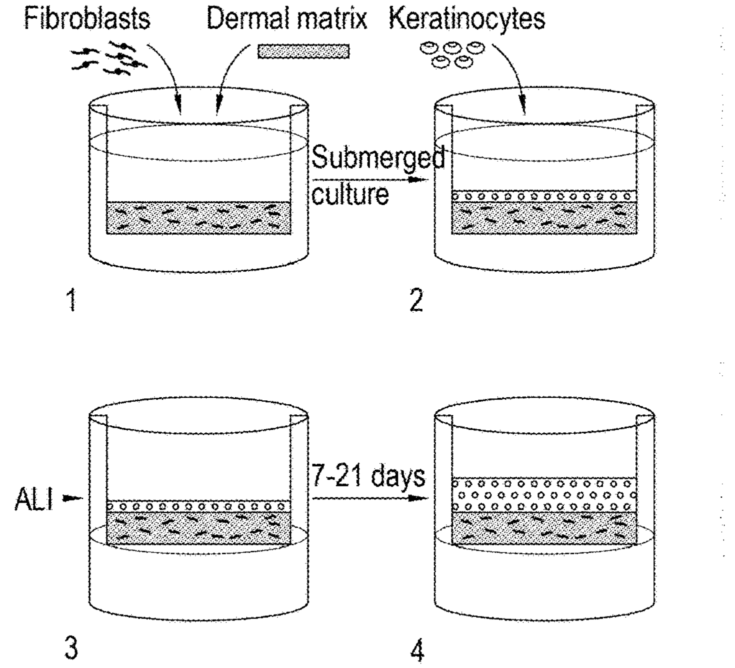
FIGS. 8A, B and C. Organotypic 3D skin cultures and the effect of chimeric anti-BDCA-2 mAb 3E5.
Figure 8B:
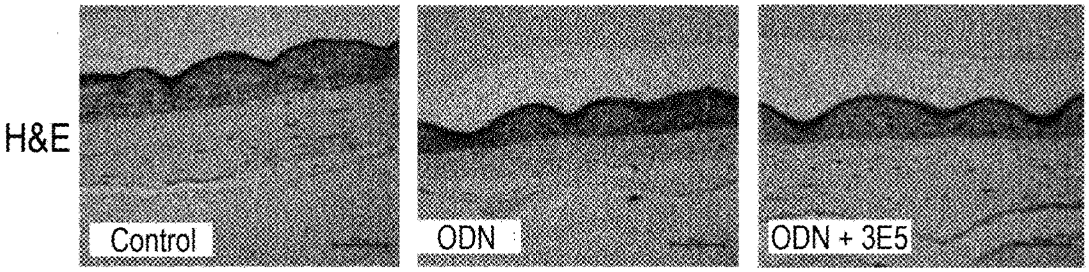
FIG. 8B Hematoxylin and eosin (H&E) staining revealed in vivo like development of epithelium.
Figure 8C:
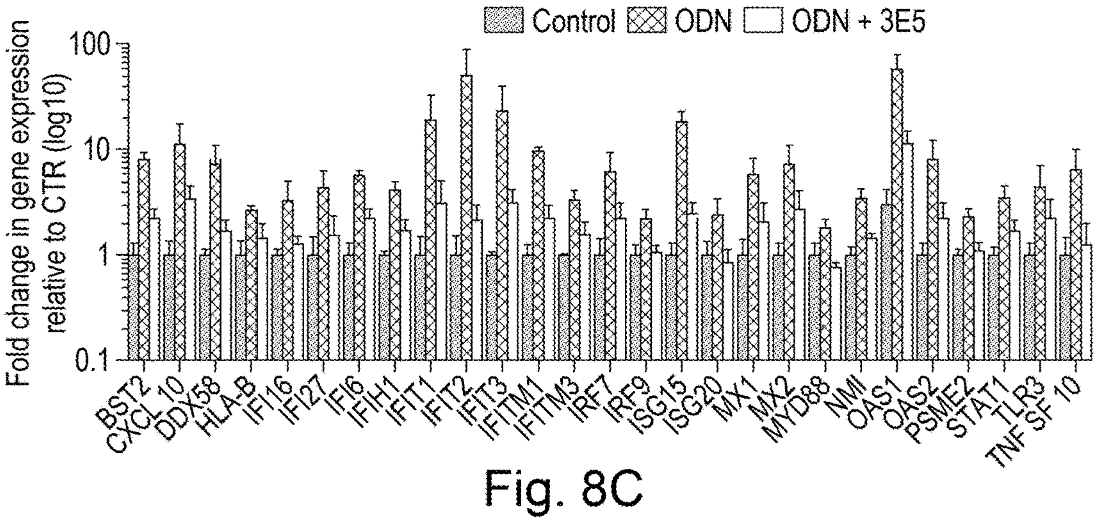
FIG. 8C shows the 27 IFN stimulated genes upregulated by ODN stimulated pDC supernatant within the epithelium relative to expression within the epithelium with resting pDC supernatant and inhibition with chimeric anti-BDCA-2 mAb 3E5.

2019; 10:1731). To confirm that chronically activated human pDCs can induce an ISG response within the skin, we utilised an organotypic 3D skin culture system as an in vitro model to mimic the microenvironment of the epidermis and allow cross-talk between the two main cellular components; fibroblasts and keratinocytes. Human primary fibroblasts were seeded into a collagen matrix, which supported the differentiation and epithelium growth of human primary keratinocytes once subjected to an air-liquid interface (ALI) (FIG. 8A). After 5 days, media was supplemented for 48 h with supernatants from pDC cultured in RPMI media (control), media plus ODN stimulation (ODN), or ODN+mAb 3E5 (ODN+3E5) to produce a final concentration of 6000 pg/ml of IFN in the ODN experiment (as determined by ELISA). Histology analysis revealed in vivo like development of the epithelium (FIG. 8B). To get a broader view of IFN-induced signalling within the epithelium dependent on ODN-stimulated pDCs, total RNA from triplicate 3D experiments was extracted and used to generate cDNA and then qRT-PCR analysis was performed on 78 genes commonly upregulated during a type I interferon response. Supernatant from chronically activated pDC (+ODN) resulted in 35 ISGs upregulated between 1.8 to 32 fold within the epithelium relative to expression within the epithelium with resting pDC supernatant (Control). Due to donor variability and the magnitude of gene-induction between triplicate experiments, only 8 genes reached statistical significance ($P>0.05$), and included ISG15, IFITM1, BST2, IFI6, IFIH1, NMI, HLA-B and IFITM3 (3 to 19-fold induction relative to control). BDCA-2 targeting with mAb 3E5 resulted in downregulation of 28 genes (>1.8-11 fold; FIG. 8C). Furthermore, BDCA2-targeted pDC supernatant did not elicit a significant type I IFN response within the epithelium, as the transcription profile mimicked epithelium cultured with unstimulated pDC supernatant (FIG. 8C). All 27 genes that were upregulated >2 fold by TLR9-stimulated pDC supernatant were downregulated by BDCA-2 targeting of pDC by 3E5 and corresponding reduction in IFN levels, similar to levels seen by control conditions (FIG. 8C).

Figure 9A:
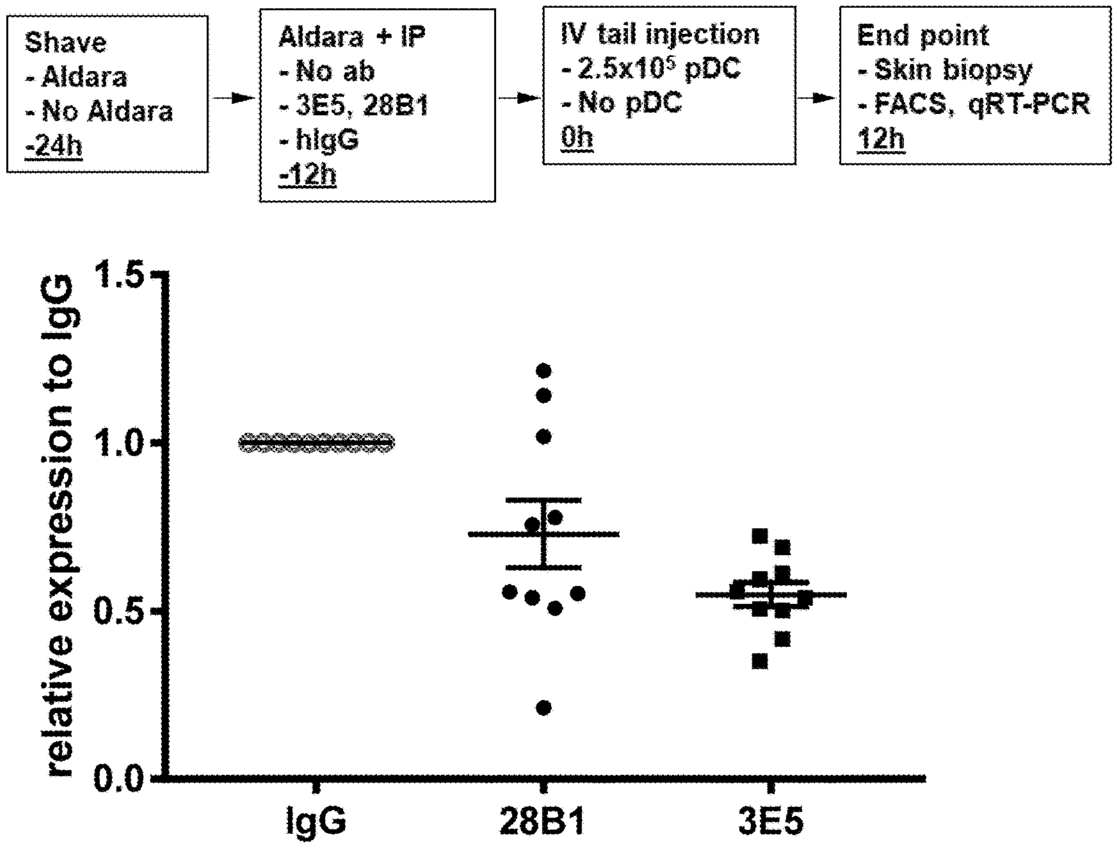
FIGS. 9A and B. Xeno-transplant mouse model of human pDC activation. Effect of chimeric anti-BDCA-2 mAbs 28B1 and 3E5 on mouse interferon gene signature. Normal human primary pDCs were tail vein injected into NOD-SCID mice and the back skin treated with Aldara cream with and without chimeric anti-BDCA2 mAbs 3E5 or 28B1 or human IgG (5 mg/kg). Total RNA from triplicate experiments was used to generate cDNA and qRT-PCR analysis of 78 genes commonly upregulated during a Type I Interferon response was performed. The IGS from the Qiagen panel were ranked for differential expression in the hIgG condition versus control (Aldara/Imiquimod alone). The 10 most differentially expressed genes were selected for analysis.
Figure 9B:
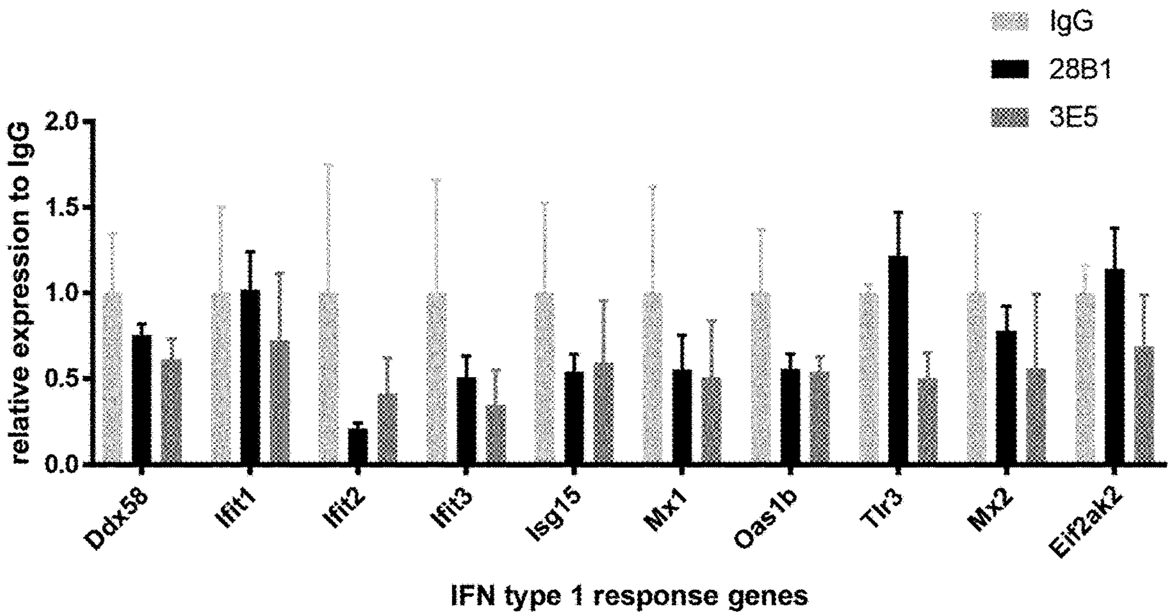

The xeno-transplant mouse model of human pDC activation was used to determine the in vivo efficacy of the chimeric mAbs 28B01 and 3E05 (FIG. 9A and FIG. 9B). The chimeric 3E05 and 28B01 mAbs and human IgG1 control mAb were injected i.p. into a NOD-SCID mouse 24 h before human pDC are injected i.v. and the ability of the mAbs to inhibit a human TLR7 agonist (Aldara cream on the mouse skin) induced mouse IFN gene signature (IGS) was examined. Aldara-induced pDC skin infiltration, as detected by human CD123+CD304+cells in the mouse treated skin, was not reduced by hIgG (0.3%), however pDC's were reduced to 0.1% with anti-BDCA-2 mAb treatment. In FIG. 9A the effects of mAbs 28B01 and 3E05 are compared to a human IgG1 control mAb. IGS from the Qiagen panel were ranked for differential expression in the hIgG condition versus control (Aldara/Imiquimod alone). The 10 most differentially expressed genes were selected for analysis and it was found that 3E5 significantly inhibited ($p<0.001$) the mouse IGS profile compared to the IgG1 control. mAb 28B01 produced less of an effect but was still significantly different from the hIgG1 control, $p<0.05$. There was a difference in the overall profile but some individual genes were significantly reduced by both antibodies (Figure. 9B).

Figure 10A:
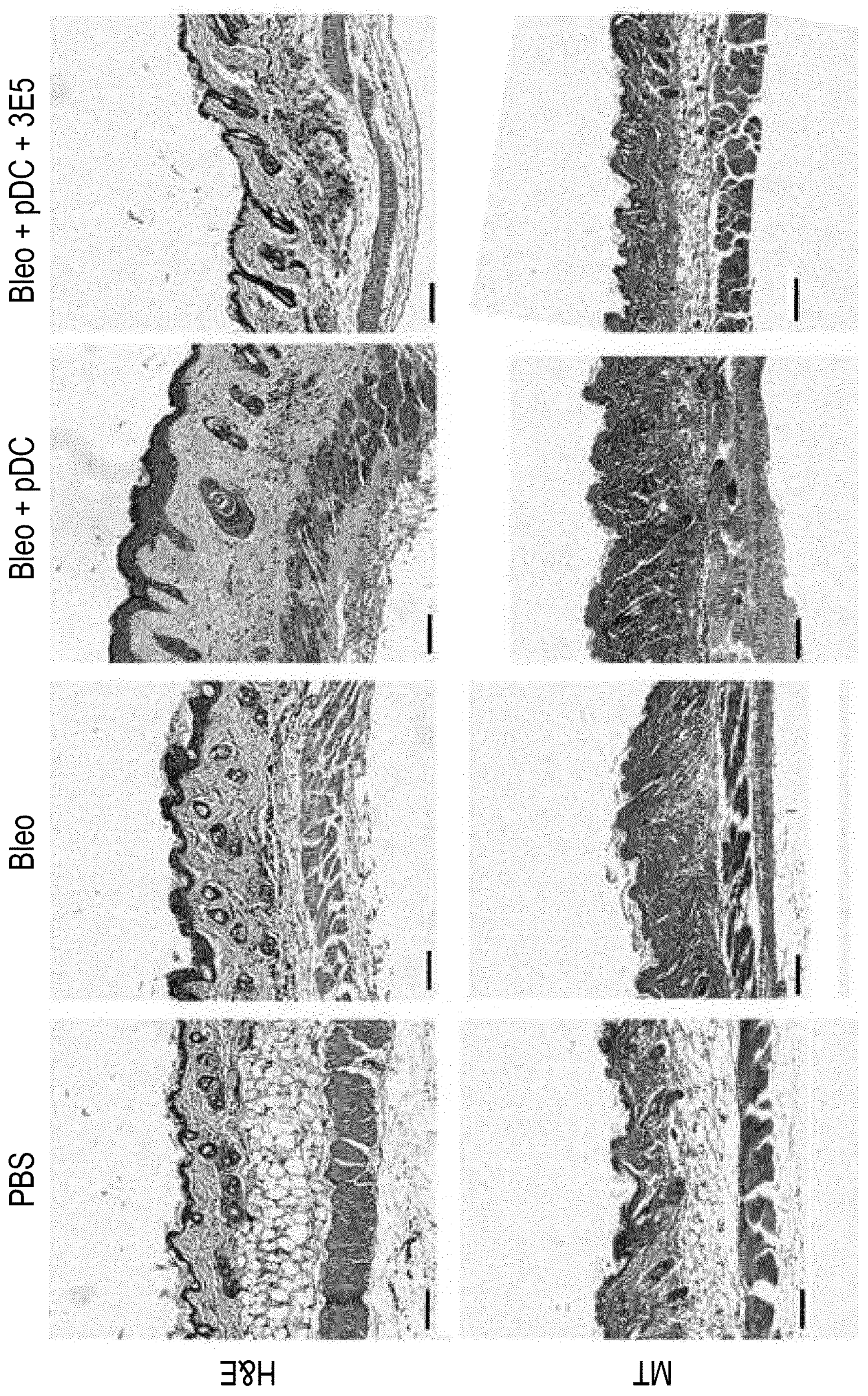
FIGS. 10A, B, C, D and E. Three-week pDC and bleomycin induced skin fibrosis model. Bleomycin (Bleo) or PBS (control, 100 μl) were injected s.c. into a single location on the shaved back of NOD-SCID mice once every other day for 3 weeks from day 0. Mice which received human PDc, ($2.5\times10^{5}$) were injected i.v. on days 0, 7 and 14. 3E5 mAb (var_6) or human IgG (2.5 mg/kg i.p.) were injected every 5 days starting on day −1 (n=5 i.p. injections per mouse) (administration schedule shown in FIG. 10E). Formalin fixed, paraffin embedded skin tissue from the treated mice were stained by haematoxylin and eosin (H&E, FIG. 10A) or Masson's trichrome (MT) stain (FIG. 10A). Epidermal and dermal skin thickness in the treated groups is shown in FIGS. 10B and 10C. The total collagen in the skin punch biopsy relative to tal protein is shown in FIG. 10D. Statistical significance (unpaired t test); P<0.05*, 0.01, 0.001*
Figure 10B:
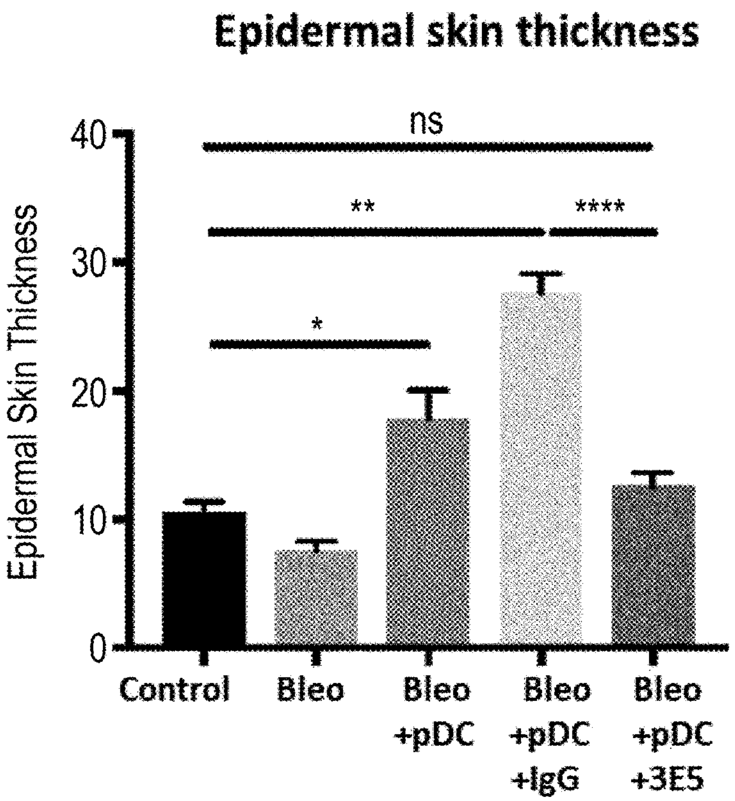
Figure 10C:
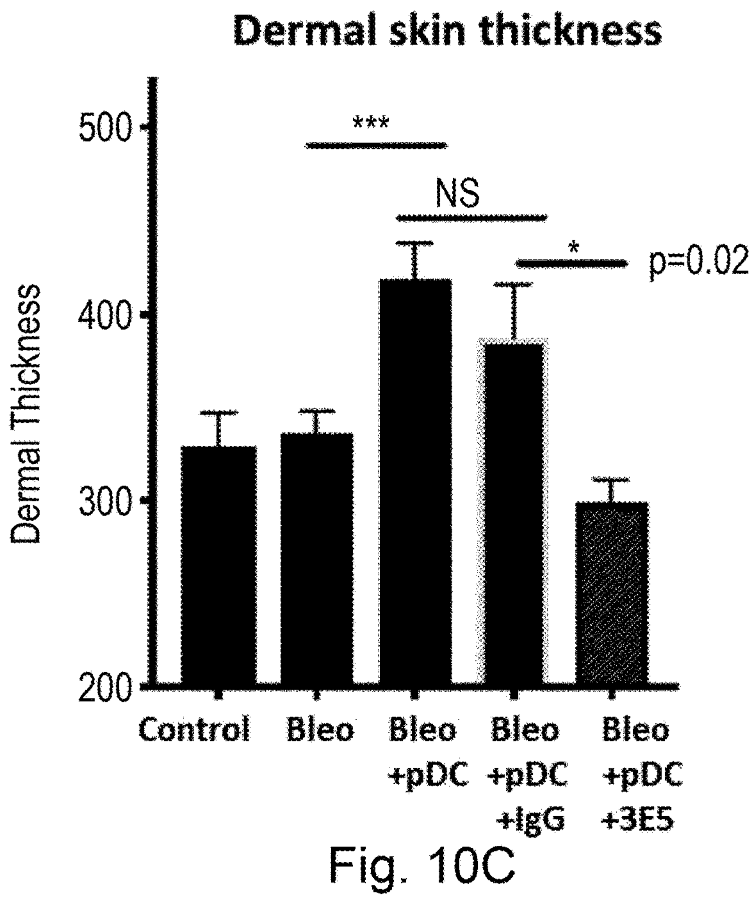
Figure 10D:
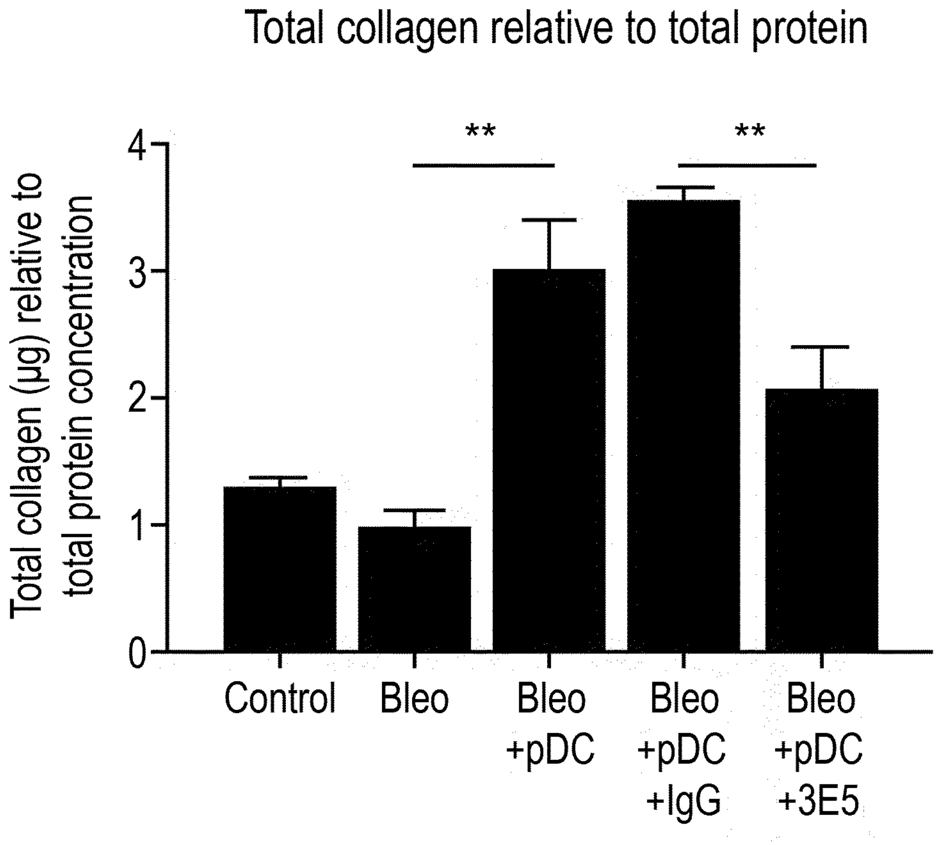
Figure 10E:
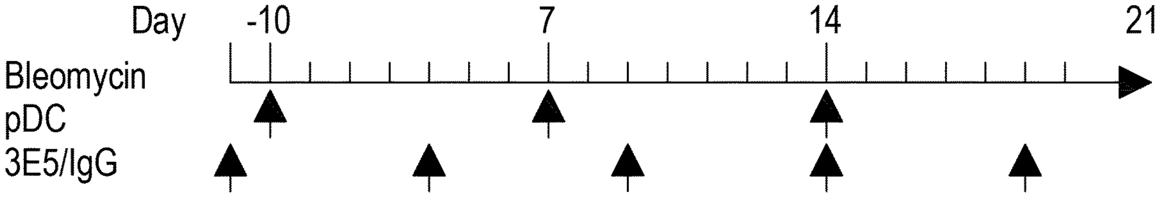
Figure 11A:
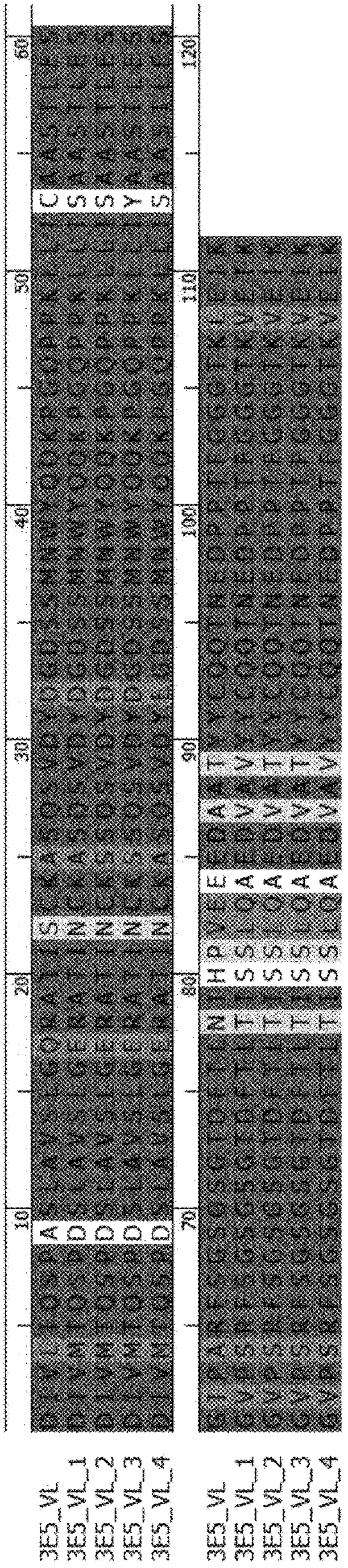
FIGS. 11A and B. Alignment of parental 3E5 sequences and 4 humanised/deimmunised variants 1 to 4. 3E5_VL is SEQ ID NO: 1. 3E5_VL_1 is SEQ ID NO: 11. 3E5_VL_2 is SEQ ID NO: 21. 3E5_VL_3 is SEQ ID NO: 31. 3E5_VL_4 is SEQ ID NO: 41. 3E5_VH is SEQ ID NO: 5. 3E5_VH_1 is SEQ ID NO: 15. 3E5_VH_2 is SEQ ID NO: 25. 3E5_VH_3 is SEQ ID NO: 35. 3E5_VH_4 is SEQ ID NO: 45.
Figure 11B:
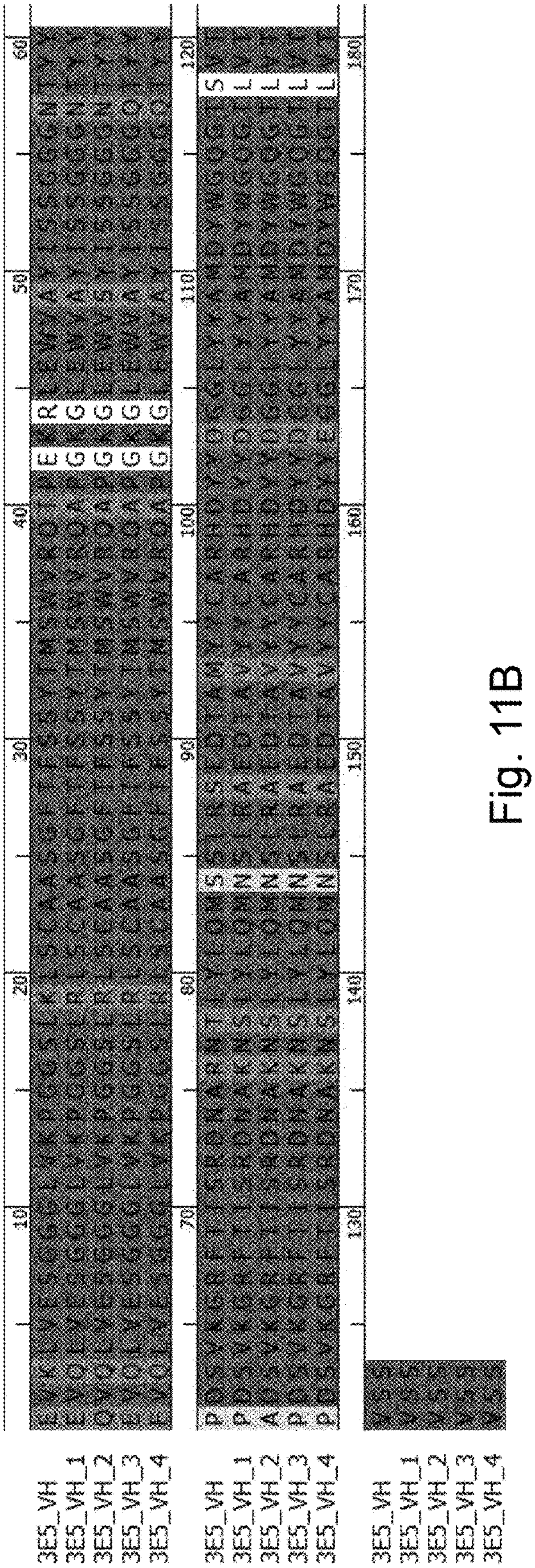

The data presented above demonstrate that chronically activated human pDCs can play a role in eliciting an immune response within the skin and that BDCA2-targeting with mAbs 3E5 and 28B1 can reduce this affect. The IFN signature has been shown to be present before the onset of clinical fibrosis in SSc (Brkic Z et al. Ann Rheum Dis. 2016; 75:1567-73) and depleting pDCs can prevent disease in a mouse model of scleroderma and could revert fibrosis in mice with established disease (Ah Kioon et al. Sci. Transl. Med. 2018; 10:eaam8458). However, whether human pDCs directly contribute to fibrosis within the skin in unclear. To address this question, skin fibrosis was induced in NOD-SCID mice by injecting bleomycin (Yamamoto et al. J Rheumatol. 1999; 26:2628-34) followed by the injection of human healthy pDC. As expected, bleomycin alone induced a limited fibrotic response at three weeks, as shown by a partially retained fatty layer and no significant increase in overall skin thickness (FIGS. 10A, B and C) or collagen content (FIG. 10D). On the contrary, mice xenotransplanted with human pDC and bleomycin showed a complete loss of the fatty layer, along with increased collagen formation (FIGS. 10A and 10D) and a 40% increase in overall skin thickness (Figures B, C). These data clearly show that human pDCs are sufficient for the induction of bleomycin-induced fibrosis within mouse skin without any adaptive immune responses by T and B cells (these cells are absent in NOD-SCID mice). It is important to note that pDC's injected on their own have no effect.

These data clearly show human pDCs to be fundamental in inducing fibrosis within mouse skin. In order to determine the therapeutic implications of BDCA-2 targeting on preventing fibrosis, the NOD-SCID bleomycin plus human pDC model was treated with humanised mAb 3E5 (var_6) and the effect on skin fibrosis was compared to hIgG administration. The pDC induced skin fibrosis was dramatically and significantly reduced by administration of mAb 3E5 compared to hIgG (FIGS. 10A-D) as demonstrated by the retention of some fatty layer tissue, similar to bleomycin-only treated mice and a significant reduction in dermal and epidermal thickness (FIGS. 10B and C) as well as significantly reducing collagen content (FIG. 10D). This is a significant finding as from the mouse data, as it would implicate pDC's in amplifying an initial fibrosis insult and that mAb 3E5 could reverse this fibrotic process. This disease mechanism may be translatable to similar human disease processes.

Epitope Mapping Analysis of 3E5 Variant 12

Based on the results obtained, we designed overlap mapping of the trypsin, chymotrypsin, ASP-N, elastase and thermolysin peptides (FIG. 13). Combining the peptides of Trypsin, Chymotrypsin, ASP-N, Elastase and Thermolysin proteolysis, 100% of the sequence of CLEC4C was covered. After Trypsin, Chymotrypsin, ASP-N, Elastase and Thermolysin proteolysis of the protein complex CLEC4C/3E5 with deuterated d0d12 cross-linker, the nLC-orbitrap MS/MS analysis detected 4 crosslinked peptides between CLEC4C and the antibody 3E5. The sequences and positions of cross-links are presented in Table 8, below.

TABLE 8

Interprotein cross-linked peptides detected between CLEC4C/3E5. 3E5-Trypsin, Chymotrypsin, ASP-N, Elastase and Thermolysin Interlink between 3E5 complementarity determining regions and CLEC4C

| Sequence | Enzyme | Protein1 | Protein2 | Sequence Protein1 | Sequence protein 2 | nAA1 | nAA2 |
|---|---|---|---|---|---|---|---|
| AASTLESGVPSRF-NENVTF-a7-b5 | CT | 3E5VL3 | CLEC4C | 54-66 of SEQ ID NO: 31 | 162-167 of SEQ ID NO: 90 | 60 | 122 |
| AASTLESGVPSRF-NENVTF-a3-b5 | CT | 3E5VL3 | CLEC4C | 54-66 of SEQ ID NO: 31 | 162-167 of SEQ ID NO: 90 | 56 | 122 |
| AASTLESGVPSRF-NENVTF-a4-b5 | CT | 3E5VL3 | CLEC4C | 54-66 of SEQ ID NO: 31 | 162-167 of SEQ ID NO: 90 | 57 | 122 |
| ISSGGGQTYYPDSVKGR-LDERCA-a9-b4 | Th | 3E5VH4 | CLEC4C | 51-67 of SEQ ID NO: 45 | 176-181 of SEQ ID NO: 90 | 59 | 135 |

CT: chymotrypsin;
Th: Thermolysin

Using chemical cross-linking, High-Mass MALDI mass spectrometry and nLC-Orbitrap mass spectrometry we were able to characterize the molecular interface between CLEC4C and 3E5. Our analysis indicates that the interaction includes the following amino acids on CLEC4C: 166 to 179 of Q8WTT0/BDCA-2 (SEQ ID NOs: 90 and 82, respectively), or residues 135 to 148 of Q8WTT0-2 (SEQ ID NO: 91), which correspond to the sequence TFWHSGEPNNLDER (SEQ ID NO: 92).

Certain Embodiments of the Invention

Among other things, the present invention provides:

1. An anti-BDCA-2 (CLEC4C) antigen binding molecule, wherein the antigen binding molecule has an equilibrium dissociation constant ($K_D$) for BDCA-2 (CLEC4C) of less than about 2 nM.
2. The anti-BDCA-2 (CLEC4C) antigen binding molecule of embodiment 1, wherein the antigen binding molecule has an equilibrium dissociation constant ($K_D$) for BDCA-2 (CLEC4C) of less than about 1 nM, less than about 0.75 nM, less than about 0.5 nM, less than about 0.4 nM, less than about 0.3 nM, less than about 0.2 nM, less than about 0.1M, less than about 0.08 nM, less than about 0.06 nM, less than about 0.05 nM, less than about 0.04 nM, less than about 0.03 nM, less than about 0.02 nM or less than about 0.01 nM.
3. An anti-BDCA-2 (CLEC4C) antigen binding molecule, wherein the antigen binding molecule has a half maximal inhibitory concentration (IC50) for inhibition of IFN secretion of less than about 2 nM.
4. The anti-BDCA-2 (CLEC4C) antigen binding molecule of embodiment 3, wherein the antigen binding molecule has a half maximal inhibitory concentration (IC50) for inhibition of IFN secretion of less than about 1.5 nM, less than about 1 nM, less than about 0.9 nM, less than about 0.8 nM, less than about 0.7 nM, less than about 0.6 nM, less than about 0.5, less than about 0.4 nM, less than about 0.3 nM, less than about 0.2 nM, or less than about 0.1 nM.
5. An anti-BDCA-2 (CLEC4C) antigen binding molecule, wherein the antigen binding molecule has an IC90 for inhibition of IFN secretion of less than about 20 nM.
6. The anti-BDCA-2 (CLEC4C) antigen binding molecule of embodiment 5, wherein the antigen binding molecule has an IC90 for inhibition of IFN secretion of less than about 15 nM, less than about 10 nM, less than about 9 nM, less than about 8 nM, less than about 7 nM, less than about 6 nM, less than about 5 nM, less than about 4 nM, less than about 3 nM, less than about 2 nM or less than about 1 nM.
7. The anti-BDCA-2 (CLEC4C) antigen binding molecule any preceding embodiment, wherein the antigen binding molecule has an equilibrium dissociation constant ($K_D$) for BDCA-2 (CLEC4C) of less than about 2 nM, a half maximal inhibitory concentration (IC50) for inhibition of IFN secretion of less than about 2 nM, and/or an IC90 for inhibition of IFN secretion of less than about 20 nM.
8. The anti-BDCA-2 (CLEC4C) antigen binding molecule of embodiment 7, wherein the antigen binding molecule has an equilibrium dissociation constant ($K_D$) for BDCA-2 (CLEC4C) of less than about 0.01 nM, a half maximal inhibitory concentration (IC50) for inhibition of IFN secretion of less than about 0.5 nM, and/or an IC90 for inhibition of IFN secretion of less than about 5 nM
9. An anti-BDCA-2 (CLEC4C) antigen binding molecule, wherein the antigen binding molecule comprises:
   - a VHCDR3 having at least 80% identity to the amino acid sequence of any one of SEQ ID NOs 48, 28, 8, 38, 58, 68 and 78; and/or
   - a VLCDR3 having at least 80% identity to the amino acid sequence of any one of SEQ ID NOs 34, 24, 44, 4, 14, 54, 64 and 74.
10. The anti-BDCA-2 (CLEC4C) antigen binding molecule of embodiment 9, wherein the antigen binding molecule comprises:
    - a VHCDR3 comprising the amino acid sequence of any one of SEQ ID NOs 48, 28, 8, 38, 58, 68 and 78; and/or
    - a VLCDR3 comprising the amino acid sequence of any one of SEQ ID NOs 34, 24, 44, 4, 14, 54, 64 and 74.
11. The anti-BDCA-2 (CLEC4C) antigen binding molecule of any one of embodiments 9 to 10, wherein the antigen binding molecule comprises:
    - a VHCDR1 having at least 80% identity to the amino acid sequence of any one of SEQ ID NOs 46, 49, 26, 29, 6, 9, 16, 19, 36, 39, 56, 59, 66, 69, 76 and 79;
    - a VHCDR2 having at least 80% identity to the amino acid sequence of any one of SEQ ID NOs 47, 50, 27, 30, 7, 10, 17, 20, 37, 40, 57, 60, 67, 70, 77 and 80; and a VHCDR3 having at least 80% identity to the amino acid sequence of any one of SEQ ID NOs 48, 28, 8, 18, 38, 58, 68 and 78; and/or a VLCDR1 having at least 80% identity to the amino acid sequence of any one of SEQ ID NOs 32, 22, 42, 2, 12, 52, 62 and 72;

a VLCDR2 having at least 80% identity to the amino acid sequence of any one of SEQ ID NOs 33, 23, 43, 3, 13, 53, 63 and 73; and a VLCDR3 having at least 80% identity to the amino acid sequence of any one of SEQ ID NOs 34, 24, 44, 4, 14, 54, 64 and 74.

12. The anti-BDCA-2 (CLEC4C) antigen binding molecule of any one of embodiments 9 to 11, wherein the antigen binding molecule comprises:

a VHCDR1 comprising the amino acid sequence of any one of SEQ ID NOs 46, 49, 26, 29, 6, 9, 16, 19, 36, 39, 56, 59, 66, 69, 76 and 79;

a VHCDR2 comprising the amino acid sequence of any one of SEQ ID NOs 47, 50, 27, 30, 7, 10, 17, 20, 37, 40, 57, 60, 67, 70, 77 and 80; and a VHCDR3 comprising the amino acid sequence of any one of SEQ ID NOs 48, 28, 8, 18, 38, 58, 68 and 78;

and/or a VLCDR1 comprising the amino acid sequence of any one of SEQ ID NOs 32, 22, 42, 2, 12, 52, 62 and 72;

a VLCDR2 comprising the amino acid sequence of any one of SEQ ID NOs 33, 23, 43, 3, 13, 53, 63 and 73; and a VLCDR3 comprising the amino acid sequence of any one of SEQ ID NOs 34, 24, 44, 4, 14, 54, 64 and 74.

13. The anti-BDCA-2 (CLEC4C) antigen binding molecule of any one of embodiments 9 to 12, wherein the antigen binding molecule is selected from the group consisting of:

(a) an anti-BDCA-2 (CLEC4C) antigen binding molecule comprising:

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

(b) an anti-BDCA-2 (CLEC4C) antigen binding molecule comprising:

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

(c) an anti-BDCA-2 (CLEC4C) antigen binding molecule comprising a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(d) an anti-BDCA-2 (CLEC4C) antigen binding molecule comprising:

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(e) an anti-BDCA-2 (CLEC4C) antigen binding molecule comprising:

a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), a VHCDR3 comprising the amino acid sequence HDYYDGGLYYAMDY (SEQ ID NO: 28); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

(f) an anti-BDCA-2 (CLEC4C) antigen binding molecule comprising:

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), a VHCDR3 comprising the amino acid sequence HDYYDGGLYYAMDY (SEQ ID NO: 28); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

(g) an anti-BDCA-2 (CLEC4C) antigen binding molecule comprising:

a heavy chain variable region comprising a VHCDR1 comprising the amino acid sequence SYTMS (SEQ ID NO: 6), a VHCDR2 comprising the amino acid sequence YISSGGGNTYYPDSVKG (SEQ ID NO: 7) and a VHCDR3 comprising the amino acid sequence HDYYDGGLYYAMDY (SEQ ID NO: 8); and a light chain variable region comprising a VLCDR1 comprising the amino acid sequence KASQSVDYDGDSSMN (SEQ ID NO: 2), a VLCDR2 comprising the amino acid sequence AASTLES (SEQ ID NO: 3) and a VLCDR3 comprising the amino acid sequence QQTNEDPPT (SEQ ID NO: 4);

(h) an anti-BDCA-2 (CLEC4C) antigen binding molecule comprising:

a heavy chain variable region comprising a VHCDR1 comprising the amino acid sequence GFTFSSY (SEQ ID NO: 9), a VHCDR2 comprising the amino acid sequence SSGGGNTY (SEQ ID NO: 10) and a VHCDR3 comprising the amino acid sequence HDYYDGGLYYAMDY (SEQ ID NO: 8); and a light chain variable region comprising a VLCDR1 comprising the amino acid sequence KASQSVDYDGDSSMN (SEQ ID NO: 2), a VLCDR2 comprising the amino acid sequence AASTLES (SEQ ID NO: 3) and a VLCDR3 comprising the amino acid sequence QQTNEDPPT (SEQ ID NO: 4);

(i) an anti-BDCA-2 (CLEC4C) antigen binding molecule comprising:

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), a VHCDR3 comprising the amino acid sequence HDYYDGGLYYAMDY (SEQ ID NO: 18); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

(j) an anti-BDCA-2 (CLEC4C) antigen binding molecule comprising:

a heavy chain variable region comprising a VHCDR1 comprising the amino acid sequence GFTFSSY (SEQ ID NO: 19), a VHCDR2 comprising the amino acid sequence SSGGGNTY (SEQ ID NO: 20), a VHCDR3 comprising the amino acid sequence HDYYDGGLYYAMDY (SEQ ID NO: 18); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

(k) an anti-BDCA-2 (CLEC4C) antigen binding molecule comprising:

a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), a VHCDR3 comprising the amino acid sequence HDYYDGGLYYAMDY (SEQ ID NO: 28); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

(l) an anti-BDCA-2 (CLEC4C) antigen binding molecule comprising:

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), a VHCDR3 comprising the amino acid sequence HDYYDGGLYYAMDY (SEQ ID NO: 28); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

(m) an anti-BDCA-2 (CLEC4C) antigen binding molecule comprising:

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), a VHCDR3 comprising the amino acid HDYYDGGLYYAMDY sequence (SEQ ID NO: 38); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

(n) an anti-BDCA-2 (CLEC4C) antigen binding molecule comprising:

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), a VHCDR3 comprising the amino acid HDYYDGGLYYAMDY sequence (SEQ ID NO: 38); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

(o) an anti-BDCA-2 (CLEC4C) antigen binding molecule comprising:

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), a VHCDR3 comprising the amino acid sequence HDYYEGGLYYAMDY (SEQ ID NO: 48); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

(p) an anti-BDCA-2 (CLEC4C) antigen binding molecule comprising:

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), a VHCDR3 comprising the amino acid sequence HDYYEGGLYYAMDY (SEQ ID NO: 48); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

(q) an anti-BDCA-2 (CLEC4C) antigen binding molecule comprising:

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(r) an anti-BDCA-2 (CLEC4C) antigen binding molecule comprising:

a heavy chain variable region comprising a VHCDR1 comprising the amino acid sequence GFTFSSY (SEQ ID NO: 19), a VHCDR2 comprising the amino acid sequence SSGGGNTY (SEQ ID NO: 20), a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(s) an anti-BDCA-2 (CLEC4C) antigen binding molecule comprising:

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), a VHCDR3 comprising the amino acid HDYYDGGLYYAMDY sequence (SEQ ID NO: 38); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(t) an anti-BDCA-2 (CLEC4C) antigen binding molecule comprising:

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), a VHCDR3 comprising the amino acid HDYYDGGLYYAMDY sequence (SEQ ID NO: 38); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(u) an anti-BDCA-2 (CLEC4C) antigen binding molecule comprising:

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(v) an anti-BDCA-2 (CLEC4C) antigen binding molecule comprising:

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(w) an anti-BDCA-2 (CLEC4C) antigen binding molecule comprising:

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

(x) an anti-BDCA-2 (CLEC4C) antigen binding molecule comprising:

a heavy chain variable region comprising a VHCDR1 comprising the amino acid sequence GFTFSSY (SEQ ID NO: 19), a VHCDR2 comprising the amino acid sequence SSGGGNTY (SEQ ID NO: 20), a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

(y) an anti-BDCA-2 (CLEC4C) antigen binding molecule comprising:

a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

(z) an anti-BDCA-2 (CLEC4C) antigen binding molecule comprising:

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

(aa) an anti-BDCA-2 (CLEC4C) antigen binding molecule comprising:

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), a VHCDR3 comprising the amino acid HDYYDGGLYYAMDY sequence (SEQ ID NO: 38); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

(bb) an anti-BDCA-2 (CLEC4C) antigen binding molecule comprising:

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), a VHCDR3 comprising the amino acid HDYYDGGLYYAMDY sequence (SEQ ID NO: 38); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

(cc) an anti-BDCA-2 (CLEC4C) antigen binding molecule comprising a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), a VHCDR3 comprising the amino acid sequence HDYYDGGLYYAMDY (SEQ ID NO: 18); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

(dd) an anti-BDCA-2 (CLEC4C) antigen binding molecule comprising:

a heavy chain variable region comprising a VHCDR1 comprising the amino acid sequence GFTFSSY (SEQ ID NO: 19), a VHCDR2 comprising the amino acid sequence SSGGGNTY (SEQ ID NO: 20), a VHCDR3 comprising the amino acid sequence HDYYDGGLYYAMDY (SEQ ID NO: 18); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

(ee) an anti-BDCA-2 (CLEC4C) antigen binding molecule comprising:

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), a VHCDR3 comprising the amino acid HDYYDGGLYYAMDY sequence (SEQ ID NO: 38); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

(ff) an anti-BDCA-2 (CLEC4C) antigen binding molecule comprising:

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), a VHCDR3 comprising the amino acid HDYYDGGLYYAMDY sequence (SEQ ID NO: 38); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

(gg) an anti-BDCA-2 (CLEC4C) antigen binding molecule comprising:

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), a VHCDR3 comprising the amino acid sequence HDYYEGGLYYAMDY (SEQ ID NO: 48); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

(hh) an anti-BDCA-2 (CLEC4C) antigen binding molecule comprising:

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), a VHCDR3 comprising the amino acid sequence HDYYEGGLYYAMDY (SEQ ID NO: 48); and a light chain variable region comprising a VLCDR1 comprising the amino acid sequence KASQSVDYDGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

(ii) an anti-BDCA-2 (CLEC4C) antigen binding molecule comprising:

a heavy chain variable region comprising a VHCDR1 comprising the amino acid sequence SYTIS (SEQ ID NO: 56), a VHCDR2 comprising the amino acid sequence YISSGGDNAYYPDSVKG (SEQ ID NO: 57), a VHCDR3 comprising the amino acid sequence HLYYGDYFYVMDY (SEQ ID NO: 58); and a light chain variable region comprising a VLCDR1 comprising the amino acid sequence KASQSVDYDGDNCLH (SEQ ID NO: 52), a VLCDR2 comprising the amino acid sequence AASNLES (SEQ ID NO: 53) and a VLCDR3 comprising the amino acid sequence QQSNEDPPT (SEQ ID NO: 54);

(jj) an anti-BDCA-2 (CLEC4C) antigen binding molecule comprising:

a heavy chain variable region comprising a VHCDR1 comprising the amino acid sequence GFTFSSY (SEQ ID NO: 59), a VHCDR2 comprising the amino acid sequence SSGGDN (SEQ ID NO: 60), a VHCDR3 comprising the amino acid sequence HLYYGDYFYVMDY (SEQ ID NO: 58); and a light chain variable region comprising a VLCDR1 comprising the amino acid sequence KASQSVDYDGDNCLH (SEQ ID NO: 52), a VLCDR2 comprising the amino acid sequence AASNLES (SEQ ID NO: 53) and a VLCDR3 comprising the amino acid sequence QQSNEDPPT (SEQ ID NO: 54);

(kk) an anti-BDCA-2 (CLEC4C) antigen binding molecule comprising:

a heavy chain variable region comprising a VHCDR1 comprising the amino acid sequence SYTMS (SEQ ID NO: 66), a VHCDR2 comprising the amino acid sequence YISGVGGDTYYPDSVKG (SEQ ID NO: 67), a VHCDR3 comprising the amino acid sequence HHYSHYFWYFDV (SEQ ID NO: 68); and a light chain variable region comprising a VLCDR1 comprising the amino acid sequence KASQSVDYDGDGFMN (SEQ ID NO: 62), a VLCDR2 comprising the amino acid sequence AASNLES (SEQ ID NO: 63) and a VLCDR3 comprising the amino acid sequence QQSNEDPPT (SEQ ID NO: 64);

(ll) an anti-BDCA-2 (CLEC4C) antigen binding molecule comprising:

a heavy chain variable region comprising a VHCDR1 comprising the amino acid sequence GFTFSSY (SEQ ID NO: 69), a VHCDR2 comprising the amino acid sequence SGVGGD (SEQ ID NO: 70), a VHCDR3 comprising the amino acid sequence HHYSHYFWYFDV (SEQ ID NO: 68); and a light chain variable region comprising a VLCDR1 comprising the amino acid sequence KASQSVDYDGDGFMN (SEQ ID NO: 62), a VLCDR2 comprising the amino acid sequence AASNLES (SEQ ID NO: 63) and a VLCDR3 comprising the amino acid sequence QQSNEDPPT (SEQ ID NO: 64);

(mm) an anti-BDCA-2 (CLEC4C) antigen binding molecule comprising:

a heavy chain variable region comprising a VHCDR1 comprising the amino acid sequence YYTMS (SEQ ID NO: 76), a VHCDR2 comprising the amino acid sequence YISSGGDNAYYPDSVRG (SEQ ID NO: 77), a VHCDR3 comprising the amino acid sequence HHYSNYFWYFDV (SEQ ID NO: 78); and a light chain variable region comprising a VLCDR1 comprising the amino acid sequence KASQSVDY-AGDSYVN (SEQ ID NO: 72), a VLCDR2 comprising the amino acid sequence AASNLES (SEQ ID NO: 73) and a VLCDR3 comprising the amino acid sequence QQSNEDPPT (SEQ ID NO: 74); and (nn) an anti-BDCA-2 (CLEC4C) antigen binding molecule comprising:

a heavy chain variable region comprising a VHCDR1 comprising the amino acid sequence GFTFSYY (SEQ ID NO: 79), a VHCDR2 comprising the amino acid sequence SSGGDN (SEQ ID NO: 80), a VHCDR3 comprising the amino acid sequence HHYSNYFWYFDV (SEQ ID NO: 78); and a light chain variable region comprising a VLCDR1 comprising the amino acid sequence KASQSVDY-AGDSYVN (SEQ ID NO: 72), a VLCDR2 comprising the amino acid sequence AASNLES (SEQ ID NO: 73) and a VLCDR3 comprising the amino acid sequence QQSNEDPPT (SEQ ID NO: 74).

14. The anti-BDCA-2 (CLEC4C) antigen binding molecule of any one of embodiments 9 to 13, wherein the antigen binding molecule comprises:

a heavy chain variable region having at least 80% identity to the amino acid sequence selected from the group consisting of SEQ ID NO: 45, SEQ ID NO: 25, SEQ ID NO: 5, SEQ ID NO: 15, SEQ ID NO: 35, SEQ ID NO: 55, SEQ ID NO: 65 and SEQ ID NO: 75; and/or a light chain variable region having at least 80% identity to the amino acid sequence selected from the group consisting of SEQ ID NO: 31, SEQ ID NO: 21, SEQ ID NO: 41, SEQ ID NO: 1, SEQ ID NO: 11, SEQ ID NO: 51, SEQ ID NO: 61 and SEQ ID NO: 71.

15. The anti-BDCA-2 (CLEC4C) antigen binding molecule of any one of embodiments 9 to 14, wherein the antigen binding molecule comprises:

a heavy chain variable region comprising the amino acid sequence selected from the group consisting of SEQ ID NO: 45, SEQ ID NO: 25, SEQ ID NO: 5, SEQ ID NO: 15, SEQ ID NO: 35, SEQ ID NO: 55, SEQ ID NO: 65 and SEQ ID NO: 75; and/or a light chain variable region comprising the amino acid sequence selected from the group consisting of SEQ ID NO: 31, SEQ ID NO: 21, SEQ ID NO: 41, SEQ ID NO: 1, SEQ ID NO: 11, SEQ ID NO: 51, SEQ ID NO: 61 and SEQ ID NO: 71.

16. The anti-BDCA-2 (CLEC4C) antigen binding molecule of any one of embodiments 9 to 15, wherein the antigen binding molecule is selected from the group consisting of
  a. a VH comprising the amino acid sequence of SEQ ID NO: 45 and a VL comprising the amino acid sequence of SEQ ID NO: 31;
  b. a VH comprising the amino acid sequence of SEQ ID NO: 25 and a VL comprising the amino acid sequence of SEQ ID NO: 21;
  c. a VH comprising the amino acid sequence of SEQ ID NO: 25 and a VL comprising the amino acid sequence of SEQ ID NO: 41;
  d. a VH comprising the amino acid sequence of SEQ ID NO: 5 and a VL comprising the amino acid sequence of SEQ ID NO: 1;
  e. a VH comprising the amino acid sequence of SEQ ID NO: 15 and a VL comprising the amino acid sequence of SEQ ID NO: 11;
  f. a VH comprising the amino acid sequence of SEQ ID NO: 25 and a VL comprising the amino acid sequence of SEQ ID NO: 11;
  g. a VH comprising the amino acid sequence of SEQ ID NO: 35 and a VL comprising the amino acid sequence of SEQ ID NO: 11;
  h. a VH comprising the amino acid sequence of SEQ ID NO: 45 and a VL comprising the amino acid sequence of SEQ ID NO: 11;
  i. a VH comprising the amino acid sequence of SEQ ID NO: 15 and a VL comprising the amino acid sequence of SEQ ID NO: 21;
  j. a VH comprising the amino acid sequence of SEQ ID NO: 35 and a VL comprising the amino acid sequence of SEQ ID NO: 21;
  k. a VH comprising the amino acid sequence of SEQ ID NO: 45 and a VL comprising the amino acid sequence of SEQ ID NO: 21;
  l. a VH comprising the amino acid sequence of SEQ ID NO: 15 and a VL comprising the amino acid sequence of SEQ ID NO: 31;
  m. a VH comprising the amino acid sequence of SEQ ID NO: 25 and a VL comprising the amino acid sequence of SEQ ID NO: 31;
  n. a VH comprising the amino acid sequence of SEQ ID NO: 35 and a VL comprising the amino acid sequence of SEQ ID NO: 31;
  o. a VH comprising the amino acid sequence of SEQ ID NO: 15 and a VL comprising the amino acid sequence of SEQ ID NO: 41;
  p. a VH comprising the amino acid sequence of SEQ ID NO: 35 and a VL comprising the amino acid sequence of SEQ ID NO: 41;
  q. a VH comprising the amino acid sequence of SEQ ID NO: 45 and a VL comprising the amino acid sequence of SEQ ID NO: 41;
  r. a VH comprising the amino acid sequence of SEQ ID NO: 55 and a VL comprising the amino acid sequence of SEQ ID NO: 51;
  s. a VH comprising the amino acid sequence of SEQ ID NO: 65 and a VL comprising the amino acid sequence of SEQ ID NO: 61; and
  t. a VH comprising the amino acid sequence of SEQ ID NO: 75 and a VL comprising the amino acid sequence of SEQ ID NO: 71.
17. The anti-BDCA-2 (CLEC4C) antigen binding molecule of any preceding embodiment wherein the anti-BDCA-2 (CLEC4C) antigen binding molecule is an antibody selected from the group consisting of 3E05_var12, 3E05_var6, 3E05_var14, 3E05, 3E05_var1, 3E05_var2, 3E05_var3, 3E05_var4, 3E05_var5, 3E05_var7, 3E05_var8, 3E05_var9, 3E05_var10, 3E05_var11, 3E05_var13, 3E05_var15, 3E05_var16, 21E06, 25E06 and 28B01.
18. The anti-BDCA-2 (CLEC4C) antigen binding molecule of embodiment 17, wherein the antibody comprises from 1 to 10, from 1 to 5 or from 1 to 2 amino acid substitutions across all 6 CDR regions.
19. The anti-BDCA-2 (CLEC4C) antigen binding molecule of embodiment 17, wherein the antibody comprises 1 or 2 amino acid substitution across all 6 CDR regions.
20. The anti-BDCA-2 (CLEC4C) antigen binding molecule of embodiment 17, wherein the antibody comprises 1 to 10, 1 to 5 or 1 to 2 amino acid substitutions in one or more framework regions.
21. The anti-BDCA-2 (CLEC4C) antigen binding molecule of embodiment 17, wherein the antibody comprises 1 or 2 amino acid substitutions in one or more framework regions.
22. The anti-BDCA-2 (CLEC4C) antigen binding molecule of any one of embodiments 18 to 21, wherein the amino acid substitutions are conservative amino acid substitutions.
23. The anti-BDCA-2 (CLEC4C) antigen binding molecule of any one of embodiments 9 to 22, wherein the antigen binding molecule has an equilibrium dissociation constant ($K_D$) for BDCA-2 (CLEC4C) of less than about 2 nM.
24. The anti-BDCA-2 (CLEC4C) antigen binding molecule of embodiment 23, wherein the antigen binding molecule has an equilibrium dissociation constant ($K_D$) for BDCA-2 (CLEC4C) of less than about 1 nM, less than about 0.75 nM, less than about 0.5 nM, less than about 0.4 nM, less than about 0.3 nM, less than about 0.2 nM, less than about 0.1M, less than about 0.08 nM, less than about 0.06 nM, less than about 0.05 nM, less than about 0.04 nM, less than about 0.03 nM, less than about 0.02 nM or less than about 0.01 nM.
25. The anti-BDCA-2 (CLEC4C) antigen binding molecule of any one of embodiments 9 to 24, wherein the antigen binding molecule has a half maximal inhibitory concentration (IC50) for inhibition of IFN secretion of less than about 2 nM.
26. The anti-BDCA-2 (CLEC4C) antigen binding molecule of embodiment 25, wherein the antigen binding molecule has a half maximal inhibitory concentration (IC50) for inhibition of IFN secretion of less than about 1.5 nM, less than about 1 nM, less than about 0.9 nM, less than about 0.8 nM, less than about 0.7 nM, less than about 0.6 nM, less than about 0.5, less than about 0.4 nM, less than about 0.3 nM, less than about 0.2 nM, or less than about 0.1 nM.
27. The anti-BDCA-2 (CLEC4C) antigen binding molecule of any one of embodiments 9 to 26, wherein the antigen binding molecule has an IC90 for inhibition of IFN secretion of less than about 20 nM.
28. The anti-BDCA-2 (CLEC4C) antigen binding molecule of embodiment 27, wherein the antigen binding molecule has an IC90 for inhibition of IFN secretion of less than about 15 nM, less than about 10 nM, less than about 9 nM, less than about 8 nM, less than about 7 nM, less than about 6 nM, less than about 5 nM, less than about 4 nM, less than about 3 nM, less than about 2 nM or less than about 1 nM.

29. The anti-BDCA-2 (CLEC4C) antigen binding molecule of any one of embodiments 9 to 28, wherein the antigen binding molecule has an equilibrium dissociation constant ($K_D$) for BDCA-2 (CLEC4C) of less than about 2 nM, a half maximal inhibitory concentration (IC50) for inhibition of IFN secretion of less than about 2 nM, and/or an IC90 for inhibition of IFN secretion of less than about 20 nM.
30. The anti-BDCA-2 (CLEC4C) antigen binding molecule of embodiment 29, wherein the antigen binding molecule has an equilibrium dissociation constant ($K_D$) for BDCA-2 (CLEC4C) of less than about 0.01 nM, a half maximal inhibitory concentration (IC50) for inhibition of IFN secretion of less than about 0.5 nM, and/or an IC90 for inhibition of IFN secretion of less than about 5 nM
31. An anti-BDCA-2 (CLEC4C) antigen binding molecule that specifically binds to BDCA-2 (CLEC4C) and competes with binding to BDCA-2 (CLEC4C) with an antigen-binding molecule of any one of embodiments 1 to 30.
32. An anti-BDCA-2 (CLEC4C) antigen binding molecule that specifically binds to BDCA-2 (CLEC4C) and inhibits the binding of BDCA-2 (CLEC4C) to an antigen binding molecule of any one of embodiments 1 to 31.
33. An anti-BDCA-2 (CLEC4C) antigen binding molecule that specifically binds to BDCA-2 (CLEC4C), wherein the anti-BDCA-2 (CLEC4C) antigen binding molecule is a humanised or deimmunised derivative of an anti-BDCA-2 (CLEC4C) antigen binding molecule of any one of embodiments 1 to 32.
34. An anti-BDCA-2 (CLEC4C) antigen binding molecule that specifically binds to BDCA-2 (CLEC4C), wherein the anti-BDCA-2 (CLEC4C) antigen binding molecule is an affinity matured mutant of an anti-BDCA-2 (CLEC4C) antigen binding molecule of any one of embodiments 1 to 33.
35. An anti-BDCA-2 (CLEC4C) antigen binding molecule that specifically binds to an epitope of BDCA-2 (CLEC4C) that is bound by an anti-BDCA-2 (CLEC4C) antigen binding molecule of any one of embodiments 1 to 34.
36. The anti-BDCA-2 (CLEC4C) antigen binding molecule of any preceding embodiment wherein the antigen binding molecule is an antibody or an antigen-binding fragment or derivative thereof.
37. The anti-BDCA-2 (CLEC4C) antigen binding molecule of embodiment 36, wherein the antigen-binding fragment or derivative thereof is Fab, F(ab')2, Fv, scFv, dAb, Fd, or a diabody.
38. The anti-BDCA-2 (CLEC4C) antigen binding molecule of any one of embodiments 1 to 36, wherein the anti-BDCA-2 (CLEC4C) antigen binding molecule is a monoclonal antibody.
39. The anti-BDCA-2 (CLEC4C) antibody or antigen-binding fragment or derivative thereof of any one of embodiments 36 to 40, wherein the antibody or antigen-binding fragment or derivative thereof is an IgA, IgD, IgE, IgG, IgM or IgY antibody or antigen-binding fragment or derivative thereof.
40. The anti-BDCA-2 (CLEC4C) antibody or antigen-binding fragment or derivative thereof of any one of embodiments 36 to 39, wherein the antibody or antigen-binding fragment or derivative thereof is an IgG antibody or antigen-binding fragment or derivative thereof.
41. The anti-BDCA-2 (CLEC4C) antibody or antigen-binding fragment or derivative thereof of any one of embodiments 36 to 40, wherein the antibody or antigen-binding fragment or derivative thereof is an IgG1 antibody or antigen-binding fragment or derivative thereof.
42. The anti-BDCA-2 (CLEC4C) antigen binding molecule of any preceding embodiment, wherein the antigen binding molecule decreases the secretion of IFNα when administered in vivo or in vitro.
43. The anti-BDCA-2 (CLEC4C) antigen binding molecule of embodiment 42 wherein the antigen binding molecule decreases the secretion of IFNα when administered in vivo or in vitro by at least about 10%, at least about 20%, at least about 30%, at least about 40%, at least about 50%, at least about 60%, at least about 70%, at least about 80%, at least about 90%, at least about 95% or at least about 99% relative to a control not comprising the anti-BDCA-2 (CLEC4C) antigen binding molecule.
44. The anti-BDCA-2 (CLEC4C) antigen binding molecule of any preceding embodiment, wherein the antigen binding molecule binds an epitope consisting of one or more amino acid residues of residues 166 to 179 of human BDCA-2 (SEQ ID NO: 82).
45. An anti-BDCA-2 (CLEC4C) antigen binding molecule, wherein the antigen binding molecule binds an epitope consisting of one or more amino acid residues of residues 166 to 179 of human BDCA-2 (SEQ ID NO: 82).
46. A pharmaceutical composition comprising an anti-BDCA-2 (CLEC4C) antigen binding molecule of any preceding embodiment and a pharmaceutically acceptable excipient.
47. A kit comprising an anti-BDCA-2 (CLEC4C) antigen binding molecule of any of embodiments 1 to 45 or a pharmaceutical composition according to embodiment 46, and further comprising an additional therapeutically active agent.
48. An anti-BDCA-2 (CLEC4C) antigen binding molecule of any one of embodiments 1 to 45, or a pharmaceutical composition according to embodiment 46, or a kit according to embodiment 47, for use in medicine.
49. An anti-BDCA-2 (CLEC4C) antigen binding molecule of any one of embodiments 1 to 45, or a pharmaceutical composition according to embodiment 46, or a kit according to embodiment 47, for use in the treatment or prevention of an inflammatory disorder or disease or an autoimmune disorder or disease.
50. The anti-BDCA-2 (CLEC4C) antigen binding molecule or pharmaceutical composition or kit for use as in embodiment 49, wherein the inflammatory or autoimmune disorder or disease is selected from the group consisting of systemic sclerosis, fibrosis (such as skin fibrosis), pemphigus vulgaris, systemic lupus erythematosus (SLE), cutaneous lupus, discoid lupus, lupus nephritis, polymyositis and dermatomyositis, psoriasis, rheumatoid arthritis, Grave's disease, morphea, inflammatory bowel disease, morphea, type I diabetes, Sjogren's disease and Hashimoto's disease.
51. The anti-BDCA-2 (CLEC4C) antigen binding molecule or pharmaceutical composition or kit for use as in embodiment 49, wherein the inflammatory disease is systemic sclerosis, fibrosis (such as skin fibrosis) or pemphigus vulgaris.

52. A method for the treatment or prevention of a BDCA-2 (CLEC4C)-mediated disease or disorder comprising administering to the subject an anti-BDCA-2 (CLEC4C) antigen binding molecule of any one of embodiments 1 to 45, or a pharmaceutical composition according to embodiment 46, or the components of the kit of embodiment 47.

53. A method for the treatment or prevention of an inflammatory disorder or disease or an autoimmune disorder or disease comprising administering to the subject an anti-BDCA-2 (CLEC4C) antigen binding molecule of any one of embodiments 1 to 45, or a pharmaceutical composition according to embodiment 46, or the components of the kit of embodiment 47.

The invention claimed is:

1. An anti-BDCA-2 (CLEC4C) antigen binding molecule comprising (a)

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

(b)

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34);

(c)

a heavy chain variable region comprising a VHCDR1 comprising the amino acid sequence SYTMS (SEQ ID NO: 26), a VHCDR2 comprising the amino acid sequence YISSGGGNTYY ADSVKG (SEQ ID NO: 27), a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(d)

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(e)

a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), a VHCDR3 comprising the amino acid sequence HDYYDGGLYYAMDY (SEQ ID NO 28); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

(f)

a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), a VHCDR3 comprising the amino acid sequence HDYYDGGLYYAMDY (SEQ ID NO: 28); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

(g)

a heavy chain variable region comprising a VHCDR1 comprising the amino acid sequence SYTMS (SEQ ID NO: 6), a VHCDR2 comprising the amino acid sequence YISSGGGNTYYPDSVKG(SEQ ID NO: 7) and a VHCDR3 comprising the amino acid sequence HDYYDGGLYYAMDY (SEQ ID NO: 8); and a light chain variable region comprising a VLCDR1 comprising the amino acid sequence KASQSVDYDGDSSMN (SEQ ID NO: 2), a VLCDR2 comprising the amino acid sequence AASTLES (SEQ ID NO: 3) and a VLCDR3 comprising the amino acid sequence QQTNEDPPT (SEQ ID NO: 4);

(h)

a heavy chain variable region comprising a VHCDR1 comprising the amino acid sequence GFTFSSY (SEQ ID NO: 9), a VHCDR2 comprising the amino acid sequence SSGGGNTY (SEQ ID NO: 10) and a VHCDR3 comprising the amino acid sequence HDYYDGGLYY AMDY (SEQ ID NO: 8); and a light chain variable region comprising a VLCDR1 comprising the amino acid sequence KASQSVDYDGDSSMN (SEQ ID NO: 2), a VLCDR2 comprising the amino acid sequence AASTLES (SEQ ID NO: 3) and a VLCDR3 comprising the amino acid sequence QQTNEDPPT (SEQ ID NO: 4);

(i)

a heavy chain variable region comprising a VHCDR1 comprising the amino acid sequence SYTMS (SEQ ID NO: 36), a VHCDR2 comprising the amino acid sequence YISSGGGQTYYPDSVKG (SEQ ID NO: 37), a VHCDR3 comprising the amino acid HDYYDGGLYYAMDY sequence (SEQ ID NO: 38); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

(j)

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), a VHCDR3 comprising the amino acid HDYYDGGLYYAMDY sequence (SEQ ID NO: 38); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

(k)

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), a VHCDR3 comprising the amino acid sequence HDYYEGGLYYAMDY (SEQ ID NO: 48); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

(l)

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), a VHCDR3 comprising the amino acid sequence HDYYEGGLYYA.MOY (SEQ ID NO: 48); and a light chain variable region comprising a VLCDR1 comprising the amino acid sequence KASQSVDYDGDSSMN (SEQ ID NO: 12), a VLCDR2 comprising the amino acid sequence AASTLES (SEQ ID NO: 13) and a VLCDR3 comprising the amino acid sequence QQTNEDPPT (SEQ ID NO: 14);

(m)

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), a VHCDR3 comprising the amino acid sequence HDYYDGGLYYAMDY (SEQ ID NO: 18); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(n)

a heavy chain variable region comprising a VHCDR1 comprising the amino acid sequence SYTMS (SEQ ID NO: 36), a VHCDR2 comprising the amino acid sequence YISSGGGQTYYPDSVKG(SEQ ID NO: 37), a VHCDR3 comprising the amino acid HDYYDGGLYYAMDY sequence (SEQ ID NO: 38); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(o)

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), a VHCDR3 comprising the amino acid HDYYDGGLYYAMDY sequence (SEQ ID NO: 38); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24);

(p)

a heavy chain variable region comprising a VHCDR1 comprising the amino acid sequence SYTMS (SEQ ID NO: 16), a VHCDR2 comprising the amino acid sequence YISSGGGNTYYPDSVKG (SEQ ID NO: 17), a VHCDR3 comprising the amino acid sequence HDYYDGGLYY AMDY (SEQ ID NO: 18); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44);

(q)

a heavy chain variable region comprising a VHCDR1 comprising the amino acid sequence SYTMS (SEQ ID NO: 36), a VHCDR2 comprising the amino acid sequence YISSGGGQTYYPDSVKG(SEQ ID NO: 37), a VHCDR3 comprising the amino acid HDYYDG-GLYY AMDY sequence (SEQ ID NO: 38); and a light chain variable region comprising a VLCDR1 comprising the amino acid sequence KASQSVDYEGDSS11N (SEQ ID NO 42), a VLCDR2 comprising the amino acid sequence AASTLES (SEQ ID NO: 43) and a VLCDR3 comprising the amino acid sequence QQTNEDPPT (SEQ ID NO: 44);

(r)

a heavy chain variable region comprising a VHCDR1 comprising the amino acid sequence GFTFSSY (SEQ ID NO: 39), a VHCDR2 comprising the amino acid sequence SSGGGQTY (SEQ ID NO: 40), a VHCDR3 comprising the amino acid HDYYDGGLYY AMDY sequence (SEQ ID NO: 38); and a light chain variable region comprising a VLCDR1 comprising the amino acid sequence KASQSVDYEGDSS11N (SEQ ID NO 42), a VLCDR2 comprising the amino acid sequence AASTLES (SEQ ID NO: 43) and a VLCDR3 comprising the amino acid sequence QQTNEDPPT (SEQ ID NO: 44);

(s)

a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), a VHCDR3 comprising the amino acid sequence HDYYEGGLYYAMDY (SEQ ID NO: 48); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44); and or (t)

a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), a VHCDR3 comprising the amino acid sequence HDYYEG-GLYYMIDY (SEQ ID NO: 48); and a light chain variable region comprising a VLCDR1 comprising the amino acid sequence KASQSVDYDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44).

2. The anti-BDCA-2 (CLEC4C) antigen binding molecule of claim 1, wherein the antigen binding molecule comprises:

a heavy chain variable region having at least 80% identity to the amino acid sequence of SEQ ID NO: 45, SEQ ID NO: 25, SEQ ID NO: 5, SEQ ID NO: 15, or SEQ ID NO: 35;

and/or a light chain variable region having at least 80% identity to the amino acid sequence of SEQ ID NO: 31, SEQ ID NO: 21, SEQ ID NO: 41, SEQ ID NO 1 or SEQ ID NO: 11.

3. The anti-BDCA-2 (CLEC4C) antigen binding molecule of claim 1, wherein the antigen binding molecule comprises:

a) a VH comprising the amino acid sequence of SEQ ID NO: 45 and a VL comprising the amino acid sequence of SEQ ID NO 31;

b) a VH comprising the amino acid sequence of SEQ ID NO: 25 and a VL comprising the amino acid sequence of SEQ ID NO: 21;

c) a VH comprising the amino acid sequence of SEQ ID NO: 25 and a VL comprising the amino acid sequence of SEQ ID NO: 41;

d) a VH comprising the amino acid sequence of SEQ ID NO: 5 and a VL comprising the amino acid sequence of SEQ ID NO: 1;

e) a VH comprising the amino acid sequence of SEQ ID NO: 15 and a VL comprising the amino acid sequence of SEQ ID NO: 11;

f) a VH comprising the amino acid sequence of SEQ ID NO: 35 and a VL comprising the amino acid sequence of SEQ ID NO: 11;

g) a VH comprising the amino acid sequence of SEQ ID NO: 45 and a VL comprising the amino acid sequence of SEQ ID NO: 11;

h) a VH comprising the amino acid sequence of SEQ ID NO: 15 and a VL comprising the amino acid sequence of SEQ ID NO 21;

i) a VH comprising the amino acid sequence of SEQ ID NO: 35 and a VL comprising the amino acid sequence of SEQ ID NO: 21;

j) a VH comprising the amino acid sequence of SEQ ID NO: 45 and a VL comprising the amino acid sequence of SEQ ID NO: 21;

k) a VH comprising the amino acid sequence of SEQ ID NO: 15 and a VL comprising the amino acid sequence of SEQ ID NO: 31;

l) a VH comprising the amino acid sequence of SEQ ID NO: 15 and a VL comprising the amino acid sequence of SEQ ID NO: 41;

m) a VH comprising the amino acid sequence of SEQ ID NO: 35 and a VL comprising the amino acid sequence of SEQ ID NO: 41; or n) a VH comprising the amino acid sequence of SEQ ID NO: 45 and a VL comprising the amino acid sequence of SEQ ID NO: 41.

4. The anti-BDCA-2 (CLEC4C) antigen binding molecule of claim 1, wherein the anti-BDCA-2 (CLEC4C) antigen binding molecule is one of the following antibodies: 3E05_var12, 3E05_var6, 3E05_var14, 3E05, 3E05_var1, 3E05_var3, 3E05_var4, 3E05_var5, 3E05_var7, 3E05_var8, 3E05_var9, 3E05_var13, 3E05_var5 or 3E05_var16.

5. The anti-BDCA-2 (CLEC4C) antigen binding molecule of claim 1, wherein the antigen binding molecule is:

a monoclonal antibody; or an antibody or an antigen binding fragment or derivative thereof.

6. The anti-BDCA-2 (CLEC4C) antigen binding molecule of claim 5, wherein the antigen binding fragment or derivative thereof is a Fab, F(ab')2, Fv, scFv, or diabody.

7. The anti-BDCA-2 (CLEC4C) antigen binding molecule of claim 5, wherein the antibody or antigen binding fragment or derivative thereof is an IgA, IgD, IgE, IgG, IgM or IgY antibody or antigen binding fragment or derivative thereof.

8. The anti-BDCA-2 (CLEC4C) antigen binding molecule of claim 1, wherein the antibody or antigen binding fragment or derivative thereof is an IgG antibody or antigen binding fragment or derivative thereof.

9. The anti-BDCA-2 (CLEC4C) antigen binding molecule of claim 8, wherein the IgG antibody or antigen binding fragment or derivative thereof is an IgGl antibody or antigen binding fragment or derivative thereof.

10. The anti-BDCA-2 (CLEC4C) antigen binding molecule of claim 1, wherein the antigen binding molecule has a half maximal inhibitory concentration (IC50) for inhibition of interferon (IFNα) secretion of less than about 2 nM.

11. The anti-BDCA-2 (CLEC4C) antigen binding molecule of claim 1, wherein the antigen binding molecule has an IC90 for inhibition of interferon-α (IFNα) secretion of less than about 20 nM.

12. The anti-BDCA-2 (CLEC4C) antigen binding molecule of claim 1, wherein the antigen binding molecule decreases the secretion of interferon-α (IFNα) when administered in vivo or in vitro.

13. A pharmaceutical composition comprising an anti-BDCA-2 (CLEC4C) antigen binding molecule of claim 1 and a pharmaceutically acceptable excipient.

14. A method of treating an inflammatory disorder or disease in a subject in need thereof, comprising administering to the subject a therapeutically effective amount of a pharmaceutical composition of claim 13.

15. The method of treating an inflammatory disorder or disease of claim 14, wherein the inflammatory disorder or disease is selected from the group consisting of systemic sclerosis, fibrosis, skin fibrosis, pemphigus vulgaris, systemic lupus erythematosus (SLE), cutaneous lupus, discoid lupus, lupus nephritis, polymyositis and dermatomyositis, psoriasis, rheumatoid arthritis, Grave's disease, morphea, inflammatory bowel disease, morphea, type I diabetes, Sjogren's disease and Hashimoto's disease.

16. The method of treating an inflammatory disorder or disease of claim 15, wherein the inflammatory disease is systemic sclerosis, fibrosis, skin fibrosis, or pemphigus vulgaris.

17. The anti-BDCA-2 (CLEC4C) antigen binding molecule of claim 1, comprising:

(i) a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), a VHCDR3 comprising the amino acid sequence HDYYDGGLYYAMDY (SEQ ID NO: 28); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24), as determined by Kabat; or (ii) a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), a VHCDR3 comprising the amino acid sequence HDYYDG-GLYYAMDY (SEQ ID NO: 28); and a light chain variable region comprising a VLCDR1 comprising the amino acid sequence KSSQSVDYDGDSSMN (SEQ ID NO: 22), a VLCDR2 comprising the amino acid sequence AASTLES (SEQ ID NO: 23) and a VLCDR3 comprising the amino acid sequence QQTNEDPPT (SEQ ID NO: 24), as determined by Chothia.

18. The anti-BDCA-2 (CLEC4C) antigen binding molecule of claim 1, comprising a heavy chain variable region comprising SEQ ID NO: 25, and a light chain variable region comprising SEQ ID NO: 21.

19. The anti-BDCA-2 (CLEC4C) antigen binding molecule of claim 1, comprising:

(i) a heavy chain variable region comprising a VHCDR1 comprising the amino acid sequence SYTMS (SEQ ID NO: 46), a VHCDR2 comprising the amino acid sequence YISSGGGQTYYPDSVKG (SEQ ID NO: 47), a VHCDR3 comprising the amino acid sequence HDYYEGGLYYAMDY (SEQ ID NO: 48); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34), as determined by Kabat; or (ii) a heavy chain variable region comprising a VHCDR1 comprising the amino acid sequence GFTFSSY (SEQ ID NO: 49), a VHCDR2 comprising the amino acid sequence SSGGGQTY (SEQ ID NO: 50), a VHCDR3 comprising the amino acid sequence HDYYEG-GLYYAMDY (SEQ ID NO: 48); and a light chain variable region comprising a VLCDR1 comprising the amino acid sequence KSSQSVDYDGDSSMN (SEQ ID NO: 32), a VLCDR2 comprising the amino acid sequence AASTLES (SEQ ID NO: 33) and a VLCDR3 comprising the amino acid sequence QQTNEDPPT (SEQ ID NO: 34), as determined by Chothia.

20. The anti-BDCA-2 (CLEC4C) antigen binding molecule of claim 1, comprising a heavy chain variable region comprising SEQ ID NO: 45, and a light chain variable region comprising SEQ ID NO: 31.

21. The anti-BDCA-2 (CLEC4C) antigen binding molecule of claim 1, comprising:

(i) a heavy chain variable region comprising a VHCDR1 comprising the amino acid sequence SYTMS (SEQ ID NO: 26), a VHCDR2 comprising the amino acid sequence YISSGGGNTYYADSVKG (SEQ ID NO: 27), a VHCDR3 comprising the amino acid sequence HDYYDGGLYYAMDY (SEQ ID NO: 28); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44), as determined by Kabat; or (ii) a heavy chain variable region comprising a VHCDR1 comprising the amino acid sequence GFTFSSY (SEQ ID NO: 29), a VHCDR2 comprising the amino acid sequence SSGGGNTY (SEQ ID NO: 30), a VHCDR3 comprising the amino acid sequence HDYYDGGLYYAMDY (SEQ ID NO: 28); and a light chain variable region comprising a VLCDR1 comprising the amino acid sequence KASQSVDYEGDSSMN (SEQ ID NO: 42), a VLCDR2 comprising the amino acid sequence AASTLES (SEQ ID NO: 43) and a VLCDR3 comprising the amino acid sequence QQTNEDPPT (SEQ ID NO: 44), as determined by Chothia.

22. The anti-BDCA-2 (CLEC4C) antigen binding molecule of claim 1, comprising a heavy chain variable region comprising SEQ ID NO: 25, and a light chain variable region comprising SEQ ID NO: 41.

23. The anti-BDCA-2 (CLEC4C) antigen binding molecule of claim 18, wherein the BDCA-2 (CLEC4C) antigen binding molecule is an IgG antibody.

24. The anti-BDCA-2 (CLEC4C) antigen binding molecule of claim 20, wherein the BDCA-2 (CLEC4C) antigen binding molecule is an IgG antibody.

25. The anti-BDCA-2 (CLEC4C) antigen binding molecule of claim 22, wherein the BDCA-2 (CLEC4C) antigen binding molecule is an IgG antibody.

* * * * *

SEQUENCE LISTING

```
<160> NUMBER OF SEQ ID NOS: 92

<210> SEQ ID NO 1
<211> LENGTH: 111
<212> TYPE: PRT
<213> ORGANISM: Artificial Sequence
<220> FEATURE:
<223> OTHER INFORMATION: Parental 3E05 VL

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Ser Met Asn Trp Tyr Gln Gln Lys Pro Gly Gln Pro Pro
        35                  40                  45

Lys Leu Leu Ile Cys Ala Ala Ser Thr Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Thr Asn
                85                  90                  95

Glu Asp Pro Pro Thr Phe Gly Gly Gly Thr Lys Leu Glu Ile Lys
            100                 105                 110


<210> SEQ ID NO 2
<211> LENGTH: 15
<212> TYPE: PRT
<213> ORGANISM: Artificial Sequence
<220> FEATURE:
<223> OTHER INFORMATION: Parental 3E05 VL CDR 1 (Kabat and Chothia)

<400> SEQUENCE: 2

Lys Ala Ser Gln Ser Val Asp Tyr Asp Gly Asp Ser Ser Met Asn
1               5                   10                  15


<210> SEQ ID NO 3
<211> LENGTH: 7
<212> TYPE: PRT
<213> ORGANISM: Artificial Sequence
<220> FEATURE:
<223> OTHER INFORMATION: Parental 3E05 VL CDR 2 (Kabat and Chothia)

<400> SEQUENCE: 3

Ala Ala Ser Thr Leu Glu Ser
1               5


<210> SEQ ID NO 4
<211> LENGTH: 9
<212> TYPE: PRT
<213> ORGANISM: Artificial Sequence
<220> FEATURE:
<223> OTHER INFORMATION: Parental 3E05 VL CDR 3 (Kabat and Chothia)

<400> SEQUENCE: 4
```

Gln Gln Thr Asn Glu Asp Pro Pro Thr
1 5

<210> SEQ ID NO 5
<211> LENGTH: 123
<212> TYPE: PRT
<213> ORGANISM: Artificial Sequence
<220> FEATURE:
<223> OTHER INFORMATION: Parental 3E05 VH

<400> SEQUENCE: 5

Glu Val Lys Leu Val Glu Ser Gly Gly Gly Leu Val Lys Pro Gly Gly
1 5 10 15

Ser Leu Lys Leu Ser Cys Ala Ala Ser Gly Phe Thr Phe Ser Ser Tyr
20 25 30

Thr Met Ser Trp Val Arg Gln Thr Pro Glu Lys Arg Leu Glu Trp Val
35 40 45

Ala Tyr Ile Ser Ser Gly Gly Gly Asn Thr Tyr Tyr Pro Asp Ser Val
50 55 60

Lys Gly Arg Phe Thr Ile Ser Arg Asp Asn Ala Arg Asn Thr Leu Tyr
65 70 75 80

Leu Gln Met Ser Ser Leu Arg Ser Glu Asp Thr Ala Met Tyr Tyr Cys
85 90 95

Ala Arg His Asp Tyr Tyr Asp Gly Gly Leu Tyr Tyr Ala Met Asp Tyr
100 105 110

Trp Gly Gln Gly Thr Ser Val Thr Val Ser Ser
115 120

<210> SEQ ID NO 6
<211> LENGTH: 5
<212> TYPE: PRT
<213> ORGANISM: Artificial Sequence
<220> FEATURE:
<223> OTHER INFORMATION: Parental 3E05 VH CDR 1 (Kabat)

<400> SEQUENCE: 6

Ser Tyr Thr Met Ser
1 5

<210> SEQ ID NO 7
<211> LENGTH: 17
<212> TYPE: PRT
<213> ORGANISM: Artificial Sequence
<220> FEATURE:
<223> OTHER INFORMATION: Parental 3E05 VH CDR 2 (Kabat)

<400> SEQUENCE: 7

Tyr Ile Ser Ser Gly Gly Gly Asn Thr Tyr Tyr Pro Asp Ser Val Lys
1 5 10 15

Gly

<210> SEQ ID NO 8
<211> LENGTH: 14
<212> TYPE: PRT
<213> ORGANISM: Artificial Sequence
<220> FEATURE:
<223> OTHER INFORMATION: Parental 3E05 VH CDR 3 (Kabat and Chothia)

<400> SEQUENCE: 8

His Asp Tyr Tyr Asp Gly Gly Leu Tyr Tyr Ala Met Asp Tyr
1 5 10

<210> SEQ ID NO 9
<211> LENGTH: 7
<212> TYPE: PRT
<213> ORGANISM: Artificial Sequence
<220> FEATURE:
<223> OTHER INFORMATION: Parental 3E05 VH CDR 1 (Chothia)

<400> SEQUENCE: 9

```
Gly Phe Thr Phe Ser Ser Tyr
1               5
```

<210> SEQ ID NO 10
<211> LENGTH: 8
<212> TYPE: PRT
<213> ORGANISM: Artificial Sequence
<220> FEATURE:
<223> OTHER INFORMATION: Parental 3E05 VH CDR 2 (Chothia)

<400> SEQUENCE: 10

```
Ser Ser Gly Gly Gly Asn Thr Tyr
1               5
```

<210> SEQ ID NO 11
<211> LENGTH: 111
<212> TYPE: PRT
<213> ORGANISM: Artificial Sequence
<220> FEATURE:
<223> OTHER INFORMATION: 3E05 VL_1

<400> SEQUENCE: 11

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Ser Met Asn Trp Tyr Gln Gln Lys Pro Gly Gln Pro Pro
        35                  40                  45

Lys Leu Leu Ile Ser Ala Ala Ser Thr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Asn
                85                  90                  95

Glu Asp Pro Pro Thr Phe Gly Gly Gly Thr Lys Val Glu Ile Lys
            100                 105                 110
```

<210> SEQ ID NO 12
<211> LENGTH: 15
<212> TYPE: PRT
<213> ORGANISM: Artificial Sequence
<220> FEATURE:
<223> OTHER INFORMATION: 3E05 VL_1 CDR 1 (Kabat and Chothia)

<400> SEQUENCE: 12

```
Lys Ala Ser Gln Ser Val Asp Tyr Asp Gly Asp Ser Ser Met Asn
1               5                   10                  15
```

<210> SEQ ID NO 13
<211> LENGTH: 7
<212> TYPE: PRT
<213> ORGANISM: Artificial Sequence
<220> FEATURE:
<223> OTHER INFORMATION: 3E05 VL_1 CDR 2 (Kabat and Chothia)

<400> SEQUENCE: 13

Ala Ala Ser Thr Leu Glu Ser
1 5

<210> SEQ ID NO 14
<211> LENGTH: 9
<212> TYPE: PRT
<213> ORGANISM: Artificial Sequence
<220> FEATURE:
<223> OTHER INFORMATION: 3E05 VL_1 CDR 3 (Kabat and Chothia)

<400> SEQUENCE: 14

Gln Gln Thr Asn Glu Asp Pro Pro Thr
1 5

<210> SEQ ID NO 15
<211> LENGTH: 123
<212> TYPE: PRT
<213> ORGANISM: Artificial Sequence
<220> FEATURE:
<223> OTHER INFORMATION: 3E05 VH_1

<400> SEQUENCE: 15

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Thr Met Ser Trp Val Arg Gln Ala Pro Gly Lys Gly Leu Glu Trp Val
35 40 45

Ala Tyr Ile Ser Ser Gly Gly Gly Asn Thr Tyr Tyr Pro Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg His Asp Tyr Tyr Asp Gly Gly Leu Tyr Tyr Ala Met Asp Tyr
100 105 110

Trp Gly Gln Gly Thr Leu Val Thr Val Ser Ser
115 120

<210> SEQ ID NO 16
<211> LENGTH: 5
<212> TYPE: PRT
<213> ORGANISM: Artificial Sequence
<220> FEATURE:
<223> OTHER INFORMATION: 3E05 VH_1 CDR 1 (Kabat)

<400> SEQUENCE: 16

Ser Tyr Thr Met Ser
1 5

<210> SEQ ID NO 17
<211> LENGTH: 17
<212> TYPE: PRT
<213> ORGANISM: Artificial Sequence
<220> FEATURE:
<223> OTHER INFORMATION: 3E05 VH_1 CDR 2 (Kabat)

<400> SEQUENCE: 17

Tyr Ile Ser Ser Gly Gly Gly Asn Thr Tyr Tyr Pro Asp Ser Val Lys
1 5 10 15

Gly

<210> SEQ ID NO 18
<211> LENGTH: 14
<212> TYPE: PRT
<213> ORGANISM: Artificial Sequence
<220> FEATURE:
<223> OTHER INFORMATION: 3E05 VH_1 CDR 3 (Kabat and Chothia)

<400> SEQUENCE: 18

His Asp Tyr Tyr Asp Gly Gly Leu Tyr Tyr Ala Met Asp Tyr
1 5 10

<210> SEQ ID NO 19
<211> LENGTH: 7
<212> TYPE: PRT
<213> ORGANISM: Artificial Sequence
<220> FEATURE:
<223> OTHER INFORMATION: 3E05 VH_1 CDR 1 (Chothia)

<400> SEQUENCE: 19

Gly Phe Thr Phe Ser Ser Tyr
1 5

<210> SEQ ID NO 20
<211> LENGTH: 8
<212> TYPE: PRT
<213> ORGANISM: Artificial Sequence
<220> FEATURE:
<223> OTHER INFORMATION: 3E05 VH_1 CDR 2 (Chothia)

<400> SEQUENCE: 20

Ser Ser Gly Gly Gly Asn Thr Tyr
1 5

<210> SEQ ID NO 21
<211> LENGTH: 111
<212> TYPE: PRT
<213> ORGANISM: Artificial Sequence
<220> FEATURE:
<223> OTHER INFORMATION: 3E05 VL_2

<400> SEQUENCE: 21

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Asp Tyr Asp
20 25 30

Gly Asp Ser Ser Met Asn Trp Tyr Gln Gln Lys Pro Gly Gln Pro Pro
35 40 45

Lys Leu Leu Ile Ser Ala Ala Ser Thr Leu Glu Ser Gly Val Pro Ser
50 55 60

Arg Phe Ser Gly Ser Gly Ser Gly Thr Asp Phe Thr Leu Thr Ile Ser
65 70 75 80

Ser Leu Gln Ala Glu Asp Val Ala Thr Tyr Tyr Cys Gln Gln Thr Asn
85 90 95

Glu Asp Pro Pro Thr Phe Gly Gly Gly Thr Lys Val Glu Ile Lys
100 105 110

<210> SEQ ID NO 22
<211> LENGTH: 15
<212> TYPE: PRT
<213> ORGANISM: Artificial Sequence
<220> FEATURE:
<223> OTHER INFORMATION: 3E05 VL_2 CDR 1 (Kabat and Chothia)

<400> SEQUENCE: 22

Lys Ser Ser Gln Ser Val Asp Tyr Asp Gly Asp Ser Ser Met Asn
1 5 10 15

<210> SEQ ID NO 23
<211> LENGTH: 7
<212> TYPE: PRT
<213> ORGANISM: Artificial Sequence
<220> FEATURE:
<223> OTHER INFORMATION: 3E05 VL_2 CDR 2 (Kabat and Chothia)

<400> SEQUENCE: 23

Ala Ala Ser Thr Leu Glu Ser
1 5

<210> SEQ ID NO 24
<211> LENGTH: 9
<212> TYPE: PRT
<213> ORGANISM: Artificial Sequence
<220> FEATURE:
<223> OTHER INFORMATION: 3E05 VL_2 CDR 3 (Kabat and Chothia)

<400> SEQUENCE: 24

Gln Gln Thr Asn Glu Asp Pro Pro Thr
1 5

<210> SEQ ID NO 25
<211> LENGTH: 123
<212> TYPE: PRT
<213> ORGANISM: Artificial Sequence
<220> FEATURE:
<223> OTHER INFORMATION: 3E05 VH_2

<400> SEQUENCE: 25

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Thr Met Ser Trp Val Arg Gln Ala Pro Gly Lys Gly Leu Glu Trp Val
35 40 45

Ser Tyr Ile Ser Ser Gly Gly Gly Asn Thr Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg His Asp Tyr Tyr Asp Gly Gly Leu Tyr Tyr Ala Met Asp Tyr
100 105 110

Trp Gly Gln Gly Thr Leu Val Thr Val Ser Ser
115 120

<210> SEQ ID NO 26
<211> LENGTH: 5
<212> TYPE: PRT
<213> ORGANISM: Artificial Sequence
<220> FEATURE:
<223> OTHER INFORMATION: 3E05 VH_2 CDR 1 (Kabat)

<400> SEQUENCE: 26

Ser Tyr Thr Met Ser
1 5

<210> SEQ ID NO 27
<211> LENGTH: 17

<212> TYPE: PRT
<213> ORGANISM: Artificial Sequence
<220> FEATURE:
<223> OTHER INFORMATION: 3E05 VH_2 CDR 2 (Kabat)

<400> SEQUENCE: 27

Tyr Ile Ser Ser Gly Gly Gly Asn Thr Tyr Tyr Ala Asp Ser Val Lys
1               5                   10                  15

Gly

<210> SEQ ID NO 28
<211> LENGTH: 14
<212> TYPE: PRT
<213> ORGANISM: Artificial Sequence
<220> FEATURE:
<223> OTHER INFORMATION: 3E05 VH_2 CDR 3 (Kabat and Chothia)

<400> SEQUENCE: 28

His Asp Tyr Tyr Asp Gly Gly Leu Tyr Tyr Ala Met Asp Tyr
1               5                   10

<210> SEQ ID NO 29
<211> LENGTH: 7
<212> TYPE: PRT
<213> ORGANISM: Artificial Sequence
<220> FEATURE:
<223> OTHER INFORMATION: 3E05 VH_2 CDR 1 (Chothia)

<400> SEQUENCE: 29

Gly Phe Thr Phe Ser Ser Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: 3E05 VH_2 CDR 2 (Chothia)

<400> SEQUENCE: 30

Ser Ser Gly Gly Gly Asn Thr Tyr
1               5

<210> SEQ ID NO 31
<211> LENGTH: 111
<212> TYPE: PRT
<213> ORGANISM: Artificial Sequence
<220> FEATURE:
<223> OTHER INFORMATION: 3E05 VL_3

<400> SEQUENCE: 31

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asp Tyr Asp
            20                  25                  30

Gly Asp Ser Ser Met Asn Trp Tyr Gln Gln Lys Pro Gly Gln Pro Pro
        35                  40                  45

Lys Leu Leu Ile Tyr Ala Ala Ser Thr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Thr Tyr Tyr Cys Gln Gln Thr Asn
                85                  90                  95

Glu Asp Pro Pro Thr Phe Gly Gly Gly Thr Lys Val Glu Ile Lys
            100                 105                 110

<210> SEQ ID NO 32
<211> LENGTH: 15
<212> TYPE: PRT
<213> ORGANISM: Artificial Sequence
<220> FEATURE:
<223> OTHER INFORMATION: 3E05 VL_3 CDR 1 (Kabat and Chothia)

<400> SEQUENCE: 32

Lys Ser Ser Gln Ser Val Asp Tyr Asp Gly Asp Ser Ser Met Asn
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: 3E05 VL_3 CDR 2 (Kabat and Chothia)

<400> SEQUENCE: 33

Ala Ala Ser Thr Leu Glu Ser
1               5

<210> SEQ ID NO 34
<211> LENGTH: 9
<212> TYPE: PRT
<213> ORGANISM: Artificial Sequence
<220> FEATURE:
<223> OTHER INFORMATION: 3E05 VL_3 CDR 3 (Kabat and Chothia)

<400> SEQUENCE: 34

Gln Gln Thr Asn Glu Asp Pro Pro Thr
1               5

<210> SEQ ID NO 35
<211> LENGTH: 123
<212> TYPE: PRT
<213> ORGANISM: Artificial Sequence
<220> FEATURE:
<223> OTHER INFORMATION: 3E05 VH_3

<400> SEQUENCE: 35

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Tyr Ile Ser Ser Gly Gly Gly Gln Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Asp Tyr Tyr Asp Gly Gly Leu Tyr Tyr Ala Met Asp Tyr
            100                 105                 110

Trp Gly Gln Gly Thr Leu Val Thr Val Ser Ser
        115                 120

<210> SEQ ID NO 36
<211> LENGTH: 5

<212> TYPE: PRT
<213> ORGANISM: Artificial Sequence
<220> FEATURE:
<223> OTHER INFORMATION: 3E05 VH_3 CDR 1 (Kabat)

<400> SEQUENCE: 36

Ser Tyr Thr Met Ser
1 5

<210> SEQ ID NO 37
<211> LENGTH: 17
<212> TYPE: PRT
<213> ORGANISM: Artificial Sequence
<220> FEATURE:
<223> OTHER INFORMATION: 3E05 VH_3 CDR 2 (Kabat)

<400> SEQUENCE: 37

Tyr Ile Ser Ser Gly Gly Gly Gln Thr Tyr Tyr Pro Asp Ser Val Lys
1 5 10 15

Gly

<210> SEQ ID NO 38
<211> LENGTH: 14
<212> TYPE: PRT
<213> ORGANISM: Artificial Sequence
<220> FEATURE:
<223> OTHER INFORMATION: 3E05 VH_3 CDR 3 (Kabat and Chothia)

<400> SEQUENCE: 38

His Asp Tyr Tyr Asp Gly Gly Leu Tyr Tyr Ala Met Asp Tyr
1 5 10

<210> SEQ ID NO 39
<211> LENGTH: 7
<212> TYPE: PRT
<213> ORGANISM: Artificial Sequence
<220> FEATURE:
<223> OTHER INFORMATION: 3E05 VH_3 CDR 1 (Chothia)

<400> SEQUENCE: 39

Gly Phe Thr Phe Ser Ser Tyr
1 5

<210> SEQ ID NO 40
<211> LENGTH: 8
<212> TYPE: PRT
<213> ORGANISM: Artificial Sequence
<220> FEATURE:
<223> OTHER INFORMATION: 3E05 VH_3 CDR 2 (Chothia)

<400> SEQUENCE: 40

Ser Ser Gly Gly Gly Gln Thr Tyr
1 5

<210> SEQ ID NO 41
<211> LENGTH: 111
<212> TYPE: PRT
<213> ORGANISM: Artificial Sequence
<220> FEATURE:
<223> OTHER INFORMATION: 3E05 VL_4

<400> SEQUENCE: 41

Asp Ile Val Met Thr Gln Ser Pro Asp Ser Leu Ala Val Ser Leu Gly
1 5 10 15

Glu Arg Ala Thr Ile Asn Cys Lys Ala Ser Gln Ser Val Asp Tyr Glu
20 25 30

Gly Asp Ser Ser Met Asn Trp Tyr Gln Gln Lys Pro Gly Gln Pro Pro
35 40 45

Lys Leu Leu Ile Ser Ala Ala Ser Thr Leu Glu Ser Gly Val Pro Ser
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Thr Asn
85 90 95

Glu Asp Pro Pro Thr Phe Gly Gly Gly Thr Lys Val Glu Ile Lys
100 105 110

<210> SEQ ID NO 42
<211> LENGTH: 15
<212> TYPE: PRT
<213> ORGANISM: Artificial Sequence
<220> FEATURE:
<223> OTHER INFORMATION: 3E05 VL_4 CDR 1 (Kabat and Chothia)

<400> SEQUENCE: 42

Lys Ala Ser Gln Ser Val Asp Tyr Glu Gly Asp Ser Ser Met Asn
1 5 10 15

<210> SEQ ID NO 43
<211> LENGTH: 7
<212> TYPE: PRT
<213> ORGANISM: Artificial Sequence
<220> FEATURE:
<223> OTHER INFORMATION: 3E05 VL_4 CDR 2 (Kabat and Chothia)

<400> SEQUENCE: 43

Ala Ala Ser Thr Leu Glu Ser
1 5

<210> SEQ ID NO 44
<211> LENGTH: 9
<212> TYPE: PRT
<213> ORGANISM: Artificial Sequence
<220> FEATURE:
<223> OTHER INFORMATION: 3E05 VL_4 CDR 3 (Kabat and Chothia)

<400> SEQUENCE: 44

Gln Gln Thr Asn Glu Asp Pro Pro Thr
1 5

<210> SEQ ID NO 45
<211> LENGTH: 123
<212> TYPE: PRT
<213> ORGANISM: Artificial Sequence
<220> FEATURE:
<223> OTHER INFORMATION: 3E05 VH_4

<400> SEQUENCE: 45

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Thr Met Ser Trp Val Arg Gln Ala Pro Gly Lys Gly Leu Glu Trp Val
35 40 45

Ala Tyr Ile Ser Ser Gly Gly Gly Gln Thr Tyr Tyr Pro Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg His Asp Tyr Tyr Glu Gly Gly Leu Tyr Tyr Ala Met Asp Tyr
100 105 110

Trp Gly Gln Gly Thr Leu Val Thr Val Ser Ser
115 120

<210> SEQ ID NO 46
<211> LENGTH: 5
<212> TYPE: PRT
<213> ORGANISM: Artificial Sequence
<220> FEATURE:
<223> OTHER INFORMATION: 3E05 VH_4 CDR 1 (Kabat)

<400> SEQUENCE: 46

Ser Tyr Thr Met Ser
1 5

<210> SEQ ID NO 47
<211> LENGTH: 17
<212> TYPE: PRT
<213> ORGANISM: Artificial Sequence
<220> FEATURE:
<223> OTHER INFORMATION: 3E05 VH_4 CDR 2 (Kabat)

<400> SEQUENCE: 47

Tyr Ile Ser Ser Gly Gly Gly Gln Thr Tyr Tyr Pro Asp Ser Val Lys
1 5 10 15

Gly

<210> SEQ ID NO 48
<211> LENGTH: 14
<212> TYPE: PRT
<213> ORGANISM: Artificial Sequence
<220> FEATURE:
<223> OTHER INFORMATION: 3E05 VH_4 CDR 3 (Kabat and Chothia)

<400> SEQUENCE: 48

His Asp Tyr Tyr Glu Gly Gly Leu Tyr Tyr Ala Met Asp Tyr
1 5 10

<210> SEQ ID NO 49
<211> LENGTH: 7
<212> TYPE: PRT
<213> ORGANISM: Artificial Sequence
<220> FEATURE:
<223> OTHER INFORMATION: 3E05 VH_4 CDR 1 (Chothia)

<400> SEQUENCE: 49

Gly Phe Thr Phe Ser Ser Tyr
1 5

<210> SEQ ID NO 50
<211> LENGTH: 8
<212> TYPE: PRT
<213> ORGANISM: Artificial Sequence
<220> FEATURE:
<223> OTHER INFORMATION: 3E05 VH_4 CDR 2 (Chothia)

<400> SEQUENCE: 50

Ser Ser Gly Gly Gly Gln Thr Tyr
1 5

<210> SEQ ID NO 51

<211> LENGTH: 111
<212> TYPE: PRT
<213> ORGANISM: Artificial Sequence
<220> FEATURE:
<223> OTHER INFORMATION: Parental 21E06 VL

<400> SEQUENCE: 51

Asp Ile Val Leu Thr Gln Ser Pro Ala Ser Leu Ala Val Ser Leu Gly
1 5 10 15

Gln Arg Ala Thr Ile Ser Cys Lys Ala Ser Gln Ser Val Asp Tyr Asp
20 25 30

Gly Asp Asn Cys Leu His Trp Phe Gln Gln Lys Pro Gly Gln Pro Pro
35 40 45

Lys Leu Leu Ile Tyr Ala Ala Ser Asn Leu Glu Ser Gly Ile Pro Ala
50 55 60

Arg Phe Ser Gly Ser Gly Ser Gly Thr Asp Phe Thr Leu Asn Ile His
65 70 75 80

Pro Val Glu Glu Glu Asp Ala Ala Thr Tyr Tyr Cys Gln Gln Ser Asn
85 90 95

Glu Asp Pro Pro Thr Phe Gly Gly Gly Thr Lys Leu Glu Ile Lys
100 105 110

<210> SEQ ID NO 52
<211> LENGTH: 15
<212> TYPE: PRT
<213> ORGANISM: Artificial Sequence
<220> FEATURE:
<223> OTHER INFORMATION: Parental 21E06 VL CDR 1 (Kabat and Chothia)

<400> SEQUENCE: 52

Lys Ala Ser Gln Ser Val Asp Tyr Asp Gly Asp Asn Cys Leu His
1 5 10 15

<210> SEQ ID NO 53
<211> LENGTH: 7
<212> TYPE: PRT
<213> ORGANISM: Artificial Sequence
<220> FEATURE:
<223> OTHER INFORMATION: Parental 21E06 VL CDR 2 (Kabat and Chothia)

<400> SEQUENCE: 53

Ala Ala Ser Asn Leu Glu Ser
1 5

<210> SEQ ID NO 54
<211> LENGTH: 9
<212> TYPE: PRT
<213> ORGANISM: Artificial Sequence
<220> FEATURE:
<223> OTHER INFORMATION: Parental 21E06 VL CDR 3 (Kabat and Chothia)

<400> SEQUENCE: 54

Gln Gln Ser Asn Glu Asp Pro Pro Thr
1 5

<210> SEQ ID NO 55
<211> LENGTH: 122
<212> TYPE: PRT
<213> ORGANISM: Artificial Sequence
<220> FEATURE:
<223> OTHER INFORMATION: Parental 21E06 VH

<400> SEQUENCE: 55

Glu Val Lys Leu Val Glu Ser Gly Gly Gly Leu Val Lys Ser Gly Gly

```
1               5                   10                  15

Ser Leu Lys Leu Ser Cys Glu Val Ser Gly Phe Thr Phe Ser Ser Tyr
            20                  25                  30

Thr Ile Ser Trp Val Arg Gln Thr Pro Glu Lys Arg Leu Glu Trp Val
        35                  40                  45

Ala Tyr Ile Ser Ser Gly Gly Asp Asn Ala Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Met Tyr Tyr Cys
                85                  90                  95

Ala Arg His Leu Tyr Tyr Gly Asp Tyr Phe Tyr Val Met Asp Tyr Trp
            100                 105                 110

Gly Gln Gly Thr Ser Val Thr Val Ser Ser
        115                 120


<210> SEQ ID NO 56
<211> LENGTH: 5
<212> TYPE: PRT
<213> ORGANISM: Artificial Sequence
<220> FEATURE:
<223> OTHER INFORMATION: Parental 21E06 VH CDR 1 (Kabat)

<400> SEQUENCE: 56

Ser Tyr Thr Ile Ser
1               5


<210> SEQ ID NO 57
<211> LENGTH: 17
<212> TYPE: PRT
<213> ORGANISM: Artificial Sequence
<220> FEATURE:
<223> OTHER INFORMATION: Parental 21E06 VH CDR 2 (Kabat)

<400> SEQUENCE: 57

Tyr Ile Ser Ser Gly Gly Asp Asn Ala Tyr Tyr Pro Asp Ser Val Lys
1               5                   10                  15

Gly


<210> SEQ ID NO 58
<211> LENGTH: 13
<212> TYPE: PRT
<213> ORGANISM: Artificial Sequence
<220> FEATURE:
<223> OTHER INFORMATION: Parental 21E06 VH CDR 3 (Kabat and Chothia)

<400> SEQUENCE: 58

His Leu Tyr Tyr Gly Asp Tyr Phe Tyr Val Met Asp Tyr
1               5                   10


<210> SEQ ID NO 59
<211> LENGTH: 7
<212> TYPE: PRT
<213> ORGANISM: Artificial Sequence
<220> FEATURE:
<223> OTHER INFORMATION: Parental 21E06 VH CDR 1 (Chothia)

<400> SEQUENCE: 59

Gly Phe Thr Phe Ser Ser Tyr
1               5


<210> SEQ ID NO 60
```

<211> LENGTH: 6
<212> TYPE: PRT
<213> ORGANISM: Artificial Sequence
<220> FEATURE:
<223> OTHER INFORMATION: Parental 21E06 VH CDR 2 (Chothia)

<400> SEQUENCE: 60

Ser Ser Gly Gly Asp Asn
1 5

<210> SEQ ID NO 61
<211> LENGTH: 111
<212> TYPE: PRT
<213> ORGANISM: Artificial Sequence
<220> FEATURE:
<223> OTHER INFORMATION: Parental 25E06 VL

<400> SEQUENCE: 61

Asp Ile Val Leu Thr Gln Ser Pro Ala Ser Leu Ala Val Ser Leu Gly
1 5 10 15

Gln Arg Ala Thr Ile Ser Cys Lys Ala Ser Gln Ser Val Asp Tyr Asp
20 25 30

Gly Asp Gly Phe Met Asn Trp Tyr Gln Gln Lys Pro Gly Gln Pro Pro
35 40 45

Lys Leu Leu Ile Tyr Ala Ala Ser Asn Leu Glu Ser Gly Ile Pro Ala
50 55 60

Arg Phe Ser Gly Ser Gly Ser Gly Ala Asp Phe Thr Leu Asn Ile His
65 70 75 80

Pro Val Glu Glu Glu Asp Ala Ala Thr Tyr Tyr Cys Gln Gln Ser Asn
85 90 95

Glu Asp Pro Pro Thr Phe Gly Gly Gly Thr Lys Leu Glu Ile Lys
100 105 110

<210> SEQ ID NO 62
<211> LENGTH: 15
<212> TYPE: PRT
<213> ORGANISM: Artificial Sequence
<220> FEATURE:
<223> OTHER INFORMATION: Parental 25E06 VL CDR 1 (Kabat and Chothia)

<400> SEQUENCE: 62

Lys Ala Ser Gln Ser Val Asp Tyr Asp Gly Asp Gly Phe Met Asn
1 5 10 15

<210> SEQ ID NO 63
<211> LENGTH: 7
<212> TYPE: PRT
<213> ORGANISM: Artificial Sequence
<220> FEATURE:
<223> OTHER INFORMATION: Parental 25E06 VL CDR 2 (Kabat and Chothia)

<400> SEQUENCE: 63

Ala Ala Ser Asn Leu Glu Ser
1 5

<210> SEQ ID NO 64
<211> LENGTH: 9
<212> TYPE: PRT
<213> ORGANISM: Artificial Sequence
<220> FEATURE:
<223> OTHER INFORMATION: Parental 25E06 VL CDR 3 (Kabat and Chothia)

<400> SEQUENCE: 64

Gln Gln Ser Asn Glu Asp Pro Pro Thr 1 5

<210> SEQ ID NO 65
<211> LENGTH: 121
<212> TYPE: PRT
<213> ORGANISM: Artificial Sequence
<220> FEATURE:
<223> OTHER INFORMATION: Parental 25E06 VH

<400> SEQUENCE: 65

Glu Val Lys Leu Val Glu Ser Gly Gly Gly Leu Val Lys Pro Gly Gly
1 5 10 15

Ser Leu Lys Leu Ser Cys Ala Ala Ser Gly Phe Thr Phe Ser Ser Tyr
20 25 30

Thr Met Ser Trp Val Arg Gln Thr Pro Glu Lys Arg Leu Glu Trp Val
35 40 45

Ala Tyr Ile Ser Gly Val Gly Gly Asp Thr Tyr Tyr Pro Asp Ser Val
50 55 60

Lys Gly Arg Phe Thr Ile Ser Arg Asp Asn Ala Arg Asn Thr Leu Tyr
65 70 75 80

Leu Gln Met Ser Ser Leu Arg Ser Glu Asp Thr Ala Met Phe Tyr Cys
85 90 95

Ala Arg His His Tyr Ser His Tyr Phe Trp Tyr Phe Asp Val Trp Gly
100 105 110

Ala Gly Thr Thr Val Thr Val Ser Ser
115 120

<210> SEQ ID NO 66
<211> LENGTH: 5
<212> TYPE: PRT
<213> ORGANISM: Artificial Sequence
<220> FEATURE:
<223> OTHER INFORMATION: Parental 25E06 VH CDR 1 (Kabat)

<400> SEQUENCE: 66

Ser Tyr Thr Met Ser
1 5

<210> SEQ ID NO 67
<211> LENGTH: 17
<212> TYPE: PRT
<213> ORGANISM: Artificial Sequence
<220> FEATURE:
<223> OTHER INFORMATION: Parental 25E06 VH CDR 2 (Kabat)

<400> SEQUENCE: 67

Tyr Ile Ser Gly Val Gly Gly Asp Thr Tyr Tyr Pro Asp Ser Val Lys
1 5 10 15

Gly

<210> SEQ ID NO 68
<211> LENGTH: 12
<212> TYPE: PRT
<213> ORGANISM: Artificial Sequence
<220> FEATURE:
<223> OTHER INFORMATION: Parental 25E06 VH CDR 3 (Kabat and Chothia)

<400> SEQUENCE: 68

His His Tyr Ser His Tyr Phe Trp Tyr Phe Asp Val
1 5 10

<210> SEQ ID NO 69

<211> LENGTH: 7
<212> TYPE: PRT
<213> ORGANISM: Artificial Sequence
<220> FEATURE:
<223> OTHER INFORMATION: Parental 25E06 VH CDR 1 (Chothia)

<400> SEQUENCE: 69

Gly Phe Thr Phe Ser Ser Tyr
1 5

<210> SEQ ID NO 70
<211> LENGTH: 6
<212> TYPE: PRT
<213> ORGANISM: Artificial Sequence
<220> FEATURE:
<223> OTHER INFORMATION: Parental 25E06 VH CDR 2 (Chothia)

<400> SEQUENCE: 70

Ser Gly Val Gly Gly Asp
1 5

<210> SEQ ID NO 71
<211> LENGTH: 111
<212> TYPE: PRT
<213> ORGANISM: Artificial Sequence
<220> FEATURE:
<223> OTHER INFORMATION: Parental 28B01 VL

<400> SEQUENCE: 71

Asp Ile Val Leu Thr Gln Ser Pro Ala Ser Leu Ala Val Ser Leu Gly
1 5 10 15

Gln Arg Ala Thr Ile Ser Cys Lys Ala Ser Gln Ser Val Asp Tyr Ala
20 25 30

Gly Asp Ser Tyr Val Asn Trp Tyr Gln Gln Lys Pro Gly Gln Pro Pro
35 40 45

Lys Leu Leu Ile Tyr Ala Ala Ser Asn Leu Glu Ser Gly Ile Pro Ala
50 55 60

Arg Phe Ser Gly Ser Gly Ser Gly Thr Asp Phe Thr Leu Asn Ile His
65 70 75 80

Pro Val Glu Glu Glu Asp Ala Ala Thr Tyr Tyr Cys Gln Gln Ser Asn
85 90 95

Glu Asp Pro Pro Thr Phe Gly Gly Gly Thr Lys Leu Glu Ile Lys
100 105 110

<210> SEQ ID NO 72
<211> LENGTH: 15
<212> TYPE: PRT
<213> ORGANISM: Artificial Sequence
<220> FEATURE:
<223> OTHER INFORMATION: Parental 28B01 VL CDR 1 (Kabat and Chothia)

<400> SEQUENCE: 72

Lys Ala Ser Gln Ser Val Asp Tyr Ala Gly Asp Ser Tyr Val Asn
1 5 10 15

<210> SEQ ID NO 73
<211> LENGTH: 7
<212> TYPE: PRT
<213> ORGANISM: Artificial Sequence
<220> FEATURE:
<223> OTHER INFORMATION: Parental 28B01 VL CDR 2 (Kabat and Chothia)

<400> SEQUENCE: 73

Ala Ala Ser Asn Leu Glu Ser 1 5

<210> SEQ ID NO 74
<211> LENGTH: 9
<212> TYPE: PRT
<213> ORGANISM: Artificial Sequence
<220> FEATURE:
<223> OTHER INFORMATION: Parental 28B01 VL CDR 3 (Kabat and Chothia)

<400> SEQUENCE: 74

Gln Gln Ser Asn Glu Asp Pro Pro Thr
1 5

<210> SEQ ID NO 75
<211> LENGTH: 121
<212> TYPE: PRT
<213> ORGANISM: Artificial Sequence
<220> FEATURE:
<223> OTHER INFORMATION: Parental 28B01 VH

<400> SEQUENCE: 75

Glu Val Lys Leu Val Glu Ser Gly Gly Gly Leu Val Lys Pro Gly Gly
1 5 10 15

Ser Leu Lys Leu Ser Cys Ala Ala Ser Gly Phe Thr Phe Ser Tyr Tyr
20 25 30

Thr Met Ser Trp Val Arg Gln Thr Pro Glu Lys Arg Leu Glu Trp Val
35 40 45

Ala Tyr Ile Ser Ser Gly Gly Asp Asn Ala Tyr Tyr Pro Asp Ser Val
50 55 60

Arg Gly Arg Phe Thr Ile Ser Arg Asp Asn Ala Arg Asn Thr Leu Tyr
65 70 75 80

Leu Gln Met Ser Ser Leu Arg Ser Glu Asp Thr Ala Met Tyr Tyr Cys
85 90 95

Ala Arg His His Tyr Ser Asn Tyr Phe Trp Tyr Phe Asp Val Trp Gly
100 105 110

Ala Gly Thr Thr Val Thr Val Ser Ser
115 120

<210> SEQ ID NO 76
<211> LENGTH: 5
<212> TYPE: PRT
<213> ORGANISM: Artificial Sequence
<220> FEATURE:
<223> OTHER INFORMATION: Parental 28B01 VH CDR 1 (Kabat)

<400> SEQUENCE: 76

Tyr Tyr Thr Met Ser
1 5

<210> SEQ ID NO 77
<211> LENGTH: 17
<212> TYPE: PRT
<213> ORGANISM: Artificial Sequence
<220> FEATURE:
<223> OTHER INFORMATION: Parental 28B01 VH CDR 2 (Kabat)

<400> SEQUENCE: 77

Tyr Ile Ser Ser Gly Gly Asp Asn Ala Tyr Tyr Pro Asp Ser Val Arg
1 5 10 15

Gly

<210> SEQ ID NO 78

<211> LENGTH: 12
<212> TYPE: PRT
<213> ORGANISM: Artificial Sequence
<220> FEATURE:
<223> OTHER INFORMATION: Parental 28B01 VH CDR 3 (Kabat and Chothia)

<400> SEQUENCE: 78

His His Tyr Ser Asn Tyr Phe Trp Tyr Phe Asp Val
1 5 10

<210> SEQ ID NO 79
<211> LENGTH: 7
<212> TYPE: PRT
<213> ORGANISM: Artificial Sequence
<220> FEATURE:
<223> OTHER INFORMATION: Parental 28B01 VH CDR 1 (Chothia)

<400> SEQUENCE: 79

Gly Phe Thr Phe Ser Tyr Tyr
1 5

<210> SEQ ID NO 80
<211> LENGTH: 6
<212> TYPE: PRT
<213> ORGANISM: Artificial Sequence
<220> FEATURE:
<223> OTHER INFORMATION: Parental 28B01 VH CDR 2 (Chothia)

<400> SEQUENCE: 80

Ser Ser Gly Gly Asp Asn
1 5

<210> SEQ ID NO 81
<211> LENGTH: 642
<212> TYPE: DNA
<213> ORGANISM: Homo sapiens

<400> SEQUENCE: 81
atggtgcctg aagaagagcc tcaagaccga gagaaaggac tctggtggtt ccagttgaag 60
gtctggtcca tggcagtcgt atccatcttg ctcctcagtg tctgtttcac tgtgagttct 120
gtggtgcctc acaattttat gtatagcaaa actgtcaaga ggctgtccaa gttacgagag 180
tatcaacagt atcatccaag cctgacctgc gtcatggaag gaaaggacat agaagattgg 240
agctgctgcc caaccccttg gacttcattt cagtctagtt gctactttat ttctactggg 300
atgcaatctt ggactaagag tcaaaagaac tgttctgtga tgggggctga tctggtggtg 360
atcaacacca gggaagaaca ggatttcatc attcagaatc tgaaaagaaa ttcttcttat 420
tttctggggc tgtcagatcc agggggtcgg cgacattggc aatgggttga ccagacacca 480
tacaatgaaa atgtcacatt ctggcactca ggtgaaccca ataaccttga tgagcgttgt 540
gcgataataa atttccgttc ttcagaagaa tggggctgga atgacattca ctgtcatgta 600
cctcagaagt caatttgcaa gatgaagaag atctacatat aa 642

<210> SEQ ID NO 82
<211> LENGTH: 213
<212> TYPE: PRT
<213> ORGANISM: Homo sapiens

<400> SEQUENCE: 82

Met Val Pro Glu Glu Glu Pro Gln Asp Arg Glu Lys Gly Leu Trp Trp
1 5 10 15

Phe Gln Leu Lys Val Trp Ser Met Ala Val Val Ser Ile Leu Leu Leu

```
            20                  25                  30

Ser Val Cys Phe Thr Val Ser Ser Val Val Pro His Asn Phe Met Tyr
        35                  40                  45

Ser Lys Thr Val Lys Arg Leu Ser Lys Leu Arg Glu Tyr Gln Gln Tyr
    50                  55                  60

His Pro Ser Leu Thr Cys Val Met Glu Gly Lys Asp Ile Glu Asp Trp
65                  70                  75                  80

Ser Cys Cys Pro Thr Pro Trp Thr Ser Phe Gln Ser Ser Cys Tyr Phe
                85                  90                  95

Ile Ser Thr Gly Met Gln Ser Trp Thr Lys Ser Gln Lys Asn Cys Ser
            100                 105                 110

Val Met Gly Ala Asp Leu Val Val Ile Asn Thr Arg Glu Glu Gln Asp
        115                 120                 125

Phe Ile Ile Gln Asn Leu Lys Arg Asn Ser Ser Tyr Phe Leu Gly Leu
    130                 135                 140

Ser Asp Pro Gly Gly Arg Arg His Trp Gln Trp Val Asp Gln Thr Pro
145                 150                 155                 160

Tyr Asn Glu Asn Val Thr Phe Trp His Ser Gly Glu Pro Asn Asn Leu
                165                 170                 175

Asp Glu Arg Cys Ala Ile Ile Asn Phe Arg Ser Ser Glu Glu Trp Gly
            180                 185                 190

Trp Asn Asp Ile His Cys His Val Pro Gln Lys Ser Ile Cys Lys Met
        195                 200                 205

Lys Lys Ile Tyr Ile
    210
```

<210> SEQ ID NO 83
<211> LENGTH: 639
<212> TYPE: DNA
<213> ORGANISM: Cynomolgus

<400> SEQUENCE: 83

```
atggtgccag aggaggagcc acaggacaga gagaagggcg tgtggtggtt tcagctgaag      60

gtgtggagcg tggccgtggt gagcatcctg ctgctgtgcg tgtgctttac cgtgagcagc     120

gtggccagcc acaattttat gtatagcaag accgtgaaga gactgagcaa gctgcaggag     180

tatcagcagt attatccaag cctgacctgc gtgatggagg gcaaggacat ggaggactgg     240

agctgctgcc caaccccatg gaccagcttt cagagcagct gctattttat cagcaccgtg     300

atgcagagct ggaccaagag ccagaataat tgcagcgtga tgggcgccga cctggtggtg     360

atcaatacca aggaggagca ggactttatc acccagaatc tgaagatcaa tagcgcctat     420

tttctgggcc tgagcgaccc aaagggctgg agacactggc agtgggtgga ccagacccca     480

tataataaga atgtgacctt ttggcacagc ggcgagccaa atagcccaga cgagagatgc     540

gccatcatca attttagaag cgaggagtgg ggctggaatg acgtgcactg ccacgtgcca     600

cagaagagca tctgcaagat gaagaagatc tatatctaa                            639
```

<210> SEQ ID NO 84
<211> LENGTH: 212
<212> TYPE: PRT
<213> ORGANISM: Cynomolgus

<400> SEQUENCE: 84

```
Met Val Pro Glu Glu Glu Pro Gln Asp Arg Glu Lys Gly Val Trp Trp
1               5                   10                  15
```

```
Phe Gln Leu Lys Val Trp Ser Val Ala Val Val Ser Ile Leu Leu Leu
            20                  25                  30

Cys Val Cys Phe Thr Val Ser Ser Val Ala Ser His Asn Phe Met Tyr
        35                  40                  45

Ser Lys Thr Val Lys Arg Leu Ser Lys Leu Gln Glu Tyr Gln Gln Tyr
    50                  55                  60

Tyr Pro Ser Leu Thr Cys Val Met Glu Gly Lys Asp Met Glu Asp Trp
65                  70                  75                  80

Ser Cys Cys Pro Thr Pro Trp Thr Ser Phe Gln Ser Ser Cys Tyr Phe
                85                  90                  95

Ile Ser Thr Val Met Gln Ser Trp Thr Lys Ser Gln Asn Asn Cys Ser
            100                 105                 110

Val Met Gly Ala Asp Leu Val Val Ile Asn Thr Lys Glu Glu Gln Asp
        115                 120                 125

Phe Ile Thr Gln Asn Leu Lys Ile Asn Ser Ala Tyr Phe Leu Gly Leu
    130                 135                 140

Ser Asp Pro Lys Gly Trp Arg His Trp Gln Trp Val Asp Gln Thr Pro
145                 150                 155                 160

Tyr Asn Lys Asn Val Thr Phe Trp His Ser Gly Glu Pro Asn Ser Pro
                165                 170                 175

Asp Glu Arg Cys Ala Ile Ile Asn Phe Arg Ser Glu Glu Trp Gly Trp
            180                 185                 190

Asn Asp Val His Cys His Val Pro Gln Lys Ser Ile Cys Lys Met Lys
        195                 200                 205

Lys Ile Tyr Ile
    210
```

<210> SEQ ID NO 85
<211> LENGTH: 525
<212> TYPE: DNA
<213> ORGANISM: Artificial Sequence
<220> FEATURE:
<223> OTHER INFORMATION: His-Human BDCA-2 DNA

<400> SEQUENCE: 85

```
catcatcatc accatcactt catgtacagc aagaccgtga agcggctgag caagctgaga     60

gagtaccagc agtaccaccc cagcctgacc tgcgtgatgg aaggcaagga catcgaggac    120

tggtcctgct gccctacccc ctggaccagc ttccagtcca gctgctactt catcagcacc    180

ggcatgcaga gctggaccaa gagccagaaa aactgcagcg tgatgggcgc cgacctggtc    240

gtgatcaaca ccagagagga acaggacttc atcatccaga acctgaagcg gaacagcagc    300

tacttcctgg gcctgagcga tcctggcggc agacggcatt ggcagtgggt ggaccagacc    360

ccctacaacg agaacgtgac cttctggcac agcggcgagc ccaacaacct ggacgagaga    420

tgcgccatca tcaacttccg gtccagcgag gaatggggct ggaacgacat ccactgccac    480

gtgccccaga aatccatctg caagatgaag aagatctaca tatga                    525
```

<210> SEQ ID NO 86
<211> LENGTH: 174
<212> TYPE: PRT
<213> ORGANISM: Artificial Sequence
<220> FEATURE:
<223> OTHER INFORMATION: His-Human BDCA-2 protein

<400> SEQUENCE: 86

```
His His His His His His Phe Met Tyr Ser Lys Thr Val Lys Arg Leu
1               5                   10                  15
```

Ser Lys Leu Arg Glu Tyr Gln Gln Tyr His Pro Ser Leu Thr Cys Val
20 25 30

Met Glu Gly Lys Asp Ile Glu Asp Trp Ser Cys Cys Pro Thr Pro Trp
35 40 45

Thr Ser Phe Gln Ser Ser Cys Tyr Phe Ile Ser Thr Gly Met Gln Ser
50 55 60

Trp Thr Lys Ser Gln Lys Asn Cys Ser Val Met Gly Ala Asp Leu Val
65 70 75 80

Val Ile Asn Thr Arg Glu Glu Gln Asp Phe Ile Ile Gln Asn Leu Lys
85 90 95

Arg Asn Ser Ser Tyr Phe Leu Gly Leu Ser Asp Pro Gly Gly Arg Arg
100 105 110

His Trp Gln Trp Val Asp Gln Thr Pro Tyr Asn Glu Asn Val Thr Phe
115 120 125

Trp His Ser Gly Glu Pro Asn Asn Leu Asp Glu Arg Cys Ala Ile Ile
130 135 140

Asn Phe Arg Ser Ser Glu Glu Trp Gly Trp Asn Asp Ile His Cys His
145 150 155 160

Val Pro Gln Lys Ser Ile Cys Lys Met Lys Lys Ile Tyr Ile
165 170

<210> SEQ ID NO 87
<211> LENGTH: 1206
<212> TYPE: DNA
<213> ORGANISM: Artificial Sequence
<220> FEATURE:
<223> OTHER INFORMATION: Fc-Human BDCA-2 DNA

<400> SEQUENCE: 87
agctgcgaca agacccacac ctgtccccct tgtcctgccc ctgaactgct gggcggacct 60
agcgtgttcc tgttcccccc aaagcccaag gacaccctga tgatcagccg gacccccgaa 120
gtgacctgcg tggtggtgga tgtgtcccac gaggaccctg aagtgaagtt caattggtac 180
gtggacggcg tggaagtgca caacgccaag accaagccca gagaggaaca gtacaacagc 240
acctaccggg tggtgtccgt gctgaccgtg ctgcaccagg actggctgaa cggcaaagag 300
tacaagtgca aggtgtccaa caaggccctg cctgccccca tcgagaaaac catcagcaag 360
gccaagggcc agccccgcga accccaggtg tacacactgc cccctagcag ggacgagctg 420
accaagaacc aggtgtccct gacctgtctc gtgaagggct tctacccctc cgatatcgcc 480
gtggaatggg agagcaacgg ccagcccgag aacaactaca agaccacccc ccctgtgctg 540
gacagcgacg gctcattctt cctgtacagc aagctgacag tggacaagag ccggtggcag 600
cagggcaacg tgttcagctg cagcgtgatg cacgaggccc tgcacaacca ctacacccag 660
aagtccctgt ccttaagccc cggcaagatc gagggccggt tcatgtactc caagaccgtg 720
aagcggctgt ccaagctgag agagtaccag cagtaccacc ccagcctgac atgcgtgatg 780
gaaggcaagg acatcgagga ctggtcctgc tgccctaccc cctggaccag cttccagtcc 840
agctgctact tcatcagcac cggcatgcag agctggacaa agagccagaa aaactgctcc 900
gtgatgggcg ccgacctggt cgtgatcaac acccgcgagg aacaggactt catcatccag 960
aacctgaagc ggaacagcag ctacttcctg ggcctgagcg atcctggcgg cagacggcat 1020
tggcagtggg tggaccagac cccctacaac gagaacgtga ccttctggca cagcggcgag 1080
cccaacaacc tggacgagag atgcgccatc atcaacttcc ggtccagcga ggaatggggc 1140
tggaacgaca tccactgcca cgtgccccag aaatccatct gcaagatgaa gaagatctac 1200
atatga 1206

<210> SEQ ID NO 88
<211> LENGTH: 400
<212> TYPE: PRT
<213> ORGANISM: Artificial Sequence
<220> FEATURE:
<223> OTHER INFORMATION: Fc-Human BDCA-2 protein

<400> SEQUENCE: 88

Ser Cys Asp Lys Thr His Thr Cys Pro Pro Cys Pro Ala Pro Glu Leu
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser His Glu Asp Pro Glu Val Lys Phe Asn Trp Tyr Val Asp Gly Val
50 55 60

Glu Val His Asn Ala Lys Thr Lys Pro Arg Glu Glu Gln Tyr Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Ala Leu Pro Ala
100 105 110

Pro Ile Glu Lys Thr Ile Ser Lys Ala Lys Gly Gln Pro Arg Glu Pro
115 120 125

Gln Val Tyr Thr Leu Pro Pro Ser Arg Asp Glu Leu Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Lys Leu
180 185 190

Thr Val Asp Lys Ser Arg Trp Gln Gln Gly Asn Val Phe Ser Cys Ser
195 200 205

Val Met His Glu Ala Leu His Asn His Tyr Thr Gln Lys Ser Leu Ser
210 215 220

Leu Ser Pro Gly Lys Ile Glu Gly Arg Phe Met Tyr Ser Lys Thr Val
225 230 235 240

Lys Arg Leu Ser Lys Leu Arg Glu Tyr Gln Gln Tyr His Pro Ser Leu
245 250 255

Thr Cys Val Met Glu Gly Lys Asp Ile Glu Asp Trp Ser Cys Cys Pro
260 265 270

Thr Pro Trp Thr Ser Phe Gln Ser Ser Cys Tyr Phe Ile Ser Thr Gly
275 280 285

Met Gln Ser Trp Thr Lys Ser Gln Lys Asn Cys Ser Val Met Gly Ala
290 295 300

Asp Leu Val Val Ile Asn Thr Arg Glu Glu Gln Asp Phe Ile Ile Gln
305 310 315 320

Asn Leu Lys Arg Asn Ser Ser Tyr Phe Leu Gly Leu Ser Asp Pro Gly
325 330 335

Gly Arg Arg His Trp Gln Trp Val Asp Gln Thr Pro Tyr Asn Glu Asn
340 345 350

Val Thr Phe Trp His Ser Gly Glu Pro Asn Asn Leu Asp Glu Arg Cys
355 360 365

Ala Ile Ile Asn Phe Arg Ser Ser Glu Glu Trp Gly Trp Asn Asp Ile
370 375 380

His Cys His Val Pro Gln Lys Ser Ile Cys Lys Met Lys Lys Ile Tyr
385 390 395 400

<210> SEQ ID NO 89
<211> LENGTH: 385
<212> TYPE: PRT
<213> ORGANISM: Homo sapiens

<400> SEQUENCE: 89

Trp Leu Ala Phe Lys Leu Lys Leu Gly Thr Ala Ala Thr Met Gly Trp
1 5 10 15

Ser Cys Ile Ile Leu Phe Leu Val Ala Thr Ala Thr Gly Val His Ser
20 25 30

Gly Asp Ala Ser Phe Thr Arg Ile Arg Thr His Thr Leu Ser Gly Arg
35 40 45

Gln Val Val Val Val Arg Leu Ala Ser Thr Lys Gly Pro Ser Val Phe
50 55 60

Pro Leu Ala Pro Ser Ser Lys Ser Thr Ser Gly Gly Thr Ala Ala Leu
65 70 75 80

Gly Cys Leu Val Lys Asp Tyr Phe Pro Glu Pro Val Thr Val Ser Trp
85 90 95

Asn Ser Gly Ala Leu Thr Ser Gly Val His Thr Phe Pro Ala Val Leu
100 105 110

Gln Ser Ser Gly Leu Tyr Ser Leu Ser Ser Val Val Thr Val Pro Ser
115 120 125

Ser Ser Leu Gly Thr Gln Thr Tyr Ile Cys Asn Val Asn His Lys Pro
130 135 140

Ser Asn Thr Lys Val Asp Lys Lys Val Glu Pro Lys Ser Cys Asp Lys
145 150 155 160

Thr His Thr Cys Pro Pro Cys Pro Ala Pro Glu Leu Leu Gly Gly Pro
165 170 175

Asp Val Phe Leu Phe Pro Pro Lys Pro Lys Asp Thr Leu Met Ile Ser
180 185 190

Arg Thr Pro Glu Val Thr Cys Val Val Val Asp Val Ser His Glu Asp
195 200 205

Pro Glu Val Lys Phe Asn Trp Tyr Val Asp Gly Val Glu Val His Asn
210 215 220

Ala Lys Thr Lys Pro Arg Glu Glu Gln Tyr Asn Ala Thr Tyr Arg Val
225 230 235 240

Val Ser Val Leu Thr Val Leu His Gln Asp Trp Leu Asn Gly Lys Glu
245 250 255

Tyr Lys Cys Lys Val Ser Asn Lys Ala Leu Pro Ala Pro Glu Glu Lys
260 265 270

Thr Ile Ser Lys Ala Lys Gly Gln Pro Arg Glu Pro Gln Val Tyr Thr
275 280 285

Leu Pro Pro Ser Arg Asp Glu Leu Thr Lys Asn Gln Val Ser Leu Thr
290 295 300

Cys Leu Val Lys Gly Phe Tyr Pro Ser Asp Ile Ala Val Glu Trp Glu
305 310 315 320

Ser Asn Gly Gln Pro Glu Asn Asn Tyr Lys Thr Thr Pro Pro Val Leu

```
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
385


<210> SEQ ID NO 90
<211> LENGTH: 213
<212> TYPE: PRT
<213> ORGANISM: Artificial Sequence
<220> FEATURE:
<223> OTHER INFORMATION: Q8WTT0 construct

<400> SEQUENCE: 90

Met Val Pro Glu Glu Glu Pro Gln Asp Arg Glu Lys Gly Leu Trp Trp
1               5                   10                  15

Phe Gln Leu Lys Val Trp Ser Met Ala Val Val Ser Ile Leu Leu Leu
            20                  25                  30

Ser Val Cys Phe Thr Val Ser Ser Val Val Pro His Asn Phe Met Tyr
        35                  40                  45

Ser Lys Thr Val Lys Arg Leu Ser Lys Leu Arg Glu Tyr Gln Gln Tyr
    50                  55                  60

His Pro Ser Leu Thr Cys Val Met Glu Gly Lys Asp Ile Glu Asp Trp
65                  70                  75                  80

Ser Cys Cys Pro Thr Pro Trp Thr Ser Phe Gln Ser Ser Cys Tyr Phe
                85                  90                  95

Ile Ser Thr Gly Met Gln Ser Trp Thr Lys Ser Gln Lys Asn Cys Ser
            100                 105                 110

Val Met Gly Ala Asp Leu Val Val Ile Asn Thr Arg Glu Glu Gln Asp
        115                 120                 125

Phe Ile Ile Gln Asn Leu Lys Arg Asn Ser Ser Tyr Phe Leu Gly Leu
    130                 135                 140

Ser Asp Pro Gly Gly Arg Arg His Trp Gln Trp Val Asp Gln Thr Pro
145                 150                 155                 160

Tyr Asn Glu Asn Val Thr Phe Trp His Ser Gly Glu Pro Asn Asn Leu
                165                 170                 175

Asp Glu Arg Cys Ala Ile Ile Asn Phe Arg Ser Ser Glu Glu Trp Gly
            180                 185                 190

Trp Asn Asp Ile His Cys His Val Pro Gln Lys Ser Ile Cys Lys Met
        195                 200                 205

Lys Lys Ile Tyr Ile
    210


<210> SEQ ID NO 91
<211> LENGTH: 182
<212> TYPE: PRT
<213> ORGANISM: Artificial Sequence
<220> FEATURE:
<223> OTHER INFORMATION: Q8WTT0-2 construct

<400> SEQUENCE: 91

Met Val Pro Glu Glu Glu Pro Gln Asp Arg Val Pro His Asn Phe Met
1               5                   10                  15
```

-continued

```
Tyr Ser Lys Thr Val Lys Arg Leu Ser Lys Leu Arg Glu Tyr Gln Gln
            20                  25                  30

Tyr His Pro Ser Leu Thr Cys Val Met Glu Gly Lys Asp Ile Glu Asp
        35                  40                  45

Trp Ser Cys Cys Pro Thr Pro Trp Thr Ser Phe Gln Ser Ser Cys Tyr
    50                  55                  60

Phe Ile Ser Thr Gly Met Gln Ser Trp Thr Lys Ser Gln Lys Asn Cys
65                  70                  75                  80

Ser Val Met Gly Ala Asp Leu Val Val Ile Asn Thr Arg Glu Glu Gln
                85                  90                  95

Asp Phe Ile Ile Gln Asn Leu Lys Arg Asn Ser Ser Tyr Phe Leu Gly
            100                 105                 110

Leu Ser Asp Pro Gly Gly Arg Arg His Trp Gln Trp Val Asp Gln Thr
        115                 120                 125

Pro Tyr Asn Glu Asn Val Thr Phe Trp His Ser Gly Glu Pro Asn Asn
    130                 135                 140

Leu Asp Glu Arg Cys Ala Ile Ile Asn Phe Arg Ser Ser Glu Glu Trp
145                 150                 155                 160

Gly Trp Asn Asp Ile His Cys His Val Pro Gln Lys Ser Ile Cys Lys
                165                 170                 175

Met Lys Lys Ile Tyr Ile
            180


<210> SEQ ID NO 92
<211> LENGTH: 14
<212> TYPE: PRT
<213> ORGANISM: Homo Sapians

<400> SEQUENCE: 92

Thr Phe Trp His Ser Gly Glu Pro Asn Asn Leu Asp Glu Arg
1               5                   10
```